United States Patent
Abrahams et al.

(10) Patent No.: US 11,827,684 B2
(45) Date of Patent: Nov. 28, 2023

(54) HUMAN INTERLEUKIN-2 CONJUGATES BIASED FOR THE INTERLEUKIN-2 RECEPTOR BETA GAMMAC DIMER AND CONJUGATED TO A NONPEPTIDIC, WATER-SOLUBLE POLYMER

(71) Applicant: Merck Sharp & Dohme LLC, Rahway, NJ (US)

(72) Inventors: Cristina Abrahams, Burlingame, CA (US); Edward Bowman, Redwood City, CA (US); Xiaofan Li, Belmont, CA (US); Songnian Lin, Holmdel, NJ (US); Willy Solis, San Mateo, CA (US); Ryan Stafford, Foster City, CA (US); Aarron Willingham, Mountain View, CA (US); Alice Yam, Belmont, CA (US); Junhao Yang, Milpitas, CA (US); Gang Yin, South San Francisco, CA (US)

(73) Assignee: Merck Sharp & Dohme LLC, Rahway, NJ (US)

(*) Notice: Subject to any disclaimer, the term of this patent is extended or adjusted under 35 U.S.C. 154(b) by 19 days.

(21) Appl. No.: 17/234,844

(22) Filed: Apr. 20, 2021

(65) Prior Publication Data
US 2021/0340207 A1 Nov. 4, 2021

Related U.S. Application Data

(60) Provisional application No. 63/013,583, filed on Apr. 22, 2020.

(51) Int. Cl.
*A61K 38/20* (2006.01)
*A61K 47/60* (2017.01)
(Continued)

(52) U.S. Cl.
CPC .......... *C07K 14/55* (2013.01); *A61K 38/2013* (2013.01); *A61K 47/545* (2017.08);
(Continued)

(58) Field of Classification Search
CPC .... A61K 38/2013; A61K 47/56; A61K 47/60; C07K 14/55
See application file for complete search history.

(56) References Cited

U.S. PATENT DOCUMENTS

| 4,766,106 A | 8/1988 | Katre et al. |
| 5,204,244 A | 4/1993 | Fell et al. |
| (Continued) | | |

FOREIGN PATENT DOCUMENTS

| CN | 101104077 A | 1/2008 |
| CN | 104231068 A | 12/2014 |
| (Continued) | | |

OTHER PUBLICATIONS

Zimmerman et al. Production of Site-Specific Antibody-Drug Conjugates Using Optimized Non-Natural Amino Acids in a Cell-Free Expression System. Bioconjugate Chemistry. 2014, vol. 25, pp. 351/361. (Year: 2014).*

(Continued)

*Primary Examiner* — Jeffrey E. Russel
(74) *Attorney, Agent, or Firm* — John David Reilly; Anna Cocuzzo

(57) ABSTRACT

Interleukin-2 (IL-2) conjugates comprising at least one or more amino acid substitutions that bias binding to the IL-2 receptor $\beta\gamma_c$ dimer over binding the IL-2 receptor $\alpha\beta\gamma_c$ trimer and a non-natural amino acid at or near the N-terminus conjugated to a water-soluble polymer are described. The IL-2 conjugates are useful for treatment and prevention of cell proliferation and cancer in a patient.

54 Claims, 38 Drawing Sheets

Specification includes a Sequence Listing.

---

CON1 [numbering scheme A]

```
         1         2         3         4         5         6         7
12345678901234567890123456789012345678901234567890123456789012345678901 2
PTSXSTKKTQLQLEHLLLDLQMILNGINNYKNPKLTAMLTKKFYMPKKATELKHLQCLEEELKPLEEVLNLA
                                   1         1         1         1
         8         9         0         1         2         3
3456789012345678901234567890123456789012345678901234567890 1 2
QSKNFHLRPRDLISNINVIVLELKGSETTFMCEYADETATIVEFLNRWITFSQSIISTLT
(SEQ ID NO: 20)
```

X is pAMF conjugated to PEG1
Amino acid substitutions are in bold and underlined

(51) Int. Cl.
| | |
|---|---|
| *C07K 14/55* | (2006.01) |
| *A61K 47/54* | (2017.01) |
| *A61P 5/00* | (2006.01) |
| *C07K 16/28* | (2006.01) |
| *A61K 38/00* | (2006.01) |

(52) U.S. Cl.
CPC ............... *A61K 47/60* (2017.08); *A61P 5/00* (2018.01); *C07K 16/2818* (2013.01); *C07K 16/2827* (2013.01); *A61K 38/00* (2013.01)

(56) References Cited

U.S. PATENT DOCUMENTS

| | | | |
|---|---|---|---|
| 5,229,109 | A | 7/1993 | Grimm et al. |
| 5,534,615 | A | 7/1996 | Baker et al. |
| 5,932,462 | A | 8/1999 | Harris et al. |
| 6,955,807 | B1 | 10/2005 | Shanafelt et al. |
| 7,642,085 | B2 | 1/2010 | Schultz et al. |
| 7,736,872 | B2 | 6/2010 | Paulsel et al. |
| 7,829,659 | B2 | 11/2010 | Grabstein et al. |
| 7,846,689 | B2 | 12/2010 | Paulsel et al. |
| 8,008,449 | B2 | 8/2011 | Korman et al. |
| 8,183,012 | B2 | 5/2012 | Schultz et al. |
| 8,354,509 | B2 | 1/2013 | Carven et al. |
| 8,431,558 | B2 | 4/2013 | Bertozzi et al. |
| 8,445,446 | B2 | 5/2013 | Deiters et al. |
| 8,541,625 | B2 | 9/2013 | Popik et al. |
| 8,680,315 | B2 | 3/2014 | Santi et al. |
| 8,703,936 | B2 | 4/2014 | Jewett et al. |
| 8,754,190 | B2 | 6/2014 | Ashley et al. |
| 9,145,361 | B2 | 9/2015 | Gee et al. |
| 9,163,271 | B2 | 10/2015 | Schultz et al. |
| 9,206,243 | B2 | 12/2015 | Len et al. |
| 9,222,940 | B2 | 12/2015 | Van Delft et al. |
| 9,266,938 | B2 | 2/2016 | Ast et al. |
| 9,428,567 | B2 | 8/2016 | Garcia et al. |
| 9,682,934 | B2 | 6/2017 | Stafford et al. |
| 9,732,134 | B2 | 8/2017 | Gavin et al. |
| 9,797,908 | B2 | 10/2017 | Deiters et al. |
| 9,861,705 | B2 | 1/2018 | Bossard et al. |
| 9,987,500 | B2 | 6/2018 | Papadopoulos et al. |
| 9,994,527 | B2 | 6/2018 | Stafford et al. |
| 10,183,890 | B2 | 1/2019 | Biguenet |
| RE47,539 | E | 7/2019 | Popik et al. |
| 10,487,133 | B2 | 11/2019 | Yin |
| 10,610,571 | B2 | 4/2020 | Ptacin et al. |
| 2012/0244112 | A1 | 9/2012 | Ast et al. |
| 2013/0189287 | A1 | 7/2013 | Bregeon et al. |
| 2013/0195795 | A1 | 8/2013 | Gavin et al. |
| 2013/0251783 | A1 | 9/2013 | Parmentier et al. |
| 2014/0356385 | A1 | 12/2014 | Dennler et al. |
| 2016/0257709 | A1 | 9/2016 | Kline et al. |
| 2017/0292139 | A1 | 10/2017 | Alfonta et al. |
| 2018/0085468 | A1 | 3/2018 | Bossard et al. |
| 2019/0008978 | A1 | 1/2019 | Huang et al. |
| 2019/0092831 | A1* | 3/2019 | Krupnick ............ A61K 47/642 |
| 2019/0144546 | A1 | 5/2019 | Stafford et al. |
| 2019/0216898 | A1 | 7/2019 | Wang et al. |
| 2019/0314455 | A1* | 10/2019 | Ptacin .................. A61K 47/542 |
| 2020/0207859 | A1 | 7/2020 | Molina |
| 2020/0317784 | A1* | 10/2020 | Nandabalan ....... A61K 39/3955 |
| 2020/0385438 | A1* | 12/2020 | Garcia ............... C07K 14/7155 |
| 2021/0046160 | A1 | 2/2021 | Ptacin et al. |
| 2021/0060169 | A1* | 3/2021 | Ikeda ................. A61K 47/545 |

FOREIGN PATENT DOCUMENTS

| | | | |
|---|---|---|---|
| EP | 2673294 | B1 | 4/2016 |
| EP | 3004062 | B1 | 7/2017 |
| EP | 2890402 | B1 | 4/2019 |
| WO | 1985000817 | A1 | 2/1985 |
| WO | 1993020849 | A1 | 10/1993 |
| WO | 1999045964 | A1 | 9/1999 |
| WO | 2002085923 | A2 | 10/2002 |
| WO | 2004070024 | A1 | 8/2004 |
| WO | 2005007121 | A2 | 1/2005 |
| WO | 2005086751 | A2 | 9/2005 |
| WO | 2006050262 | A2 | 5/2006 |
| WO | 2006121168 | A1 | 11/2006 |
| WO | 2007134181 | A2 | 11/2007 |
| WO | 2008003473 | A2 | 1/2008 |
| WO | 2009061853 | A2 | 5/2009 |
| WO | 2009114335 | A3 | 9/2009 |
| WO | 2010014258 | A2 | 2/2010 |
| WO | 2010085495 | A1 | 7/2010 |
| WO | 2012065086 | A1 | 5/2012 |
| WO | 2012075045 | A2 | 6/2012 |
| WO | 2013185115 | A1 | 12/2013 |
| WO | 2014036492 | A1 | 3/2014 |
| WO | 2014189370 | A1 | 11/2014 |
| WO | 2015006555 | A2 | 1/2015 |
| WO | 2015112800 | A1 | 7/2015 |
| WO | 2015193897 | A1 | 12/2015 |
| WO | 2016025385 | A1 | 2/2016 |
| WO | 2016115168 | A1 | 7/2016 |
| WO | 2017106767 | A1 | 6/2017 |
| WO | 2017136818 | A2 | 8/2017 |
| WO | 2017190684 | A1 | 11/2017 |
| WO | 2019014267 | A1 | 1/2019 |
| WO | 2019028419 | A1 | 2/2019 |
| WO | 2019028425 | A1 | 2/2019 |
| WO | 2019125732 | A1 | 6/2019 |
| WO | WO-2019131964 | A1 * | 7/2019 ............. A61K 38/20 |
| WO | 2019185705 | A1 | 10/2019 |
| WO | 2019185706 | A1 | 10/2019 |
| WO | WO-2020056066 | A1 * | 3/2020 ............. A61K 38/00 |
| WO | 2020163532 | A1 | 8/2020 |
| WO | 2021030706 | A1 | 2/2021 |
| WO | WO-2021091986 | A1 * | 5/2021 ......... A61K 38/2066 |
| WO | 2021140416 | A2 | 7/2021 |
| WO | WO-2022076859 | A1 * | 4/2022 | |

OTHER PUBLICATIONS

Arenas-Ramirez, N. et al., Improved cancer immunotherapy by a CD25-mimobody conferring selectivity to human interleukin-2, Sci Transl Med, 2016, 1-12, 8:367ra166.

Azoulay, M. et al., Glutamine analogues as potential antimalarials, Eur. J. Med. Chem., 1991, 201-205, 26.

Baert et al., Influence of Immunogenicity on the long term efficacy of Infliximab in Crohns disease, New England Journal Med., 2003, pp. 601-608, 348.

Barton, Derek H.R. et al., Synthesis of Novel a-Amino-Acids and Derivatives Using Radical Chemistry: Synthesis of L- and D-a-Amino-Adipic Acids, L-a-aminopimelic Acid and Appropriate Unsaturated Derivatives, Tetrahedron Letters, 1987, 4297-4308, 43.

Beniaminovitz et al., Prevention of rejection in cardiac transplantation by blockade of the interleukin 2 receptor with a monoclonal antibody, New England Journal of Medicine, 2000, pp. 613-619, 342.

Bentebibel, S.E. et al., The Novel IL-2 Cytokine Immune Agonist NKTR-214 Harnesses the Adaptive and Innate Immune System for the Treatment of Solid Cancers, Society for Immunotherapy of Cancer 2017 Annual Meeting (SITC 2017), 2017, 1, Poster 77.

Boyman, O. et al., The role of interleukin-2 during homeostatis and activation of the immune system, Nature, 2012, 180-190, 12.

Carmenate, T. et al., Human IL-2 Mutein with Higher Antitumor Efficacy Than Wild Type IL-2, Journal of Immunology, 2013, 6230-6238, 190(12).

Charych, D. et al., Combining complementary mechanisms of immune activation: NKTR-214, a biased IL-2 pathway agonist and immune checkpoint antagonists, Annals of Oncology, 2016, 1 (1078P), 27 (S6).

Charych, D. et al., Modeling the receptor pharmacology, pharmacokinetis, and pharmacodynamics of NKTR-214, a kinetically-controlled interleukin-2 (IL2) receptor agonist for cancer immunotherapy, PLoS ONE, 2017, 1-24, 12(7): e20179431.

Charych, D. et al., NKTR-214, an Engineered Cytokine with Biased IL2 Receptor Binding, Increased Tumor Exposure, and Marked Efficacy in Mouse Tumor Models, Clin Cancer Res, 2016, 680-690, 22(3).

(56) References Cited

OTHER PUBLICATIONS

Chastagner, P. et al., Lack of intermediate-affinity interleukin-2 receptor in mice leads to dependence on Interkeukin-2 receptor alpha, beta and gamma chain expression for T cell growth, Eur J Immunol, 1996, 201-206, 26.
Chen, X. et al., A novel human IL-2 mutein with minimal systemic toxicity exerts greater antitumor efficacy than wild-type IL-2, Cell Death & Disease, 2018, 1-12, 9:989.
Christie, Bradley D. et al., Synthesis of optically pure pipecolates from L-asparagine. Application to the total synthesis of (+)-apovincamine through amino acid decarbonylation and iminium ion cyclization, J. Org. Chem., 1985, 1239-1246, 50.
Craig, J. Cymerman et al., Absolute configuration of the enantiomers of 7-chloro-4-[[4-(diethylamino)-1-methylbutyl]amino]quinoline (chloroquine), J. Org. Chem., 1988, 1167-1170, 53.
Defour, G., THOR-707, an engineered not-alpha IL-2, for the treatment of solid tumors induces strong Immunological responses in vivo, CSCO Immunotherapy Seminar Mar. 22-23, 2019 (Shanghi, China), 2019, 1-12, N/A.
Deiters, A. et al., Site-specific PEGylation of proteins containing unnatural amino acids, Bioorg Med Chem Lett, 2004, 5743-5745, 14.
Diab, A. et al., NKTR-214 (CD-122-biased agonist) plus nivolumab in patients with advanced solid tumors: Preliminary phase 1/2 results of Pivot, ClinicalTrials gov NCT02983045, 2018, 1-22, N/A.
Diab, A. et al., Pivot-02: Preliminary safety, efficacy and biomarker results from dose escalation of the Phase 1/2 study of CD-122-biased agonist NKTR-214 plus nivolumab in patients . . . , SITC 2017, 2017, 1, Poster O20.
Dien, V.T. et al., Expansion of the genetic code via expansion of the genetic alphabet, Curr Opin Chem Biol, 2018, 196-202, 46.
Dien, V.T. et al., Progress Toward a Semi-Synthetic Organism with an Unrestricted Expanded Genetic Alphabet, J Am Chem Soc, 2018, 16115-16123, 140.
Dozier, J.K. et al., Site-Specific PEGylation of Therapeutic Proteins, Int. J. Mol. Sci., 2015, 25831-25864, 16(10).
Feldman, A.W. et al., Chemical Stabilization of Unnatural Nucleotide Triphosphates for the in Vivo Expansion of the Genetic Alphabet, J. Am. Chem. Soc., 2017, 2464-2467, 139(6).
Feldman, A.W. et al., Expansion of the Genetic Alphabet: A Chemist's Approach to Synthetic Biology, Acc. Chem. Res., 2018, 394-403, 51(2).
Floros, T. et al., Anticancer Cytokines: Biology and Clinical Effects of IFN-alpha2, IL-2, IL-15, IL-21, and IL-12, Semin. Oncol., 2015, 539-548, 42(4).
Friedman, Orrie M. et al., Synthesis of Derivatives of Glutamine as Model Substrates for Anti-tumor Agents, J. Am. Chem. Soc., 1959, 3750-3752, 81.
GenBank accession No. JX206457, 3 pages, (2012).
Ghosh et al., Natalizumab for active Crohns disease, New England J. Med., 2003, pp. 24-32, 348.
Gillies, S.D. et al., A Low-Toxicity IL-2-based Immunocytokine Retains Antitumor Activity Despite its High Degree of IL-2 receptor Selectivity, Clin. Cancer Res., 2011, 3673-3686, 17(11).
Goodson, R.J. et al., Site-Directed Pegylation of Recombinant IL-2 at its Glycosylation Site, Biotechnology, 1990, 343-346, 8(4).
Hamid et al., Safety and Tumor Responses with Lambrolizumab (Anti-PD-1) in Melanoma, New Eng. J. Med., 2013, 134-144, 369(2).
Hancock, S.M. et al., Expanding the Genetic Code of Yeast for Incorporation of Diverse Unnatural Amino Acids via a Pyrrolysyl-tRNA Synthetase/IRNA Pair, JACS, 2010, 14819-14824, 132.
Heaton, K.M. et al., Characterization of lymphokine-activated killing by human peripheral blood mononuclear cells stimulated with interleukin 2 (IL-2) analogs specific for the intermediate affinity IL-2 receptor, Cellular Immunology, 1993, 167-179, 147.
Heaton, K.M. et al., Human interleukin 2 analogues that preferentially bind the intermediate-affinity interleukin 2 receptor lead to reduced secondary cytokine secretion: implications for the use of these interleukin 2 analogues in cancer immunotherapy, Cancer Research, 1993, 2597-2602, 53.
Hurwitz, M.E. et al., A Novel Immune Agonist, NKTR-214, Increases the No. of Activity of CD8+ Tumor Infiltrating Lymphocytes in Patients with Advance Renal Cell Carcinoma, Poster Session C, ASCO Feb. 18, 2017, 2017, 1, Poster Abstract #454.
Jiang, T. et al., Role of IL-2 in cancer immunotherapy, Oncolmmunology, 2016, 1-10, 5(6):e1163462.
Joseph, I.B. et al., THOR-707, A novel not-alpha IL-2, elicits durable pharmacodynamic responses in non-human primates and, efficacy as single agent and in combination with anti PD-1 in multiple syngeneic mouse models, American Association of Cancer Research (AACR) Annual Meeting 2019, 2019, 1, Poster.
Khalili, S. et al., Mechanistic modeling of a new kinetically-controlled CD122 agonist for cancer immunotherapy: NKTR-214 pharmacokinetics, pharmacodynamics, and receptor pharmacology, AACR Annual Meeting, Apr. 2017, 2017, 1-2, Poster Abstract 1617.
King, F.E. et al., A New Synthesis of Glutamine and of y-Dipeptides of Glutamic Acid from Phthylated Intermediates, J. Chem. Soc., 1949, 3315-3319, N/A.
Klein, C. et al., Cergutuzumab amunaleukin (CEA-IL2v), a CEA-targeted IL-2 variant-based immunocytokine for combination cancer immunotherapy: Overcoming limitations of aldesleukin and conventional IL-2-based Immunocytokines, Oncolmmunology, 2017, 1-15, 6(3):e1277306.
Koskinen, Ari M.P. et al., Synthesis of 4-Substituted Prolines as Conformationally Constrained Amino Acid Analogues, J. Org. Chem., 1989, 1859-1866, 54.
Krieg, et al., Improved IL-2 immunotherapy by selective stimulation of IL-2 receptors on lymphocytes and endothelial cells, PNAS USA, 2010, 11906-11911, 107.
Langowski, J.L. et al., The CD122-biased immunostimulatory cytokine NKTR-214 combined with checkpoint blockade leads to mobilization of anti-tumor immunity and synergistic activity, 2016 CR-CIMT-EATIR-AACR Cancer Immunotherapy Conference, 2016, 1, Poster Abstract 311.
Lazear, E. et al., Targeting of IL-2 to cytotoxic lymphocytes as an improved method of cytokine-driven Immunotherapy, Oncolmmunology, 2017, 1-3, 6(2) e1265721.
Letourneau, S. et al., IL-2/anti-IL-2 antibody complexes show strong biological activity by avoiding interaction with IL-2 receptor alpha subunit CD25, PNAS USA, 2010, 2171-2176, 107.
Levin, A.M. et al., Exploiting a natural conformational switch to engineer an Interleukin-2 superkine, Nature, 2012, 629-533, 484(7395).
Losey, H.C. et al., Abstract 4280: Utilizing a selective agonist of the intermediate-affinity IL-2 receptor with an Improved pharmacokinetic profile leads to an enhanced . . . , AACR 2015, 2015, 1-2, Poster for Abstract 4280.
Lotze, M.T. et al., In vivo administration of purified human interleukin 2. II. Half life, immunologic effects, and expansion of peripheral lymphoid cells in vivo with recombinant IL 2, The Journal of Immunology, 2017, 2865-2875, 135.
Matsoukas, John M. et al., Differences in Backbone Structure between Angiotensin II Agonists and Type I Antagonist, J. Med. Chem., 1995, 4660-4669, 38.
Meghnem, D. et al., Cutting Edge: Differential Fine-Tuning of IL-2- and IL-15-Dependent Functions by Targeting Their Common IL-2/15Rbeta/gammac, The Journal of Immunology, 2017, 4563-4568, 198(12).
Merchant, F. et al., Preclinical characterization of IL-2 Superkines engineered with biased CD8+ T cell stimulating properties, Journal for Immuno Therapy of Cancer, 2018, 1-2, 6 (Suppl 1).
Milgrom et al., Treatment of allergic asthma with monoclonal anti IgE antibody, New England Journal Med., 1999, pp. 1966-1973, 341.
Milla, et al., THOR-707: Using Synthetic Biology to Reprogram the Therapeutic Activity of Interleukin-2 (IL-2), 2019 American Society of Clinical Oncology (ASCO) Annual Meeting Poster (May 15, 2019), 2019, 1, Abstract 2603.
Milla, M. et al., THOR-707: An engineered IL-2 for the treatment of solid tumors with superior preclinical efficacy and safety evidence, 2018 Society for Immunotherapy of Cancer (SITC) 33rd Annual Meeting Poster, 2018, 1, Abstract P417.
Plieth, Jacob, Cytokine therapy focus—interleukin-2 claims the early lead. EP Vantage, Evaluate, 2018, 1-3, N/A.

(56) References Cited

OTHER PUBLICATIONS

Roessler, E. et al., Cooperative interactions between the interleukin 2 receptor alpha and beta chains alter the Interleukin 2-binding affinity of the receptor subunits, PNAS USA, 1994, 3344-3347, 91.

Rosentrater, E.E. et al., Determination of the Relative potency of a Selective Agonist of the Intermediate-Affinity IL-2 Receptor on Lymphocytes from Human, Cynomolgus Monkey and Mouse, Clinical Research, 2015, 1-2, Poster Abstract 4281.

Sakaguchi, S. et al., Immunologic self-tolerance maintained by activated T cells expressing IL-2 receptor alpha-chains (CD25). Breakdown of a single mechanism of self-tolerance causes various autoimmune diseases, The Journal of Immunology, 1995, 1151-1164, 155(3).

Sauve, K. et al., Localization in human interleukin 2 of the binding site to the alpha chain (p55) of the interleukin 2 receptor, Proc. Natl. Acad. Sci., USA, 1991, 4636-4640, 88.

Sharma, M. et al., NKTR-214 enhances anti-tumor T cell immune responses induced by checkpoint blockade or vaccination, SITC 2017, 2017, 1, Poster P140.

Shimizu, Y. et al., Cell-free translation systems for protein engineering, The FEBS Journal, 2006, 4133-4140, 273.

Siegel, J.P. et al., Interleukin-2 Toxicity, Journal of Clinical Oncology, 1991, 694-704, 9(4).

Sim, G.C. et al., IL2 Variant Circumvents ICOS+ Regulatory T-cell Expansion and Promotes NK Cell Activation, Cancer Immunology Research, 2016, 983-995, 4(11).

Sivakumar, P.V. et al., Comparison of Vascular Leak Syndrome in Mice treated with IL21 or IL2, Comparative Medicine, 2013, 13-21, 63(1).

Slagle, C.J. et al., Click Conjugation of Cloaked Peptide Ligands to Microbubbles, Bioconjugate Chemistry, 2018, 1534-1543, 29(5).

Slamon et al., Use of chemotherapy plus a monoclonal antibody against HER2 for metastatic breast cancer that overexpresses HER2, New England J. Med., 2001, pp. 783-792, 344.

Sockolosky, J.T. et al., Selective targeting of engineered T cells using orthogonal IL-2 cytokine-receptor complexes, Science, 2018, 1037-1042, 359(6379).

Stauber, D.J. et al., Crystal Structure of the IL-2 signaling complex: Paradigm for a heterotrimeric cytokine receptor, PNAS, 2006, 2788-2793, 103(8).

Subasinghe, Nalin et al., Quisqualic Acid Analogues: Synthesis of Beta-Heterocyclic 2-Aminopropanoic Acid Derivatives and Their Activity at a Novel Quisqualate-Sensitized Site, J. Med. Chem., 1992, 4602-4607, 35.

Sun, Lei et al., First-In-Human dose Selection of ALKS 4230, an Investigational Immunotherapeutic Agent, Cancer Research, 2017, 1-2, Poster Abstract 4088.

Sun, Lei et al., Pharmacokinetics and Pharmacodynamic Effects of ALKS 4230, an Investigational Immunotherapeutic Agent, in Cynomolgus Monkeys After Intravenous and Subcutaneous Administration, SITC 2018, 2018, 1-2, Poster Abstract P425.

Vaishampayan, U.N. et al., A Phase 1 Trial of ALKS 4230, an Engineered Cytokine Activator of NK and Effector T Cells, in Patients with Advanced Solid Tumors, ASCO 2017, 2017, 1-2, Abstract TPS3111.

Vaishampayan, U.N. et al., Safety, pharmacokinetics and pharmacodynamic effects of ALKS 4230 in patients with advanced solid tumors from the ongoing dose escalation portion of a first in human (F11-1) study, SITC 2018, 2018, 1-2, Poster Abstract P423.

Van Gool, F. et al., Interleukin-5-producing group 2 innate lymphoid cells control eosinophilia induced by Interleukin-2 therapy, Blood, 2014, 3572-3576, 124(24).

Van Haelst Pisani, C. et al., Administration of Interleukin-2 (IL-2) Results in Increased Plasma Concentrations of IL-5 and Eosinophilia in Patients with Cancer, Blood, 1991, 1538-1544, 78.

Vazquez-Lombardi, R. et al., Potent antitumour activity of the interleukin-2-Fc fusion proteins requires Fc-mediated depletion of regulatory T-cells, Nature Communications, 2017, 1-12, 8:15373.

Waldmann, Thomas A., The Shared and Contrasting Roles of IL2 and IL15 in the Life and Death of Normal and Neoplastic Lymphocytes: Implications for Cancer Therapy, Cancer Immunology Research, 2015, 219-227, 3(3).

Walker, J. et al., Combination of NKTR-214 and radiotherapy (RT) to reverse anergy and expand tumor-specific CD8 T Cells, SITC 2017, 2017, 1, Poster Abstract P274.

Wang, L. et al., Enhanced Anti-tumor Activity of the Combination of Entinostat and NKTR-214 in Renal and Colon Cancer Tumor Models, AACR Annual Meeting 2018, 2018, 1, Poster 17.

Wang, Pin et al., Incorporation of Trifluoroisoleucine into Proteins in Vivo, JACS, 2003, 6900-6906, 125.

Wang, X. et al., Structure of the Quaternary Complex of Interleukin-2 with its alpha, beta, and gamma c Receptors, Science, 2005, 1159-1163, 310.

Yamaguchi, Y. et al., Role of IL-5 in IL-2-induced eosinophilia. In vivo and in vitro expression of IL-5 mRNA by IL-2, The Journal of Immunology, 1990, 873-877, 145.

Yin, Gang et al., RF1 attenuation enables efficient non-natural amino acid incorporation for production of homogeneous antibody drug conjugates, Scientific Reports, 2017, 1-13, 7:3026.

Young, T.S. et al., Beyond the canonical 20 amino acids: expanding the genetic lexicon, The Journal of Biological Chemistry, 2010, 11039-11044, 285.

Zhang, J. et al., Studies of nucleoside transporters using novel autofluorescent nucleoside probes, Biochemistry, 2006, 1087-1098, 45(4).

Zhang, Y. et al., A Semi-Synthetic Organism that Stores and Retrieves Increased Genetic Information, Nature, 2017, 644-647, 551(7682).

Zhang, Y. et al., A semisynthetic organism engineered for the stable expansion of the genetic alphabet, PNAS USA, 2017, 1317-1322, 114(6).

International Preliminary Report Patentability and Written Opinion for PCTUS2021028054, dated Oct. 25, 2022, 7 pages.

* cited by examiner

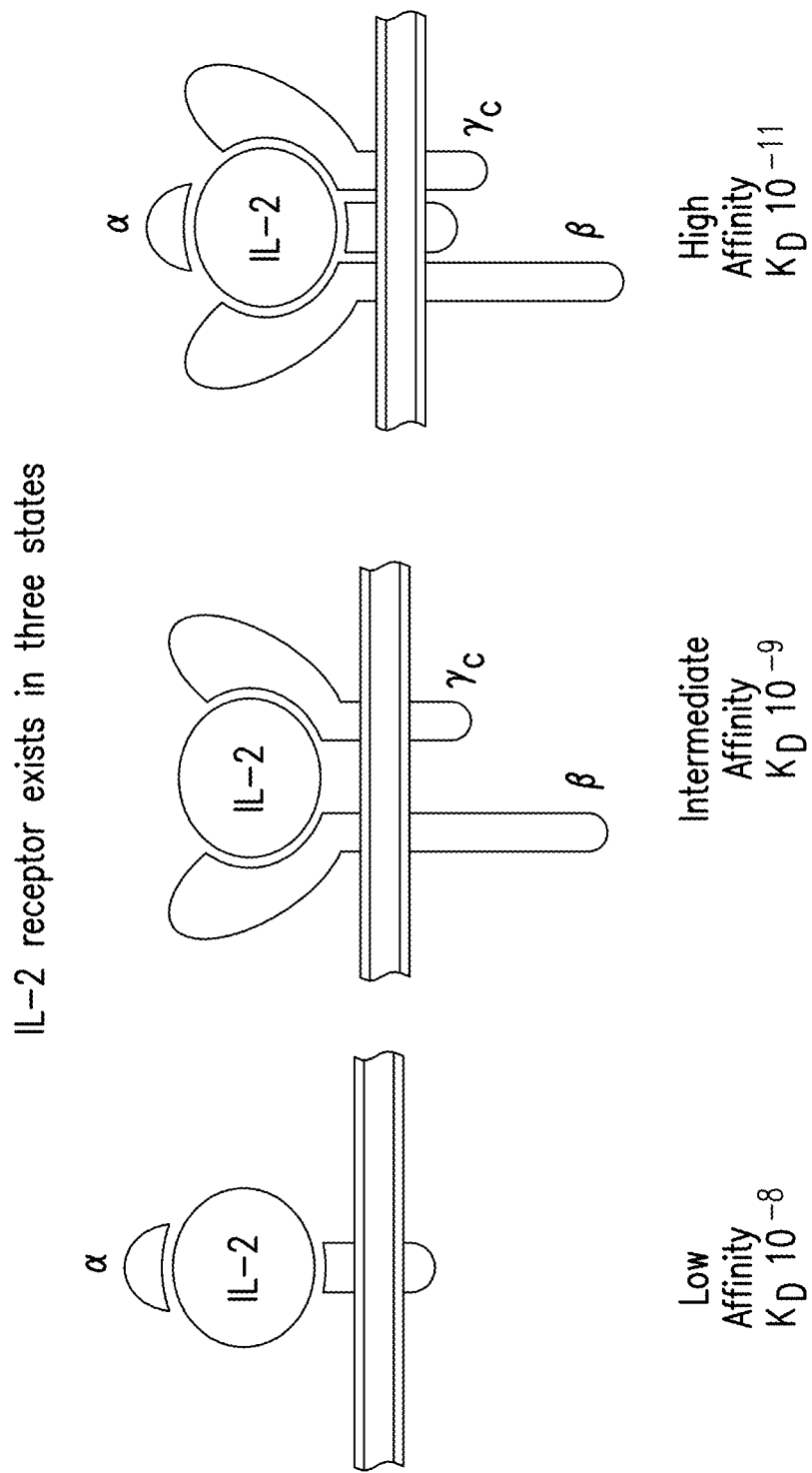

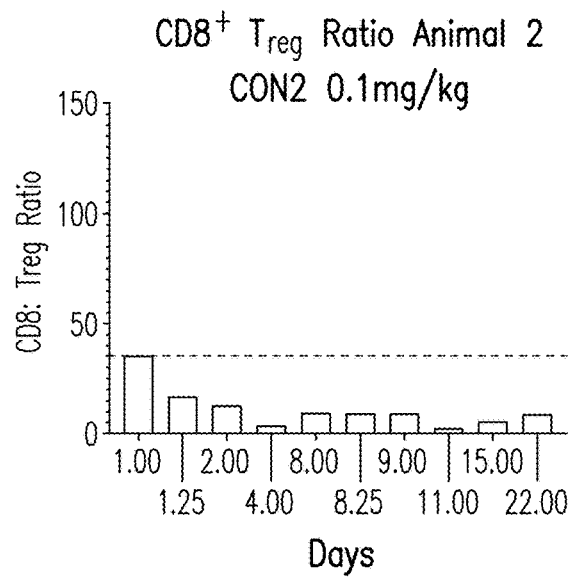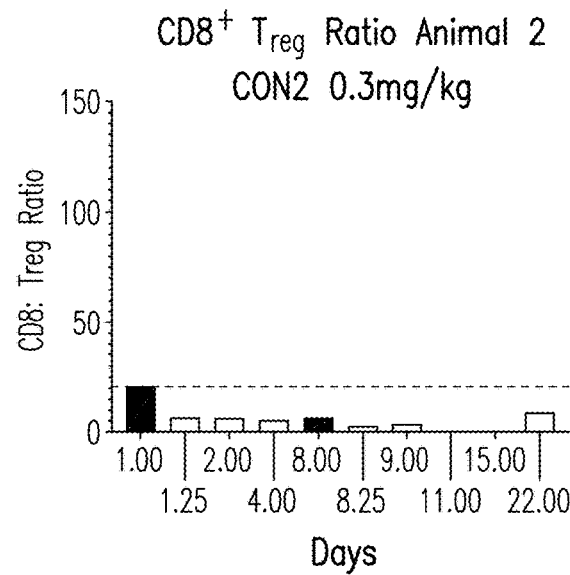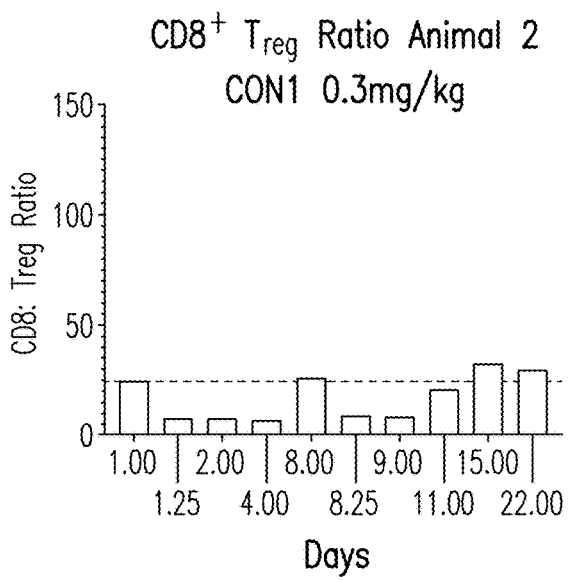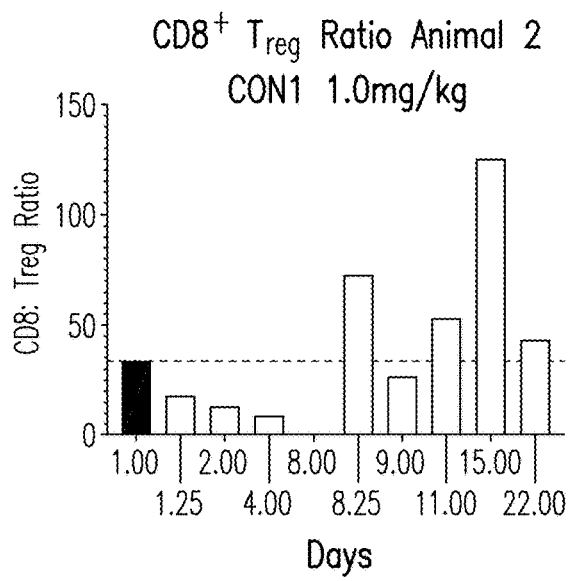
FIG. 13B

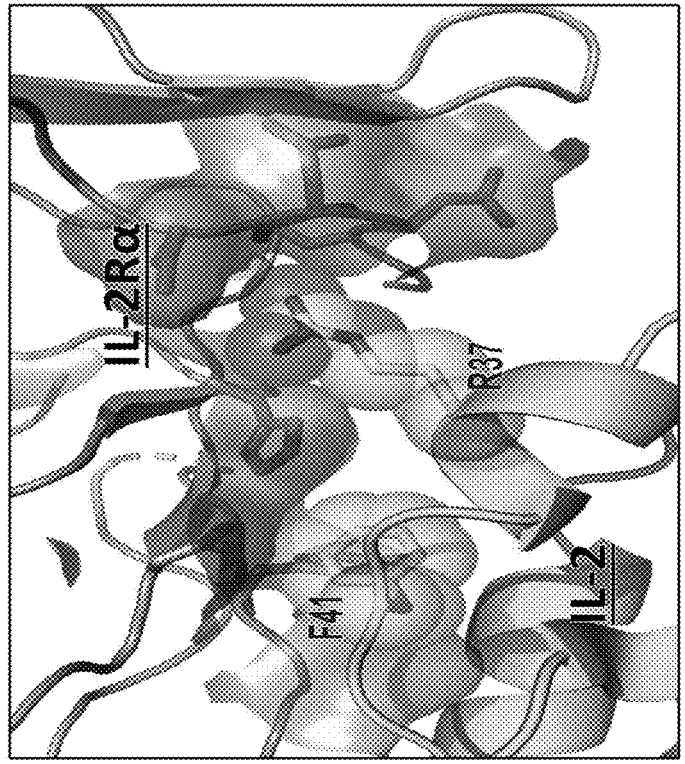
Panel B – Mutant IL-2 R37A/F41K substitutions at the IL-2Rα interface
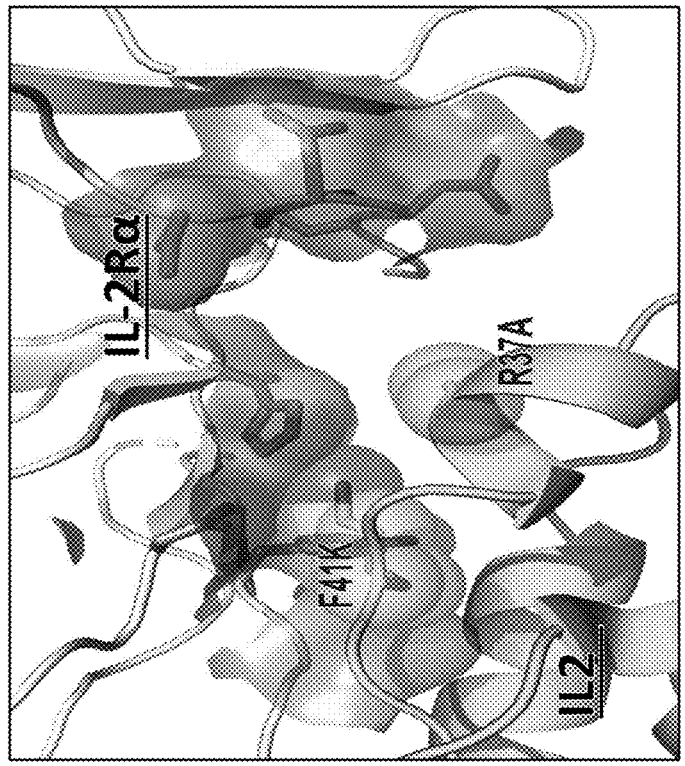
Panel A – Native IL-2 R37/F41

Native human IL-2 (mature)

```
         1         2         3         4         5         6         7
1234567890123456789012345678901234567890123456789012345678901234567890123
APTSSSTKKTQLQLEHLLLDLQMILNGINNYKNPKLTRMLTFKFYMPKKATELKHLQCLEEELKPLEEVLNLA 8         9         1         1         1         1
                            0         1         2         3
4567890123456789012345678901234567890123456789012345678901234567890123
QSKNFHLRPRDLISNINVIVLELKGSETTFMCEYADETATIVEFLNRWITFCQSIISTLT
```

(SEQ ID NO: 1)

FIG. 15A

Aldesleukin [numbering scheme A]

```
         1         2         3         4         5         6         7
1234567890123456789012345678901234567890123456789012345678901234567890123456789012
PTSSSTKKTQLQLEHLLLDLQMILNGINNYKNPKLTRMLTFKFYMPKKATELKHLQCLEEELKPLEEVLNLA 8         9         1         1         1         1
                             0         1         2         3
345678901234567890123456789012345678901234567890123456789012
QSKNFHLRPRDLISNINVIVLELKGSETTFMCEYADETATIVEFLNRWITFSQSIISTLT
(SEQ ID NO: 2)
```

FIG. 15B

Aldesleukin [numbering scheme B]

```
         1         2         3         4         5         6         7
2345678901234567890123456789012345678901234567890123456789012345678901234567890123
PTSSSTKKTQLQLEHLLLDLQMILNGINNYKNPKLTRMLTFKFYMPKKATELKHLQCLEEELKPLEEVLNLA 8         9        10        11        12        13
4567890123456789012345678901234567890123456789012345678901234567890123
QSKNFHLRPRDLISNINVIVLELKGSETTFMCEYADETATIVEFLNRWITFSQSIISTLT
(SEQ ID NO: 2)
```

FIG. 15C

CON1 [numbering scheme A]
```
         1         2         3         4         5         6         7
123456789012345678901234567890123456789012345678901234567890123456789012
PTSXSTKKTQLQLEHLLLDLQMILNGINNYKNPKLTAMLTKKFYMPKKATELKHLQCLEEELKPLEEVLNLA
        8         9         1         1         1         1
345678901234567890123456789012345678901234567890123456789012
QSKNFHLRPRDLISNINIVLELKGSETTFMCEYADETATIVEFLNRWITFSQSIISTLT
                                          0         1         2         3
(SEQ ID NO: 20)
```

X is pAMF conjugated to PEG1
Amino acid substitutions are in bold and underlined

FIG.15D

CON1 [numbering scheme B]

```
         1         2         3         4         5         6         7
23456789012345678901234567890123456789012345678901234567890123456789012 3
PTSXSTKKTQLQLEHLLLDLQMILNGINNYKNPKLTAMLTKKFYMPKKATELKHLQCLEEELKPLEEVLNLA
         8         9        10        11        12        13
4567890123456789012345678901234567890123456789012345678901 23
QSKNFHLRPRDLISNINVIVLELKGSETTFMCEYADETATIVEFLNRWITFSQSIISTLT
(SEQ ID NO: 20)
```

X is pAMF conjugated to PEG1
Amino acid substitutions are bold and underlined

FIG. 15E

```
                           SEQUENCE LISTING

<160> NUMBER OF SEQ ID NOS: 54

<210> SEQ ID NO 1
<211> LENGTH: 133
<212> TYPE: PRT
<213> ORGANISM: Homo sapiens

<400> SEQUENCE: 1

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 2
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110
```

```
Ile Val Glu Phe Leu Asn Arg Trp Ile Thr Phe Ser Gln Ser Ile Ile
            115                 120                 125

Ser Thr Leu Thr
    130

<210> SEQ ID NO 3
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: A, another amino acid, any non-natural amino
      acid, or absent
<220> FEATURE:
<221> NAME/KEY: SITE
<222> LOCATION: (1)..(10)
<223> OTHER INFORMATION: Comprises only one non-natural amino acid and
      the non-natural amino acid is conjugated to a nonpeptidic, water
      soluble polymer
<220> FEATURE:
<221> NAME/KEY: SITE
<222> LOCATION: (1)..(133)
<223> OTHER INFORMATION: At least one of the amino acids at positions
      37, 38, 41, 42, 43, 45, 61, 62, 64, 65, 68, 72, and 107 is not
      the amino acid at the corresponding position in native IL-2
<220> FEATURE:
<221> NAME/KEY: MOD_RES
<222> LOCATION: (2)..(2)
<223> OTHER INFORMATION: P, another amino acid, or any non-natural
      amino acid
<220> FEATURE:
<221> NAME/KEY: MOD_RES
<222> LOCATION: (3)..(3)
<223> OTHER INFORMATION: T, another amino acid, or any non-natural
      amino acid
<220> FEATURE:
<221> NAME/KEY: MOD_RES
<222> LOCATION: (4)..(4)
<223> OTHER INFORMATION: S, another amino acid, or any non-natural
      amino acid
<220> FEATURE:
<221> NAME/KEY: MOD_RES
<222> LOCATION: (5)..(5)
<223> OTHER INFORMATION: S, another amino acid, or any non-natural
      amino acid
<220> FEATURE:
<221> NAME/KEY: MOD_RES
<222> LOCATION: (6)..(6)
<223> OTHER INFORMATION: S, another amino acid, or any non-natural
      amino acid
<220> FEATURE:
<221> NAME/KEY: MOD_RES
<222> LOCATION: (7)..(7)
<223> OTHER INFORMATION: T, another amino acid, or any non-natural
      amino acid
<220> FEATURE:
<221> NAME/KEY: MOD_RES
<222> LOCATION: (8)..(8)
<223> OTHER INFORMATION: K, another amino acid, or any non-natural
      amino acid
<220> FEATURE:
<221> NAME/KEY: MOD_RES
<222> LOCATION: (9)..(9)
<223> OTHER INFORMATION: K, another amino acid, or any non-natural
      amino acid
<220> FEATURE:
<221> NAME/KEY: MOD_RES
<222> LOCATION: (10)..(10)
<223> OTHER INFORMATION: T, another amino acid, or any non-natural
      amino acid
```

```
<220> FEATURE:
<221> NAME/KEY: MOD_RES
<222> LOCATION: (35)..(35)
<223> OTHER INFORMATION: K or another amino acid
<220> FEATURE:
<221> NAME/KEY: MOD_RES
<222> LOCATION: (37)..(37)
<223> OTHER INFORMATION: T or another amino acid
<220> FEATURE:
<221> NAME/KEY: MOD_RES
<222> LOCATION: (38)..(38)
<223> OTHER INFORMATION: R or another amino acid
<220> FEATURE:
<221> NAME/KEY: MOD_RES
<222> LOCATION: (41)..(41)
<223> OTHER INFORMATION: T or another amino acid
<220> FEATURE:
<221> NAME/KEY: MOD_RES
<222> LOCATION: (42)..(42)
<223> OTHER INFORMATION: F or another amino acid
<220> FEATURE:
<221> NAME/KEY: MOD_RES
<222> LOCATION: (43)..(43)
<223> OTHER INFORMATION: K or another amino acid
<220> FEATURE:
<221> NAME/KEY: MOD_RES
<222> LOCATION: (45)..(45)
<223> OTHER INFORMATION: Y or another amino acid
<220> FEATURE:
<221> NAME/KEY: MOD_RES
<222> LOCATION: (61)..(61)
<223> OTHER INFORMATION: E or another amino acid
<220> FEATURE:
<221> NAME/KEY: MOD_RES
<222> LOCATION: (62)..(62)
<223> OTHER INFORMATION: E or another amino acid
<220> FEATURE:
<221> NAME/KEY: MOD_RES
<222> LOCATION: (64)..(64)
<223> OTHER INFORMATION: K or another amino acid
<220> FEATURE:
<221> NAME/KEY: MOD_RES
<222> LOCATION: (65)..(65)
<223> OTHER INFORMATION: P or another amino acid
<220> FEATURE:
<221> NAME/KEY: MOD_RES
<222> LOCATION: (68)..(68)
<223> OTHER INFORMATION: E or another amino acid
<220> FEATURE:
<221> NAME/KEY: MOD_RES
<222> LOCATION: (72)..(72)
<223> OTHER INFORMATION: L or another amino acid
<220> FEATURE:
<221> NAME/KEY: MOD_RES
<222> LOCATION: (107)..(107)
<223> OTHER INFORMATION: Y or another amino acid
<220> FEATURE:
<221> NAME/KEY: MOD_RES
<222> LOCATION: (125)..(125)
<223> OTHER INFORMATION: C or another amino acid

<400> SEQUENCE: 3

Xaa Xaa Xaa Xaa Xaa Xaa Xaa Xaa Xaa Xaa Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Xaa Leu Xaa Xaa Met Leu Xaa Xaa Xaa Phe Xaa Met Pro Lys
        35                  40                  45

Lys Ala Thr Glu Leu Lys His Leu Gln Cys Leu Glu Xaa Xaa Leu Xaa
    50                  55                  60

Xaa Leu Glu Xaa Val Leu Asn Xaa Ala Gln Ser Lys Asn Phe His Leu
65                  70                  75                  80
```

```
Arg Pro Arg Asp Leu Ile Ser Asn Ile Asn Val Ile Val Leu Glu Leu
                85                  90                  95

Lys Gly Ser Glu Thr Thr Phe Met Cys Glu Xaa Ala Asp Glu Thr Ala
            100                 105                 110

Thr Ile Val Glu Phe Leu Asn Arg Trp Ile Thr Phe Xaa Gln Ser Ile
        115                 120                 125

Ile Ser Thr Leu Thr
        130

<210> SEQ ID NO 4
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: P, another amino acid, or any non-natural
      amino acid
<220> FEATURE:
<221> NAME/KEY: SITE
<222> LOCATION: (1)..(9)
<223> OTHER INFORMATION: Comprises only one non-natural amino acid and
      the non-natural amino acid is conjugated to a nonpeptidic, water
      soluble polymer
<220> FEATURE:
<221> NAME/KEY: SITE
<222> LOCATION: (1)..(132)
<223> OTHER INFORMATION: At least one of the amino acids at positions
      36, 37, 40, 41, 42, 44, 60, 61, 63, 64, 69, 71, and 106 is not
      the amino acid at the corresponding position in aldesleukin
<220> FEATURE:
<221> NAME/KEY: MOD_RES
<222> LOCATION: (2)..(2)
<223> OTHER INFORMATION: T, another amino acid, or any non-natural
      amino acid
<220> FEATURE:
<221> NAME/KEY: MOD_RES
<222> LOCATION: (3)..(3)
<223> OTHER INFORMATION: S, another amino acid, or any non-natural
      amino acid
<220> FEATURE:
<221> NAME/KEY: MOD_RES
<222> LOCATION: (4)..(4)
<223> OTHER INFORMATION: S, another amino acid, or any non-natural
      amino acid
<220> FEATURE:
<221> NAME/KEY: MOD_RES
<222> LOCATION: (5)..(5)
<223> OTHER INFORMATION: S, another amino acid, or any non-natural
      amino acid
<220> FEATURE:
<221> NAME/KEY: MOD_RES
<222> LOCATION: (6)..(6)
<223> OTHER INFORMATION: T, another amino acid, or any non-natural
      amino acid
<220> FEATURE:
<221> NAME/KEY: MOD_RES
<222> LOCATION: (7)..(7)
<223> OTHER INFORMATION: K, another amino acid, or any non-natural
      amino acid
<220> FEATURE:
<221> NAME/KEY: MOD_RES
<222> LOCATION: (8)..(8)
<223> OTHER INFORMATION: K, another amino acid, or any non-natural
      amino acid
<220> FEATURE:
<221> NAME/KEY: MOD_RES
<222> LOCATION: (9)..(9)
<223> OTHER INFORMATION: T, another amino acid, or any non-natural
      amino acid
```

```
<220> FEATURE:
<221> NAME/KEY: MOD_RES
<222> LOCATION: (34)..(34)
<223> OTHER INFORMATION: K or another amino acid
<220> FEATURE:
<221> NAME/KEY: MOD_RES
<222> LOCATION: (36)..(36)
<223> OTHER INFORMATION: T or another amino acid
<220> FEATURE:
<221> NAME/KEY: MOD_RES
<222> LOCATION: (37)..(37)
<223> OTHER INFORMATION: R or another amino acid
<220> FEATURE:
<221> NAME/KEY: MOD_RES
<222> LOCATION: (40)..(40)
<223> OTHER INFORMATION: T or another amino acid
<220> FEATURE:
<221> NAME/KEY: MOD_RES
<222> LOCATION: (41)..(41)
<223> OTHER INFORMATION: F or another amino acid
<220> FEATURE:
<221> NAME/KEY: MOD_RES
<222> LOCATION: (42)..(42)
<223> OTHER INFORMATION: K or another amino acid
<220> FEATURE:
<221> NAME/KEY: MOD_RES
<222> LOCATION: (44)..(44)
<223> OTHER INFORMATION: Y or another amino acid
<220> FEATURE:
<221> NAME/KEY: MOD_RES
<222> LOCATION: (60)..(60)
<223> OTHER INFORMATION: E or another amino acid
<220> FEATURE:
<221> NAME/KEY: MOD_RES
<222> LOCATION: (61)..(61)
<223> OTHER INFORMATION: E or another amino acid
<220> FEATURE:
<221> NAME/KEY: MOD_RES
<222> LOCATION: (63)..(63)
<223> OTHER INFORMATION: K or another amino acid
<220> FEATURE:
<221> NAME/KEY: MOD_RES
<222> LOCATION: (64)..(64)
<223> OTHER INFORMATION: P or another amino acid
<220> FEATURE:
<221> NAME/KEY: MOD_RES
<222> LOCATION: (67)..(67)
<223> OTHER INFORMATION: E or another amino acid
<220> FEATURE:
<221> NAME/KEY: MOD_RES
<222> LOCATION: (71)..(71)
<223> OTHER INFORMATION: L or another amino acid
<220> FEATURE:
<221> NAME/KEY: MOD_RES
<222> LOCATION: (106)..(106)
<223> OTHER INFORMATION: Y or another amino acid
<220> FEATURE:
<221> NAME/KEY: MOD_RES
<222> LOCATION: (124)..(124)
<223> OTHER INFORMATION: C or another amino acid

<400> SEQUENCE: 4

Xaa Xaa Xaa Xaa Xaa Xaa Xaa Xaa Xaa Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Xaa Leu Xaa Xaa Met Leu Xaa Xaa Xaa Phe Xaa Met Pro Lys Lys
        35                  40                  45

Ala Thr Glu Leu Lys His Leu Gln Cys Leu Glu Xaa Xaa Leu Xaa Xaa
    50                  55                  60

Leu Glu Xaa Val Leu Asn Xaa Ala Gln Ser Lys Asn Phe His Leu Arg
65                  70                  75                  80
```

```
Pro Arg Asp Leu Ile Ser Asn Ile Asn Val Ile Val Leu Glu Leu Lys
            85                  90                  95

Gly Ser Glu Thr Thr Phe Met Cys Glu Xaa Ala Asp Glu Thr Ala Thr
        100                 105                 110

Ile Val Glu Phe Leu Asn Arg Trp Ile Thr Phe Xaa Gln Ser Ile Ile
        115                 120                 125

Ser Thr Leu Thr
        130

<210> SEQ ID NO 5
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(132)
<223> OTHER INFORMATION: At least one of the amino acids at positions
      36, 37, 40, 41, 42, 44, 60, 61, 63, 64, 69, 71, and 106 is not
      the amino acid at the corresponding position in native human IL-2
<220> FEATURE:
<221> NAME/KEY: MOD_RES
<222> LOCATION: (4)..(4)
<223> OTHER INFORMATION: Any non-natural amino acid conjugated to a
      nonpeptidic, water soluble polymer
<220> FEATURE:
<221> NAME/KEY: MOD_RES
<222> LOCATION: (34)..(34)
<223> OTHER INFORMATION: K or another amino acid
<220> FEATURE:
<221> NAME/KEY: MOD_RES
<222> LOCATION: (36)..(36)
<223> OTHER INFORMATION: T or another amino acid
<220> FEATURE:
<221> NAME/KEY: MOD_RES
<222> LOCATION: (37)..(37)
<223> OTHER INFORMATION: R or another amino acid
<220> FEATURE:
<221> NAME/KEY: MOD_RES
<222> LOCATION: (40)..(40)
<223> OTHER INFORMATION: T or another amino acid
<220> FEATURE:
<221> NAME/KEY: MOD_RES
<222> LOCATION: (41)..(41)
<223> OTHER INFORMATION: F or another amino acid
<220> FEATURE:
<221> NAME/KEY: MOD_RES
<222> LOCATION: (42)..(42)
<223> OTHER INFORMATION: K or another amino acid
<220> FEATURE:
<221> NAME/KEY: MOD_RES
<222> LOCATION: (44)..(44)
<223> OTHER INFORMATION: Y or another amino acid
<220> FEATURE:
<221> NAME/KEY: MOD_RES
<222> LOCATION: (60)..(60)
<223> OTHER INFORMATION: E or another amino acid
<220> FEATURE:
<221> NAME/KEY: MOD_RES
<222> LOCATION: (61)..(61)
<223> OTHER INFORMATION: E or another amino acid
<220> FEATURE:
<221> NAME/KEY: MOD_RES
<222> LOCATION: (63)..(63)
<223> OTHER INFORMATION: K or another amino acid
<220> FEATURE:
<221> NAME/KEY: MOD_RES
<222> LOCATION: (64)..(64)
<223> OTHER INFORMATION: P or another amino acid
<220> FEATURE:
<221> NAME/KEY: MOD_RES
<222> LOCATION: (67)..(67)
<223> OTHER INFORMATION: E or another amino acid
```

```
<220> FEATURE:
<221> NAME/KEY: MOD_RES
<222> LOCATION: (71)..(71)
<223> OTHER INFORMATION: L or another amino acid
<220> FEATURE:
<221> NAME/KEY: MOD_RES
<222> LOCATION: (106)..(106)
<223> OTHER INFORMATION: Y or another amino acid
<220> FEATURE:
<221> NAME/KEY: MOD_RES
<222> LOCATION: (124)..(124)
<223> OTHER INFORMATION: C or another amino acid

<400> SEQUENCE: 5

Pro Thr Ser Xaa Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Xaa Leu Xaa Xaa Met Leu Xaa Xaa Xaa Phe Xaa Met Pro Lys Lys
        35                  40                  45

Ala Thr Glu Leu Lys His Leu Gln Cys Leu Glu Xaa Xaa Leu Xaa Xaa
50                  55                  60

Leu Glu Xaa Val Leu Asn Xaa Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Xaa Ala Asp Glu Thr Ala Thr
            100                 105                 110

Ile Val Glu Phe Leu Asn Arg Trp Ile Thr Phe Xaa Gln Ser Ile Ile
        115                 120                 125

Ser Thr Leu Thr
    130

<210> SEQ ID NO 6
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Any non-natural amino acid conjugated to a
      nonpeptidic, water soluble polymer
<220> FEATURE:
<221> NAME/KEY: MOD_RES
<222> LOCATION: (37)..(37)
<223> OTHER INFORMATION: Any amino acid except R
<220> FEATURE:
<221> NAME/KEY: MOD_RES
<222> LOCATION: (41)..(41)
<223> OTHER INFORMATION: Any amino acid except F
<220> FEATURE:
<221> NAME/KEY: MOD_RES
<222> LOCATION: (124)..(124)
<223> OTHER INFORMATION: Any amino acid except C

<400> SEQUENCE: 6

Pro Thr Ser Xaa Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Xaa Met Leu Thr Xaa Lys Phe Tyr Met Pro Lys Lys
        35                  40                  45
```

```
Ala Thr Glu Leu Lys His Leu Gln Cys Leu Glu Glu Glu Leu Lys Pro
 50                  55                  60

Leu Glu Glu Val Leu Asn Leu Ala Gln Ser Lys Asn Phe His Leu Arg
 65                  70                  75                  80

Pro Arg Asp Leu Ile Ser Asn Ile Asn Val Ile Val Leu Glu Leu Lys
                 85                  90                  95

Gly Ser Glu Thr Thr Phe Met Cys Glu Tyr Ala Asp Glu Thr Ala Thr
                100                 105                 110

Ile Val Glu Phe Leu Asn Arg Trp Ile Thr Phe Xaa Gln Ser Ile Ile
                115                 120                 125

Ser Thr Leu Thr
            130
```

<210> SEQ ID NO 7
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: Any non-natural amino acid conjugated to a
      nonpeptidic, water soluble polymer
<220> FEATURE:
<221> NAME/KEY: MOD_RES
<222> LOCATION: (38)..(38)
<223> OTHER INFORMATION: Any amino acid except R
<220> FEATURE:
<221> NAME/KEY: MOD_RES
<222> LOCATION: (42)..(42)
<223> OTHER INFORMATION: Any amino acid except F
<220> FEATURE:
<221> NAME/KEY: MOD_RES
<222> LOCATION: (125)..(125)
<223> OTHER INFORMATION: Any amino acid except C

<400> SEQUENCE: 7

```
Ala Pro Thr Ser Xaa Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
                 20                  25                  30

Asn Pro Lys Leu Thr Xaa Met Leu Thr Xaa Lys Phe Tyr Met Pro Lys
                 35                  40                  45

Lys Ala Thr Glu Leu Lys His Leu Gln Cys Leu Glu Glu Glu Leu Lys
 50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Xaa Gln Ser Ile
                115                 120                 125

Ile Ser Thr Leu Thr
            130
```

<210> SEQ ID NO 8
<211> LENGTH: 132
<212> TYPE: PRT
<213> ORGANISM: Artificial Sequence

```
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Any non-natural amino acid conjugated to a
      nonpeptidic, water soluble polymer
<220> FEATURE:
<221> NAME/KEY: MOD_RES
<222> LOCATION: (124)..(124)
<223> OTHER INFORMATION: A or S

<400> SEQUENCE: 8

Pro Thr Ser Xaa Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Lys Lys Phe Tyr Met Pro Lys Lys
        35                  40                  45

Ala Thr Glu Leu Lys His Leu Gln Cys Leu Glu Glu Glu Leu Lys Pro
50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Xaa Gln Ser Ile Ile
        115                 120                 125

Ser Thr Leu Thr
    130

<210> SEQ ID NO 9
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: Any non-natural amino acid conjugated to a
      nonpeptidic, water soluble polymer
<220> FEATURE:
<221> NAME/KEY: MOD_RES
<222> LOCATION: (125)..(125)
<223> OTHER INFORMATION: A or S

<400> SEQUENCE: 9

Ala Pro Thr Ser Xaa Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Ala Met Leu Thr Lys Lys Phe Tyr Met Pro Lys
        35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95
```

```
Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Xaa Gln Ser Ile
        115                 120                 125

Ile Ser Thr Leu Thr
        130

<210> SEQ ID NO 10
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Any non-natural amino acid conjugated to a
      nonpeptidic, water soluble polymer

<400> SEQUENCE: 10

Pro Thr Ser Xaa Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Lys Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
        130

<210> SEQ ID NO 11
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: Any non-natural amino acid conjugated to a
      nonpeptidic, water soluble polymer

<400> SEQUENCE: 11

Ala Pro Thr Ser Xaa Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Ala Met Leu Thr Lys Lys Phe Tyr Met Pro Lys
        35                  40                  45

Lys Ala Thr Glu Leu Lys His Leu Gln Cys Leu Glu Glu Glu Leu Lys
    50                  55                  60
```

```
Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 12
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: pAMF conjugated to a nonpeptidic, water
      soluble polymer

<400> SEQUENCE: 12

Pro Thr Ser Xaa Ser Thr Lys Lys Thr Gln Leu Gln Leu Glu His Leu
 1               5                  10                  15

Leu Leu Asp Leu Gln Met Ile Leu Asn Gly Ile Asn Asn Tyr Lys Asn
             20                  25                  30

Pro Lys Leu Thr Ala Met Leu Thr Lys Lys Phe Tyr Met Pro Lys Lys
         35                  40                  45

Ala Thr Glu Leu Lys His Leu Gln Cys Leu Glu Glu Glu Leu Lys Pro
     50                  55                  60

Leu Glu Glu Val Leu Asn Leu Ala Gln Ser Lys Asn Phe His Leu Arg
 65                  70                  75                  80

Pro Arg Asp Leu Ile Ser Asn Ile Asn Val Ile Val Leu Glu Leu Lys
                 85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
        130

<210> SEQ ID NO 13
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: pAMF conjugated to a nonpeptidic, water
      soluble polymer

<400> SEQUENCE: 13

Ala Pro Thr Ser Xaa Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
             20                  25                  30
```

```
Asn Pro Lys Leu Thr Ala Met Leu Thr Lys Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 14
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: pAMF conjugated to PEG

<400> SEQUENCE: 14

Pro Thr Ser Xaa Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
                20                  25                  30

Pro Lys Leu Thr Ala Met Leu Thr Lys Lys Phe Tyr Met Pro Lys Lys
            35                  40                  45

Ala Thr Glu Leu Lys His Leu Gln Cys Leu Glu Glu Glu Leu Lys Pro
        50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 15
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: pAMF conjugated to PEG
```

<400> SEQUENCE: 15

Ala Pro Thr Ser Xaa Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Ala Met Leu Thr Lys Lys Phe Tyr Met Pro Lys
        35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
            115                 120                 125

Ile Ser Thr Leu Thr
    130

<210> SEQ ID NO 16
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: pAMF conjugated to mPEG

<400> SEQUENCE: 16

Pro Thr Ser Xaa Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Lys Lys Phe Tyr Met Pro Lys Lys
        35                  40                  45

Ala Thr Glu Leu Lys His Leu Gln Cys Leu Glu Glu Glu Leu Lys Pro
50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
            115                 120                 125

Ser Thr Leu Thr
    130

<210> SEQ ID NO 17
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

```
<220> FEATURE:
<221> NAME/KEY: MOD_RES
<222> LOCATION: (5)..(5)
<223> OTHER INFORMATION: pAMF conjugated to mPEG

<400> SEQUENCE: 17

Ala Pro Thr Ser Xaa Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Ala Met Leu Thr Lys Lys Phe Tyr Met Pro Lys
        35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 18
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: pAMF conjugated to 30 kDa mPEG

<400> SEQUENCE: 18

Pro Thr Ser Xaa Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Lys Lys Phe Tyr Met Pro Lys Lys
        35                  40                  45

Ala Thr Glu Leu Lys His Leu Gln Cys Leu Glu Glu Glu Leu Lys Pro
50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
        130
```

```
<210> SEQ ID NO 19
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: pAMF conjugated to 30 kDa mPEG

<400> SEQUENCE: 19

Ala Pro Thr Ser Xaa Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Ala Met Leu Thr Lys Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 20
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: pAMF conjugated to PEG1 by a triazole linkage
      (CON1)

<400> SEQUENCE: 20

Pro Thr Ser Xaa Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Lys Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110
```

```
Ile Val Glu Phe Leu Asn Arg Trp Ile Thr Phe Ser Gln Ser Ile Ile
            115                 120                 125

Ser Thr Leu Thr
    130

<210> SEQ ID NO 21
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: pAMF conjugated to PEG1 by a triazole linkage

<400> SEQUENCE: 21

Ala Pro Thr Ser Xaa Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Ala Met Leu Thr Lys Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130

<210> SEQ ID NO 22
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: pAMF conjugated to PEG1 by a triazole linkage
      (CON2)

<400> SEQUENCE: 22

Pro Thr Ser Xaa Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80
```

```
Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 23
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Pro Thr Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Lys Lys Phe Tyr Met Pro Lys Lys
        35                  40                  45

Ala Thr Glu Leu Lys His Leu Gln Cys Leu Glu Thr Ser Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr Gly Gly Ser His His His His His His
    130                 135                 140

<210> SEQ ID NO 24
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Pro Thr Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Asp Phe Lys Phe Tyr Met Pro Lys Lys
        35                  40                  45

Ala Thr Glu Leu Lys His Leu Gln Cys Leu Glu Thr Ser Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95
```

```
Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr Gly Gly Ser His His His His His His
    130                 135                 140

<210> SEQ ID NO 25
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Pro Thr Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Asp Lys Lys Phe Tyr Met Pro Lys Lys
        35                  40                  45

Ala Thr Glu Leu Lys His Leu Gln Cys Leu Glu Glu Ser Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr Gly Gly Ser His His His His His
    130                 135                 140

<210> SEQ ID NO 26
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Pro Thr Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Asp Lys Lys Phe Tyr Met Pro Lys Lys
        35                  40                  45

Ala Thr Glu Leu Lys His Leu Gln Cys Leu Glu Thr Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110
```

```
Ile Val Glu Phe Leu Asn Arg Trp Ile Thr Phe Ser Gln Ser Ile Ile
        115                 120                 125

Ser Thr Leu Thr Gly Gly Ser His His His His His
    130                 135                 140

<210> SEQ ID NO 27
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Pro Thr Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Phe Lys Phe Tyr Met Pro Lys Lys
        35                  40                  45

Ala Thr Glu Leu Lys His Leu Gln Cys Leu Glu Thr Ser Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr Gly Gly Ser His His His His His
    130                 135                 140

<210> SEQ ID NO 28
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Pro Thr Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Lys Lys Phe Tyr Met Pro Lys Lys
        35                  40                  45

Ala Thr Glu Leu Lys His Leu Gln Cys Leu Glu Glu Ser Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110
```

```
Ile Val Glu Phe Leu Asn Arg Trp Ile Thr Phe Ser Gln Ser Ile Ile
        115                 120                 125

Ser Thr Leu Thr Gly Gly Ser His His His His His
        130                 135                 140
```

<210> SEQ ID NO 29
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

```
Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Lys Lys Phe Tyr Met Pro Lys Lys
        35                  40                  45

Ala Thr Glu Leu Lys His Leu Gln Cys Leu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr Gly Gly Ser His His His His His
        130                 135                 140
```

<210> SEQ ID NO 30
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

```
Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Asp Phe Lys Phe Tyr Met Pro Lys Lys
        35                  40                  45

Ala Thr Glu Leu Lys His Leu Gln Cys Leu Glu Glu Ser Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110
```

```
Ile Val Glu Phe Leu Asn Arg Trp Ile Thr Phe Ser Gln Ser Ile Ile
            115                 120                 125

Ser Thr Leu Thr Gly Gly Ser His His His His His
        130                 135                 140

<210> SEQ ID NO 31
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Pro Thr Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Asp Phe Lys Phe Tyr Met Pro Lys Lys
        35                  40                  45

Ala Thr Glu Leu Lys His Leu Gln Cys Leu Glu Thr Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
            115                 120                 125

Ser Thr Leu Thr Gly Gly Ser His His His His His
        130                 135                 140

<210> SEQ ID NO 32
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Pro Thr Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Asp Lys Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110
```

```
Ile Val Glu Phe Leu Asn Arg Trp Ile Thr Phe Ser Gln Ser Ile Ile
        115                 120                 125

Ser Thr Leu Thr Gly Gly Ser His His His His His
    130                 135                 140

<210> SEQ ID NO 33
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Lys Lys Phe Tyr Met Pro Lys Lys
        35                  40                  45

Ala Thr Glu Leu Lys His Leu Gln Cys Leu Glu Glu Ser Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr Gly Gly Ser His His His His His
    130                 135                 140

<210> SEQ ID NO 34
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Lys Lys Phe Tyr Met Pro Lys Lys
        35                  40                  45

Ala Thr Glu Leu Lys His Leu Gln Cys Leu Glu Thr Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110
```

Ile Val Glu Phe Leu Asn Arg Trp Ile Thr Phe Ser Gln Ser Ile Ile
            115                 120                 125

Ser Thr Leu Thr Gly Gly Ser His His His His His
        130                 135                 140

<210> SEQ ID NO 35
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Asp Phe Lys Phe Tyr Met Pro Lys Lys
        35                  40                  45

Ala Thr Glu Leu Lys His Leu Gln Cys Leu Glu Glu Ser Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
            115                 120                 125

Ser Thr Leu Thr Gly Gly Ser His His His His His
        130                 135                 140

<210> SEQ ID NO 36
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Asp Phe Lys Phe Tyr Met Pro Lys Lys
        35                  40                  45

Ala Thr Glu Leu Lys His Leu Gln Cys Leu Glu Thr Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

```
Ile Val Glu Phe Leu Asn Arg Trp Ile Thr Phe Ser Gln Ser Ile Ile
        115                 120                 125

Ser Thr Leu Thr Gly Gly Ser His His His His His
    130                 135                 140

<210> SEQ ID NO 37
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Pro Thr Ser Ser Thr Lys Lys Thr Gln Leu Gln Leu Glu His Leu
1               5                  10                  15

Leu Leu Asp Leu Gln Met Ile Leu Asn Gly Ile Asn Asn Tyr Lys Asn
            20                  25                  30

Pro Lys Leu Thr Arg Met Leu Asp Lys Phe Tyr Met Pro Lys Lys
        35                  40                  45

Ala Thr Glu Leu Lys His Leu Gln Cys Leu Glu Glu Glu Leu Lys Pro
 50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr Gly Gly Ser His His His His His
    130                 135                 140

<210> SEQ ID NO 38
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Pro Thr Ser Ser Thr Lys Lys Thr Gln Leu Gln Leu Glu His Leu
1               5                  10                  15

Leu Leu Asp Leu Gln Met Ile Leu Asn Gly Ile Asn Asn Tyr Lys Asn
            20                  25                  30

Pro Lys Leu Thr Ala Met Leu Thr Phe Lys Phe Tyr Met Pro Lys Lys
        35                  40                  45

Ala Thr Glu Leu Lys His Leu Gln Cys Leu Glu Glu Ser Leu Lys Pro
 50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110
```

```
Ile Val Glu Phe Leu Asn Arg Trp Ile Thr Phe Ser Gln Ser Ile Ile
        115                 120                 125

Ser Thr Leu Thr Gly Gly Ser His His His His His
        130                 135                 140

<210> SEQ ID NO 39
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Phe Lys Phe Tyr Met Pro Lys Lys
        35                  40                  45

Ala Thr Glu Leu Lys His Leu Gln Cys Leu Glu Thr Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr Gly Gly Ser His His His His His
        130                 135                 140

<210> SEQ ID NO 40
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Lys Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110
```

Ile Val Glu Phe Leu Asn Arg Trp Ile Thr Phe Ser Gln Ser Ile Ile
            115                 120                 125

Ser Thr Leu Thr Gly Gly Ser His His His His His His
    130                 135                 140

<210> SEQ ID NO 41
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Asp Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
            115                 120                 125

Ser Thr Leu Thr Gly Gly Ser His His His His His His
    130                 135                 140

<210> SEQ ID NO 42
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: A, another amino acid, any non-natural amino
      acid, or absent
<220> FEATURE:
<221> NAME/KEY: SITE
<222> LOCATION: (1)..(10)
<223> OTHER INFORMATION: Comprises only one non-natural amino acid
<220> FEATURE:
<221> NAME/KEY: SITE
<222> LOCATION: (1)..(133)
<223> OTHER INFORMATION: At least one of the amino acids at positions
      37, 38, 41, 42, 43, 45, 61, 62, 64, 65, 68, 72, and 107 is not
      the amino acid at the corresponding position in native IL-2
<220> FEATURE:
<221> NAME/KEY: MOD_RES
<222> LOCATION: (2)..(2)
<223> OTHER INFORMATION: P, another amino acid, or any non-natural
      amino acid
<220> FEATURE:
<221> NAME/KEY: MOD_RES
<222> LOCATION: (3)..(3)
<223> OTHER INFORMATION: T, another amino acid, or any non-natural
      amino acid

```
-continued

<220> FEATURE:
<221> NAME/KEY: MOD_RES
<222> LOCATION: (4)..(4)
<223> OTHER INFORMATION: S, another amino acid, or any non-natural
      amino acid
<220> FEATURE:
<221> NAME/KEY: MOD_RES
<222> LOCATION: (5)..(5)
<223> OTHER INFORMATION: S, another amino acid, or any non-natural
      amino acid
<220> FEATURE:
<221> NAME/KEY: MOD_RES
<222> LOCATION: (6)..(6)
<223> OTHER INFORMATION: S, another amino acid, or any non-natural
      amino acid
<220> FEATURE:
<221> NAME/KEY: MOD_RES
<222> LOCATION: (7)..(7)
<223> OTHER INFORMATION: T, another amino acid, or any non-natural
      amino acid
<220> FEATURE:
<221> NAME/KEY: MOD_RES
<222> LOCATION: (8)..(8)
<223> OTHER INFORMATION: K, another amino acid, or any non-natural
      amino acid
<220> FEATURE:
<221> NAME/KEY: MOD_RES
<222> LOCATION: (9)..(9)
<223> OTHER INFORMATION: K, another amino acid, or any non-natural
      amino acid
<220> FEATURE:
<221> NAME/KEY: MOD_RES
<222> LOCATION: (10)..(10)
<223> OTHER INFORMATION: T, another amino acid, or any non-natural
      amino acid
<220> FEATURE:
<221> NAME/KEY: MOD_RES
<222> LOCATION: (35)..(35)
<223> OTHER INFORMATION: K or another amino acid
<220> FEATURE:
<221> NAME/KEY: MOD_RES
<222> LOCATION: (37)..(37)
<223> OTHER INFORMATION: T or another amino acid
<220> FEATURE:
<221> NAME/KEY: MOD_RES
<222> LOCATION: (38)..(38)
<223> OTHER INFORMATION: R or another amino acid
<220> FEATURE:
<221> NAME/KEY: MOD_RES
<222> LOCATION: (41)..(41)
<223> OTHER INFORMATION: T or another amino acid
<220> FEATURE:
<221> NAME/KEY: MOD_RES
<222> LOCATION: (42)..(42)
<223> OTHER INFORMATION: F or another amino acid
<220> FEATURE:
<221> NAME/KEY: MOD_RES
<222> LOCATION: (43)..(43)
<223> OTHER INFORMATION: K or another amino acid
<220> FEATURE:
<221> NAME/KEY: MOD_RES
<222> LOCATION: (45)..(45)
<223> OTHER INFORMATION: Y or another amino acid
<220> FEATURE:
<221> NAME/KEY: MOD_RES
<222> LOCATION: (61)..(61)
<223> OTHER INFORMATION: E or another amino acid
<220> FEATURE:
<221> NAME/KEY: MOD_RES
<222> LOCATION: (62)..(62)
<223> OTHER INFORMATION: E or another amino acid
<220> FEATURE:
<221> NAME/KEY: MOD_RES
<222> LOCATION: (64)..(64)
<223> OTHER INFORMATION: K or another amino acid
<220> FEATURE:
<221> NAME/KEY: MOD_RES
<222> LOCATION: (65)..(65)
<223> OTHER INFORMATION: P or another amino acid
```

```
<220> FEATURE:
<221> NAME/KEY: MOD_RES
<222> LOCATION: (68)..(68)
<223> OTHER INFORMATION: E or another amino acid
<220> FEATURE:
<221> NAME/KEY: MOD_RES
<222> LOCATION: (72)..(72)
<223> OTHER INFORMATION: L or another amino acid
<220> FEATURE:
<221> NAME/KEY: MOD_RES
<222> LOCATION: (107)..(107)
<223> OTHER INFORMATION: Y or another amino acid
<220> FEATURE:
<221> NAME/KEY: MOD_RES
<222> LOCATION: (125)..(125)
<223> OTHER INFORMATION: C or another amino acid

<400> SEQUENCE: 42

Xaa Xaa Xaa Xaa Xaa Xaa Xaa Xaa Xaa Xaa Gln Leu Gln Leu Glu His
 1               5                  10                  15

Leu Leu Leu Asp Leu Gln Met Ile Leu Asn Gly Ile Asn Asn Tyr Lys
             20                  25                  30

Asn Pro Xaa Leu Xaa Xaa Met Leu Xaa Xaa Phe Xaa Met Pro Lys
         35                  40                  45

Lys Ala Thr Glu Leu Lys His Leu Gln Cys Leu Glu Xaa Xaa Leu Xaa
 50                  55                  60

Xaa Leu Glu Xaa Val Leu Asn Xaa Ala Gln Ser Lys Asn Phe His Leu
 65                  70                  75                  80

Arg Pro Arg Asp Leu Ile Ser Asn Ile Asn Val Ile Val Leu Glu Leu
             85                  90                  95

Lys Gly Ser Glu Thr Thr Phe Met Cys Glu Xaa Ala Asp Glu Thr Ala
            100                 105                 110

Thr Ile Val Glu Phe Leu Asn Arg Trp Ile Thr Phe Xaa Gln Ser Ile
            115                 120                 125

Ile Ser Thr Leu Thr
            130

<210> SEQ ID NO 43
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: P, another amino acid, or any non-natural
      amino acid
<220> FEATURE:
<221> NAME/KEY: SITE
<222> LOCATION: (1)..(9)
<223> OTHER INFORMATION: Comprises only one non-natural amino acid
<220> FEATURE:
<221> NAME/KEY: SITE
<222> LOCATION: (1)..(132)
<223> OTHER INFORMATION: At least one of the amino acids at positions
      36, 37, 40, 41, 42, 44, 60, 61, 63, 64, 69, 71, and 106 is not
      the amino acid at the corresponding position in aldesleukin
<220> FEATURE:
<221> NAME/KEY: MOD_RES
<222> LOCATION: (2)..(2)
<223> OTHER INFORMATION: T, another amino acid, or any non-natural
      amino acid
<220> FEATURE:
<221> NAME/KEY: MOD_RES
<222> LOCATION: (3)..(3)
<223> OTHER INFORMATION: S, another amino acid, or any non-natural
      amino acid
```

```
<220> FEATURE:
<221> NAME/KEY: MOD_RES
<222> LOCATION: (4)..(4)
<223> OTHER INFORMATION: S, another amino acid, or any non-natural
      amino acid
<220> FEATURE:
<221> NAME/KEY: MOD_RES
<222> LOCATION: (5)..(5)
<223> OTHER INFORMATION: S, another amino acid, or any non-natural
      amino acid
<220> FEATURE:
<221> NAME/KEY: MOD_RES
<222> LOCATION: (6)..(6)
<223> OTHER INFORMATION: T, another amino acid, or any non-natural
      amino acid
<220> FEATURE:
<221> NAME/KEY: MOD_RES
<222> LOCATION: (7)..(7)
<223> OTHER INFORMATION: K, another amino acid, or any non-natural
      amino acid
<220> FEATURE:
<221> NAME/KEY: MOD_RES
<222> LOCATION: (8)..(8)
<223> OTHER INFORMATION: K, another amino acid, or any non-natural
      amino acid
<220> FEATURE:
<221> NAME/KEY: MOD_RES
<222> LOCATION: (9)..(9)
<223> OTHER INFORMATION: T, another amino acid, or any non-natural
      amino acid
<220> FEATURE:
<221> NAME/KEY: MOD_RES
<222> LOCATION: (34)..(34)
<223> OTHER INFORMATION: K or another amino acid
<220> FEATURE:
<221> NAME/KEY: MOD_RES
<222> LOCATION: (36)..(36)
<223> OTHER INFORMATION: T or another amino acid
<220> FEATURE:
<221> NAME/KEY: MOD_RES
<222> LOCATION: (37)..(37)
<223> OTHER INFORMATION: R or another amino acid
<220> FEATURE:
<221> NAME/KEY: MOD_RES
<222> LOCATION: (40)..(40)
<223> OTHER INFORMATION: T or another amino acid
<220> FEATURE:
<221> NAME/KEY: MOD_RES
<222> LOCATION: (41)..(41)
<223> OTHER INFORMATION: F or another amino acid
<220> FEATURE:
<221> NAME/KEY: MOD_RES
<222> LOCATION: (42)..(42)
<223> OTHER INFORMATION: K or another amino acid
<220> FEATURE:
<221> NAME/KEY: MOD_RES
<222> LOCATION: (44)..(44)
<223> OTHER INFORMATION: Y or another amino acid
<220> FEATURE:
<221> NAME/KEY: MOD_RES
<222> LOCATION: (60)..(60)
<223> OTHER INFORMATION: E or another amino acid
<220> FEATURE:
<221> NAME/KEY: MOD_RES
<222> LOCATION: (61)..(61)
<223> OTHER INFORMATION: E or another amino acid
<220> FEATURE:
<221> NAME/KEY: MOD_RES
<222> LOCATION: (63)..(63)
<223> OTHER INFORMATION: K or another amino acid
<220> FEATURE:
<221> NAME/KEY: MOD_RES
<222> LOCATION: (64)..(64)
<223> OTHER INFORMATION: P or another amino acid
<220> FEATURE:
<221> NAME/KEY: MOD_RES
<222> LOCATION: (67)..(67)
<223> OTHER INFORMATION: E or another amino acid
```

```
<220> FEATURE:
<221> NAME/KEY: MOD_RES
<222> LOCATION: (71)..(71)
<223> OTHER INFORMATION: L or another amino acid
<220> FEATURE:
<221> NAME/KEY: MOD_RES
<222> LOCATION: (106)..(106)
<223> OTHER INFORMATION: Y or another amino acid
<220> FEATURE:
<221> NAME/KEY: MOD_RES
<222> LOCATION: (124)..(124)
<223> OTHER INFORMATION: C or another amino acid

<400> SEQUENCE: 43

Xaa Xaa Xaa Xaa Xaa Xaa Xaa Xaa Xaa Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Xaa Leu Xaa Xaa Met Leu Xaa Xaa Xaa Phe Xaa Met Pro Lys Lys
        35                  40                  45

Ala Thr Glu Leu Lys His Leu Gln Cys Leu Glu Xaa Xaa Leu Xaa Xaa
50                  55                  60

Leu Glu Xaa Val Leu Asn Xaa Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Xaa Ala Asp Glu Thr Ala Thr
            100                 105                 110

Ile Val Glu Phe Leu Asn Arg Trp Ile Thr Phe Xaa Gln Ser Ile Ile
        115                 120                 125

Ser Thr Leu Thr
    130

<210> SEQ ID NO 44
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(132)
<223> OTHER INFORMATION: At least one of the amino acids at positions
      36, 37, 40, 41, 42, 44, 60, 61, 63, 64, 69, 71, and 106 is not
      the amino acid at the corresponding position in native human IL-2
<220> FEATURE:
<221> NAME/KEY: MOD_RES
<222> LOCATION: (4)..(4)
<223> OTHER INFORMATION: Any non-natural amino acid conjugated to a
      nonpeptidic, water-soluble polymer
<220> FEATURE:
<221> NAME/KEY: MOD_RES
<222> LOCATION: (34)..(34)
<223> OTHER INFORMATION: K or another amino acid
<220> FEATURE:
<221> NAME/KEY: MOD_RES
<222> LOCATION: (36)..(36)
<223> OTHER INFORMATION: T or another amino acid
<220> FEATURE:
<221> NAME/KEY: MOD_RES
<222> LOCATION: (37)..(37)
<223> OTHER INFORMATION: R or another amino acid
<220> FEATURE:
<221> NAME/KEY: MOD_RES
<222> LOCATION: (40)..(40)
<223> OTHER INFORMATION: T or another amino acid
```

```
<220> FEATURE:
<221> NAME/KEY: MOD_RES
<222> LOCATION: (41)..(41)
<223> OTHER INFORMATION: F or another amino acid
<220> FEATURE:
<221> NAME/KEY: MOD_RES
<222> LOCATION: (42)..(42)
<223> OTHER INFORMATION: K or another amino acid
<220> FEATURE:
<221> NAME/KEY: MOD_RES
<222> LOCATION: (44)..(44)
<223> OTHER INFORMATION: Y or another amino acid
<220> FEATURE:
<221> NAME/KEY: MOD_RES
<222> LOCATION: (60)..(60)
<223> OTHER INFORMATION: E or another amino acid
<220> FEATURE:
<221> NAME/KEY: MOD_RES
<222> LOCATION: (61)..(61)
<223> OTHER INFORMATION: E or another amino acid
<220> FEATURE:
<221> NAME/KEY: MOD_RES
<222> LOCATION: (63)..(63)
<223> OTHER INFORMATION: K or another amino acid
<220> FEATURE:
<221> NAME/KEY: MOD_RES
<222> LOCATION: (64)..(64)
<223> OTHER INFORMATION: P or another amino acid
<220> FEATURE:
<221> NAME/KEY: MOD_RES
<222> LOCATION: (67)..(67)
<223> OTHER INFORMATION: E or another amino acid
<220> FEATURE:
<221> NAME/KEY: MOD_RES
<222> LOCATION: (71)..(71)
<223> OTHER INFORMATION: L or another amino acid
<220> FEATURE:
<221> NAME/KEY: MOD_RES
<222> LOCATION: (106)..(106)
<223> OTHER INFORMATION: Y or another amino acid
<220> FEATURE:
<221> NAME/KEY: MOD_RES
<222> LOCATION: (124)..(124)
<223> OTHER INFORMATION: C or another amino acid

<400> SEQUENCE: 44

Pro Thr Ser Xaa Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Xaa Leu Xaa Xaa Met Leu Xaa Xaa Xaa Phe Xaa Met Pro Lys Lys
        35                  40                  45

Ala Thr Glu Leu Lys His Leu Gln Cys Leu Glu Xaa Xaa Leu Xaa Xaa
    50                  55                  60

Leu Glu Xaa Val Leu Asn Xaa Ala Gln Ser Lys Asn Phe His Leu Arg
65              70                  75                  80

Pro Arg Asp Leu Ile Ser Asn Ile Asn Val Ile Leu Glu Leu Lys
                85                  90                  95

Gly Ser Glu Thr Thr Phe Met Cys Glu Xaa Ala Asp Glu Thr Ala Thr
            100                 105                 110

Ile Val Glu Phe Leu Asn Arg Trp Ile Thr Phe Xaa Gln Ser Ile Ile
        115                 120                 125

Ser Thr Leu Thr
    130

<210> SEQ ID NO 45
<211> LENGTH: 132
<212> TYPE: PRT
<213> ORGANISM: Artificial Sequence
```

```
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Any non-natural amino acid
<220> FEATURE:
<221> NAME/KEY: MOD_RES
<222> LOCATION: (37)..(37)
<223> OTHER INFORMATION: Any amino acid except R
<220> FEATURE:
<221> NAME/KEY: MOD_RES
<222> LOCATION: (41)..(41)
<223> OTHER INFORMATION: Any amino acid except F
<220> FEATURE:
<221> NAME/KEY: MOD_RES
<222> LOCATION: (124)..(124)
<223> OTHER INFORMATION: Any amino acid except C

<400> SEQUENCE: 45

Pro Thr Ser Xaa Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Xaa Met Leu Thr Xaa Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Xaa Gln Ser Ile Ile
        115                 120                 125

Ser Thr Leu Thr
    130

<210> SEQ ID NO 46
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: Any non-natural amino acid
<220> FEATURE:
<221> NAME/KEY: MOD_RES
<222> LOCATION: (38)..(38)
<223> OTHER INFORMATION: Any amino acid except R
<220> FEATURE:
<221> NAME/KEY: MOD_RES
<222> LOCATION: (42)..(42)
<223> OTHER INFORMATION: Any amino acid except F
<220> FEATURE:
<221> NAME/KEY: MOD_RES
<222> LOCATION: (125)..(125)
<223> OTHER INFORMATION: Any amino acid except C
```

<400> SEQUENCE: 46

```
Ala Pro Thr Ser Xaa Ser Thr Lys Lys Thr Gln Leu Gln Leu Glu His
1               5                   10                  15
Leu Leu Leu Asp Leu Gln Met Ile Leu Asn Gly Ile Asn Asn Tyr Lys
            20                  25                  30
Asn Pro Lys Leu Thr Xaa Met Leu Thr Xaa Lys Phe Tyr Met Pro Lys
        35                  40                  45
Lys Ala Thr Glu Leu Lys His Leu Gln Cys Leu Glu Glu Glu Leu Lys
    50                  55                  60
Pro Leu Glu Glu Val Leu Asn Leu Ala Gln Ser Lys Asn Phe His Leu
65                  70                  75                  80
Arg Pro Arg Asp Leu Ile Ser Asn Ile Asn Val Ile Val Leu Glu Leu
                85                  90                  95
Lys Gly Ser Glu Thr Thr Phe Met Cys Glu Tyr Ala Asp Glu Thr Ala
            100                 105                 110
Thr Ile Val Glu Phe Leu Asn Arg Trp Ile Thr Phe Xaa Gln Ser Ile
        115                 120                 125
Ile Ser Thr Leu Thr
            130
```

<210> SEQ ID NO 47
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Any non-natural amino acid
<220> FEATURE:
<221> NAME/KEY: MOD_RES
<222> LOCATION: (124)..(124)
<223> OTHER INFORMATION: A or S

<400> SEQUENCE: 47

```
Pro Thr Ser Xaa Ser Thr Lys Lys Thr Gln Leu Gln Leu Glu His Leu
1               5                   10                  15
Leu Leu Asp Leu Gln Met Ile Leu Asn Gly Ile Asn Asn Tyr Lys Asn
            20                  25                  30
Pro Lys Leu Thr Ala Met Leu Thr Lys Lys Phe Tyr Met Pro Lys Lys
        35                  40                  45
Ala Thr Glu Leu Lys His Leu Gln Cys Leu Glu Glu Glu Leu Lys Pro
    50                  55                  60
Leu Glu Glu Val Leu Asn Leu Ala Gln Ser Lys Asn Phe His Leu Arg
65                  70                  75                  80
Pro Arg Asp Leu Ile Ser Asn Ile Asn Val Ile Val Leu Glu Leu Lys
                85                  90                  95
Gly Ser Glu Thr Thr Phe Met Cys Glu Tyr Ala Asp Glu Thr Ala Thr
            100                 105                 110
Ile Val Glu Phe Leu Asn Arg Trp Ile Thr Phe Xaa Gln Ser Ile Ile
        115                 120                 125
Ser Thr Leu Thr
            130
```

```
<210> SEQ ID NO 48
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: Any non-natural amino acid
<220> FEATURE:
<221> NAME/KEY: MOD_RES
<222> LOCATION: (125)..(125)
<223> OTHER INFORMATION: A or S

<400> SEQUENCE: 48

Ala Pro Thr Ser Xaa Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Ala Met Leu Thr Lys Lys Phe Tyr Met Pro Lys
        35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Xaa Gln Ser Ile
        115                 120                 125

Ile Ser Thr Leu Thr
            130

<210> SEQ ID NO 49
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Any non-natural amino acid

<400> SEQUENCE: 49

Pro Thr Ser Xaa Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Lys Lys Phe Tyr Met Pro Lys Lys
        35                  40                  45

Ala Thr Glu Leu Lys His Leu Gln Cys Leu Glu Glu Glu Leu Lys Pro
50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95
```

```
Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 50
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: Any non-natural amino acid

<400> SEQUENCE: 50

Ala Pro Thr Ser Xaa Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Ala Met Leu Thr Lys Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130

<210> SEQ ID NO 51
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: pAMF

<400> SEQUENCE: 51

Pro Thr Ser Xaa Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Lys Lys Phe Tyr Met Pro Lys Lys
        35                  40                  45

Ala Thr Glu Leu Lys His Leu Gln Cys Leu Glu Glu Glu Leu Lys Pro
    50                  55                  60
```

```
Leu Glu Glu Val Leu Asn Leu Ala Gln Ser Lys Asn Phe His Leu Arg
 65                  70                  75                  80

Pro Arg Asp Leu Ile Ser Asn Ile Asn Val Ile Val Leu Glu Leu Lys
                 85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 52
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: pAMF

<400> SEQUENCE: 52

Ala Pro Thr Ser Xaa Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Ala Met Leu Thr Lys Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130

<210> SEQ ID NO 53
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60
```

```
Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
            85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Cys Gln Ser Ile Ile
        115                 120                 125

Ser Thr Leu Thr
    130

<210> SEQ ID NO 54
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 54

His His His His His His
1               5
```

HUMAN INTERLEUKIN-2 CONJUGATES BIASED FOR THE INTERLEUKIN-2 RECEPTOR BETA GAMMAC DIMER AND CONJUGATED TO A NONPEPTIDIC, WATER-SOLUBLE POLYMER

CROSS REFERENCE TO RELATED APPLICATIONS

This application claims benefit of U.S. Provisional Application No. 63/013,583, filed Apr. 22, 2020, which is herein incorporated by reference in its entirety.

REFERENCE TO SEQUENCE LISTING SUBMITTED ELECTRONICALLY

The instant application contains a Sequence Listing which has been submitted electronically in ASCII format and is hereby incorporated by reference in its entirety. Said ASCII copy, created on Apr. 7, 2021, is named "24982USNP_SEQTXT_07APRIL2021.txt" and is 85,882 bytes in size.

BACKGROUND OF THE INVENTION

(1) Field of the Invention

The present invention relates to interleukin-2 (IL-2) conjugates comprising at least one or more amino acid substitutions that bias binding to the IL-2 receptor $\beta\gamma_c$ dimer over binding the IL-2 receptor $\alpha\beta\gamma_c$ trimer and a non-natural amino acid at or near the N-terminus conjugated to a nonpeptidic, water-soluble polymer. The IL-2 conjugates are useful for treatment and prevention of cell proliferation and cancer in a patient.

(2) Description of Related Art

Interleukin-2 (IL-2) was identified in 1965 as a factor produced in leukocyte cultures which when transferred, induced leukocyte blast formation. The factor behind this activity, the second cytokine to be identified over four decades ago, was initially called T-cell growth factor (TCGF). TCGF was named IL-2 in 1979 and in 1983 the cDNA for IL-2 was cloned. The first approval for IL-2 as a treatment for cancer (metastatic melanoma) occurred merely 8 years later.

The IL-2 protein is a four alpha helix cytokine measuring 15.5 kDa. IL-2 is produced by a number of cell types including NK T cells, CD8 T cells, mast cells and dendritic cells, but the main producers of IL-2 are antigen stimulated helper (CD4) T cells.

The effects of IL-2 are mediated by a complex receptor system comprised of three protein subunits, IL-2Rα (CD25), IL-2Rβ (CD122) and the common gamma chain (γc/CD132) (See FIG. 1). CD25 binds IL-2 with low affinity (no signal transduction). CD122 and CD132 form an intermediate affinity dimeric receptor (Kd, $10^{-9}$ M) which is expressed on CD8 T cells and NK cells. CD25, CD122, and CD132 form the high affinity trimer receptor system (Kd, $10^{-11}$ M) that binds IL-2 with high affinity and is expressed on regulatory T cells (Tregs), activated T cells and endothelial cells. Due to this differential affinity, IL-2Rαβγc expressing cells will preferentially bind IL-2. A high dose of IL-2 activates the βγc dimer, resulting in activation of the immune response. A high dose of IL-2 also activates the αβγc trimer on Tregs, which suppresses activation of the immune response and may lead to tolerance of tumor antigens.

Binding of IL-2 to either IL-2Rβγ$_c$ or IL-2Rαβγ$_c$ induces multiple signaling pathways and the transcription of target genes. These pathways include the Jak/Stat pathway, the MAPK pathway and the PI3K pathway. Through these pathways, this potent cytokine induces activation, proliferation and cytokine production and differentiation of CD4 and CD8 T cells, and the activation of NK cells to promote their cytolytic functions. In addition, IL-2 promotes the induction of regulatory T cells (T$_{regs}$) which are inhibitory to the immune response. Discovered in 1999, the T$_{reg}$ component of IL-2 biology illustrated the effect of IL-2 in both promoting or contracting the inflammatory immune response against foreign invaders such as pathogens or cancer; and added a level of nuance to the understanding of how high IL-2 doses promoted anti-tumor immunity by affecting the function of CD8 T cells and NK cells.

IL-2 in Cancer Immunotherapy

IL-2 was the first cytokine, and immunotherapy, to be used successfully to treat cancer. In 1992, aldesleukin, a non-glycosylated human recombinant IL-2 analog (des-alanyl-1, serine-125 human IL-2), was approved by the U.S. Food and Drug Administration (FDA) for the treatment of Renal Cell Carcinoma (RCC) and Metastatic Melanoma. In these settings, high dose aldesleukin led to approximately 10% complete responses, however with dose limiting toxicities. Due to the short half-life of IL-2 (about one hour in humans) treatment of patients with IL-2 requires administration of approximately 3 mg by IV infusion over a 15-minute period every 8 hours for 14 doses over 5 days; following a 5 day break the course is repeated. An additional 1-2 courses of treatment might be given after 6-12 weeks.

Many patients treated with the high dose IL-2 regimen present with vascular leak syndrome (VLS) beginning 3-4 days after starting therapy; this effect was often dose limiting at days 5-10 of treatment, resulting in Intensive Care Unit admission. This syndrome is characterized by an increase in vascular permeability and extravasation of fluids and proteins from capillaries into tissues resulting in interstitial edema, decrease in organ perfusion and organ damage. Quantification of the most prominent Grade 3 and Grade 4 adverse events associated with IL-2 include hypotension and impaired renal function. Because administration of aldesleukin at the approved recommended doses can cause severe side effects, including VLS and impaired neutrophil function, FDA requires aldesleukin be marketed with a black box warning. Moreover, the commercial formulation of aldesleukin includes the presence of sodium dodecyl sulfate, a substance that appears to be required to maintain optimal activity through conformational stability. See Arakawa et al., 1994, Int. J. Peptide Protein Res. 43:583-587.

As the utility of IL-2 in the clinic has been hampered by its short half-life and by dose limiting toxicities, investigations have been concentrated towards mitigating these issues. Studies of the cellular and molecular mechanisms that result in VLS have implicated the interaction of IL-2 with CD25, the IL-2Rα chain, as the cause of VLS. Data supporting this hypothesis demonstrates that either half-life extended mutants of IL-2 that fail to interact with IL-2Rα or antibodies that block the IL-2-IL-2Rα binding interaction and confer prolonged half-life, provide efficacy in mouse models of cancer without inducing vascular leak. To confirm this effect using genetic deletions, bone marrow chimeras using mice harboring a deletion of CD25 in either only the immune system or only in the non-immune tissues found that the effect of IL-2 required only CD25 to be present in the non-immune tissues. These studies demonstrated the possibility of engineering a half-life extended IL-2 molecule that lacks the toxicity driving features while retaining the anti-neoplastic activity of wild-type IL-2.

After decades of attempts at engineering IL-2 molecules, positive data has emerged from the clinic. Progress in producing a half-life extended, biased, low-dose IL-2 has seemingly been accomplished by Nektar Therapeutics with a pegylated pro-drug form of aldesleukin called bempegaldesleukin (NKTR-214; See U.S. Pat. No. 9,861,705). Bempegaldesleukin has about six of its 11 lysine residues conjugated to hydrolysable bi-10 kDa polyethylene glycol (PEG) molecules such as to form an inactive prodrug. After four of the six PEG moieties are hydrolyzed, the bempegaldesleukin gains activity, with one or two of the remaining PEGs putatively positioned in a manner that biases binding of the molecule away from the IL-2Rα. Pegylation also endows bempegaldesleukin with a greatly increased half-life compared to wild-type native IL-2 (days compared to minutes) with prolonged exposure.

In addition to the treatment of proliferative diseases and disorders, IL-2 also has been suggested for the treatment of hepatitis C virus (HCV) infection, human immunodeficiency virus (HIV) infection, acute myeloid leukemia, non-Hodgkin's lymphoma, cutaneous T-cell lymphoma, juvenile rheumatoid arthritis, atopic dermatitis, breast cancer, and bladder cancer.

In light of the toxicity of aldesleukin and its relatively short half-life, there is a need for IL-2 analogs with reduced toxicity and extended half-life. Unmet improvements include stability, selectivity for instance at the various IL-2 receptor forms, dosing regimens, and limiting side effects. IL-2 muteins and conjugates may provide improved therapeutics for treating malignant melanoma, renal cell cancer, and other conditions receptive to IL-2 therapy.

BRIEF SUMMARY OF THE INVENTION

The present invention provides herein interleukin 2 (IL-2) polypeptides having at least one or more amino acid substitutions that bias binding to the IL-2 receptor $\beta\gamma_c$ dimer (IL-2R$\beta\gamma_c$) over the IL-2 receptor $\alpha\beta\gamma_c$ trimer (IL-2R$\beta\gamma_c$), a non-natural amino acid at or near the N-terminus of the IL-2 polypeptide conjugated to a nonpeptidic, water-soluble polymer, and an amino acid sequence with at least 80% identity otherwise to the amino acid sequence wild-type or native human IL-2. These IL-2 conjugates have a binding affinity to the IL-2R$\beta\gamma_c$ that is substantially similar to that of native IL-2 and has reduced or no detectable binding affinity for the IL-2R$\alpha$ compared to native IL-2 as determined by Surface Plasmon Resonance (SPR) assay. Thus, these IL-2 conjugates have reduced toxicity compared to compared to commercially available IL-2 polypeptides and a plasma half-life of at least five times that of commercially available IL-2 polypeptides.

The present invention provides an interleukin 2 (IL-2) conjugate comprising an IL-2 polypeptide comprising an amino acid sequence with at least 80%, 85%, 90%, 95%, 98%, or 99% identity to the amino acid sequence set forth in SEQ ID NO: 53 and further comprising: (i) one or more amino acid substitutions that reduce(s) affinity of the IL-2 polypeptide for the human IL-2 receptor $\alpha\beta\gamma_c$ trimer (IL-2R$\alpha\beta\gamma_c$) relative to wild-type human IL-2; and (ii) a substitution of an amino acid at or near the N-terminus of the IL-2 polypeptide with a non-natural amino acid conjugated to a nonpeptidic, water-soluble polymer or an insertion of a non-natural amino acid conjugated to a nonpeptidic, water-soluble polymer at or near the N-terminus of the IL-2 polypeptide; wherein the IL-2 polypeptide has substantially similar binding affinity for the human IL-2 receptor $\beta\gamma_c$ dimer (IL-2R$\beta\gamma_c$) relative to wild-type human IL-2.

In further embodiments, the IL-2 polypeptide amino acid sequence comprises at least 80%, 85%, 90%, 95%, 98%, or 99% identity with amino acid sequence set forth in SEQ ID: 2 with the proviso that the IL-2 polypeptide comprises at least amino acids E15, H16, L19, D20, D84, N88, V91, Q126, T123, and I129, wherein the amino acid positions correspond to the positions set forth in the amino acid sequence of SEQ ID NO: 53.

In further embodiments, the IL-2 polypeptide amino acid sequence comprises at least 80% identity with amino acid sequence set forth in SEQ ID: 2 with the proviso that the IL-2 polypeptide comprises at least amino acids E15, H16, L19, D20, D84, N88, V91, Q126, T123, and I129, wherein the amino acid positions correspond to the positions set forth in the amino acid sequence of SEQ ID NO: 53. In further embodiments, the IL-2 polypeptide amino acid sequence comprises at least 90% identity with amino acid sequence set forth in SEQ ID: 2 with the proviso that the IL-2 polypeptide comprises at least amino acids E15, H16, L19, D20, D84, N88, V91, Q126, T123, and I129, wherein the amino acid positions correspond to the positions set forth in the amino acid sequence of SEQ ID NO: 53. In further embodiments, the IL-2 polypeptide amino acid sequence comprises at least 95% identity with amino acid sequence set forth in SEQ ID: 2 with the proviso that the IL-2 polypeptide comprises at least amino acids E15, H16, L19, D20, D84, N88, V91, Q126, T123, and I129, wherein the amino acid positions correspond to the positions set forth in the amino acid sequence of SEQ ID NO: 53. In further embodiments, the IL-2 polypeptide amino acid sequence comprises at least 98% identity with amino acid sequence set forth in SEQ ID: 2 with the proviso that the IL-2 polypeptide comprises at least amino acids E15, H16, L19, D20, D84, N88, V91, Q126, T123, and I129, wherein the amino acid positions correspond to the positions set forth in the amino acid sequence of SEQ ID NO: 53.

In a further embodiment, the IL-2 polypeptide conjugate has reduced or no detectable binding to the human IL-2 receptor α monomer (IL-2Rα) compared to native IL-2 as determined by an SPR assay.

In a further embodiment, the one or more amino acid substitutions are independently selected from the group consisting of K34, T36, R37, T40, F41, K42, F43, Y44, E60, K63, P64, E67, L71, M103, C104, and Y106, wherein the amino acid substitution positions correspond to the position of the amino acid in the amino acid sequence set forth in SEQ ID NO: 53. In a further embodiment, the one or more amino acid substitutions in the IL-2 polypeptide are at positions R37 and F41. In a further embodiment, the amino acid substitutions in the IL-2 polypeptide are R37A and F41K. In a further embodiment, the IL-2 polypeptide further includes a substitution of the cysteine residue at position 124 with an amino acid selected from the group consisting of A and S, wherein the amino acid position corresponds to the position of the amino acid in the amino acid sequence set forth in SEQ ID NO: 53. In a further embodiment, the IL-2 polypeptide further includes an N-terminal alanine residue or methionine residue. In a further embodiment, the IL-2 polypeptide further includes a C-terminal HIS6 tag (SEQ ID NO: 54).

In a further embodiment, the non-natural amino acid is substituted for an amino acid corresponding to a position within the first 10 amino acids of the amino acid sequence as set forth in SEQ ID NO: 2 or inserted within said sequence. In a further embodiment, the non-natural amino acid is substituted for an amino acid corresponding to a position within the sequence from P1 to Q10 of the amino acid sequence as set forth in SEQ ID NO: 2 or inserted within said sequence between P1 through Q10. In a further embodiment, the non-natural amino acid is substituted for an amino acid at position P1, T2, S3, S4, S5, T6, K7, K8, or T9 or linked to the N-terminal amino acid by an amide linkage. In a further embodiment, the non-natural amino acid is inserted after the amino acid at position P1, T2, S3, S4, S5, T6, K7, K8, or T9. In a further embodiment, the non-natural amino acid is located at the amino acid position corresponding to position 4 of the amino acid sequence set forth in SEQ ID NO: 2.

In a further embodiment, the non-natural amino acid comprises a functional group and the nonpeptidic, water-soluble polymer is linked to a reactive group that is capable of reacting with the functional group to form a covalent linkage. In a further embodiment, the non-natural amino acid is selected from the group consisting of p-azidomethyl-L-phenylalanine, p-azido-L-phenylalanine, p-acetyl-L-phenylalanine, N6-azidoethoxy-L-lysine, N6-propargylethoxy-L-lysine (PraK), BCN-L-lysine, norbornene lysine, TCO-lysine, methyltetrazine lysine, allyloxycarbonyllysine, 2-amino-8-oxononanoic acid, O-methyl-L-tyrosine, L-3-(2-naphthyl)alanine, 3-methyl-phenylalanine, O-4-allyl-L-tyrosine, 4-propyl-L-tyrosine, tri-O-acetyl-GlcNAc-serine, L-Dopa, fluorinated phenylalanine, isopropyl-L-phenylalanine, p-benzoyl-L-phenylalanine, L-phosphoserine, phosphonoserine, phosphonotyrosine, p-iodo-phenylalanine, p-bromophenylalanine, p-amino-L-phenylalanine, isopropyl-L-phenylalanine, p-propargyloxy-phenylalanine, 2-amino-3-((2-((3-(benzyloxy)-3-oxopropyl)amino)ethyl) selanyl)propanoic acid, 2-amino-3-(phenyl selanyl)propanoic, selenocysteine, m-acetylphenylalanine, and p-propargyloxyphenylalanine. In a further embodiment, the non-natural amino acid is p-azidomethyl-L-phenylalanine.

In a further embodiment, the nonpeptidic, water-soluble polymer has an average molecular weight between 1 kDa and 100 kDa. In a further embodiment, the nonpeptidic, water-soluble polymer has an average molecular weight of about 30 kDa. In a further embodiment, the nonpeptidic, water-soluble polymer is polyethylene glycol (PEG), poly (propylene glycol) (PPG), copolymers of ethylene glycol and propylene glycol, poly(oxyethylated polyol), poly (olefinic alcohol), poly(vinylpyrrolidone), poly(hydroxyalkylmethacrylamide), poly(hydroxyalkylmethacrylate), poly (saccharides), poly(a-hydroxy acid), poly(vinyl alcohol), polyphosphazene, polyoxazolines (POZ), poly(N-acryloylmorpholine), or a combination thereof. In a further embodiment, the nonpeptidic, water-soluble polymer is a linear or branched PEG.

In a further embodiment, the nonpeptidic, water-soluble polymer linked to the reactive group has the formula:

(RG)-(linker)-(POLY)-x wherein RG is a reactive group that is capable of forming a covalent linkage with the functional group of a non-natural amino acid; linker is a covalent bond or a substituted or non-substituted $C_{1-20}$ alkyl; POLY is a nonpeptidic, water-soluble polymer; and x is an alcohol or methyl group at the terminus of the POLY.

In a further embodiment, the reactive group of the nonpeptidic, water-soluble polymer comprises an alkyne and the functional group of the non-natural amino acid comprises an azide or the reactive group of the nonpeptidic, water-soluble polymer comprises an azide and the functional group of the non-natural amino acid comprises an alkyne.

In a further embodiment, the nonpeptidic, water-soluble polymer conjugated to the reactive group has the formula:

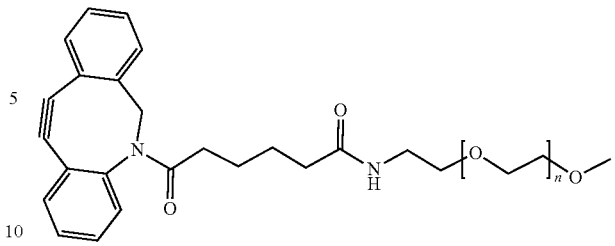

wherein n is about 681.

In a further embodiment, the IL-2 conjugate comprises the amino acid sequence set forth in SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, or SEQ ID NO: 21.

In a further embodiment, the interleukin 2 (IL-2) conjugate comprising the formula:

(SEQ ID NO: 20)

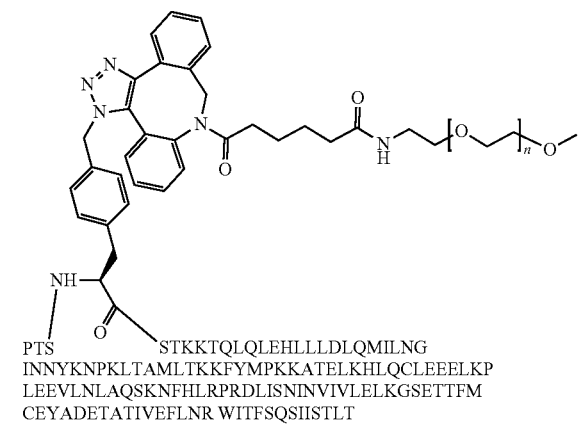

PTS STKKTQLQLEHLLLDLQMILNG
INNYKNPKLTAMLTKKFYMPKKATELKHLQCLEEELKP
LEEVLNLAQSKNFHLRPRDLISNINVIVLELKGSETTFM
CEYADETATIVEFLNR WITFSQSIISTLT wherein n is about 681, or a regioisomer thereof comprising the formula (SEQ ID NO: 20)

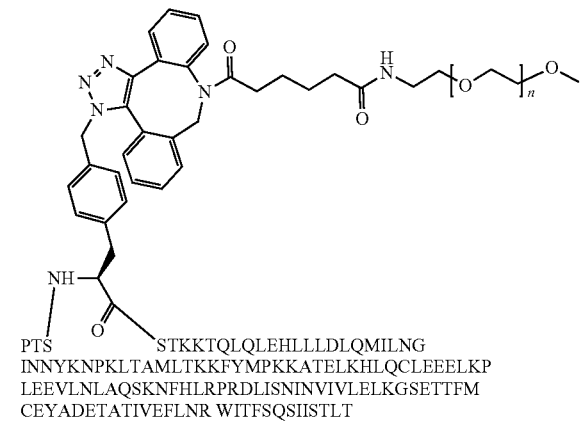

PTS STKKTQLQLEHLLLDLQMILNG
INNYKNPKLTAMLTKKFYMPKKATELKHLQCLEEELKP
LEEVLNLAQSKNFHLRPRDLISNINVIVLELKGSETTFM
CEYADETATIVEFLNR WITFSQSIISTLT wherein n is about 681.

In a further embodiment, the present invention provides a composition comprising: the IL-2 conjugate of any one of the foregoing embodiments and a pharmaceutically acceptable carrier or excipient.

In a further embodiment, the present invention provides a method for treating a proliferative disease or cancer in an individual, comprising: administering a therapeutically effective amount of any embodiment of IL-2 conjugate disclosed herein or composition thereof to an individual in need thereof to treat the proliferative disease or cancer in the individual.

In a further embodiment, the present invention provides a combination therapy for treating a proliferative disease or cancer in an individual, comprising: administering a therapeutically effective amount of any embodiment of IL-2 conjugate disclosed herein or composition thereof to an individual in need thereof, and administering a therapeutically effective amount of a therapeutic agent to the individual, to treat the proliferative disease or cancer in the individual. In a further embodiment, the therapeutic agent is an anti-PD1 antibody or anti-PDL1 antibody. In a further embodiment, the IL-2 conjugate or composition is administered before the therapeutic agent is administered. In a further embodiment, the IL-2 conjugate or composition is administered after the therapeutic agent is administered. In a further embodiment, the IL-2 conjugate or composition is administered concurrently with the therapeutic agent.

The present invention further provides for the use of the IL-2 conjugate of any embodiment of IL-2 conjugate disclosed herein or composition thereof for the treatment of a proliferative disease or cancer. In a further embodiment, is provided the use of the IL-2 conjugate of any embodiment of IL-2 conjugate disclosed herein or composition thereof and a therapeutic agent for the treatment of a proliferative disease or cancer. In a further embodiment, the therapeutic agent is an anti-PD1 antibody or anti-PDL1 antibody.

The present invention further provides for the use of the IL-2 conjugate of any embodiment of IL-2 conjugate disclosed herein or composition thereof for the manufacture of a medicament for the treatment of a proliferative disease or cancer.

The present invention further provides an IL-2 conjugate comprising an IL-2 polypeptide comprising an amino acid sequence with at least 80% identity to the amino acid sequence set forth in SEQ ID NO: 53 and further comprising: (i) one or more amino acid substitutions selected from the group consisting of K34, T36, R37, T40, F41, K42, F43, Y44, E60, E61, K63, P64, E67, L71, M103, C104, and Y106; and (ii) a substitution of an amino acid at or near the N-terminus of the IL-2 polypeptide with a non-natural amino acid conjugated to a nonpeptidic, water-soluble polymer or an insertion of a non-natural amino acid conjugated to a nonpeptidic, water-soluble polymer at or near the N-terminus of the IL-2 polypeptide, wherein the amino acid positions correspond to the positions set forth in the amino acid sequence of SEQ ID NO: 53.

In particular embodiments, the IL-2 polypeptide comprises an amino acid sequence with at least 85% identity to the amino acid sequence set forth in SEQ ID NO: 53 and further comprises: (i) one or more amino acid substitutions selected from the group consisting of K34, T36, R37, T40, F41, K42, F43, Y44, E60, E61, K63, P64, E67, L71, M103, C104, and Y106; and (ii) a substitution of an amino acid at or near the N-terminus of the IL-2 polypeptide with a non-natural amino acid conjugated to a nonpeptidic, water-soluble polymer or an insertion of a non-natural amino acid conjugated to a nonpeptidic, water-soluble polymer at or near the N-terminus of the IL-2 polypeptide, wherein the amino acid positions correspond to the positions set forth in the amino acid sequence of SEQ ID NO: 53.

In particular embodiments, the IL-2 polypeptide comprises an amino acid sequence with at least 90% identity to the amino acid sequence set forth in SEQ ID NO: 53 and further comprises: (i) one or more amino acid substitutions selected from the group consisting of K34, T36, R37, T40, F41, K42, F43, Y44, E60, E61, K63, P64, E67, L71, M103, C104, and Y106; and (ii) a substitution of an amino acid at or near the N-terminus of the IL-2 polypeptide with a non-natural amino acid conjugated to a nonpeptidic, water-soluble polymer or an insertion of a non-natural amino acid conjugated to a nonpeptidic, water-soluble polymer at or near the N-terminus of the IL-2 polypeptide, wherein the amino acid positions correspond to the positions set forth in the amino acid sequence of SEQ ID NO: 53.

In particular embodiments, the IL-2 polypeptide comprises an amino acid sequence with at least 95% identity to the amino acid sequence set forth in SEQ ID NO: 53 and further comprises: (i) one or more amino acid substitutions selected from the group consisting of K34, T36, R37, T40, F41, K42, F43, Y44, E60, E61, K63, P64, E67, L71, M103, C104, and Y106; and (ii) a substitution of an amino acid at or near the N-terminus of the IL-2 polypeptide with a non-natural amino acid conjugated to a nonpeptidic, water-soluble polymer or an insertion of a non-natural amino acid conjugated to a nonpeptidic, water-soluble polymer at or near the N-terminus of the IL-2 polypeptide, wherein the amino acid positions correspond to the positions set forth in the amino acid sequence of SEQ ID NO: 53.

In a further embodiment, the one or more amino acid substitutions in the IL-2 polypeptide are at positions R37 and F41. In a further embodiment, the amino acid substitutions in the IL-2 polypeptide are R37A and F41K. In a further embodiment, the IL-2 polypeptide further includes a substitution of the cysteine residue at position 124 with an amino acid selected from the group consisting of A and S, wherein the amino acid position corresponds to the position of the amino acid in the amino acid sequence set forth in SEQ ID NO: 53. In a further embodiment, the IL-2 polypeptide further includes an N-terminal alanine residue.

In a further embodiment, the non-natural amino acid is substituted for an amino acid corresponding to a position within the first 10 amino acids of the amino acid sequence as set forth in SEQ ID NO: 2 or inserted within said sequence. In a further embodiment, the non-natural amino acid is substituted for an amino acid corresponding to a position within the sequence from P1 to Q10 of the amino acid sequence as set forth in SEQ ID NO: 2 or inserted within said sequence between P1 through Q10. In a further embodiment, the non-natural amino acid is substituted for an amino acid at position P1, T2, S3, S4, S5, T6, K7, K8, or T9 or linked to the N-terminal amino acid by an amide linkage. In a further embodiment, the non-natural amino acid is located at the amino acid position corresponding to position 4 of the amino acid sequence set forth in SEQ ID NO: 2.

In a further embodiment, the non-natural amino acid comprises a functional group and the nonpeptidic, water-soluble polymer is linked to a reactive group that is capable of reacting with the functional group to form a covalent linkage. In a further embodiment, the non-natural amino acid is selected from the group consisting of p-azidomethyl-L-phenylalanine, p-azido-L-phenylalanine, p-acetyl-L-phenylalanine, N6-azidoethoxy-L-lysine, N6-propargylethoxy-L-lysine (PraK), BCN-L-lysine, norbornene lysine, TCO-lysine, methyltetrazine lysine, allyloxycarbonyllysine, 2-amino-8-oxononanoic acid, O-methyl-L-tyrosine, L-3-(2-naphthyl)alanine, 3-methyl-phenylalanine, O-4-allyl-L-tyrosine, 4-propyl-L-tyrosine, tri-O-acetyl-GlcNAc-serine, L-Dopa, fluorinated phenylalanine, isopropyl-L-phenylalanine, p-benzoyl-L-phenylalanine, L-phosphoserine, phosphonoserine, phosphonotyrosine, p-iodo-phenylalanine, p-bromophenylalanine, p-amino-L-phenylalanine, isopropyl-L-phenylalanine, p-propargyloxy-phenylalanine, 2-amino-3-((2-((3-(benzyloxy)-3-oxopropyl)amino)ethyl) selanyl)propanoic acid, 2-amino-3-(phenyl selanyl)propanoic, selenocysteine, m-acetylphenylalanine, and p-propargyloxyphenylalanine. In a further embodiment, the non-natural amino acid is p-azidomethyl-L-phenylalanine.

In a further embodiment, the nonpeptidic, water-soluble polymer has an average molecular weight between 1 kDa and 100 kDa. In a further embodiment, the nonpeptidic, water-soluble polymer has an average molecular weight of about 30 kDa. In a further embodiment, the nonpeptidic, water-soluble polymer is polyethylene glycol (PEG), poly (propylene glycol) (PPG), copolymers of ethylene glycol and propylene glycol, poly(oxyethylated polyol), poly (olefinic alcohol), poly(vinylpyrrolidone), poly(hydroxyalkylmethacrylamide), poly(hydroxyalkylmethacrylate), poly (saccharides), poly(a-hydroxy acid), poly(vinyl alcohol), polyphosphazene, polyoxazolines (POZ), poly(N-acryloylmorpholine), or a combination thereof. In a further embodiment, the nonpeptidic, water-soluble polymer is a linear or branched PEG.

In a further embodiment, the nonpeptidic, water-soluble polymer linked to the reactive group has the formula:

(RG)-(linker)-(POLY)-x wherein RG is a reactive group that is capable of forming a covalent linkage with the functional group of a non-natural amino acid; linker is a covalent bond or a substituted or non-substituted $C_{1-20}$ alkyl; POLY is a nonpeptidic, water-soluble polymer; and x is an alcohol or methyl group at the terminus of the POLY.

In a further embodiment, the reactive group of the nonpeptidic, water-soluble polymer comprises an alkyne and the functional group of the non-natural amino acid comprises an azide or the reactive group of the nonpeptidic, water-soluble polymer comprises an azide and the functional group of the non-natural amino acid comprises an alkyne.

In a further embodiment, the nonpeptidic, water-soluble polymer conjugated to the reactive group has the formula:

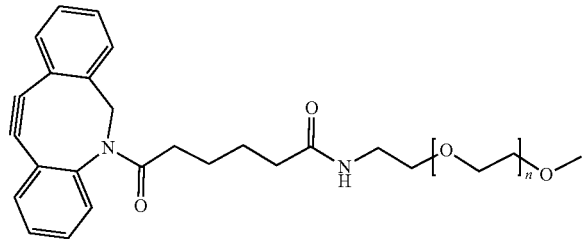

wherein n is about 681.

In a further embodiment, the IL-2 conjugate comprises the amino acid sequence set forth in SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, or SEQ ID NO: 21.

The present invention further provides a composition comprising: the IL-2 conjugate of any embodiment of IL-2 conjugate disclosed herein and a pharmaceutically acceptable carrier or excipient.

The present invention further provides a method for treating a proliferative disease or cancer in an individual, comprising: administering a therapeutically effective amount of the IL-2 conjugate of any embodiment of IL-2 conjugate disclosed herein or composition thereof to an individual in need thereof to treat the proliferative disease or cancer in the individual.

The present invention further provides a combination therapy for treating a proliferative disease or cancer in an individual, comprising: administering a therapeutically effective amount of the IL-2 conjugate of any embodiment of IL-2 conjugate disclosed herein or composition thereof to an individual in need thereof, and administering a therapeutically effective amount of a therapeutic agent to the individual, to treat the proliferative disease or cancer in the individual. In a further embodiment, the therapeutic agent is an anti-PD1 antibody or anti-PDL1 antibody. In a further embodiment, the IL-2 conjugate or composition is administered before the therapeutic agent is administered. In a further embodiment, the IL-2 conjugate or composition is administered after the therapeutic agent is administered. In a further embodiment, the IL-2 conjugate or composition is administered concurrently with the therapeutic agent.

The present invention further provides for the use of the IL-2 conjugate of any embodiment of IL-2 conjugate disclosed herein or composition thereof for the treatment of a proliferative disease or cancer.

The present invention further provides for the use of the IL-2 conjugate of any embodiment of IL-2 conjugate disclosed herein or composition thereof and a therapeutic agent for the treatment of a proliferative disease or cancer. In a further embodiment, the therapeutic agent is an anti-PD1 antibody or anti-PDL1 antibody.

The present invention further provides for the use of the IL-2 conjugate of any embodiment of IL-2 conjugate disclosed herein or composition thereof for the manufacture of a medicament for the treatment of a proliferative disease or cancer.

The present invention further provides an IL-2 conjugate comprising the amino acid sequence set forth in SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, or SEQ ID NO: 21. In a further embodiment, the present invention provides a pharmaceutical composition comprising the IL-2 conjugate and a pharmaceutically acceptable carrier or excipient.

The present invention further provides an IL-2 moiety comprising an amino acid sequence set forth in SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, or SEQ ID NO: 52.

The present invention further provides an interleukin 2 (IL-2) conjugate comprising an IL-2 polypeptide comprising an amino acid sequence with at least 80%, 85%, 90%, 95%, 98%, or 99% identity to the amino acid sequence set forth in SEQ ID NO: 53 and further comprising: a substitution of an amino acid at or near the N-terminus of the IL-2 polypeptide with a non-natural amino acid conjugated to a nonpeptidic, water-soluble polymer or an insertion of a non-natural amino acid conjugated to a nonpeptidic, water-soluble polymer at or near the N-terminus of the IL-2 polypeptide, with the proviso that the IL-2 polypeptide comprises at least amino acids E15, H16, L19, D20, K34, T36, R37, T40, F41, K42, F43, Y44, E60, E61, K63, P64, E67, L71, D84, N88, V91, M103, C104, Y106, Q126, T123, and I129, wherein the amino acid positions correspond to the positions set forth in the amino acid sequence of SEQ ID NO: 53.

In a further embodiment, the IL-2 polypeptide further includes a substitution of the cysteine residue at position 124 with an amino acid selected from the group consisting of A and S.

In a further embodiment, the IL-2 polypeptide further includes an N-terminal alanine residue.

In a further embodiment, the non-natural amino acid is substituted for an amino acid corresponding to a position within the first 10 amino acids of the amino acid sequence as set forth in SEQ ID NO: 2 or inserted within said sequence. In a further embodiment, the non-natural amino acid is substituted for an amino acid corresponding to a position within the sequence from P1 to Q10 of the amino acid sequence as set forth in SEQ ID NO: 2 or inserted within said sequence between P1 through Q10. In a further embodiment, the non-natural amino acid is substituted for an amino acid at position P1, T2, S3, S4, S5, T6, K7, K8, or T9 or linked to the N-terminal amino acid by an amide linkage. In a further embodiment, the non-natural amino acid is located at the amino acid position corresponding to position 4 of the amino acid sequence set forth in SEQ ID NO: 2.

In a further embodiment, the non-natural amino acid comprises a functional group and the water-soluble polymer is linked to a reactive group that is capable of reacting with the functional group to form a covalent linkage.

In a further embodiment, the non-natural amino acid comprises a functional group and the nonpeptidic, water-soluble polymer is linked to a reactive group that is capable of reacting with the functional group to form a covalent linkage. In a further embodiment, the non-natural amino acid is selected from the group consisting of p-azidomethyl-L-phenylalanine, p-azido-L-phenylalanine, p-acetyl-L-phenylalanine, N6-azidoethoxy-L-lysine, N6-propargylethoxy-L-lysine (PraK), BCN-L-lysine, norbornene lysine, TCO-lysine, methyltetrazine lysine, allyloxycarbonyllysine, 2-amino-8-oxononanoic acid, O-methyl-L-tyrosine, L-3-(2-naphthyl)alanine, 3-methyl-phenylalanine, O-4-allyl-L-tyrosine, 4-propyl-L-tyrosine, tri-O-acetyl-GlcNAc-serine, L-Dopa, fluorinated phenylalanine, isopropyl-L-phenylalanine, p-benzoyl-L-phenylalanine, L-phosphoserine, phosphonoserine, phosphonotyrosine, p-iodo-phenylalanine, p-bromophenylalanine, p-amino-L-phenylalanine, isopropyl-L-phenylalanine, p-propargyloxy-phenylalanine, 2-amino-3-((2-((3-(benzyloxy)-3-oxopropyl)amino)ethyl) selanyl)propanoic acid, 2-amino-3-(phenyl selanyl)propanoic, selenocysteine, m-acetylphenylalanine, and p-propargyloxyphenylalanine. In a further embodiment, the non-natural amino acid is p-azidomethyl-L-phenylalanine.

In a further embodiment, the nonpeptidic, water-soluble polymer has an average molecular weight between 1 kDa and 100 kDa. In a further embodiment, the nonpeptidic, water-soluble polymer has an average molecular weight of about 30 kDa. In a further embodiment, The IL-2 conjugate of claim 65, wherein the nonpeptidic, water-soluble polymer is polyethylene glycol (PEG), poly(propylene glycol) (PPG), copolymers of ethylene glycol and propylene glycol, poly(oxyethylated polyol), poly(olefinic alcohol), poly(vinylpyrrolidone), poly(hydroxyalkylmethacrylamide), poly (hydroxyalkylmethacrylate), poly(saccharides), poly(a-hydroxy acid), poly(vinyl alcohol), polyphosphazene, polyoxazolines (POZ), poly(N-acryloylmorpholine), or a combination thereof. In a further embodiment, the nonpeptidic, water-soluble polymer is a linear or branched PEG.

In a further embodiment, the reactive group of the non-peptidic, water-soluble polymer comprises an alkyne and the functional group of the non-natural amino acid comprises an azide or the reactive group of the nonpeptidic, water-soluble polymer comprises an azide and the functional group of the non-natural amino acid comprises an alkyne.

In a further embodiment, the nonpeptidic, water-soluble polymer, which comprises the alkyne, has the formula:

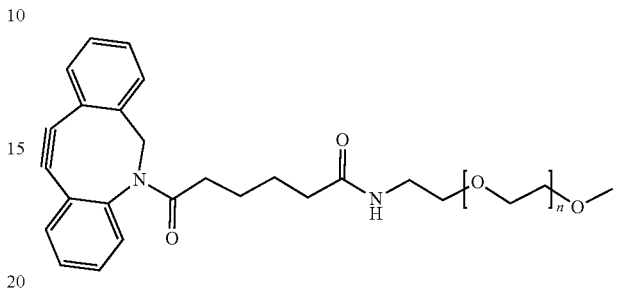

wherein n is about 681.

In a further embodiment, the IL-2 conjugate comprises the amino acid sequence set forth in SEQ ID NO: 22.

The present invention further provides for any embodiment disclosed herein in which the non-natural amino acid is not specifically identified as being substituted for the serine residue at position four as it corresponds to position four of SEQ ID NO:2, embodiments wherein the substitution or insertion of the non-natural amino acid is within the N-terminal region, for example, (i) a substitution of an amino acid within the first 30 amino acids of the N-terminus of the IL-2 polypeptide with a non-natural amino acid conjugated to a nonpeptidic, water-soluble polymer or an insertion of a non-natural amino acid conjugated to a non-peptidic, water-soluble polymer within the first 30 amino acids of the N-terminus of the IL-2 polypeptide or (ii) a substitution of an amino acid within the first 20 amino acids of the N-terminus of the IL-2 polypeptide with a non-natural amino acid conjugated to a nonpeptidic, water-soluble polymer or an insertion of a non-natural amino acid conjugated to a nonpeptidic, water-soluble polymer within the first 20 amino acids of the N-terminus of the IL-2 polypeptide.

Thus, the present invention provides (a) IL-2 conjugate comprising an IL-2 polypeptide comprising an amino acid sequence with at least 80%, 85%, 90%, 95%, 98%, or 99% identity to the amino acid sequence set forth in SEQ ID NO: 53 and further comprising: (i) one or more amino acid substitutions that reduce(s) affinity of the IL-2 polypeptide for the human IL-2R$\beta\gamma_c$ relative to wild-type human IL-2; and (ii) a substitution of an amino acid within the N-terminal region of the IL-2 polypeptide with a non-natural amino acid conjugated to a nonpeptidic, water-soluble polymer or an insertion of a non-natural amino acid conjugated to a non-peptidic, water-soluble polymer within the N-terminal region of the IL-2 polypeptide; wherein the IL-2 polypeptide has substantially similar binding affinity for the human IL-2R$\beta\gamma_c$ relative to wild-type human IL-2.

In particular embodiments, the present invention provides (a) IL-2 conjugate comprising an IL-2 polypeptide comprising an amino acid sequence with at least 80%, 85%, 90%, 95%, 98%, or 99% identity to the amino acid sequence set forth in SEQ ID NO: 53 and further comprising: (i) one or more amino acid substitutions that reduce(s) affinity of the IL-2 polypeptide for the human IL-2R$\alpha\beta\gamma_c$ relative to wild-type human IL-2; and (ii) a substitution of an amino acid within the first 30 amino acids of the N-terminus of the IL-2 polypeptide with a non-natural amino acid conjugated to a nonpeptidic, water-soluble polymer or an insertion of a non-natural amino acid conjugated to a nonpeptidic, water-soluble polymer within the first 30 amino acids of the N-terminus of the IL-2 polypeptide; wherein the IL-2 polypeptide has substantially similar binding affinity for the human IL-2Rβγ$_c$ relative to wild-type human IL-2; and (b) IL-2 conjugate comprising an IL-2 polypeptide comprising an amino acid sequence with at least 80%, 85%, 90%, 95%, 98%, or 99% identity to the amino acid sequence set forth in SEQ ID NO: 53 and further comprising: (i) one or more amino acid substitutions that reduce(s) affinity of the IL-2 polypeptide for the human IL-2Rαβγ$_c$ relative to wild-type human IL-2; and (ii) a substitution of an amino acid within the first 20 amino acids of the N-terminus of the IL-2 polypeptide with a non-natural amino acid conjugated to a nonpeptidic, water-soluble polymer or an insertion of a non-natural amino acid conjugated to a nonpeptidic, water-soluble polymer within the first 20 amino acids of the N-terminus of the IL-2 polypeptide; wherein the IL-2 polypeptide has substantially similar binding affinity for the human IL-2Rβγ$_c$ relative to wild-type human IL-2.

BRIEF DESCRIPTION OF THE DRAWINGS

FIG. 1 shows the interaction of IL-2 with the low affinity (α), intermediate affinity (βγ$_c$), and high affinity (αβγ$_c$) IL-2 receptors. IL-2 binds the α monomer with low_affinity (no signal transduction). IL-2 binds the βγ$_c$ dimer with intermediate affinity. The βγ$_c$ dimer is expressed on CD8$^+$ T cells and NK cells. IL-2 binds the αβγ$_c$ trimer with high affinity. The αβγ$_c$ trimer is expressed on T$_{regs}$ and activated T cells. High doses of IL-2 activate the βγ$_c$ dimer, which activates the immune response. However, high doses also activate the αβγ$_c$ trimer on T$_{regs}$, which suppresses activation of the immune response and may lead to tolerance of tumor antigens.

FIG. 10A shows changes in tumor infiltrating CD8 T cells (clone 53-6.7) following a single intravenous dose of 5 mg/kg CON1 or CON2 as measured by flow cytometry and standardized as percentage of total live cells. Data is presented as mean values±SEM (n=5 per group).

Figure 10A:
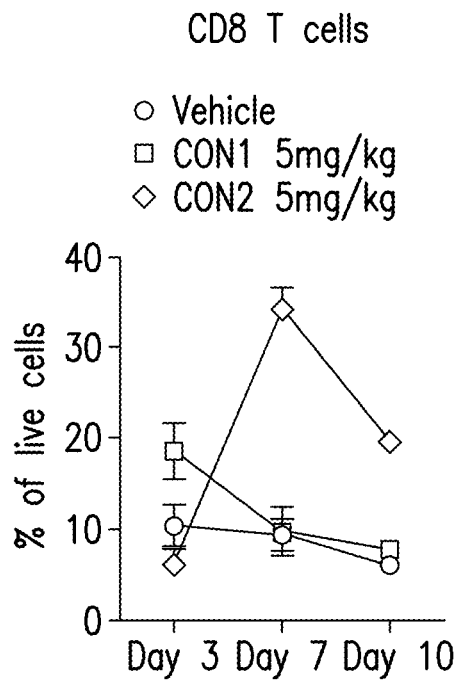
FIG. 10A-J shows immune cell alterations and tumor response following a single intravenous dose of 5 mg/kg CON1 or CON2 in animals bearing B16F10 tumors. Single cell suspensions from B16F10 tumors harvested on days 3, 7, and 10 after treatment were prepared using the Miltenyi Biotec Inc. kit (cat #130-096-730).
Figure 10B:
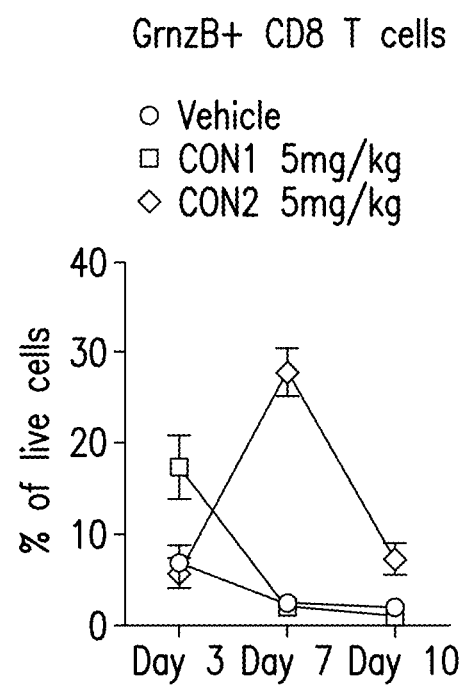

FIG. 10B shows changes in tumor infiltrating Granzyme B (GrnzB+, clone GB11) expressing CD8 T cells following a single intravenous dose of 5 mg/kg CON1 or CON2 as measured by flow cytometry and standardized as percentage of total live cells. Data is presented as mean values±SEM (n=5 per group).

Figure 10C:
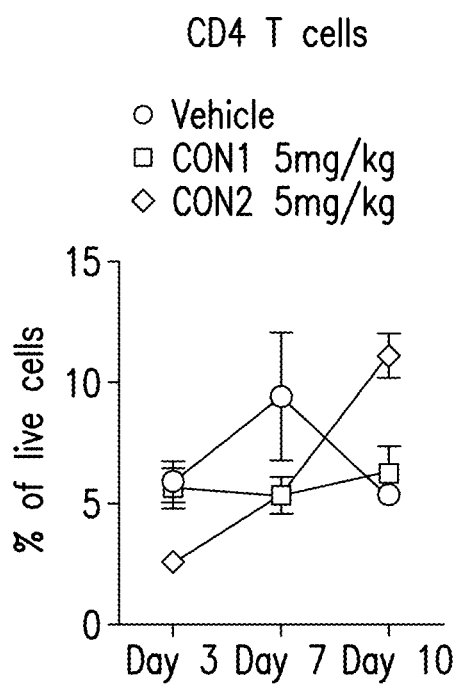

FIG. 10C shows changes in tumor infiltrating CD4 T cells (clone GK1.5) following a single intravenous dose of 5 mg/kg CON1 or CON2 as measured by flow cytometry and standardized as percentage of total live cells. Data is presented as mean values±SEM (n=5 per group).

Figure 10D:
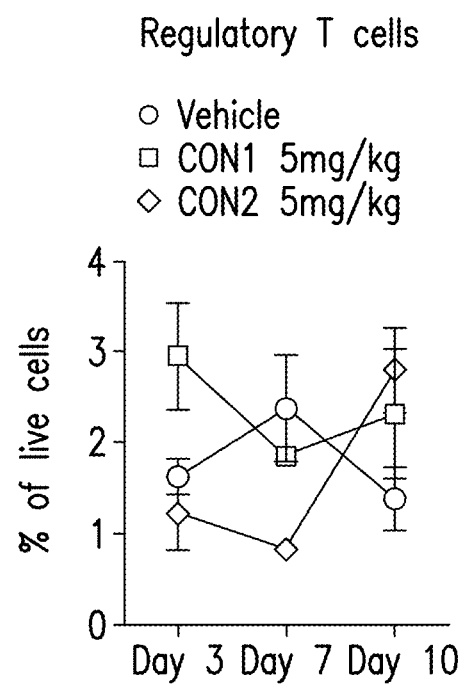

FIG. 10D shows changes in tumor infiltrating Foxp3+ (clone FJK-16s) CD4 regulatory T cells ($T_{regs}$) following a single intravenous dose of 5 mg/kg CON1 or CON2 as measured by flow cytometry and standardized as percentage of total live cells. Data is presented as mean values±SEM (n=5 per group).

Figure 10E:
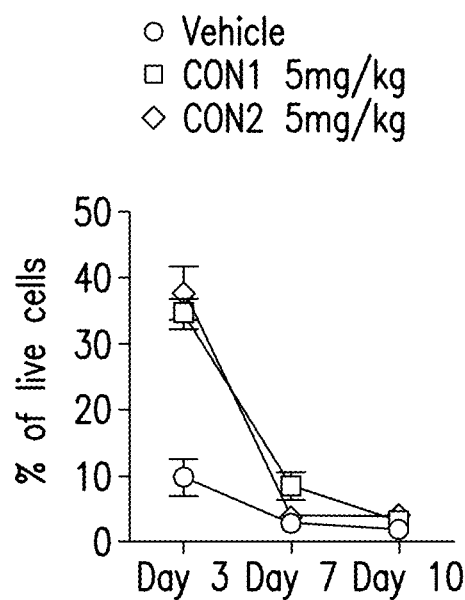

FIG. 10E shows changes in tumor infiltrating NKp46+ (clone 29A1.4) total NK cells following a single intravenous dose of 5 mg/kg CON1 or CON2 as measured by flow cytometry and standardized as percentage of total live cells. Data is presented as mean values SEM (n=5 per group).

Figure 10F:
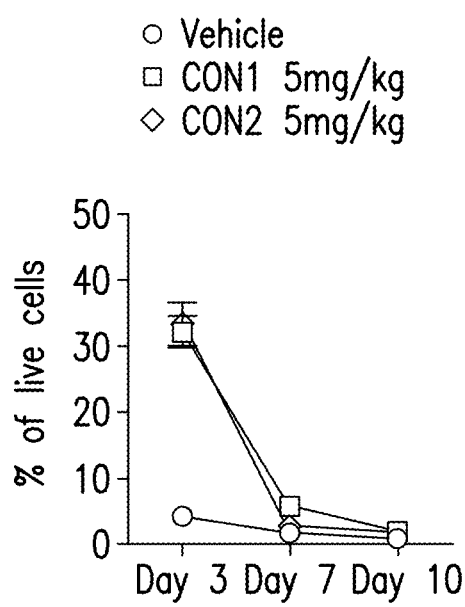

FIG. 10F shows changes in tumor infiltrating NKp46+ Thy1.2+ (Clone 53-2.1) NKT cells following a single intravenous dose of 5 mg/kg CON1 or CON2 as measured by flow cytometry and standardized as percentage of total live cells. Data is presented as mean values SEM (n=5 per group).

Figure 10G:
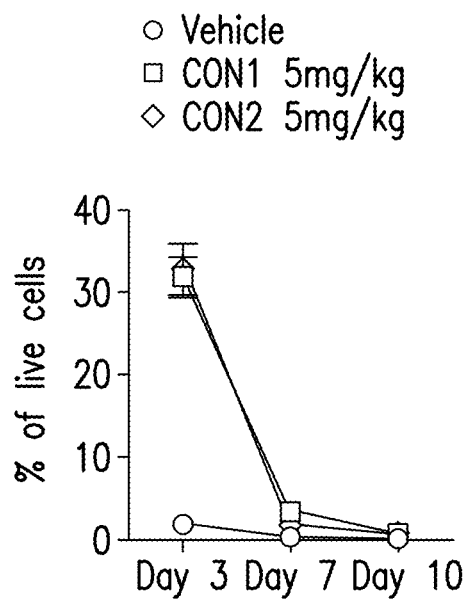

FIG. 10G shows changes in tumor infiltrating GmzB+ expressing NKT cells following a single intravenous dose of 5 mg/kg CON1 or CON2 as measured by flow cytometry and standardized as percentage of total live cells. Data is presented as mean values±SEM (n=5 per group).

Figure 10H:
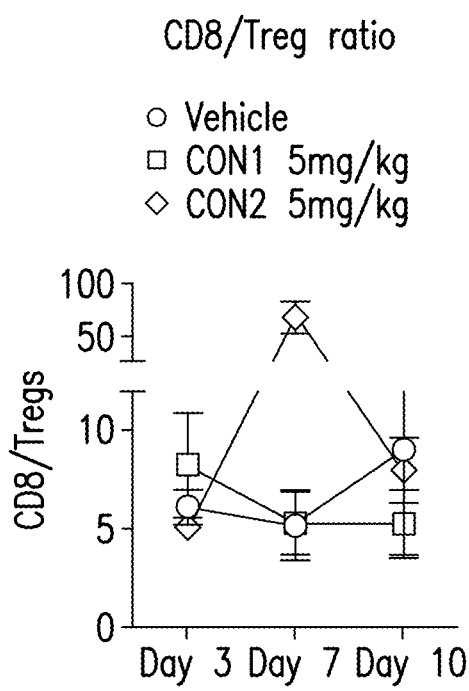

FIG. 10H shows changes in therapeutic ratios of CD8 to $T_{reg}$ in B16F10 tumors following a single intravenous dose of 5 mg/kg CON1 or CON2. Data is presented as mean values±SEM (n=5 per group).

Figure 10I:
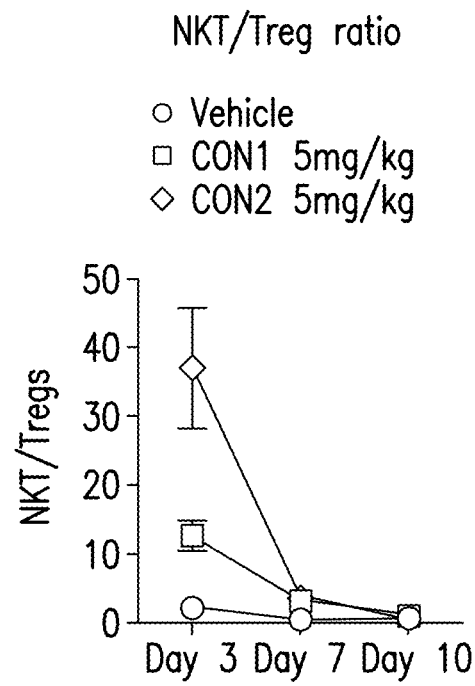

FIG. 10I shows changes in therapeutic ratios of NKT to $T_{reg}$ in B16F10 tumors following a single intravenous dose of 5 mg/kg CON1 or CON2. Data is presented as mean values±SEM (n=5 per group).

Figure 10J:
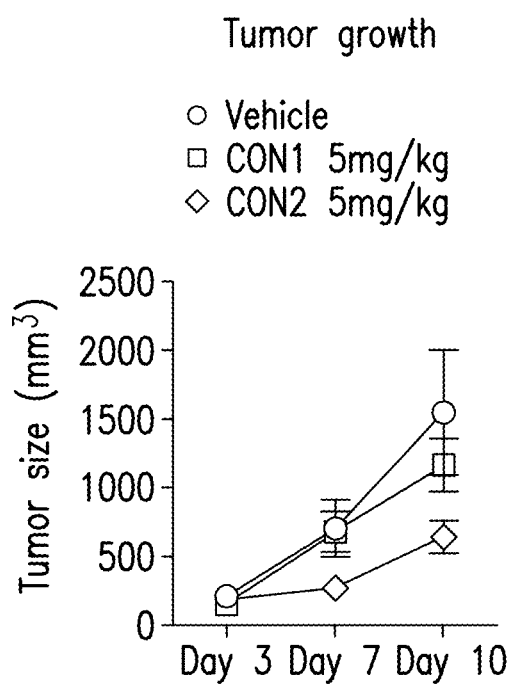

FIG. 10J shows B16F10 tumor growth curves in response to a single intravenous dose of 5 mg/kg CON1 or CON2. Data is presented as mean values±SEM (n=5 per group).

Figure 11:
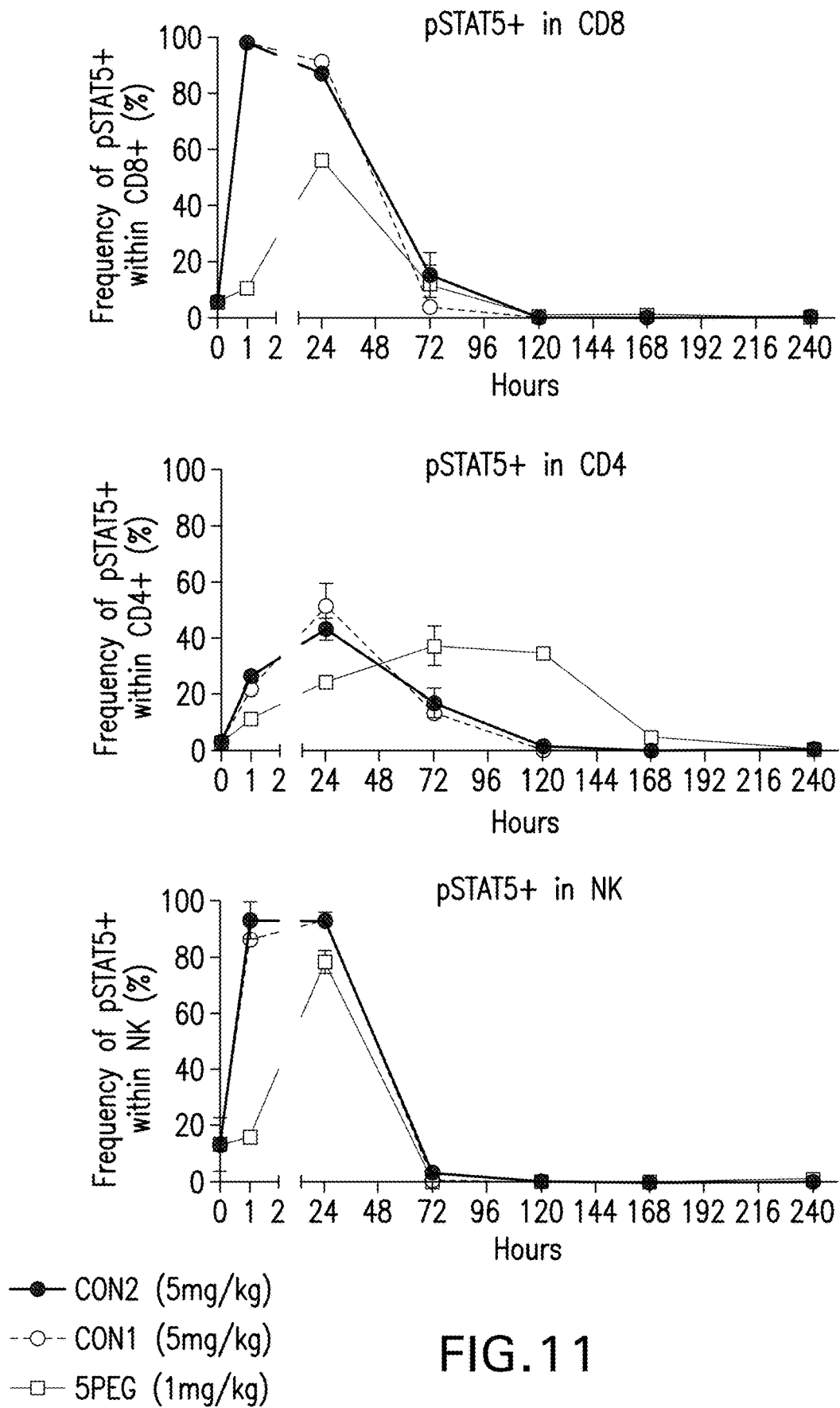

FIG. 11 shows that CON2 and CON1 has fast and robust pSTAT5 in vivo activity in blood of naïve mice compared to NKTR-214 analog 5PEG when injected into mice intravenously at 5 mg/kg dose for CON2 and CON1 and at 1 mg/kg dose for 5PEG. After injection, the blood was collected at 1 hour, 1, 3, 5, 7, and 10 days post injection. The collected whole blood was immediately fixed and permeabilized to stain for lineage markers and for phospho-STAT5. CD4, CD8+, and NK cells from five mice for each group were gated to monitor pSTAT5 by flow cytometry in each time point for each compound.

FIG. 12A-12J show key results from a repeat-dose pharmacokinetic (PK), pharmacodynamic (PD) study of CON1 and CON2 in non-human primates (NHP). Experimentally naïve male cynomolgus monkeys were randomly assigned to two groups (n=2/group). Animals were given IV bolus doses of 0.3 and 1 mg/kg CON1 (Lot No. ADC-004D) or 0.1 and 0.3 mg/kg CON2 (Lot No. ADC-0048) on days 1 and 8 and monitored for two weeks after the last dose. Following drug administration (indicated by dotted back lines), blood samples were collected at several timepoints for hematology analysis (complete blood cell count and differential) and to characterize various lymphocyte populations by flow cytometry methods.

Figure 12A:
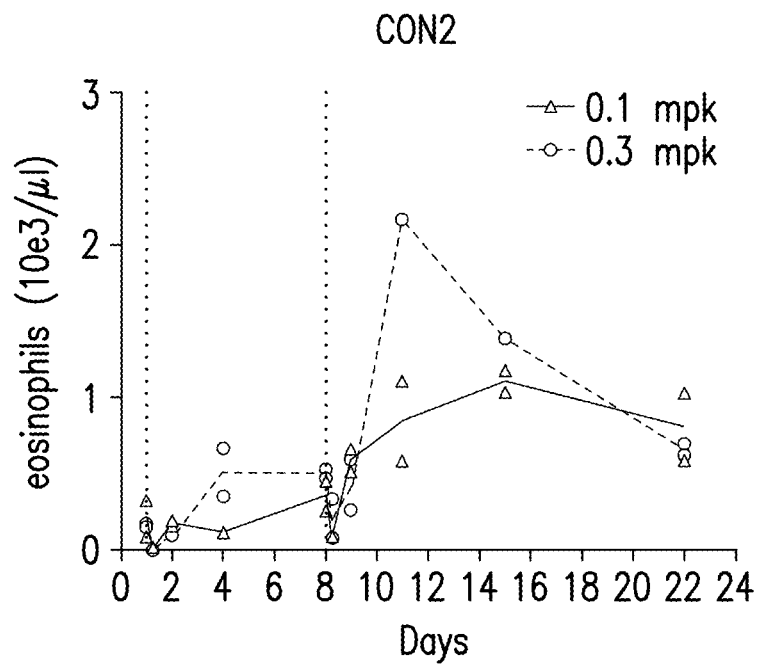
Figure 12B:
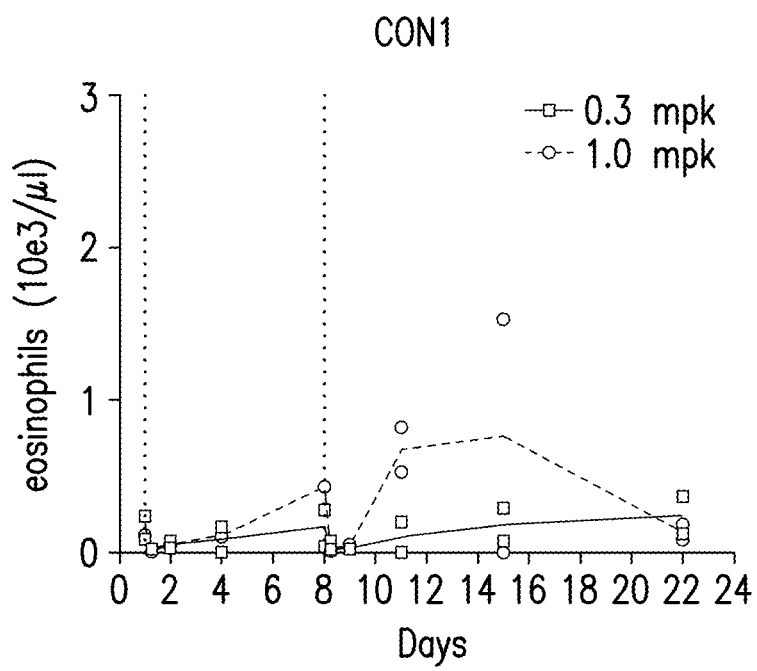

FIG. 12A and FIG. 12B show CON1 or CON2-related changes in eosinophils in NHP at the indicated doses. Individual animal data are plotted at indicated time points and the solid and dashed lines represents the average value of two animals whenever available, or of a single animal in each group.

Figure 12C:
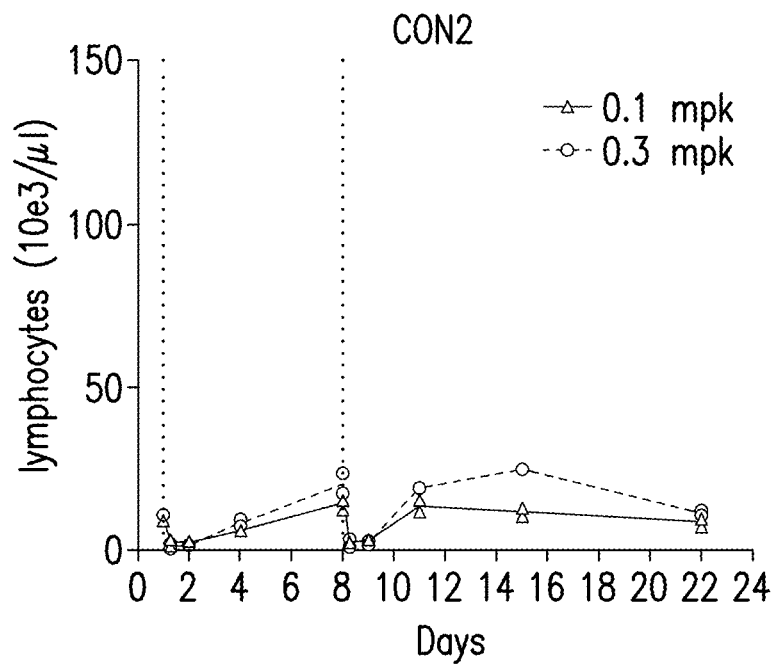
Figure 12D:
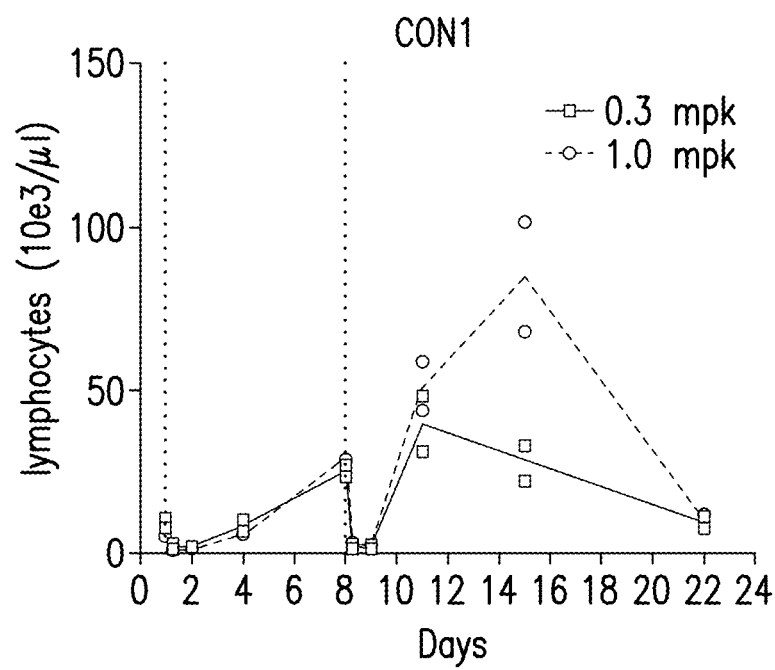

FIG. 12C and FIG. 12D show CON1 or CON2-related changes in total lymphocytes in NHP at the indicated doses. Individual animal data are plotted at indicated time points and the solid and dashed lines represent the average value of two animals whenever available or of a single animal in each group.

Figure 12E:
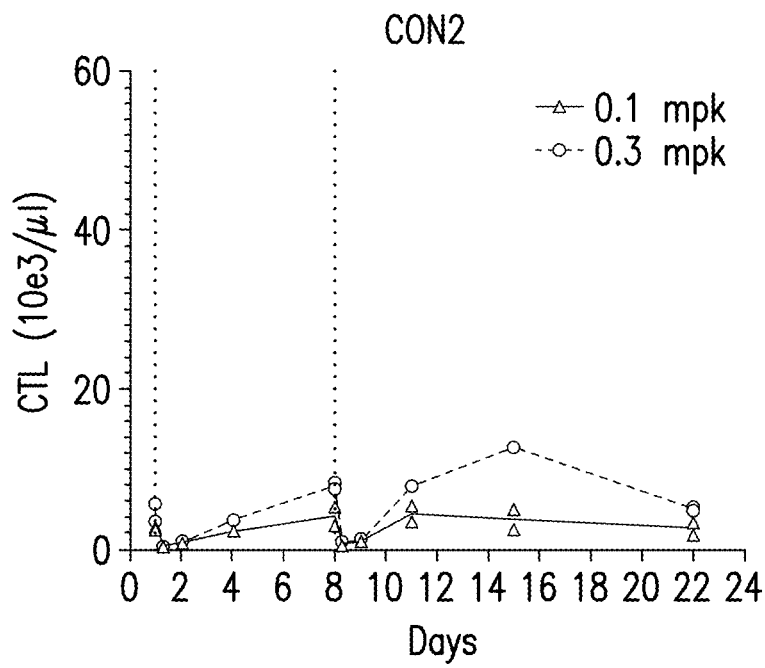
Figure 12F:
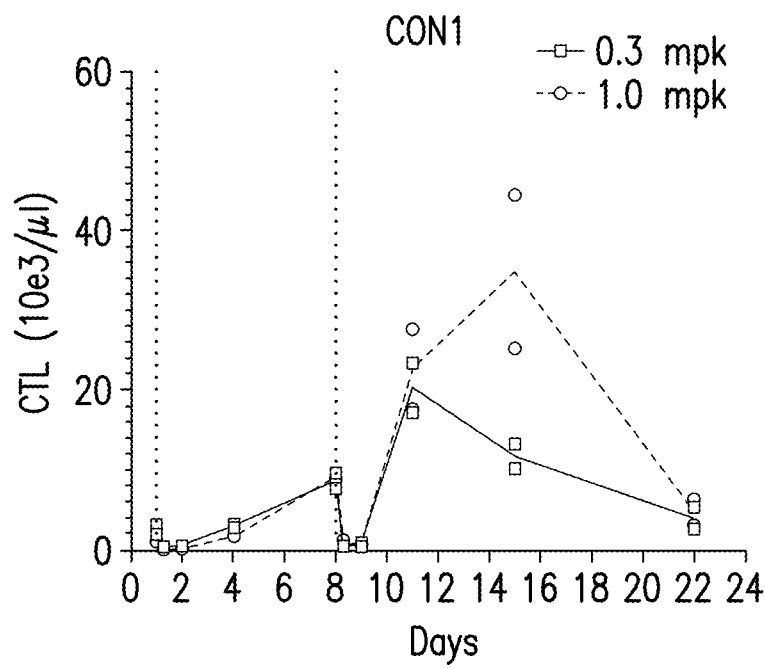

FIG. 12E and FIG. 12F show CON1 or CON2-related changes in FACs based profiling cytotoxic T-cells (CTLs) in NHP at the indicated doses. Individual animal data are plotted at indicated time points and the solid and dashed lines represent the average value of two animals whenever available or of a single animal in each group.

Figure 12G:
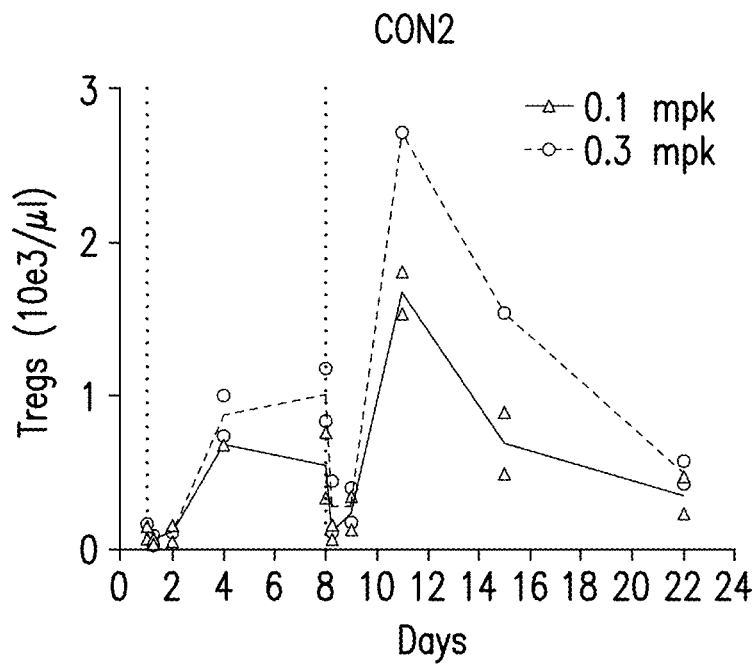
Figure 12H:
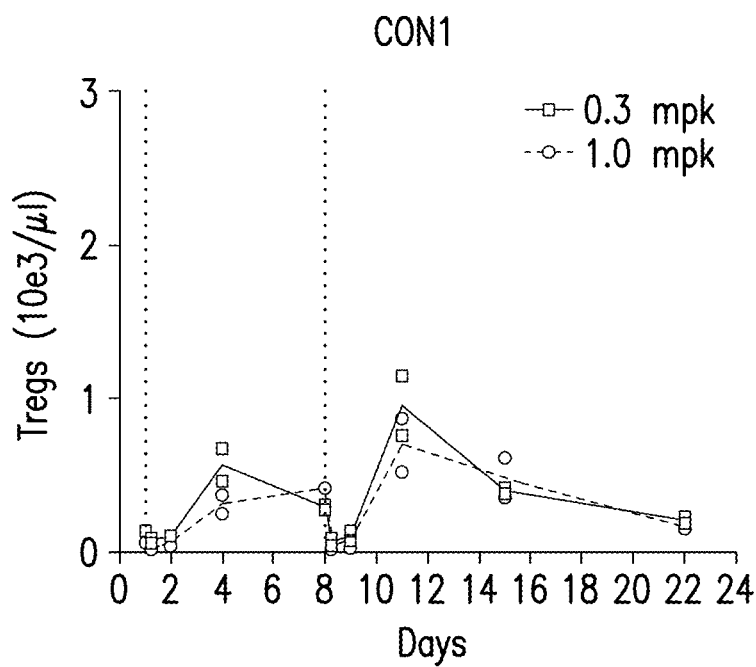

FIG. 12G and FIG. 12H show CON1- and CON2-related changes in FACs based profiling of regulatory T cells ($T_{reg}$ cells) in NHP at the indicated doses following dosing with CON1 or CON2. Individual animal data are plotted at indicated time points and the solid line represents the average value of two animals whenever available or of a single animal in each group.

Figure 12I:
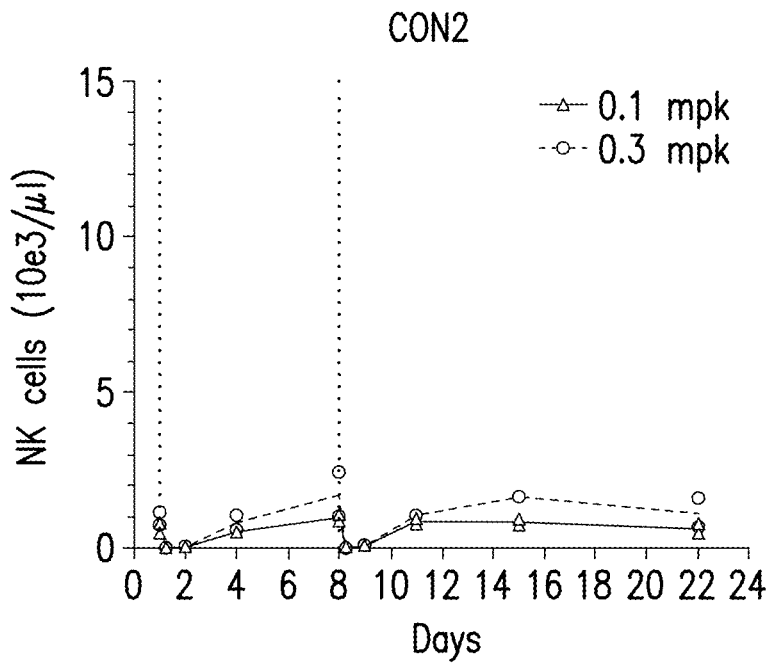
Figure 12J:
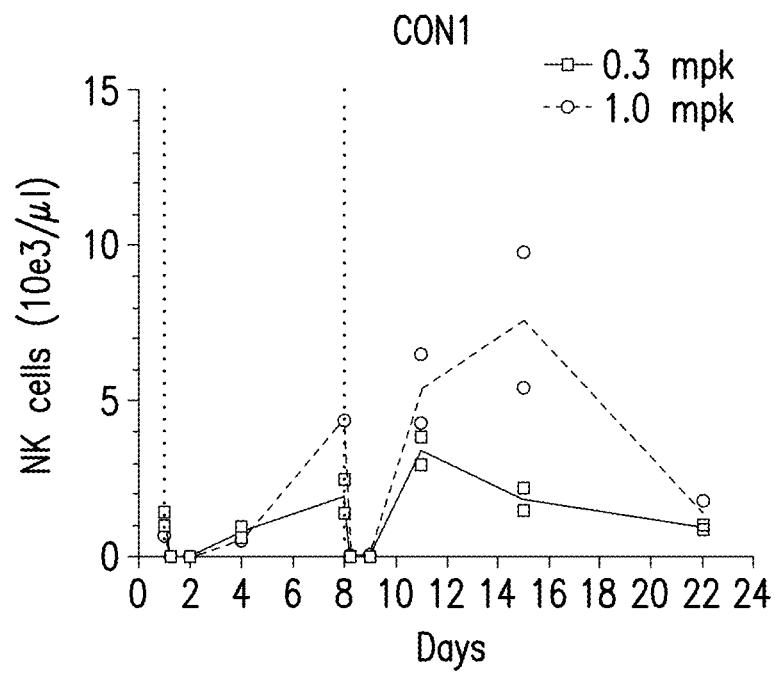

FIG. 12I and FIG. 12J show CON1 or CON2-related changes in FACs based profiling of natural killer cells (NK cells) in NHP at the indicated doses. Individual animal data are plotted at indicated time points and the solid line represents the average value of two animals whenever available or of a single animal in each group.

Figure 13A:
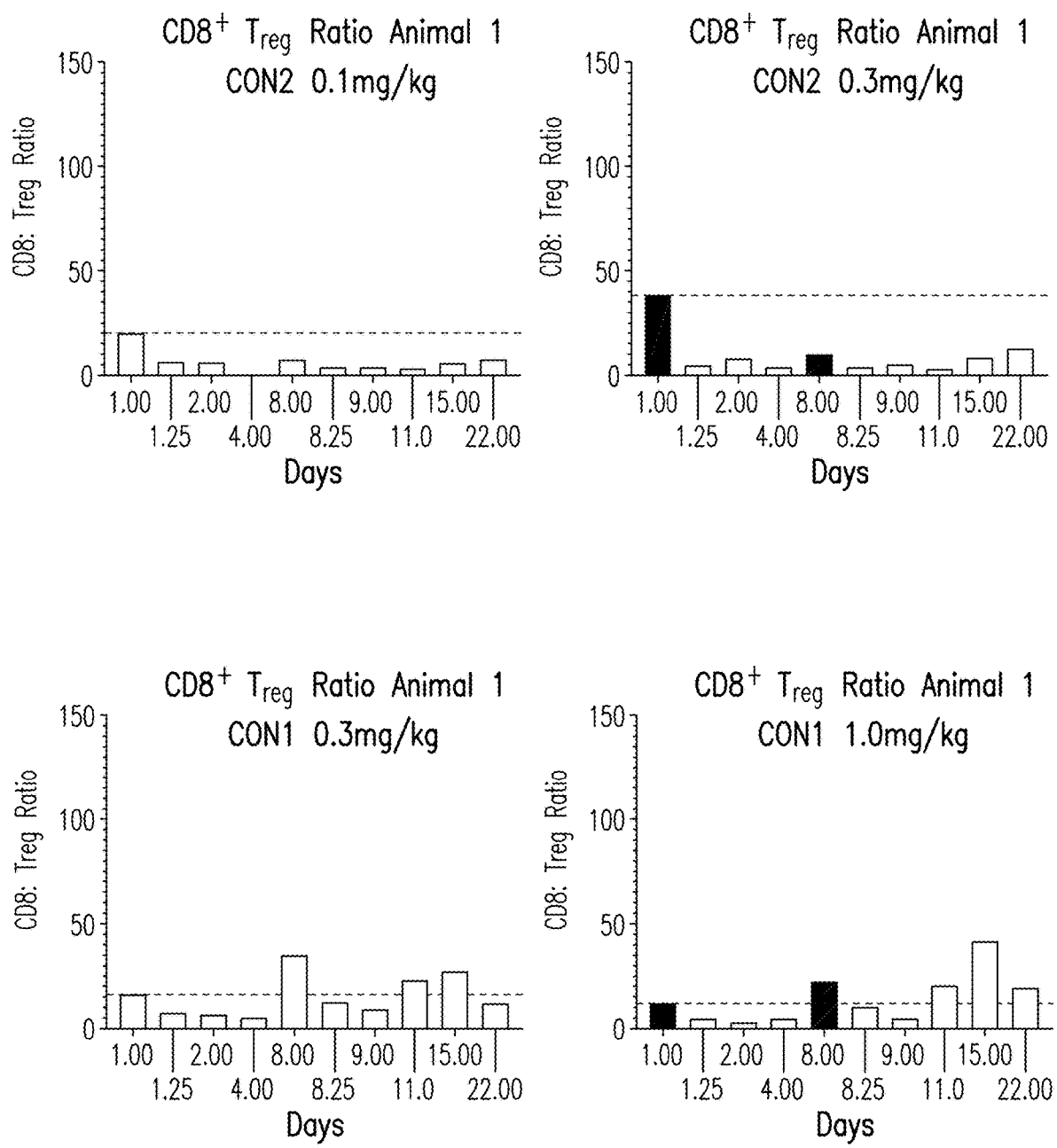

FIG. 13A and FIG. 13B show the CON1- and CON2-related changes in $CD8^+:T_{reg}$ ratios in NHP dosed as described in FIG. 12E through FIG. 12H. Individual animal data at the indicated time points are shown as bar graphs. The dashed line in each graph represents pre-dose levels for each animal.

Figure 14A:
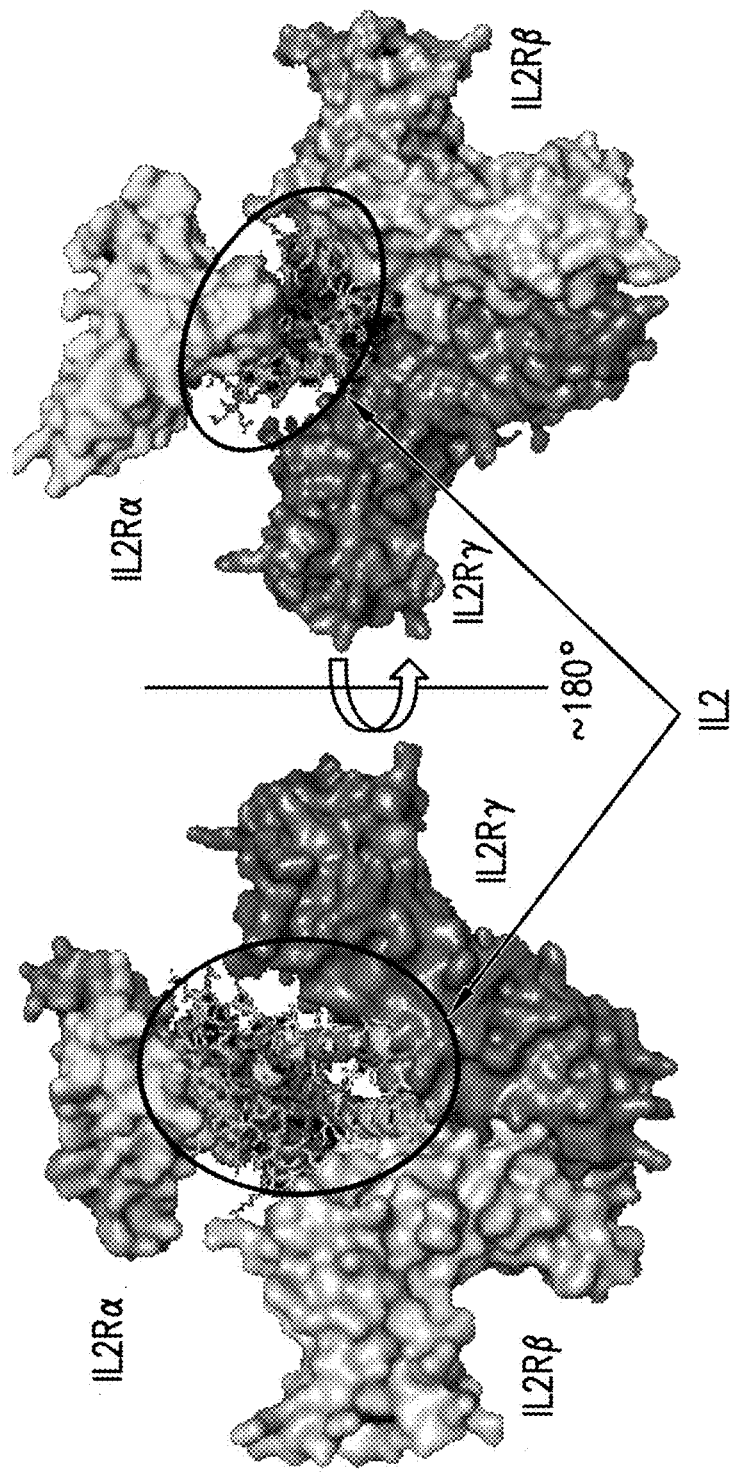

FIG. 14A shows IL-2 (aldesleukin) interaction with the IL-2Rαβγ trimer.

FIG. 14B shows in Panel A native IL-2 R37/F41 residues at the interface with IL-2Rα and highlights their interactions with the IL-2Rα residues. Panel B shows an IL-2 mutant with R37A/F41K substitutions at the interface with IL-2Rα showing the F41K substitution clash with IL-2Rα residues and loss of the R37A substitution electrostatic interaction.

FIG. 15A shows the sequence for mature native human IL-2.

FIG. 15B shows the sequence for mature aldesleukin with amino acid positions determined by number scheme A.

FIG. 15C shows the sequence for mature aldesleukin with amino acid positions determined by number scheme B.

FIG. 15D shows the sequence for mature CON1 with amino acid positions determined by number scheme A.

FIG. 15E shows the sequence for mature CON1 with amino acid positions determined by number scheme B.

Figure 16A:
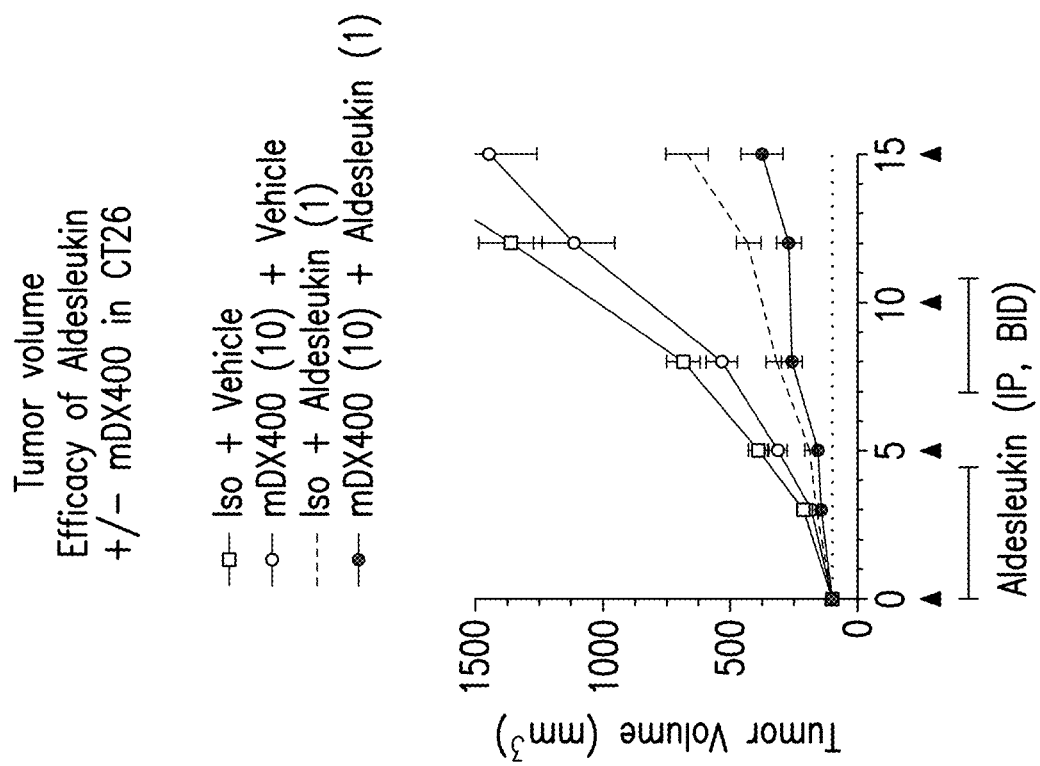

FIG. 16A shows the efficacy of aldesleukin at a 1 mg/kg dose for reducing tumor volume as a monotherapy or combination therapy with mDX400 in the CT26 mouse model.

Figure 16B:
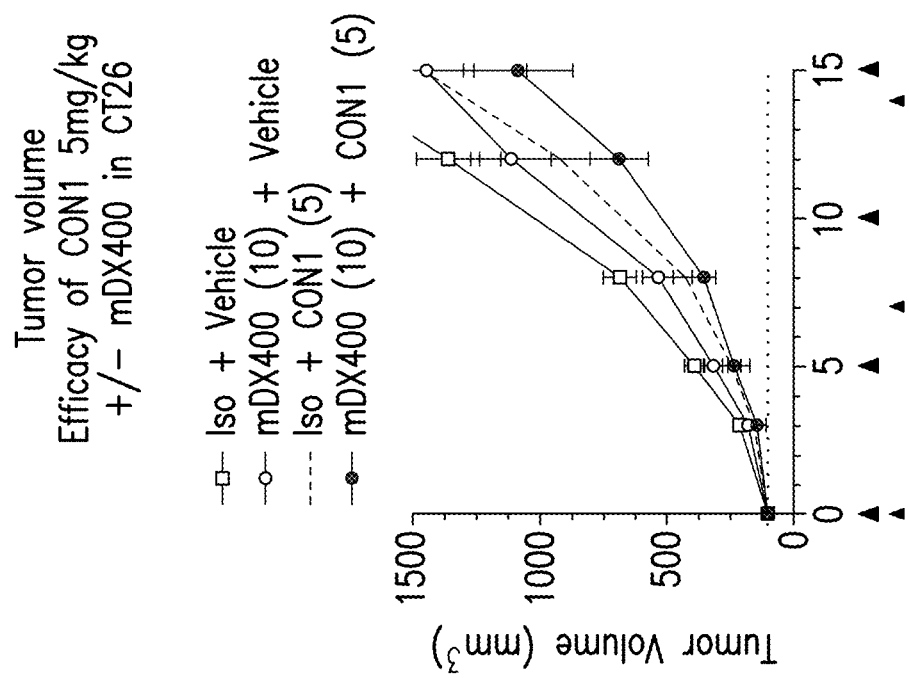

FIG. 16B shows the efficacy of CON1 at a 5 mg/kg dose for reducing tumor volume as a monotherapy or combination therapy with mDX400 in the CT26 mouse model.

Figure 16C:
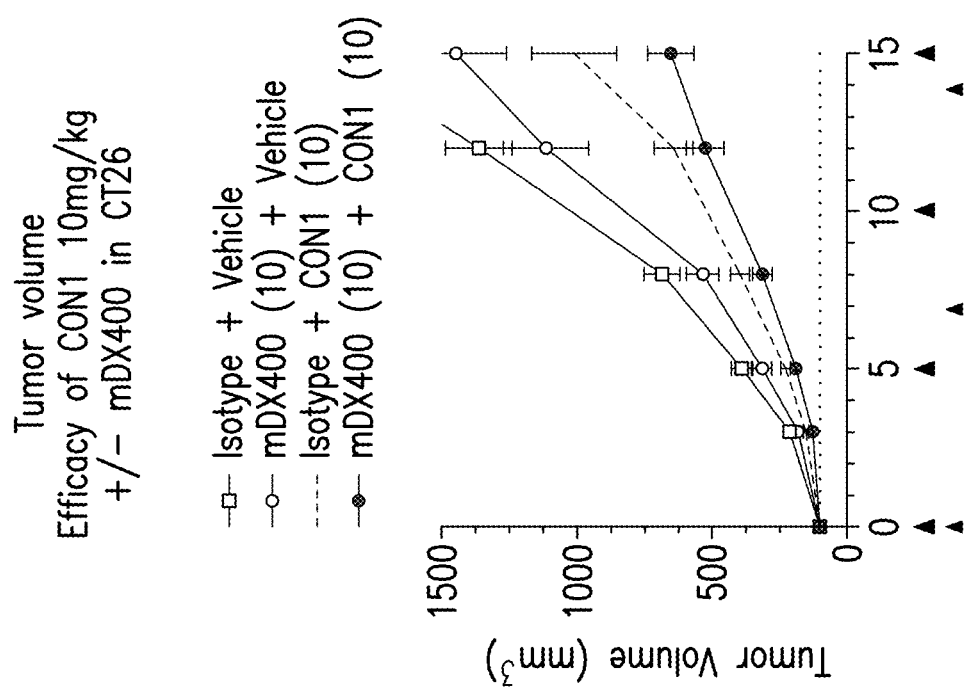

FIG. 16C shows the efficacy of CON1 at a 10 mg/kg dose for reducing tumor volume as a monotherapy or combination therapy with mDX400 in the CT26 mouse model.

Figure 17A:
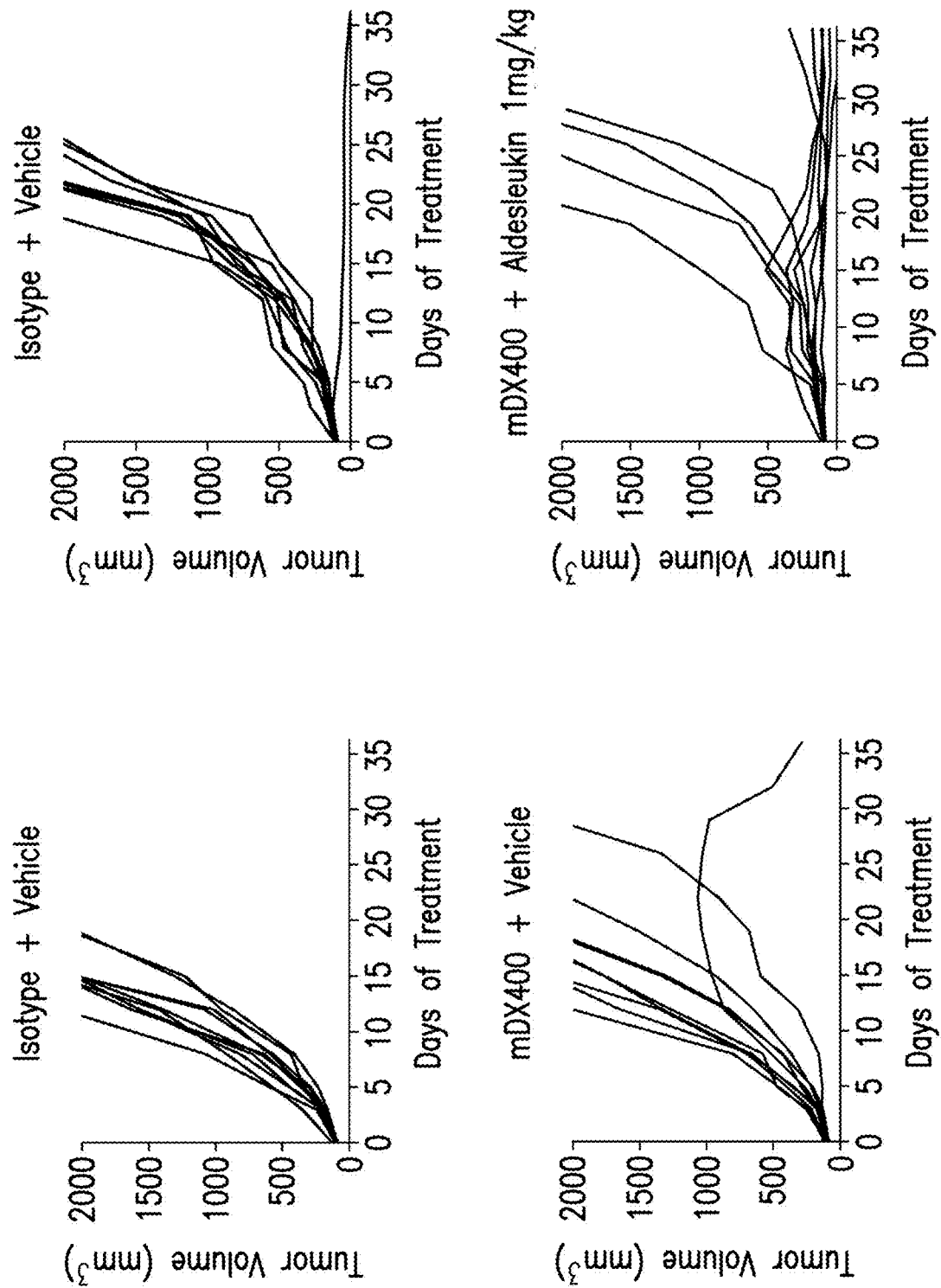

FIG. 17A shows the individual animal tumor volumes for each treatment group shown in FIG. 16A.

Figure 17B:
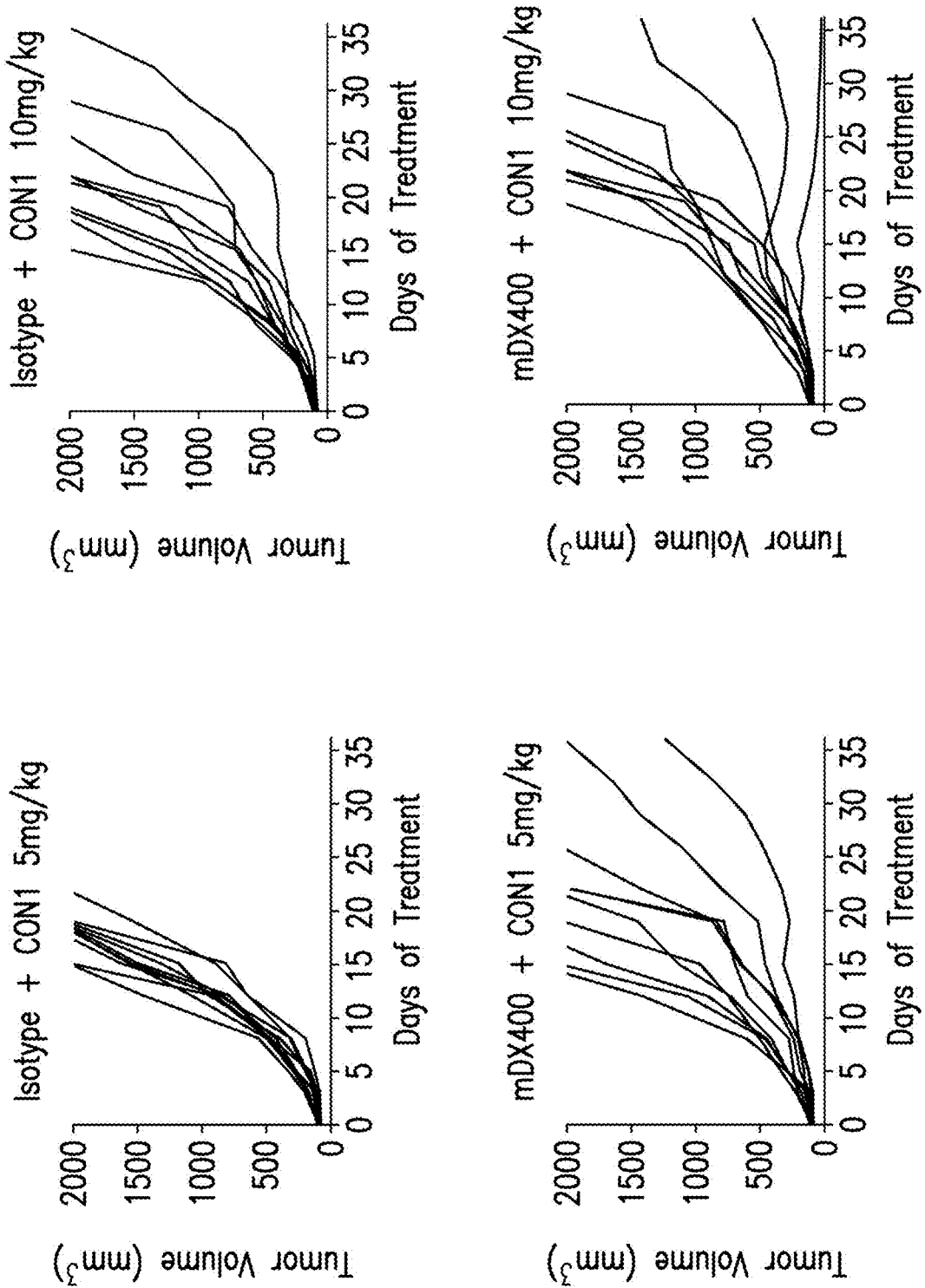

FIG. 17B shows the individual animal tumor volumes for each treatment group shown in FIG. 16B.

Figure 18A:
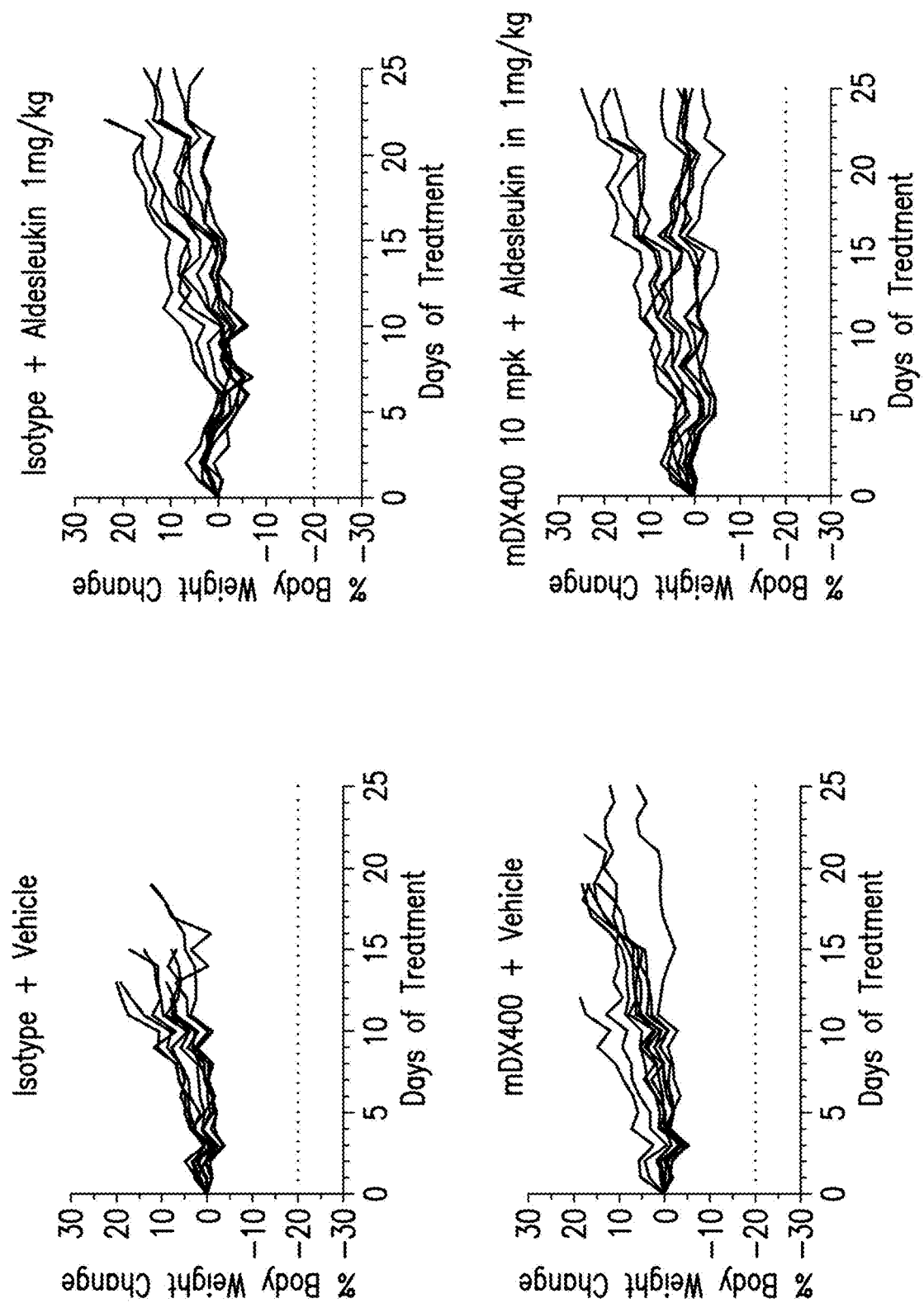

FIG. 18A shows the changes in weight for the individual animals in each treatment group shown in FIG. 16A.

Figure 18B:
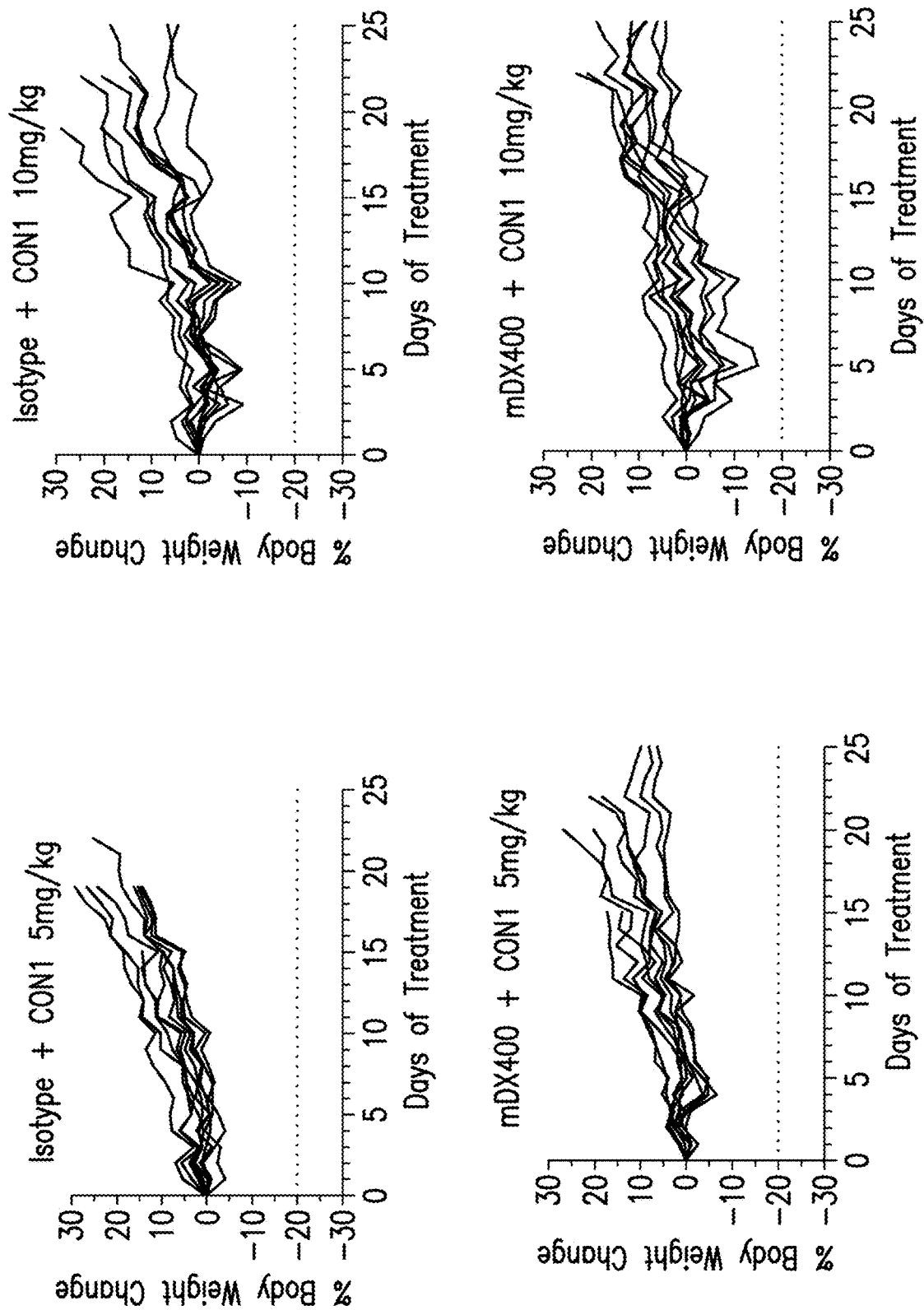

FIG. 18B shows the changes in weight for the individual animals in each treatment group shown in FIG. 16B.

DETAILED DESCRIPTION OF THE INVENTION

Definitions

As used herein, the term "interleukin-2" or "IL-2" as used herein, refers to any wild-type or native IL-2 from any vertebrate source, including mammals such as primates (e.g. humans) and rodents (e.g., mice and rats), unless otherwise indicated. The term encompasses unprocessed IL-2 as well as any mature form of IL-2 that lacks the N-terminal leader signal sequence. The term also encompasses naturally occurring variants of IL-2, e.g. splice variants or allelic variants. The amino acid sequence of mature human IL-2 is shown in SEQ ID NO: 1. Unprocessed human IL-2 additionally comprises an N-terminal 20 amino acid signal peptide, which is absent in the mature human IL-2 molecule. Human mature IL-2 has three cysteine residues, namely, C58, C105, and C125, of which C58 and C105 are linked intramolecularly by a disulfide bond (Tsuji et al., 1987, J. Biochem. 26: 129-134). Recombinant mature human IL-2 with a deletion of the N-terminal alanine residue (desAla1 or desA1) and a substitution of serine for the cysteine at position 125 (C125S substitution) and expressed in $E.\ coli$ has been found to be biologically active after in vitro refolding (Wang et al., 1984, Science, 224: 1431-1433; Yun et al., 1988, Kor. J. Biochem. 22: 120-126). This molecule has the nonproprietary name of aldesleukin.

In the art there are two schemes for numbering the amino acid positions in desA1 IL-2 molecules as illustrated in FIGS. 15A-15D. In numbering scheme A, the amino acids in desA1 IL-2 molecules are numbered beginning with number 1 for the penultimate amino acid at the N-terminus (FIGS. 15B, 15C, and 15D). In numbering scheme B, the amino acids in desA1 IL-2 molecules are numbered according to the amino acid sequence of native mature IL-2, thus beginning with number 2 for the penultimate amino acid at the N-terminus (FIG. 15E).

As used herein, amino acid positions may be denoted as follows: Amino acid followed immediately by Position Number; e.g., Trp26 or W26. Where there is a substitution made, the substituted amino acid follows the Position Number; e.g., Trp26Cys or W26C. Trp26Cys or W26C in this non-limiting example denotes that the amino acid Tryptophan (Trp or W) at position 26 is changed to a Cysteine (Cys or C).

As used herein, the term "IL-2 mutant" or "mutant IL-2 polypeptide" or "mutant IL-2" as used herein refers to an IL-2 polypeptide, either native human IL-2 or desAla1, C125S IL-2 (e.g., aldesleukin) either of which has at least one amino acid substitution with a natural amino acid that affects or inhibits the interaction of IL-2 with CD25. IL-2 mutant polypeptides may further include a C125S or A substitution. The IL-2 mutant may be full-length, i.e., has an N-terminal alanine residue and truncated, i.e., lacks the N-terminal alanine. Unless otherwise indicated, an IL-2 mutant may be referred to herein as an IL-2 mutant peptide sequence, an IL-2 mutant polypeptide, IL-2 mutant protein or IL-2 mutant analog.

As used herein, the term "IL-2 moiety," refers to an IL-2 mutant or a desAla1, C125S IL-2 (e.g., aldesleukin), either of which has human IL-2 activity and at least one non-natural amino acid having a functional group, e.g. an electrophilic group or a nucleophilic group, suitable for reaction with a reactive group of a nonpeptidic, water-soluble polymer. As will be explained in further detail below, one of ordinary skill in the art can determine whether any given IL-2 moiety has IL-2 activity.

As used herein, the term "IL-2 conjugate" refers to an IL-2 moiety conjugated to a nonpeptidic, water-soluble polymer. The IL-2 moiety can be directly linked to the reactive group of, or within, the nonpeptidic, water-soluble polymer via a covalent bond, or the IL-2 moiety can be indirectly linked to the nonpeptidic, water-soluble polymer via the functional group of a linker linked to the nonpeptidic, water-soluble polymer.

As used herein, the term "PEG," "polyethylene glycol" and "poly(ethylene glycol)" as used herein, are interchangeable and encompass any nonpeptidic, water-soluble poly (ethylene oxide). Typically, PEGs for use in accordance with the invention comprise the following formula "—$(OCH_2CH_2)_n$—" where (n) is 2 to 4000. As used herein, PEG also includes "—$CH_2CH_2$— $O(CH_2CH_2O)_n$— $CH_2CH_2$—" and "—$(OCH_2CH_2)_nO$—," depending upon whether or not the terminal oxygens have been displaced, e.g., during a synthetic transformation. Throughout the specification and claims, it should be remembered that the term "PEG" includes structures having various terminal or "end capping" groups and so forth. The term "PEG" also means a polymer that contains a majority, that is to say, greater than 50%, of —$OCH_2CH_2$— repeating subunits. With respect to specific forms, the PEG can take any number of a variety of molecular weights, as well as structures or geometries such as "branched," "linear," "forked," "multi-functional," and the like, to be described in greater detail below.

As used herein, the term "water-soluble" as in a "nonpeptidic water-soluble polymer" polymer is any nonpeptidic polymer that is soluble in water at room temperature. Typically, a water-soluble polymer will transmit at least about 75%, more preferably at least about 95%, of light transmitted by the same solution after filtering. On a weight basis, a water-soluble polymer will preferably beat least about 35% (by weight) soluble in water, more preferably at least about 50% (by weight) soluble in water, still more preferably about 70% (by weight) soluble in water, and still more preferably about 85% (by weight) soluble in water. It is most preferred, however, that the water-soluble polymer is about 95% (by weight) soluble in water or completely soluble in water.

Molecular weight in the context of a nonpeptidic, water-soluble polymer, such as PEG, can be expressed as either a number average molecular weight or a weight average molecular weight. Unless otherwise indicated, all references to molecular weight herein refer to the weight average molecular weight. Both molecular weight determinations, number average and weight average, can be measured using gel permeation chromatography or other liquid chromatography techniques.

Other methods for measuring molecular weight values can also be used, such as the use of end-group analysis or the measurement of colligative properties (e.g., freezing-point depression, boiling-point elevation, or osmotic pressure) to determine number average molecular weight or the use of light scattering techniques, ultracentrifugation or viscometry to determine weight average molecular weight. The polymers of the invention are typically polydisperse (i.e., number average molecular weight and weight average molecular weight of the polymers are not equal), possessing low polydispersity values of preferably less than about 1.2, more preferably less than about 1.15, still more preferably less than about 1.10, yet still more preferably less than about 1.05, and most preferably less than about 1.03.

As used herein, the term "active," "reactive" or "activated" when used in conjunction with a particular functional group or reactive group, refers to a reactive functional or reactive group that reacts readily with an electrophile or a nucleophile on another molecule. This is in contrast to those groups that require strong catalysts or highly impractical reaction conditions in order to react (i.e., a "non-reactive" or "inert" group). As used herein, a reactive group interacts with a functional group to form a covalent linkage between the two.

As used herein, the term "functional group" or "reactive group" any synonym thereof is meant to encompass protected forms thereof as well as unprotected forms.

As used herein, the term "linker" refers to a molecular moiety that is capable of forming at least two covalent bonds between a reactive group and a nonpeptidic, water-soluble polymer.

As used herein, the term "hydrolytically stable" linkage or bond refers to a chemical bond, typically a covalent bond, which is substantially stable in water, that is to say, does not undergo hydrolysis under physiological conditions to any appreciable extent over an extended period of time. Examples of hydrolytically stable linkages include, but are not limited to, the following: carbon-carbon bonds (e.g., in aliphatic chains), ethers, amides, urethanes, triazole, and the like. Generally, a hydrolytically stable linkage is one that exhibits a rate of hydrolysis of less than about 1-2% per day under physiological conditions. Hydrolysis rates of representative chemical bonds can be found in most standard chemistry textbooks.

As used herein, the term "amino acid" refers to the twenty common naturally occurring amino acids. Naturally occurring amino acids include alanine (Ala; A), arginine (Arg; R), asparagine (Asn; N), aspartic acid (Asp; D), cysteine (Cys; C); glutamic acid (Glu; E), glutamine (Gln; Q), glycine (Gly; G); histidine (His; H), isoleucine (Ile; I), leucine (Leu; L), lysine (Lys; K), methionine (Met; M), phenylalanine (Phe; F), praline (Pro; P), serine (Ser; S), threonine (Thr; T), tryptophan (Trp; W), tyrosine (Tyr; Y), and valine (Val; V).

Naturally encoded amino acids are the proteinogenic amino acids known to those of skill in the art. They include the 20 common amino acids (alanine, arginine, asparagine, aspartic acid, cysteine, glutamine, glutamic acid, glycine, histidine, isoleucine, leucine, lysine, methionine, phenylalanine, praline, serine, threonine, tryptophan, tyrosine, and valine) and the less common pyrrolysine and selenocysteine. Naturally encoded amino acids include post-translational variants of the 22 naturally occurring amino acids such as prenylated amino acids, isoprenylated amino acids, myrisoylated amino acids, palmitoylated amino acids, N-linked glycosylated amino acids, O-linked glycosylated amino acids, phosphorylated amino acids and acylated amino acids.

As used herein, the term "non-natural amino acid" or "NNAA" or "unnatural amino acid" or "UAA" all refer to an amino acid that is not a proteinogenic amino acid, or a post-translationally modified variant thereof. In particular, the term refers to an amino acid that is not one of the 20 common amino acids or pyrrolysine or selenocysteine, or post-translationally modified variants thereof. Examples of non-natural amino acids include but are not limited to p-azidomethyl-L-phenylalanine, p-azido-L-phenylalanine, p-acetyl-L-phenylalanine, N6-azidoethoxy-L-lysine, N6-propargylethoxy-L-lysine (PraK), BCN-L-lysine, norbornene lysine, TCO-lysine, methyltetrazine lysine, allyloxycarbonyllysine, 2-amino-8-oxononanoic acid, O-methyl-L-tyrosine, L-3-(2-naphthyl)alanine, 3-methylphenylalanine, O-4-allyl-L-tyrosine, 4-propyl-L-tyrosine, tri-O-acetyl-GlcNAc-serine, L-Dopa, fluorinated phenylalanine, isopropyl-L-phenylalanine, p-benzoyl-L-phenylalanine, L-phosphoserine, phosphonoserine, phosphonotyrosine, p-iodo-phenylalanine, p-bromophenylalanine, p-amino-L-phenylalanine, isopropyl-L-phenylalanine, p-propargyloxy-phenylalanine, 2-amino-3-((2-((3-(benzyloxy)-3-oxopropyl)amino)ethyl)selanyl)propanoic acid, 2-amino-3-(phenyl selanyl)propanoic, selenocysteine, m-acetylphenylalanine, and p-propargyloxyphenylalanine.

As used herein, the term "orthogonal" refers to a molecule (e.g., an orthogonal tRNA (O-tRNA) and/or an orthogonal aminoacyl tRNA synthetase (O—RS)) that functions with endogenous components of a cell with reduced efficiency as compared to a corresponding molecule that is endogenous to the cell or translation system, or that fails to function with endogenous components of the cell. In the context of tRNAs and aminoacyl-tRNA synthetases, orthogonal refers to an inability or reduced efficiency, e.g., less than 20% efficient, less than 10% efficient, less than 5% efficient, or less than 1% efficient, of an orthogonal tRNA to function with an endogenous tRNA synthetase compared to an endogenous tRNA to function with the endogenous tRNA synthetase, or of an orthogonal aminoacyl-tRNA synthetase to function with an endogenous tRNA compared to an endogenous tRNA synthetase to function with the endogenous tRNA. The orthogonal molecule lacks a functional endogenous complementary molecule in the cell. For example, an orthogonal tRNA in a cell is aminoacylated by any endogenous RS of the cell with reduced or even zero efficiency, when compared to aminoacylation of an endogenous tRNA by the endogenous RS. In another example, an orthogonal RS aminoacylates any endogenous tRNA in a cell of interest with reduced or even zero efficiency, as compared to aminoacylation of the endogenous tRNA by an endogenous RS. A second orthogonal molecule can be introduced into the cell that functions with the first orthogonal molecule. For example, an orthogonal tRNA/RS pair includes introduced complementary components that function together in the cell with an efficiency (e.g., 50% efficiency, 60% efficiency, 70% efficiency, 75% efficiency, 80% efficiency, 90% efficiency, 95% efficiency, or 99% or more efficiency) to that of a corresponding tRNA/RS endogenous pair.

As used herein, the term "complementary" refers to components of an orthogonal pair, O-tRNA and O—RS that can function together, e.g., the O—RS aminoacylates the O-tRNA.

As used herein, the term "translation system" refers to the collective set of components that incorporate a naturally occurring amino acid into a growing polypeptide chain (protein). Components of a translation system can include, e.g., ribosomes, tRNAs, synthetases, mRNA, amino acids, and the like. The components for an orthogonal translation system include for example O—RS, O-tRNAs, non-natural amino acids, etc.), which can be added to an in vitro or in vivo translation system, e.g., cell-free, a eukaryotic cell, e.g., a yeast cell, a mammalian cell, a plant cell, an algae cell, a fungus cell, an insect cell, and/or the like.

As used herein, "combination therapy" refers to treatment of a human or animal individual comprising administering a first therapeutic agent and a second therapeutic agent consecutively or concurrently to the individual. In general, the first and second therapeutic agents are administered to the individual separately and not as a mixture; however, there may be embodiments where the first and second therapeutic agents are mixed prior to administration.

As used herein, "combination product" is defined as in 21 CFR 3.2(e) and includes:

1. A product comprised of two or more regulated components, i.e., drug/device, biologic/device, drug/biologic, or drug/device/biologic, that are physically, chemically, or otherwise combined or mixed and produced as a single entity;
2. Two or more separate products packaged together in a single package or as a unit and comprised of drug and device products, device and biological products, or biological and drug products;
3. A drug, device, or biological product packaged separately that according to its investigational plan or proposed labeling is intended for use only with an approved individually specified drug, device, or biological product where both are required to achieve the intended use, indication, or effect and where upon approval of the proposed product the labeling of the approved product would need to be changed, e.g., to reflect a change in intended use, dosage form, strength, route of administration, or significant change in dose; or
4. Any investigational drug, device, or biological product packaged separately that according to its proposed labeling is for use only with another individually specified investigational drug, device, or biological product where both are required to achieve the intended use, indication, or effect.

For example, an IL-2 conjugate of the present invention and a medical delivery device for administering the therapeutic agent is a combination product.

As used herein, the term "medical delivery device" or "device" or "medication delivery device" are used interchangeably and has the definition set forth in Section 201(h) of the Food, Drug, and Cosmetic Act, which defines a device as an instrument, apparatus, implement, machine, contrivance, implant, in vitro reagent, or other similar or related article, including a component part, or accessory which is: (i) recognized in the official National Formulary, or the United States Pharmacopoeia, or any supplement to them, (ii) intended for use in the diagnosis of disease or other conditions, or in the cure, mitigation, treatment, or prevention of disease, in man or other animals, or (iii) intended to affect the structure or any function of the body of man or other animals, and which does not achieve its primary intended purposes through chemical action within or on the body of man or other animals and which does not achieve its primary intended purposes through chemical action within or on the body of man or other animals and which is not dependent upon being metabolized for the achievement of its primary intended purposes. The term "device" does not include software functions excluded pursuant to section 520(o). Examples of devices include medical pens and autoinjectors.

As used herein, the term "treating" or "treatment" of any disease or disorder refers, in certain embodiments, to ameliorating a disease or disorder that exists in a subject. In another embodiment, "treating" or "treatment" includes ameliorating at least one physical parameter, which may be indiscernible by the subject. In yet another embodiment, "treating" or "treatment" includes modulating the disease or disorder, either physically (e.g., stabilization of a discernible symptom) or physiologically (e.g., stabilization of a physical parameter) or both. In yet another embodiment, "treating" or "treatment" includes delaying or preventing the onset of the disease or disorder.

As used herein, the term "therapeutically effective amount" or "effective amount" refers to an amount of a protein or composition that when administered to a subject is effective to treat a disease or disorder. In some embodiments, a therapeutically effective amount or effective amount refers to an amount of a protein or composition that when administered to a subject is effective to prevent or ameliorate a disease, the progression of the disease, or result in amelioration of symptoms.

As used herein, the term "substantially similar" or "substantially the same," as used herein, denotes a sufficiently high degree of similarity between two or more numeric values, for example, receptor binding affinity, $EC_{50}$, etc., such that one of skill in the art would consider the difference between the two or more values to be of little or no biological and/or statistical significance within the context of the biological characteristic measured by said value. In some embodiments, the two or more substantially similar values may be within 5% to 100% of each other.

As used herein, the term "at or near the N-terminus" with respect to IL-2 refers to an amino acid at the N-terminus of the IL-2 or a position within the first 10 amino acids comprising the IL-2.

As used herein, the term "N-terminal region" with respect to IL-2 refers to an amino acid at the N-terminus of the IL-2 or a position within the first 20 or 30 amino acids comprising the IL-2.

Interleukin Conjugates

The present invention provides herein interleukin 2 (IL-2) polypeptides having at least one or more amino acid substitutions that bias binding to the IL-2 receptor $\beta\gamma_c$ dimer (IL-2R$\beta\gamma_c$) over the IL-2 receptor $\alpha\beta\gamma_c$ trimer (IL-2R$\alpha\beta\gamma_c$), a non-natural amino acid at or near the N-terminus of the IL-2 polypeptide conjugated to a nonpeptidic, water-soluble polymer or an insertion of a non-natural amino acid conjugated to a nonpeptidic, water-soluble polymer at or near the N-terminus of the IL-2 polypeptide, and an amino acid sequence with at least 80% to 95% identity otherwise to the amino acid sequence wild-type or native human IL-2. These IL-2 conjugates have no detectable binding to the IL-2R$\alpha$ while maintaining binding to the IL-2R$\beta\gamma_c$ at a level similar to that of native IL-2 as determined by SPR assay. Furthermore, these IL-2 conjugates polypeptides have reduced toxicity compared to compared to commercially available IL-2 polypeptides and a plasma half-life of at least five times that of commercially available IL-2 polypeptides.

The present invention provides IL-2 moieties comprising a NNAA as disclosed herein suitable for conjugating to any nonpeptidic, water-soluble polymer as disclosed herein to provide an IL-2 conjugate as disclosed herein. Exemplary IL-2 moieties include the following embodiments, wherein in each embodiment the NNAA therein has or includes a functional group capable of forming a covalent bond with a reactive group within or linked to a nonpeptidic, water-soluble polymer.

The present invention provides an IL-2 moiety comprising or consisting of the amino acid sequence (SEQ ID NO: 42)
XXXXXXXXXXQLQLEHLLLDLQMILNGINNYKNPXLXXMLXXXFXMPKKA

TELKHLQCLEXXLXXLEXVLNXAQSKNFHLRPRDLISNINVIVLELKGSE

TTFMCEXADETATIVEFLNRWITFXQSIISTLT wherein X1 is A, another amino acid, NNAA, or absent; X2 is P, another amino acid, or NNAA; X3 is T, another amino acid, or NNAA; X4 is S, another amino acid, or NNAA; X5 is S, another amino acid, or NNAA; X6 is S, another amino acid, or NNAA; X7 is T, another amino acid, or NNAA; X8 is K, another amino acid, or NNAA; X9 is K, another amino acid, or NNAA; X10 is T, another amino acid, or NNAA; X35 is K or another amino acid; X37 is T or another amino acid; X38 is R or another amino acid; X41 is T or another amino acid; X42 is F or another amino acid; X43 is K or another amino acid; X45 is Y or another amino acid; X61 is E or another amino acid; X62 is E or another amino acid; X64 is K or another amino acid; X65 is P or another amino acid; X68 is E or another amino acid; X72 is L or another amino acid; X107 is Y or another amino acid; X125 is C or another amino acid; with the proviso that (i) X1-X10 comprises only one NNAA and (ii) at least one of the amino acids at positions 35, 37, 38, 41, 42, 43, 45, 61, 62, 64, 65, 68, 72, and 107 is not the amino acid at the corresponding position in the amino acid sequence of SEQ ID NO: 1. In particular embodiments, amino acid X125 is any amino acid other than C, which in a further embodiment may be amino acid A or S.

In further embodiments of the amino acid sequence set forth in SEQ ID NO: 42, at least two of the amino acids selected from positions 35, 37, 38, 41, 42, 43, 45, 61, 62, 64, 65, 68, 72, and 107 are not the amino acid at their corresponding amino acid positions in the amino acid sequence of SEQ ID NO: 1. In further embodiments of the amino acid sequence set forth in SEQ ID NO: 42, at least two of the amino acids selected from positions 35, 37, 38, 41, 42, 43, 45, 61, 62, 64, 65, 68, 72, and 107 are not the amino acid at their corresponding positions in the amino acid sequence of SEQ ID NO: 1 and amino acid X125 is any amino acid other than C, which in a further embodiment may be amino acid A or S. In further embodiments of the above amino acid sequence of SEQ ID NO: 42, NNAA is conjugated to a nonpeptidic, water-soluble polymer. In particular embodiments, the NNAA is para-azidomethylphenylalanine. In further embodiments, the nonpeptidic, water-soluble polymer is polyethylene glycol (PEG).

In a further embodiment, provided is an IL-2 moiety comprising or consisting of (SEQ ID NO: 43)
XXXXXXXXXQLQLEHLLLDLQMILNGINNYKNPXLXXMLXXXFXMPKKAT

ELKHLQCLEXXLXXLEXVLNXAQSKNFHLRPRDLISNINVIVLELKGSET

TFMCEXADETATIVEFLNRWITFXQSIISTLT wherein X1 is P, another amino acid, or NNAA; X2 is T, another amino acid, or NNAA; X3 is S, another amino acid, or NNAA; X4 is S, another amino acid, or NNAA; X5 is S, another amino acid, or NNAA; X6 is T, another amino acid, or NNAA; X7 is K, another amino acid, or NNAA; X8 is K, another amino acid, or NNAA; X9 is T, another amino acid, or NNAA; X34 is K or another amino acid; X36 is T or another amino acid; X37 is R or another amino acid; X40 is T or another amino acid; X41 is F or another amino acid; X42 is K or another amino acid; X44 is Y or another amino acid; X60 is E or another amino acid; X61 is E or another amino acid; X63 is K or another amino acid; X64 is P or another amino acid; X67 is E or another amino acid; X71 is L or another amino acid; X106 is Y or another amino acid; and X124 is C or another amino acid; with the proviso that (i) X1-X9 comprises only one NNAA and (ii) at least one of the amino acids at positions 34, 36, 37, 40, 41, 42, 44, 60, 61, 63, 64, 67, 71, and 106 is not the amino acid at the corresponding position the amino acid sequence of SEQ ID NO: 2. In particular embodiments, amino acid X124 is any amino acid other than C, which in a further embodiment may be amino acid A or S.

In further embodiments of the amino acid sequence set forth in SEQ ID NO: 43, at least two of the amino acids selected from positions 34, 36, 37, 40, 41, 42, 44, 60, 61, 63, 64, 67, 71, and 106 are not the amino acid at their corresponding amino acid positions in the amino acid sequence of SEQ ID NO: 2. In further embodiments of the amino acid sequence set forth in SEQ ID NO: 43, at least two of the amino acids selected from positions 34, 36, 37, 40, 41, 42, 44, 60, 61, 63, 64, 67, 71, and 106 are not the amino acid at their corresponding positions in the amino acid sequence of SEQ ID NO: 2 and amino acid X124 is any amino acid other than C, which in a further embodiment may be amino acid A or S. In further embodiments of the above amino acid sequence of SEQ ID NO: 43, NNAA is conjugated to a nonpeptidic, water-soluble polymer. In particular embodiments, the NNAA is para-azidomethylphenylalanine. In further embodiments, the nonpeptidic, water-soluble polymer is PEG.

In a further embodiment, provided is an IL-2 moiety comprising or consisting of (SEQ ID NO: 44)
PTSXSTKKTQLQLEHLLLDLQMILNGINNYKNPXLXXMLXXXFXMPKKAT

ELKHLQCLEXXLXXLEXVLNXAQSKNFHLRPRDLISNINVIVLELKGSET

TFMCEXADETATIVEFLNRWITFXQSIISTLT wherein X4 is a NNAA conjugated to a nonpeptidic, water-soluble polymer; X34 is K or another amino acid; X36 is T or another amino acid; X37 is R or another amino acid; X40 is T or another amino acid; X41 is F or another amino acid; X42 is K or another amino acid; X44 is Y or another amino acid; X60 is E or another amino acid; X61 is E or another amino acid; X63 is K or another amino acid; X64 is P or another amino acid; X67 is E or another amino acid; X71 is L or another amino acid; X106 is Y or another amino acid; and X124 is C or another amino acid; with the proviso that at least one of the amino acids at positions 34, 36, 37, 40, 41, 42, 44, 60, 61, 63, 64, 67, 71, and 106 is not the amino acid at the corresponding position in the amino acid sequence of SEQ ID NO: 2. In particular embodiments, amino acid X124 is any amino acid other than C, which in a further embodiment may be amino acid A or S.

In further embodiments of the amino acid sequence set forth in SEQ ID NO: 44, at least two of the amino acids selected from positions 34, 36, 37, 40, 41, 42, 44, 60, 61, 63, 64, 67, 71, and 106 are not the amino acid at their corresponding amino acid positions in the amino acid sequence of SEQ ID NO: 2. In further embodiments of the amino acid sequence set forth in SEQ ID NO: 42, at least two of the amino acids selected from positions 34, 36, 37, 40, 41, 42, 44, 60, 61, 63, 64, 67, 71, and 106 are not the amino acid at their corresponding positions in the amino acid sequence of SEQ ID NO: 2 and amino acid X124 is any amino acid other than C, which in a further embodiment may be amino acid A or S. In particular embodiments, the NNAA is para-azidomethylphenylalanine. In further embodiments, the nonpeptidic, water-soluble polymer is PEG.

In a further embodiment, provided is an IL-2 moiety comprising or consisting of (SEQ ID NO: 45)
PTSXSTKKTQLQLEHLLLDLQMILNGINNYKNPKLTXMLTXKFYMPKKAT

ELKHLQCLEEELKPLEEVLNLAQSKNFHLRPRDLISNINVIVLELKGSET

TFMCEYADETATIVEFLNRWITFXQSIISTLT wherein X4 is a NNAA; X37 any amino acid except R; X41 is any amino acid except F; and X124 is any amino acid except C.

In a further embodiment, provided is an IL-2 moiety comprising or consisting of (SEQ ID NO: 46)
APTSXSTKKTQLQLEHLLLDLQMILNGINNYKNPKLTXMLTXKFYMPKKA

TELKHLQCLEEELKPLEEVLNLAQSKNFHLRPRDLISNINVIVLELKGSE

TTFMCEYADETATIVEFLNRWITFXQSIISTLT wherein X5 is a NNAA; X38 any amino acid except R; X42 is any amino acid except F; and X125 is any amino acid except C.

In a further embodiment, provided is an IL-2 moiety comprising or consisting of (SEQ ID NO: 47)
PTSXSTKKTQLQLEHLLLDLQMILNGINNYKNPKLTAMLTKKFYMPKKAT

ELKHLQCLEEELKPLEEVLNLAQSKNFHLRPRDLISNINVIVLELKGSET

TFMCEYADETATIVEFLNRWITFXQSIISTLT wherein X4 is a NNAA and X124 is A or S.

In a further embodiment, provided is an IL-2 moiety comprising or consisting of (SEQ ID NO: 48)
APTSXSTKKTQLQLEHLLLDLQMILNGINNYKNPKLTAMLTKKFYMPKKA

TELKHLQCLEEELKPLEEVLNLAQSKNFHLRPRDLISNINVIVLELKGSE

TTFMCEYADETATIVEFLNRWITFXQSIISTLT wherein X5 is a NNAA and X125 is A or S.

In a further embodiment, provided is an IL-2 moiety comprising or consisting of (SEQ ID NO: 49)
PTSXSTKKTQLQLEHLLLDLQMILNGINNYKNPKLTAMLTKKFYMPKKAT

ELKHLQCLEEELKPLEEVLNLAQSKNFHLRPRDLISNINVIVLELKGSET

TFMCEYADETATIVEFLNRWITFSQSIISTLT wherein X4 is a NNAA.

In a further embodiment, provided is an IL-2 moiety comprising or consisting of (SEQ ID NO: 50)
APTSXSTKKTQLQLEHLLLDLQMILNGINNYKNPKLTAMLTKKFYMPKKA

TELKHLQCLEEELKPLEEVLNLAQSKNFHLRPRDLISNINVIVLELKGSE

TTFMCEYADETATIVEFLNRWITFSQSIISTLT wherein X5 is a NNAA.

In a further embodiment, provided is an IL-2 moiety comprising or consisting of (SEQ ID NO: 51)
PTSXSTKKTQLQLEHLLLDLQMILNGINNYKNPKLTAMLTKKFYMPKKAT

ELKHLQCLEEELKPLEEVLNLAQSKNFHLRPRDLISNINVIVLELKGSET

TFMCEYADETATIVEFLNRWITFSQSIISTLT wherein X4 is a para-azidomethylphenylalanine.

In a further embodiment, provided is an IL-2 moiety comprising or consisting of (SEQ ID NO: 52)
APTSXSTKKTQLQLEHLLLDLQMILNGINNYKNPKLTAMLTKKFYMPKKA

TELKHLQCLEEELKPLEEVLNLAQSKNFHLRPRDLISNINVIVLELKGSE

TTFMCEYADETATIVEFLNRWITFSQSIISTLT wherein X5 is a para-azidomethylphenylalanine.

The present invention provides IL-2 conjugates comprising a NNAA as disclosed herein conjugated to any nonpeptidic, water-soluble polymer as disclosed herein. Exemplary IL-2 conjugates include the following embodiments.

The present invention provides an IL-2 conjugate comprising or consisting of the amino acid sequence (SEQ ID NO: 3)
XXXXXXXXXXQLQLEHLLLDLQMILNGINNYKNPXLXXMLXXXFXMPKKA

TELKHLQCLEXXLXXLEXVLNXAQSKNFHLRPRDLISNINVIVLELKGSE

TTFMCEXADETATIVEFLNRWITFXQSIISTLT wherein X1 is A, another amino acid, NNAA, or absent; X2 is P, another amino acid, or NNAA; X3 is T, another amino acid, or NNAA; X4 is S, another amino acid, or NNAA; X5 is S, another amino acid, or NNAA; X6 is S, another amino acid, or NNAA; X7 is T, another amino acid, or NNAA; X8 is K, another amino acid, or NNAA; X9 is K, another amino acid, or NNAA; X10 is T, another amino acid, or NNAA; X35 is K or another amino acid; X37 is T or another amino acid; X38 is R or another amino acid; X41 is T or another amino acid; X42 is F or another amino acid; X43 is K or another amino acid; X45 is Y or another amino acid; X61 is E or another amino acid; X62 is E or another amino acid; X64 is K or another amino acid; X65 is P or another amino acid; X68 is E or another amino acid; X72 is L or another amino acid; X107 is Y or another amino acid; X125 is C or another amino acid; with the proviso that (i) X1-X10 comprises only one NNAA and the NNAA is conjugated to a nonpeptidic, water-soluble polymer and (ii) at least one of the amino acids at positions 35, 37, 38, 41, 42, 43, 45, 61, 62, 64, 65, 68, 72, and 107 is not the amino acid at the corresponding position in the amino acid sequence of SEQ ID NO: 1. In particular embodiments, amino acid X124 is any amino acid other than C, which in a further embodiment may be amino acid A or S.

In further embodiments of the amino acid sequence set forth in SEQ ID NO: 3, at least two of the amino acids selected from positions 35, 37, 38, 41, 42, 43, 45, 61, 62, 64, 65, 68, 72, and 107 are not the amino acid at their corresponding amino acid positions in the amino acid sequence of SEQ ID NO: 1. In further embodiments of the amino acid sequence set forth in SEQ ID NO: 3, at least two of the amino acids selected from positions 35, 37, 38, 41, 42, 43, 45, 61, 62, 64, 65, 68, 72, and 107 are not the amino acid at their corresponding positions in the amino acid sequence of SEQ ID NO: 1 and amino acid X125 is any amino acid other than C, which in a further embodiment may be amino acid A or S. In particular embodiments, the NNAA is para-azidomethylphenylalanine. In further embodiments, the nonpeptidic, water-soluble polymer is PEG.

In a further embodiment, provided is an IL-2 conjugate comprising or consisting of

```
                                        (SEQ ID NO: 4)
XXXXXXXXXQLQLEHLLLDLQMILNGINNYKNPXLXXMLXXXFXMPKKAT

ELKHLQCLEXXLXXLEXVLNXAQSKNFHLRPRDLISNINVIVLELKGSET

TFMCEXADETATIVEFLNRWITFXQSIISTLT
``` wherein X1 is P, another amino acid, or NNAA; X2 is T, another amino acid, or NNAA; X3 is S, another amino acid, or NNAA; X4 is S, another amino acid, or NNAA; X5 is S, another amino acid, or NNAA; X6 is T, another amino acid, or NNAA; X7 is K, another amino acid, or NNAA; X8 is K, another amino acid, or NNAA; X9 is T, another amino acid, or NNAA; X34 is K or another amino acid; X36 is T or another amino acid; X37 is R or another amino acid; X40 is T or another amino acid; X41 is F or another amino acid; X42 is K or another amino acid; X44 is Y or another amino acid; X60 is E or another amino acid; X61 is E or another amino acid; X63 is K or another amino acid; X64 is P or another amino acid; X67 is E or another amino acid; X71 is L or another amino acid; X106 is Y or another amino acid; and X124 is C or another amino acid; with the proviso that (i) X1-X9 comprises only one NNAA and the NNAA is conjugated to a nonpeptidic, water-soluble polymer and (ii) at least one of the amino acids at positions 34, 36, 37, 40, 41, 42, 44, 60, 61, 63, 64, 67, 71, and 106 is not the amino acid at the corresponding position in the amino acid sequence of SEQ ID NO: 2. In particular embodiments, amino acid X124 is any amino acid other than C, which in a further embodiment may be amino acid A or S.

In further embodiments of the amino acid sequence set forth in SEQ ID NO: 4, at least two of the amino acids selected from positions 34, 36, 37, 40, 41, 42, 44, 60, 61, 63, 64, 67, 71, and 106 are not the amino acid at their corresponding amino acid positions in the amino acid sequence of SEQ ID NO: 2. In further embodiments of the amino acid sequence set forth in SEQ ID NO: 4, at least two of the amino acids selected from positions 34, 36, 37, 40, 41, 42, 44, 60, 61, 63, 64, 67, 71, and 106 are not the amino acid at their corresponding positions in the amino acid sequence of SEQ ID NO: 2 and amino acid X125 is any amino acid other than C, which in a further embodiment may be amino acid A or S. In particular embodiments, the NNAA is para-azidomethylphenylalanine. In further embodiments, the nonpeptidic, water-soluble polymer is PEG.

In a further embodiment, provided is an IL-2 conjugate comprising or consisting of

```
                                        (SEQ ID NO: 5)
PTSXSTKKTQLQLEHLLLDLQMILNGINNYKNPXLXXMLXXXFXMPKKAT

ELKHLQCLEXXLXXLEXVLNXAQSKNFHLRPRDLISNINVIVLELKGSET

TFMCEXADETATIVEFLNRWITFXQSIISTLT
``` wherein X4 is a NNAA conjugated to a nonpeptidic, water-soluble polymer; X34 is K or another amino acid; X36 is T or another amino acid; X37 is R or another amino acid; X40 is T or another amino acid; X41 is F or another amino acid; X42 is K or another amino acid; X44 is Y or another amino acid; X60 is E or another amino acid; X61 is E or another amino acid; X63 is K or another amino acid; X64 is P or another amino acid; X67 is E or another amino acid; X71 is L or another amino acid; X106 is Y or another amino acid; and X124 is C or another amino acid; with the proviso that at least one of the amino acids at positions 34, 36, 37, 40, 41, 42, 44, 60, 61, 63, 64, 67, 71, and 106 is not the amino acid at the corresponding position in the amino acid sequence of SEQ ID NO: 2. In particular embodiments, amino acid X124 is any amino acid other than C, which in a further embodiment may be amino acid A or S.

In further embodiments of the amino acid sequence set forth in SEQ ID NO: 5, at least two of the amino acids selected from positions 34, 36, 37, 40, 41, 42, 44, 60, 61, 63, 64, 67, 71, and 106 are not the amino acid at their corresponding amino acid positions in the amino acid sequence of SEQ ID NO: 2. In further embodiments of the amino acid sequence set forth in SEQ ID NO: 4, at least two of the amino acids selected from positions 34, 36, 37, 40, 41, 42, 44, 60, 61, 63, 64, 67, 71, and 106 are not the amino acid at their corresponding positions in the amino acid sequence of SEQ ID NO: 2 and amino acid X125 is any amino acid other than C, which in a further embodiment may be amino acid A or S. In particular embodiments, the NNAA is para-azidomethylphenylalanine. In further embodiments, the nonpeptidic, water-soluble polymer is PEG.

In a further embodiment, provided is an IL-2 conjugate comprising or consisting of

```
                                        (SEQ ID NO: 6)
PTSXSTKKTQLQLEHLLLDLQMILNGINNYKNPKLTXMLTXKFYMPKKAT

ELKHLQCLEEELKPLEEVLNLAQSKNFHLRPRDLISNINVIVLELKGSET

TFMCEYADETATIVEFLNRWITFXQSIISTLT
``` wherein X4 is a NNAA conjugated to a nonpeptidic, water-soluble polymer; X37 any amino acid except R; X41 is any amino acid except F; and X124 is any amino acid except C.

In a further embodiment, provided is an IL-2 conjugate comprising or consisting of

```
                                        (SEQ ID NO: 7)
APTSXSTKKTQLQLEHLLLDLQMILNGINNYKNPKLTXMLTXKFYMPKKA

TELKHLQCLEEELKPLEEVLNLAQSKNFHLRPRDLISNINVIVLELKGSE

TTFMCEYADETATIVEFLNRWITFXQSIISTLT
``` wherein X5 is a NNAA conjugated to a nonpeptidic, water-soluble polymer; X38 any amino acid except R; X42 is any amino acid except F; and X125 is any amino acid except C.

In a further embodiment, provided is an IL-2 conjugate comprising or consisting of

```
                                        (SEQ ID NO: 8)
PTSXSTKKTQLQLEHLLLDLQMILNGINNYKNPKLTAMLTKKFYMPKK

ATELKHLQCLEEELKPLEEVLNLAQSKNFHLRPRDLISNINVIVLELK

GSETTFMCEYADETATIVEFLNRWITFXQSIISTLT
``` wherein X4 is a NNAA conjugated to a nonpeptidic, water-soluble polymer and X124 is A or S.

In a further embodiment, provided is an IL-2 conjugate comprising or consisting of (SEQ ID NO: 9)
APTSXSTKKTQLQLEHLLLDLQMILNGINNYKNPKLTAMLTKKFYMPK

KATELKHLQCLEEELKPLEEVLNLAQSKNFHLRPRDLISNINVIVLEL

KGSETTFMCEYADETATIVEFLNRWITFXQSIISTLT wherein X5 is a NNAA conjugated to a nonpeptidic, water-soluble polymer and X125 is A or S.

In a further embodiment, provided is an IL-2 conjugate comprising or consisting of (SEQ ID NO: 10)
PTSXSTKKTQLQLEHLLLDLQMILNGINNYKNPKLTAMLTKKFYMPKK

ATELKHLQCLEEELKPLEEVLNLAQSKNFHLRPRDLISNINVIVLELK

GSETTFMCEYADETATIVEFLNRWITFSQSIISTLT wherein X4 is a NNAA conjugated to a nonpeptidic, water-soluble polymer.

In a further embodiment, provided is an IL-2 conjugate comprising or consisting of (SEQ ID NO: 11)
APTSXSTKKTQLQLEHLLLDLQMILNGINNYKNPKLTAMLTKKFYMPK

KATELKHLQCLEEELKPLEEVLNLAQSKNFHLRPRDLISNINVIVLEL

KGSETTFMCEYADETATIVEFLNRWITFSQSIISTLT wherein X5 is a NNAA conjugated to a nonpeptidic, water-soluble polymer.

In a further embodiment, provided is an IL-2 conjugate comprising or consisting of (SEQ ID NO: 12)
PTSXSTKKTQLQLEHLLLDLQMILNGINNYKNPKLTAMLTKKFYMPKK

ATELKHLQCLEEELKPLEEVLNLAQSKNFHLRPRDLISNINVIVLELK

GSETTFMCEYADETATIVEFLNRWITFSQSIISTLT wherein X4 is a para-azidomethylphenylalanine conjugated to a nonpeptidic, water-soluble polymer.

In a further embodiment, provided is an IL-2 conjugate comprising or consisting of (SEQ ID NO: 13)
APTSXSTKKTQLQLEHLLLDLQMILNGINNYKNPKLTAMLTKKFYMPK

KATELKHLQCLEEELKPLEEVLNLAQSKNFHLRPRDLISNINVIVLEL

KGSETTFMCEYADETATIVEFLNRWITFSQSIISTLT wherein X5 is a para-azidomethylphenylalanine conjugated to a nonpeptidic, water-soluble polymer.

In a further embodiment, provided is an IL-2 conjugate comprising or consisting of (SEQ ID NO: 14)
PTSXSTKKTQLQLEHLLLDLQMILNGINNYKNPKLTAMLTKKFYMPKK

ATELKHLQCLEEELKPLEEVLNLAQSKNFHLRPRDLISNINVIVLELK

GSETTFMCEYADETATIVEFLNRWITFSQSIISTLT wherein X4 is a para-azidomethyphenyllalanine conjugated to PEG.

In a further embodiment, provided is an IL-2 conjugate comprising or consisting of (SEQ ID NO: 15)
APTSXSTKKTQLQLEHLLLDLQMILNGINNYKNPKLTAMLTKKFYMPK

KATELKHLQCLEEELKPLEEVLNLAQSKNFHLRPRDLISNINVIVLEL

KGSETTFMCEYADETATIVEFLNRWITFSQSIISTLT wherein X5 is a para-azidomethylphenylalanine conjugated PEG.

In a further embodiment, provided is an IL-2 conjugate comprising or consisting of (SEQ ID NO: 16)
PTSXSTKKTQLQLEHLLLDLQMILNGINNYKNPKLTAMLTKKFYMPKK

ATELKHLQCLEEELKPLEEVLNLAQSKNFHLRPRDLISNINVIVLELK

GSETTFMCEYADETATIVEFLNRWITFSQSIISTLT wherein X4 is a para-azidomethylphenylalanine conjugated to PEG end-capped with a methyl group (mPEG).

In a further embodiment, provided is an IL-2 conjugate comprising or consisting of (SEQ ID NO: 17)
APTSXSTKKTQLQLEHLLLDLQMILNGINNYKNPKLTAMLTKKFYMPK

KATELKHLQCLEEELKPLEEVLNLAQSKNFHLRPRDLISNINVIVLEL

KGSETTFMCEYADETATIVEFLNRWITFSQSIISTLT wherein X5 is a para-azidomethylphenylalanine conjugated to mPEG.

In a further embodiment, provided is an IL-2 conjugate comprising or consisting of (SEQ ID NO: 18)
PTSXSTKKTQLQLEHLLLDLQMILNGINNYKNPKLTAMLTKKFYMPKK

ATELKHLQCLEEELKPLEEVLNLAQSKNFHLRPRDLISNINVIVLELK

GSETTFMCEYADETATIVEFLNRWITFSQSIISTLT wherein X4 is a para-azidomethylphenylalanine conjugated to PEG end-capped with a 30 kDa mPEG.

In a further embodiment, provided is an IL-2 conjugate comprising or consisting of (SEQ ID NO: 19)
APTSXSTKKTQLQLEHLLLDLQMILNGINNYKNPKLTAMLTKKFYMPK

KATELKHLQCLEEELKPLEEVLNLAQSKNFHLRPRDLISNINVIVLEL

KGSETTFMCEYADETATIVEFLNRWITFSQSIISTLT wherein X5 is a para-azidomethylphenylalanine conjugated to 30 kDa mPEG.

In a further embodiment, provided is an IL-2 conjugate comprising or consisting of (SEQ ID NO: 20)
PTSXSTKKTQLQLEHLLLDLQMILNGINNYKNPKLTAMLTKKFYMPKK

ATELKHLQCLEEELKPLEEVLNLAQSKNFHLRPRDLISNINVIVLELK

GSETTFMCEYADETATIVEFLNRWITFSQSIISTLT wherein X4 is a para-azidomethylphenylalanine conjugated to DBCO_30 kDa PEG (PEG1) by a triazole linkage, wherein PEG1 has the formula

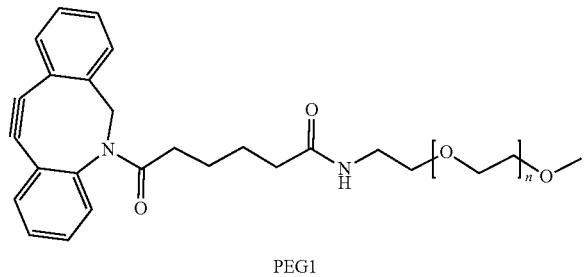

PEG1 wherein n is about 681.

In a further embodiment, provided is an IL-2 conjugate comprising or consisting of (SEQ ID NO: 21)
APTSXSTKKTQLQLEHLLLDLQMILNGINNYKNPKLTAMLTKKFYMPK

KATELKHLQCLEEELKPLEEVLNLAQSKNFHLRPRDLISNINVIVLEL

KGSETTFMCEYADETATIVEFLNRWITFSQSIISTLT wherein X5 is a para-azidomethylphenylalanine conjugated to PEG1 by a triazole linkage.

Stauber et al., Proc. Natl. Acad. Sci (USA) 103:2788-2793 (2006), teaches that the nature of the IL-2/IL-2Rα interface comprises a hydrophobic center dominated by IL-2Rα residues $L2^α$, $M25^α$, $L42^α$, and $Y43^α$ and IL-2 residues $F42^{IL-2}$, $F44^{IL-2}$, $Y45^{IL-2}$, $P65^{IL-2}$, and $L72^{IL-2}$, and a polar periphery featuring five ion pairs ($K38^α/E61^{IL-2}$, $R36^α/E62^{IL-2}$, $E1^α/K35^{IL-2}$, $D6^α/R38^{IL-2}$, and $E29^α/K43^{IL-2}$.

Stauber et al. further teaches that for IL-2 binding to IL-2Rβ, $D20^{IL2}$ and $H16^{IL2}$ seem to be the most critical residues; $D20^{IL2}$ hydrogen bonds to $H133^β$ and $Y134^β$, whereas $H16^{IL2}$ is tucked into a slot created by $Y134^β$, $Q188^β$, and the methyl groups of $T74^β$ and $T73^β$. Major van der Waals contacts in the interface are also made with $R41^β$, $V75^β$, $H133^β$, $L19^{IL2}$, $D84^{IL2}$, $N88^{IL2}$, and $V91^{IL2}$.

Stauber et al. further teaches that for IL-2 binding to IL-2Rγ$_c$, IL-2 with a buried surface area of 72 Å$^2$ and one hydrogen bond, $Q126^{IL2}$ is the most critical IL-2 residue that contacts γ$_c$ in accordance with biochemical data. $E15^{IL2}$, $T123^{IL2}$, and $I129^{IL2}$ contribute other significant interactions to the IL-2/γ$_c$ interface.

Thus, the present invention provides IL-2 moieties and IL-2 conjugates as disclosed herein in which the IL-2 polypeptide amino acid sequence with the exception of the substitution of the NNAA and the substitution of the one or more amino acids that reduce(s) affinity of the IL-2 polypeptide for the human IL-2 receptor αβγ$_c$ trimer (IL-2Rαβγ$_c$) relative to wild-type human IL-2 or abrogate binding to the IL-2Rα, has at least 80%, 85%, 90%, 95%, 98%, or 100% identity with amino acid sequence set forth in SEQ ID NO:1 for native IL-2, SEQ ID NO: 53 for desA1_IL-2, or SEQ ID NO: 2 for aldesleukin. In further embodiments, the IL-2 polypeptide amino acid sequence comprising the IL-2 moiety or conjugate has at least 80%, 85%, 90%, 95%, 98%, or 99% identity with amino acid sequence set forth in SEQ ID NO:1 for native SEQ ID NO: 53 for desA1_IL-2, or SEQ ID NO: 2 for aldesleukin with the proviso that the IL-2 polypeptide comprises at least amino acids E15, H16, L19, D20, D84, N88, V91, Q126, T123, and I129 (according to numbering scheme B).

The present invention further provides for any embodiment disclosed herein in which the non-natural amino acid is not specifically identified as being substituted for the serine residue at position four as it corresponds to position four of SEQ ID NO:2, embodiments wherein the substitution or insertion of the non-natural amino acid is within the N-terminal region, for example, (i) a substitution of an amino acid within the first 30 amino acids of the N-terminus of the IL-2 polypeptide with a non-natural amino acid conjugated to a nonpeptidic, water-soluble polymer or an insertion of a non-natural amino acid conjugated to a nonpeptidic, water-soluble polymer within the first 30 amino acids of the N-terminus of the IL-2 polypeptide or (ii) a substitution of an amino acid within the first 20 amino acids of the N-terminus of the IL-2 polypeptide with a non-natural amino acid conjugated to a nonpeptidic, water-soluble polymer or an insertion of a non-natural amino acid conjugated to a nonpeptidic, water-soluble polymer within the first 20 amino acids of the N-terminus of the IL-2 polypeptide.

Thus, the present invention provides (a) IL-2 conjugate comprising an IL-2 polypeptide comprising an amino acid sequence with at least 80%, 85%, 90%, 95%, 98%, or 99% identity to the amino acid sequence set forth in SEQ ID NO: 53 and further comprising: (i) one or more amino acid substitutions that reduce(s) affinity of the IL-2 polypeptide for the human IL-2Rαβγ$_c$ relative to wild-type human IL-2; and (ii) a substitution of an amino acid within the N-terminal region of the IL-2 polypeptide with a non-natural amino acid conjugated to a nonpeptidic, water-soluble polymer or an insertion of a non-natural amino acid conjugated to a nonpeptidic, water-soluble polymer within the N-terminal region of the IL-2 polypeptide; wherein the IL-2 polypeptide has substantially similar binding affinity for the human IL-2Rβγ$_c$ relative to wild-type human IL-2.

In a particular embodiment, the present invention provides an IL-2 conjugate comprising an IL-2 polypeptide comprising an amino acid sequence with at least 80%, 85%, 90%, 95%, 98%, or 99% identity to the amino acid sequence set forth in SEQ ID NO: 53 and further comprising: (i) one or more amino acid substitutions that reduce(s) affinity of the IL-2 polypeptide for the human IL-2Rαβγ$_c$ relative to wild-type human IL-2; and (ii) a substitution of an amino acid within the N-terminal region comprising the first 30 amino acids of the N-terminus of the IL-2 polypeptide with a non-natural amino acid conjugated to a nonpeptidic, water-soluble polymer or an insertion of a non-natural amino acid conjugated to a nonpeptidic, water-soluble polymer within the N-terminal region comprising the first 30 amino acids of the N-terminus of the IL-2 polypeptide; wherein the IL-2 polypeptide has substantially similar binding affinity for the human IL-2Rβγ$_c$ relative to wild-type human IL-2.

In a particular embodiment, the present invention provides an IL-2 conjugate comprising an IL-2 polypeptide comprising an amino acid sequence with at least 80%, 85%, 90%, 95%, 98%, or 99% identity to the amino acid sequence set forth in SEQ ID NO: 53 and further comprising: (i) one or more amino acid substitutions that reduce(s) affinity of the IL-2 polypeptide for the human IL-2Rαβγ$_c$ relative to wild-type human IL-2; and (ii) a substitution of an amino acid within the N-terminal region comprising the first 20 amino acids of the N-terminus of the IL-2 polypeptide with a non-natural amino acid conjugated to a nonpeptidic, water-soluble polymer or an insertion of a non-natural amino acid conjugated to a nonpeptidic, water-soluble polymer within the N-terminal region comprising the first 20 amino acids of the N-terminus of the IL-2 polypeptide; wherein the IL-2 polypeptide has substantially similar binding affinity for the human IL-2Rβγ$_c$ relative to wild-type human IL-2.

Nonpeptidic Water-Soluble Polymers

Provided herein are conjugates comprising an IL-2 mutant comprising a non-natural amino acid (IL-2 moiety) attached via the non-natural amino acid to a nonpeptidic, water-soluble polymer. With respect to the water-soluble polymer, in certain embodiments, the nonpeptidic, water-soluble polymer is nonpeptidic, nontoxic, non-naturally occurring and biocompatible. With respect to biocompatibility, a substance is considered biocompatible if the beneficial effects associated with use of the substance alone or with another substance (e.g., an active agent such as an IL-2 moiety) in connection with living tissues (e.g., administration to a patient) outweighs any deleterious effects as evaluated by a clinician, e.g., a physician. With respect to non-immunogenicity, a substance is considered non-immunogenic if the intended use of the substance in vivo does not produce an undesired immune response (e.g., the formation of antibodies) or, if an immune response is produced, that such a response is not deemed clinically significant or important as evaluated by a clinician. It is particularly preferred that the nonpeptidic, water-soluble polymer is biocompatible and non-immunogenic.

Further, the polymer is typically characterized as having from two to about 300 termini. Examples of such polymers include, but are not limited to, poly(alkylene glycols) such as polyethylene glycol ("PEG"), poly(propylene glycol) ("PPG"), copolymers of ethylene glycol and propylene glycol and the like, poly(oxyethylated polyol), poly(olefinic alcohol), poly(vinylpyrrolidone), poly(hydroxyalkylmethacrylamide), poly(hydroxy-alkylmethacrylate), poly(saccharides), poly(α-hydroxy acid), poly(vinyl alcohol), polyphosphazene, polyoxazolines ("POZ") (which are described m WO2008/106186), poly(N-acryloylmorpholine), and combinations of any of the foregoing.

The nonpeptidic, water-soluble polymer is not limited to a particular structure and can be linear (e.g., an end capped, e.g., alkoxy PEG or a bifunctional PEG), branched or multi-armed (e.g., forked PEG or PEG attached to a polyol core), a dendritic (or star) architecture, each with or without one or more degradable linkages. Moreover, the internal structure of the nonpeptidic, water-soluble polymer can be organized in any number of different repeat patterns and can be selected from the group consisting of homopolymer, alternating copolymer, random copolymer, block copolymer, alternating tripolymer, random tripolymer, and block tripolymer.

Typically, activated PEG and other activated nonpeptidic, water-soluble polymers (i.e., polymeric reagents) are activated with a suitable reactive group appropriate for coupling to the functional group of an unnatural amino acid within the IL-2 moiety. Thus, a polymeric reagent will possess a reactive group for reaction with the functional group of the non-natural amino acid within the IL-2 moiety. Representative polymeric reagents and methods for conjugating these polymers to an active moiety are known in the art and further described in Zalipsky, S., et al., "Use of Functionalized Poly(Ethylene Glycols) for Modification of Polypeptides" in Polyethylene Glycol Chemistry: Biotechnical and Biomedical Applications, J. M. Harris, Plenus Press, New York (1992), and in Zalipsky (1995) Advanced Drug Reviews 16:157-182. Exemplary reactive groups suitable for coupling to a functional group of a non-natural amino acid within an IL-2 moiety include hydroxyl, maleimide, ester, acetal, ketal, amine, carboxyl, aldehyde, aldehyde hydrate, ketone, vinyl ketone, thione, thiol, vinyl sulfone, hydrazine, alkyne, azide, among others. In particular embodiments, the reactive group is an alkyne, for example, a strained alkyne, as described below, which is capable of forming a covalent linkage with an azide comprising the functional group of a non-natural amino acid within an IL-2 moiety.

In certain embodiments, the polymeric reagent used to prepare the conjugates described herein is prepared without the use of phosgene. Such an approach stands in contrast to, for example, the disclosure set forth in U.S. Pat. No. 4,902,502, which specifically describes forming a chloroformate and subsequent used to form a PEG active ester, which is then reacted with a non-natural amino acid of the IL-2 moiety. Use of phosgene leads to the formation of hydrogen chloride, which can lead to chain cleavage in the polymer, thereby increasing impurities, which may not be able to be removed using conventional techniques. Thus, without wishing to be bound by theory, IL-2 moiety conjugates prepared from polymeric reagents formed without the use of phosgene provides higher quality compositions that are substantially absent polymer chain degradation products. Also, in one or more embodiments, the linker between the nonpeptidic, water-soluble polymer and the functional group is not a carbamate-containing linker.

Typically, the weight-average molecular weight of the nonpeptidic, water-soluble polymer in the conjugate is from about 100 Daltons (Da) to about 150,000 Da. Exemplary ranges, however, include weight-average molecular weights in the range of greater than 5,000 Da to about 100,000 Da, in the range of from about 6,000 Da to about 90,000 Da, in the range of from about 10,000 Da to about 85,000 Da, in the range of greater than 10,000 Da to about 85,000 Da, in the range of from about 20,000 Da to about 85,000 Da, in the range of from about 53,000 Da to about 85,000 Da, in the range of from about 25,000 Da to about 120,000 Da, in the range of from about 29,000 Da to about 120,000 Da, in the range of from about 35,000 Da to about 120,000 Da, and in the range of from about 40,000 Da to about 120,000 Da. For any given nonpeptidic, water-soluble polymer, PEGs having a molecular weight in one or more of these ranges are preferred.

Exemplary weight-average molecular weights for the nonpeptidic, water-soluble polymer include about 100 Da, about 200 Da, about 300 Da, about 400 Da, about 500 Da, about 600 Da, about 700 Da, about 750 Da, about 800 Da, about 900 Da, about 1,000 Da, about 1,500 Da, about 2,000 Da, about 2,200 Da, about 2,500 Da, about 3,000 Da, about 4,000 Da, about 4,400 Da, about 4,500 Da, about 5,000 Da, about 5,500 Da, about 6,000 Da, about 7,000 Da, about 7,500 Da, about 8,000 Da, about 9,000 Da, about 10,000 Da, about 11,000 Da, about 12,000 Da, about 13,000 Da, about 14,000 Da, about 15,000 Da, about 20,000 Da, about 22,500 Da, about 25,000 Da, about 30,000 Da, about 35,000 Da, about 40,000 Da, about 45,000 Da, about 50,000 Da, about 55,000 Da, about 60,000 Da, about 65,000 Da, about 70,000 Da, and about 75,000 Da. Branched versions of the nonpeptidic, water-soluble polymer (e.g., a branched 40,000 Da nonpeptidic, water-soluble polymer comprised of two 20,000 Dalton polymers, or a branched 20,000 Da nonpeptidic, water-soluble polymer comprised of two 10,000 Dalton polymers) having a total molecular weight of any of the foregoing can also be used. In one or more embodiments, the conjugate will not have any PEG moieties attached, either directly or indirectly, having a weight average molecular weight of less than about 6,000 Daltons.

When used as the nonpeptidic, PEGs will typically comprise a number of ($OCH_2CH_2$) monomers (or ($CH_2CH_2O$) monomers, depending on how the PEG is defined). As used throughout the description, the number of repeating units is identified by the subscript "n" in "($OCH_2CH_2$)$_n$." Thus, the value of (n) typically falls within one or more of the following ranges: from 2 to about 3400, from about 100 to about 2300, from about 100 to about 2270, from about 136 to about 2050, from about 225 to about 1930, from about 450 to about 1930, from about 1200 to about 1930, from about 568 to about 2727, from about 660 to about 2730, from about 795 to about 2730, from about 795 to about 2730, from about 909 to about 2730, and from about 1,200 to about 1,900. For any given polymer in which the molecular weight is known, it is possible to determine the number of repeating units (i.e., "n") by dividing the total weight-average molecular weight of the polymer by the molecular weight of the repeating monomer.

In one embodiment, the polymer for use herein is an end-capped polymer, that is, a polymer having at least one terminus capped with a relatively inert group, such as a lower C1-6 alkoxy group, although a hydroxyl group can also be used. When the polymer is PEG, for example, it may be desirable to use a methoxy-PEG (commonly referred to as mPEG), which is a linear form of PEG wherein one terminus of the polymer is a methoxy (—$OCH_3$) group, while the other terminus is a hydroxyl or other reactive group that can be optionally chemically modified.

In certain embodiments, free or unbound PEG is a linear polymer terminated at each end with hydroxyl groups: HO—$CH_2CH_2O$—($CH_2CH_2O$)$_n$—$CH_2CH_2$—OH, wherein (n) typically ranges from zero to about 4,000. The above polymer, alpha-, omega-dihydroxylpoly(ethylene glycol), can be represented in brief form as HO-PEG-OH where it is understood that the -PEG- symbol can represent the following structural unit: —$CH_2CH_2O$—($CH_2CH_2O$)$_n$—$CH_2CH_2$—, wherein (n) is as defined as above.

Another type of PEG useful in one or more embodiments is methoxy-PEG-OH, or mPEG in brief, in which one terminus is the relatively inert methoxy group, while the other terminus is a hydroxyl group. The formula of mPEG is given below. $CH_3O$—$CH_2CH_2O$—($CH_2CH_2O$)$_n$—$CH_2CH_2$—OH wherein (n) is as described above.

Multi-armed or branched PEG molecules, such as those described in U.S. Pat. No. 5,932,462, can also be used as the PEG polymer. For example, PEG can have the formula:

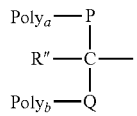

wherein poly$_a$ and poly$_b$ are PEG backbones (either the same or different), such as methoxy poly(ethylene glycol); R″ is a nonreactive moiety, such as H, methyl, or a PEG backbone; and P and Q are nonreactive linkages.

In addition, the PEG can comprise a forked PEG. An example of a forked PEG is represented by the following formula:

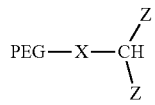

wherein X is a linker of one or more atoms and each Z is an activated terminal group linked to CH by a chain of atoms of defined length. International Patent Application Publication WO 99/45964 discloses various forked PEG structures capable of use in one or more embodiments of the present invention. The chain of atoms linking the Z functional groups to the branching carbon atom serve as a tethering group and may comprise, for example, alkyl chains, ether chains, ester chains, amide chains and combinations thereof.

The PEG polymer may comprise a pendant PEG molecule having reactive groups, such as carboxyl, covalently attached along the length of the PEG rather than at the end of the PEG chain. The pendant reactive groups can be attached to the PEG directly or through a linker, such as an alkylene group.

Those of ordinary skill in the art will recognize that the foregoing discussion concerning nonpeptidic, water-soluble polymer is by no means exhaustive and is merely illustrative, and that all polymeric materials having the qualities described above are contemplated. As used herein, the term "polymeric reagent" generally refers to an entire molecule, which can comprise a water-soluble polymer segment and a functional group.

Typically, for any given conjugate, there will be one to three nonpeptidic, water-soluble polymers covalently attached to one or more IL-2 moieties having IL-2 activity. In some instances, however, the conjugate may have 1, 2, 3, 4, 5, 6, 7, 8 or more nonpeptidic, water-soluble polymers individually attached to an IL-2 moiety. The nonpeptidic, water-soluble polymers are typically attached to side chains of site-specific non-natural amino acids, described in detail below.

With respect to the polymeric reagents, those described here and elsewhere can be purchased from commercial sources or prepared from commercially available starting materials. In addition, methods for preparing the polymeric reagents are described in the literature.

The attachment between the non-natural amino acid of the IL-2 moiety and the nonpeptidic, water-soluble polymer can be direct, wherein no intervening atoms are located between the IL-2 moiety and the nonpeptidic, water-soluble polymer, or indirect, wherein one or more atoms are located between the IL-2 moiety and the nonpeptidic, water-soluble polymer. With respect to the indirect attachment, a "linker" serves as a spacer between the functional group and the nonpeptidic, water-soluble polymer. The one or more atoms making up the linker can include one or more of carbon atoms, nitrogen atoms, sulfur atoms, oxygen atoms, and combinations thereof. The linker can comprise an amide, secondary amine, carbamate, thioether, and/or disulfide group. Nonlimiting examples of specific linkers include those selected from the group consisting of —O—, —S—, —S—, —C(O)—, —C(O)—NH—, —NH—C(O)—NH—, —O—C(O)—NH—, —C(S)—, —$CH_2$—, —$CH_2$—$CH_2$—, —$CH_2$—$CH_2$—$CH_2$—, —$CH_2$—$CH_2$—$CH_2$—$CH_2$—, —O—$CH_2$—, —$CH_2$—O—, —O—$CH_2$—$CH_2$—, —$CH_2$—O—$CH_2$—, —$CH_2$—$CH_2$—O—, —O—$CH_2$—$CH_2$—$CH_2$—, —$CH_2$—O—$CH_2$—$CH_2$—, —$CH_2$—$CH_2$—O—$CH_2$—, —$CH_2$—$CH_2$—$CH_2$—O—, —O—$CH_2$—$CH_2$—$CH_2$—$CH_2$—, —$CH_2$—O—$CH_2$—$CH_2$—$CH_2$—, —$CH_2$—$CH_2$—O—$CH_2$—$CH_2$—, —$CH_2$—$CH_2$—$CH_2$—O—$CH_2$—, —$CH_2$—$CH_2$—$CH_2$—$CH_2$—O—, —C(O)—NH—$CH_2$—, —C(O)—NH—$CH_2$—$CH_2$—, —$CH_2$—C(O)—NH—$CH_2$—, —$CH_2$—$CH_2$—C(O)—NH—, —C(O)—NH—$CH_2$—$CH_2$—$CH_2$—, —$CH_2$—C(O)—NH—$CH_2$—$CH_2$—, —$CH_2$—$CH_2$—C(O)—NH—$CH_2$—, —$CH_2$—$CH_2$— $CH_2$—C(O)—NH—, —C(O)—NH—CH$_2$—CH$_2$—CH$_2$—CH$_2$—, —CH$_2$—C(O)—NH—CH$_2$—CH$_2$—CH$_2$—, —CH$_2$—CH$_2$—C(O)—NH—CH$_2$—CH$_2$—, —CH$_2$—CH$_2$—CH$_2$—C(O)—NH—CH$_2$—, —CH$_2$—CH$_2$—CH$_2$—C(O)—NH—CH$_2$—CH$_2$—, —CH$_2$—CH$_2$—CH$_2$—CH$_2$—C(O)—NH—, —C(O)—O—CH$_2$—, —CH$_2$—C(O)—O—CH$_2$—, —CH$_2$—CH$_2$—C(O)—O—CH$_2$—, —C(O)—O—CH$_2$—CH$_2$—, —NH—C(O)—CH$_2$—, —CH$_2$—NH—C(O)—CH$_2$—, —CH$_2$—CH$_2$—NH—C(O)—CH$_2$—, —NH—C(O)—CH$_2$—CH$_2$—, —CH$_2$—NH—C(O)—CH$_2$—CH$_2$—, —CH$_2$—CH$_2$—NH—C(O)—CH$_2$—CH$_2$—, —C(O)—NH—CH$_2$—, —C(O)—NH—CH$_2$—CH$_2$—, —O—C(O)—NH—CH$_2$—CH$_2$—, —O—C(O)—NH—CH$_2$—CH$_2$—, —NH—CH$_2$—, —NH—CH$_2$—CH$_2$—, —CH$_2$—NH—CH$_2$—, —CH$_2$—CH$_2$—NH—CH$_2$—, —C(O)—CH$_2$—, —C(O)—CH$_2$—CH$_2$—, —CH$_2$—C(O)—CH$_2$—, —CH$_2$—CH$_2$—C(O)—CH$_2$—, —CH$_2$—CH$_2$—C(O)—CH$_2$—CH$_2$—, —CH$_2$—CH$_2$—C(O)—, —CH$_2$—CH$_2$—CH$_2$—C(O)—NH—CH$_2$—CH$_2$—NH—, —CH$_2$—CH$_2$—CH$_2$—C(O)—NH—CH$_2$—CH$_2$—NH—C(O)—, —CH$_2$—CH$_2$—CH$_2$—C(O)—NH—CH$_2$—CH$_2$—NH—C(O)—CH$_2$—, —CH$_2$—CH$_2$—CH$_2$—C(O)—NH—CH$_2$—CH$_2$—N—H—C(O)—CH$_2$—CH$_2$—, —O—C(O)—NH—[CH$_2$]$_h$—(OCH$_2$CH$_2$)$_j$—, bivalent cycloalkyl group, —O—, —S—, an amino acid, —N(R$^6$)—, and combinations of two or more of any of the foregoing, wherein R$^6$ is H or an organic radical selected from the group consisting of alkyl, substituted alkyl, alkenyl, substituted alkenyl, alkynyl, substituted alkynyl, aryl and substituted aryl, (h) is zero to six, and (J) is zero to 20. Other specific spacer moieties have the following formulas: —C(O)—NH—(CH$_2$)$_{1-6}$—NH—C(O)—NH—C(O)—NH—(CH$_2$)$_{1-6}$—NH—C(O)—, and —O—C(O)—NH—(CH$_2$)$_{1-6}$—NH—C(O)—, wherein the subscript values following each methylene indicate the number of methylene groups contained in the formula, e.g., (CH$_2$)$_{1-6}$ means that the formula can contain 1, 2, 3, 4, 5 or 6 methylene groups. Additionally, any of the above linkers may further include an ethylene oxide oligomer chain comprising 1 to 20 ethylene oxide monomer units [i.e., —(CH$_2$CH$_2$O)$_{1-20}$]. That is, the ethylene oxide oligomer chain can occur before or after the linker, and optionally in between any two atoms of a linker comprised of two or more atoms. Also, the oligomer chain would not be considered part of the linker if the oligomer is adjacent to a polymer segment and merely represent an extension of the polymer segment. In particular embodiments, the linker comprises 1, 2, 3, 4, 5, 6, 7, 8, 9, or 10 carbon atoms. Exemplary linkers include but are not limited to

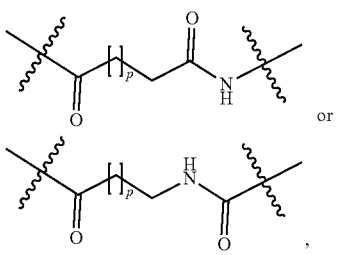

wherein p is an integer from 1 to 10 and the wavy lines indicate bonds linked to N of DBCO on the left and to C of PEG on the right. In particular embodiments, p is 1, 3, or 5.

Any molecular mass for a PEG can be used as practically desired, including but not limited to, from about 100 Da to 100,000 Da or more as desired (including but not limited to, sometimes 0.1-50 kDa or 10-40 kDa). Branched chain PEGs, including but not limited to, PEG molecules with each chain having a molecular weight (MW) ranging from 1-100 kDa (including but not limited to, 1-50 kDa or 5-20 kDa) can also be used. A wide range of PEG molecules are described in, including but not limited to, the Shearwater Polymers, Inc. catalog, and the Nektar Therapeutics catalog, incorporated herein by reference.

Generally, at least one terminus of the nonpeptidic, water-soluble polymer, e.g., PEG molecule, is available for reaction with the non-natural amino acid of the IL-2 moiety. For example, nonpeptidic, water-soluble polymer bearing alkyne or azide reactive groups for reaction with non-natural amino acid side chains can be used to attach the nonpeptidic, water-soluble polymer to site-specific non-natural amino acids within the IL-2 moiety comprising the corresponding azide or alkyne group, respectively, as described herein. In particular embodiment, when the site-specific non-natural amino acid comprises an azide, then the nonpeptidic, water-soluble polymer will typically contain either an alkyne reactive group to effect formation of the [3+2]cycloaddition product (triazole). Alternatively, if the site-specific non-natural amino acid comprises an alkyne, then the nonpeptidic, water-soluble polymer will typically contain an azide reactive group to effect formation of the [3+2] Huisgen cycloaddition product. If the site-specific non-natural amino acid comprises a carbonyl group functional group, the nonpeptidic, water-soluble polymer will typically comprise a potent nucleophile reactive group (including but not limited to, a hydrazide, hydrazine, hydroxylamine, or semicarbazide functionality) in order to effect formation of corresponding hydrazone, oxime, and semicarbazone linkages, respectively. In other alternatives, a reverse of the orientation of the reactive and functional groups described herein can be used, i.e., an azide in the site-specific non-natural amino acid can be reacted with a nonpeptidic, water-soluble polymer containing within, or linked to, an alkyne.

In certain embodiments, the nonpeptidic, water-soluble polymer is an azide- or alkyne-containing polymer comprising a nonpeptidic, water-soluble polymer backbone having an average molecular weight from about 1,000 Da to about 100,000 Da.

Non-Natural Amino Acids

The non-natural amino acid can be any non-natural amino acid deemed suitable by the practitioner. In particular embodiments, the non-natural amino acid comprises a functional group useful for forming a covalent bond to a reactive group present within a nonpeptidic, water-soluble polymer or on a linker linked to the nonpeptidic, water-soluble polymer. In certain embodiments, the functional group is selected from the group consisting of amino, carboxy, acetyl, hydrazino, hydrazido, semicarbazido, sulfanyl, azido, and alkynyl with the proviso that the functional group is selected as being capable of forming a covalent bond with the reactive group within or linked to the nonpeptidic, water-soluble polymer. Modified amino acids are also described in, for example, WO2013185115 and WO2015006555, each of which is incorporated herein by reference in its entirety.

In certain embodiments, the amino acid residue is according to any of the following formulas:

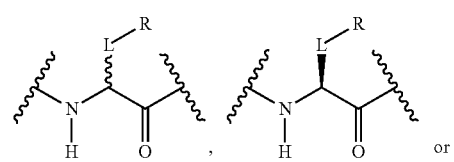

-continued

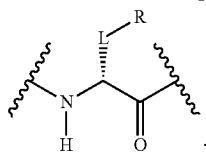

Those of skill in the art will recognize that proteins are generally comprised of L-amino acids. However, with non-natural amino acids, the present methods and compositions provide the practitioner with the ability to use L, D, or racemic non-natural amino acids at the site-specific positions. In certain embodiments, the non-natural amino acids described herein include D-versions of the natural amino acids and racemic versions of the natural amino acids.

In the above formulas, the wavy lines indicate bonds that connect to the remainder of the polypeptide chains of the proteins. These non-natural amino acids can be incorporated into polypeptide chains just as natural amino acids are incorporated into the same polypeptide chains. In certain embodiments, the non-natural amino acids are incorporated into the polypeptide chain via amide bonds as indicated in the formulas.

In some embodiments, the site-specific non-natural amino acids include side chain functional groups that react efficiently and selectively with reactive groups and are not found in the 20 common amino acids (including but not limited to, azido, ketone, aldehyde and aminooxy groups) to form stable conjugates. For example, the IL-2 moiety that includes a site-specific non-natural amino acid containing an azido functional group can be reacted with a reactive group of a nonpeptidic, water-soluble polymer containing an alkyne moiety to form a stable conjugate resulting from the selective reaction of the azide and the alkyne groups to form a Huisgen [3+2]cycloaddition product.

Exemplary site-specific non-natural amino acids that may be suitable for use in the present invention and that are useful for reactions with nonpeptidic water-soluble polymers include, but are not limited to, those with carbonyl, aminooxy, hydrazine, hydrazide, semicarbazide, azide, and alkyne functional groups. In some embodiments, site-specific non-natural amino acids comprise a saccharide moiety. Examples of such amino acids include N-acetyl-L-glucosaminyl-L-serine, N-acetyl-L-galactosaminyl-L-serine, N-acetyl-L-glucosaminyl-L-threonine, N-acetyl-L-glucosaminyl-L-asparagine and O-mannosaminyl-L-serine. Examples of such amino acids also include examples where the naturally-occurring N- or O-linkage between the amino acid and the saccharide is replaced by a covalent linkage not commonly found in nature-including but not limited to, an alkene, an oxime, a thioether, an amide and the like. Examples of such amino acids also include saccharides that are not commonly found in naturally-occurring proteins such as 2-deoxy-glucose, 2-deoxygalactose and the like.

Specific examples of unnatural amino acids that may be suitable for use in the present invention include, but are not limited to, p-azidomethyl-L-phenylalanine, p-azido-L-phenylalanine, p-acetyl-L-phenylalanine, N6-azidoethoxy-L-lysine, N6-propargylethoxy-L-lysine (PraK), BCN-L-lysine, norbornene lysine, TCO-lysine, methyltetrazine lysine, allyloxycarbonyllysine, 2-amino-8-oxononanoic acid, 2 O-methyl-L-tyrosine, L-3-(2-naphthyl)alanine, 3-methylphenylalanine, O-4-allyl-L-tyrosine, 4-propyl-L-tyrosine, tri-O-acetyl-GlcNAc-serine, L-Dopa, fluorinated phenylalanine, isopropyl-L-phenylalanine, p-benzoyl-L-phenylalanine, L-phosphoserine, phosphonoserine, phosphonotyrosine, p-iodo-phenylalanine, p-bromophenylalanine, p-amino-L-phenylalanine, isopropyl-L-phenylalanine, p-propargyloxy-phenylalanine, 2-amino-3-((2-((3-(benzyloxy)-3-oxopropyl)amino)ethyl)selanyl)propanoic acid, 2-amino-3-(phenyl selanyl)propanoic, selenocysteine, m-acetylphenylalanine, and p-propargyloxyphenylalanine, and the like. Examples of structures of a variety of unnatural amino acids that may be suitable for use in the present invention are provided in, for example, WO 2002085923 entitled "In vivo incorporation of unnatural amino acids." See also Kiick et al., (2002) Incorporation of azides into recombinant proteins for chemoselective modification by the Staudinger ligation, PNAS 99:19-24, for additional methionine analogs.

Many of the non-natural amino acids suitable for use in the present invention are commercially available, e.g., from Sigma (USA) or Aldrich (Milwaukee, Wis., USA). Those that are not commercially available are optionally synthesized as provided herein or as provided in various publications or using standard methods known to those of skill in the art. For organic synthesis techniques, see, e.g., Organic Chemistry by Fessendon and Fessendon, (1982, Second Edition, Willard Grant Press, Boston Mass.); Advanced Organic Chemistry by March (Third Edition, 1985, Wiley and Sons, New York); and Advanced Organic Chemistry by Carey and Sundberg (Third Edition, Parts A and B, 1990, Plenum Press, New York). Additional publications describing the synthesis of unnatural amino acids include, e.g., WO 2002/085923 entitled "In vivo incorporation of Unnatural Amino Acids;" Matsoukas et al., (1995) J. Med. Chem., 38, 4660-4669; King, F. E. & Kidd, D. A. A. (1949) A New Synthesis of Glutamine and of y-Dipeptides of Glutamic Acid from Phthylated Intermediates. J. Chem. Soc., 3315-3319; Friedman, 0. M. & Chatterrji, R. (1959) Synthesis of Derivatives of Glutamine as Model Substrates for Anti-Tumor Agents. J. Am. Chem. Soc. 81, 3750-3752; Craig, J. C. et al. (1988) Absolute Configuration of the Enantiomers of 7-Chloro-4 [[4-(diethyl amino)-1-methylbutyl]amino] quinoline (Chloroquine). J. Org. Chem. 53, 1167-1170; Azoulay, M., Vilmont, M. & Frappier, F. (1991) Glutamine analogues as Potential Antimalarials, Eur. J. Med. Chem. 26, 201-5; Koskinen, A. M. P. & Rapoport, H. (1989) Synthesis of 4-Substituted Pralines as Conformationally Constrained Amino Acid Analogues. J. Org. Chem. 54, 1859-1866; Christie, B. D. & Rapoport, H. (1985) Synthesis of Optically Pure Pipecolates from L-Asparagine. Application to the Total Synthesis of (+)-Apovincamine through Amino Acid Decarbonylation and lminium Ion Cyclization. J. Org. Chem. 1989:1859-1866; Barton et al., (1987) Synthesis of Novel a-Amino-Acids and Derivatives Using Radical Chemistry: Synthesis of L- and D-a-Amino-Adipic Acids, L-a-aminopimelic Acid and Appropriate Unsaturated Derivatives. Tetrahedron Lett. 43:4297-4308; and, Subasinghe et al., (1992) Quisqualic acid analogues: synthesis of beta-heterocyclic 2-aminopropanoic acid derivatives and their activity at a novel quisqualate-sensitized site. J. Med. Chem. 35:4602-7. See also, patent applications entitled "Protein Arrays," filed Dec. 22, 2003, Ser. No. 10/744,899 and Ser. No. 60/435,821 filed on Dec. 22, 2002.

The unique reactivity of azide and alkyne groups makes such groups extremely useful for the selective modification of polypeptides and other biological molecules. Organic azides, particularly aliphatic azides, and alkynes are generally stable toward common reactive chemical conditions. In particular, both the azide and the alkyne functional or reactive groups are inert toward the side chains (i.e., R groups) of the 20 common amino acids found in naturally-occurring polypeptides. When brought into close proximity, the "spring-loaded" nature of the azide and alkyne groups is revealed, and they react selectively and efficiently via Huisgen [3+2] cycloaddition reaction to generate the corresponding triazole. See, e.g., Chin J., et al., Science 301:964-7 (2003); Wang, Q., et al., J. Am. Chem. Soc. 125, 3192-3193 (2003); Chin, J. W., et al., J. Am. Chem. Soc. 124:9026-9027 (2002).

Because the Huisgen cycloadditionareaction involves a selective cycloaddition reaction (see, e.g., Padwa, A., in COMPREHENSIVE ORGANIC SYNTHESIS, Vol. 4, (ed. Trost, B. M., 1991), p. 1069-1109; Huisgen, R. in 1,3-DIPOLAR CYCLOADDITION CHEMISTRY, (ed. Padwa, A., 1984), p. 1-176) rather than a nucleophilic substitution, the incorporation of site-specific non-natural amino acids bearing azide and alkyne-containing side chains permits the resultant polypeptides to be modified selectively at the position of the site-specific non-natural amino acid. Cycloaddition reaction involving azide or alkyne-containing protein can be carried out at room temperature under aqueous conditions by the addition of Cu(II) (including but not limited to, in the form of a catalytic amount of $CuSO_4$) in the presence of a reducing agent for reducing Cu(II) to Cu(I), in situ, in catalytic amount. See, e.g., Wang, Q., et al., J. Am. Chem. Soc. 125, 3192-3193 (2003); Tomoe, C. W., et al., J. Org. Chem. 67:3057-3064 (2002); Rostovtsev, et al., Angew. Chem. Int. Ed. 41:2596-2599 (2002). Exemplary reducing agents include, but are not limited to, ascorbate, metallic copper, quinine, hydroquinone, vitamin K, glutathione, cysteine, $Fe^2Co^{2+}$, and an applied electric potential.

In some cases, where a Huisgen [3+2] cycloaddition reaction between an azide and an alkyne is desired, the antigen-binding polypeptide comprises a site-specific non-natural amino acid comprising an alkyne moiety and the water-soluble polymer to be attached to the amino acid comprises an azide moiety. Alternatively, the converse reaction (i.e., with the azide moiety on the amino acid and the alkyne moiety present on the nonpeptidic, water-soluble polymer) can also be performed.

The azide functional group can also be reacted selectively with a nonpeptidic, water-soluble polymer containing an aryl ester and appropriately functionalized with an aryl phosphine moiety to generate an amide linkage. The aryl phosphine group reduces the azide in situ and the resulting amine then reacts efficiently with a proximal ester linkage to generate the corresponding amide. See, e.g., E. Saxon and C. Bertozzi, Science 287, 2007-2010 (2000). The azide-containing amino acid can be either an alkyl azide (including but not limited to, 2-amino-6-azido-1-hexanoic acid) or an aryl azide (p-azido-phenylalanine).

Exemplary azide-containing amino acids include the following:

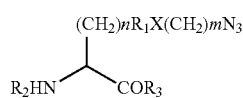

wherein n is 0-10; $R_1$ is an alkyl, aryl, substituted alkyl, substituted aryl or not present; X is O, N, S, or not present; m is 0-10; $R_2$ is H, an amino acid, a polypeptide, or an amino terminus modification group, and $R_3$ is H, an amino acid, a polypeptide, or a carboxy terminus modification group. In some embodiments, n is 1, $R_1$ is phenyl, X is not present, m is 0 and the azide moiety is positioned para to the alkyl side chain. In some embodiments, n is 0-4 and $R_1$ and X are not present, and m is 0. In some embodiments, n is 1, $R_1$ is phenyl, X is 0, m is 2 and the p-azidoethoxy moiety is positioned in the para position relative to the alkyl side chain.

Azide-containing amino acids are available from commercial sources. For instance, 4-azidophenylalanine can be obtained from Chem-Impex International, Inc. (Wood Dale, Ill.). For those azide-containing amino acids that are not commercially available, the azide group can be prepared relatively readily using standard methods known to those of skill in the art, including but not limited to, via displacement of a suitable leaving group (including but not limited to, halide, mesylate, tosylate) or via opening of a suitably protected lactone. See, e.g., Advanced Organic Chemistry by March (Third Edition, 1985, Wiley and Sons, New York).

In certain embodiments, the non-natural amino acid is according to Formula I:

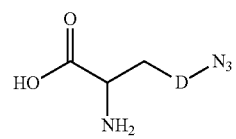

or a salt thereof, wherein: D is —Ar—$W_3$— or —$W_1$—$Y_1$—C(O)—$Y_2$—$W_2$—; Ar is each of $W_1$, $W_2$, and W3 is independently a single bond or lower alkylene; each

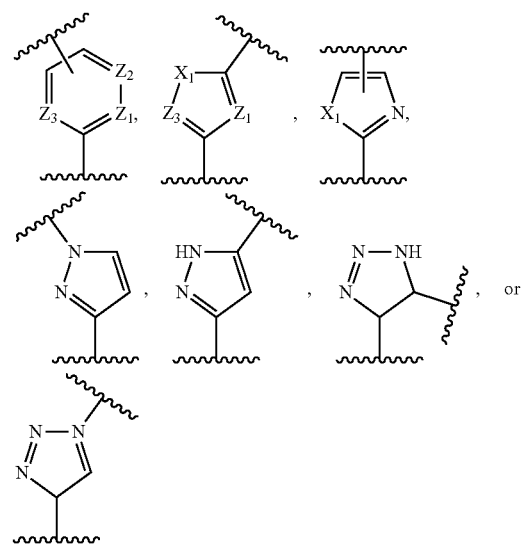

$X_1$ is independently -NH—, —O—, or —S—; each $Y_1$ is independently a single bond, —NH—, or —O—; each $Y_2$ is independently a single bond, —NH—, —O—, or an N-linked or C-linked pyrrolidinylene; and one of $Z_1$, $Z_2$, and $Z_3$ is —N— and the others of $Z_1$, $Z_2$, and $Z_3$ are independently —CH—, and wherein the wavy line indicates a bond to an adjacent atom.

In certain embodiments, the non-natural amino acid is according to formula II:

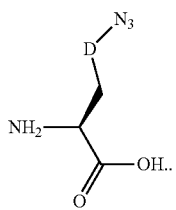

where D is a defined in the context of formula I. In certain embodiments, the non-natural amino acid is according formula IIb:

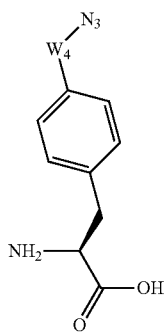

or a salt thereof, wherein $W_4$ is $C_1$-$C_{10}$ alkylene. In a further embodiment, $W_4$ is $C_1$-$C_5$ alkylene. In an embodiment, $W_4$ is $C_1$-$C_3$ alkylene. In an embodiment, $W_4$ is $C_1$ alkylene.

In particular embodiments, the non-natural amino acid is p-azidomethylpheylalanine (pAMF):

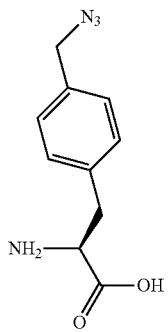

or a salt thereof. Such non-natural amino acids may be in the form of a salt or may be incorporated into a non-natural amino acid polypeptide, polymer, polysaccharide, or a polynucleotide and optionally post translationally modified.

Linkers

In certain embodiments, the IL-2 moieties can be linked to the nonpeptidic, water-soluble polymers with one or more linkers capable of reacting with an IL-2 moiety amino acid and with a nonpeptidic, water-soluble polymer group. The one or more linkers can be any linkers apparent to those of skill in the art.

Useful linkers include those described herein. In certain embodiments, the linker is any divalent or multivalent linker known to those of skill in the art. Useful divalent linkers include alkylene, substituted alkylene, heteroalkylene, substituted heteroalkylene, arylene, substituted arylene, heteroarylene, and substituted heteroarylene. In certain embodiments, the linker is $C_{1-10}$ alkylene or $C_{1-10}$ heteroalkylene. In some embodiments, the $C_{1-10}$ heteroalkylene is PEG.

In general, the linker is hydrolytically stable. Hydrolytically stable linkages are linkages that are substantially stable in water and do not react with water at physiological pH values, including but not limited to, under physiological conditions for an extended period of time, perhaps even indefinitely.

The linker may have a wide range of molecular weights or molecular lengths. Larger or smaller molecular weight linkers may be used to provide a desired spatial relationship or conformation between the IL-2 moiety and the linked nonpeptidic, water-soluble polymer. Linkers having longer or shorter molecular length may also be used to provide a desired space or flexibility between the moiety and the linked nonpeptidic, water-soluble polymer. Similarly, a linker having a particular shape or conformation may be utilized to impart a particular shape or conformation to the polypeptide or the linked entity, either before or after the polypeptide reaches its target. This optimization of the spatial relationship between the polypeptide and the linked entity may provide new, modulated, or desired properties to the molecule.

In certain embodiments, the nonpeptidic, water-soluble polymers can be linked to the linkers, referred to herein as a linker-nonpeptidic, water-soluble polymer, with one or more linker groups capable of reacting with an IL-2 moiety functional group. The one or more linkers can be any linkers apparent to those of skill in the art or those set forth herein. In specific embodiments, the nonpeptidic, water-soluble polymer conjugated to the reactive group has the formula:

(RG)-(linker)-(POLY)-x wherein RG is a reactive group that is capable of forming a covalent linkage with the functional group of a non-natural amino acid; linker is a covalent bond or a substituted or non-substituted $C_{1-20}$ alkyl; POLY is a nonpeptidic, water-soluble polymer; and x is an alcohol or methyl group at the terminus of the POLY.

In particular embodiments, POLY is polyethylene glycol (PEG) having a molecular weight from about 5 to about 100 kilo Daltons (kDa). In certain embodiments, the polyethylene glycol has a molecular weight of 10,000, 20,000, or 30,000 kDa. Each ethylene glycol unit of the polyethylene glycol has a molecular weight of about 44 Da. Thus, a 30 kDa PEG comprises about 681 ethylene glycol units. An exemplary (RG)-(linker)-(POLY)-x molecule has the formula

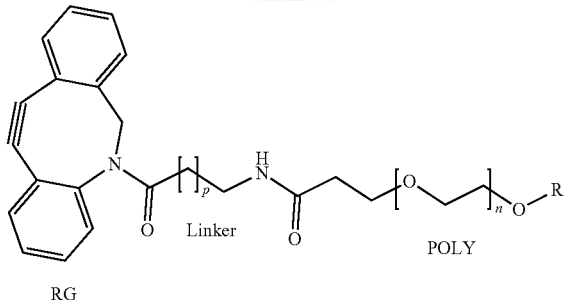

RG / Linker / POLY wherein p is an integer from 1 to 10; n is an integer from 1 to 5,000; and, R is an end-capping group selected from methyl and H. In particular embodiments, p is an integer from 1-6.

In particular embodiments, POLY is polyethylene glycol (PEG) having a molecular weight from about 5 to about 100 kilo Daltons (kDa). In certain embodiments, the polyethylene glycol has a molecular weight of 10,000, 20,000, or 30,000 kDa. Each ethylene glycol unit of the polyethylene glycol has a molecular weight of about 44 Da. Thus, a 30 kDa PEG comprises about 681 ethylene glycol units.

Other useful linker-PEG moieties are described in U.S. Pat. Nos. 8,680,315 and 8,754,190, the contents of which are hereby incorporated by reference in their entirety.

Exemplary Conjugates

In certain embodiments, provided herein are conjugates according to the Formula:

(COMP)$_n$-QQ-LL-POLY-$x$ wherein COMP is a non-natural amino acid of an IL-2 moiety, as described above; QQ is a divalent residue of a conjugating group; LL is an optional linker; n is an integer from one to five, POLY is a nonpeptidic, water-soluble polymer as described herein, and x is methyl or alcohol. As discussed above, the IL-2 moiety may be linked to one or more than one nonpeptidic, water-soluble polymer, where each nonpeptidic, water-soluble polymer is linked to a COMP residue of the IL-2 moiety.

Conjugating groups facilitate conjugation of a reactive group described herein to a functional group described herein. In certain embodiments, the conjugated conjugating group linkage is designated QQ herein. Conjugating groups can react via any suitable reaction mechanism known to those of skill in the art. In certain embodiments, a conjugating group reacts through a [3+2] alkyne-azide cycloaddition reaction, inverse-electron demand Diels-Alder ligation reaction, thiol-electrophile reaction, or carbonyl-oxyamine reaction, as described in detail herein. In certain embodiments, the conjugating group comprises an alkyne, strained alkyne, tetrazine, thiol, para-acetyl-phenylalanine residue, oxyamine, maleimide, or azide.

In certain embodiments, the conjugating group is:

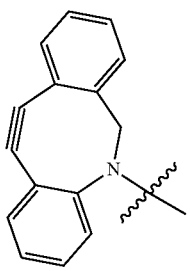 [SMILES: *N1Cc2ccccc2C#Cc2ccccc21]

wherein the wavy line indicates a bond to an adjacent atom, e.g., a carbon residue of a linker, PEG, or linker-PEG.

Additional conjugating groups are described in, for example, U.S. Patent Publication No. 2014/0356385, U.S. Patent Publication No. 2013/0189287, U.S. Patent Publication No. 2013/0251783, U.S. Pat. Nos. 8,703,936, 9,145,361, 9,222,940, and 8,431,558.

After conjugation, a divalent residue "QQ" of the conjugating group is formed and is bonded to the residue of a second compound. The structure of the divalent residue is determined by the type of conjugation reaction employed to form the conjugate.

In certain embodiments when a conjugate is formed through a [3+2]alkyne-azide cycloaddition reaction, the divalent residue of the conjugating group comprises a triazole ring or fused cyclic group comprising a triazole ring. In certain embodiment when a conjugate is formed through a strain-promoted [3+2] alkyne-azide cycloaddition (SPAAC) reaction, the divalent residue of the conjugating group is:

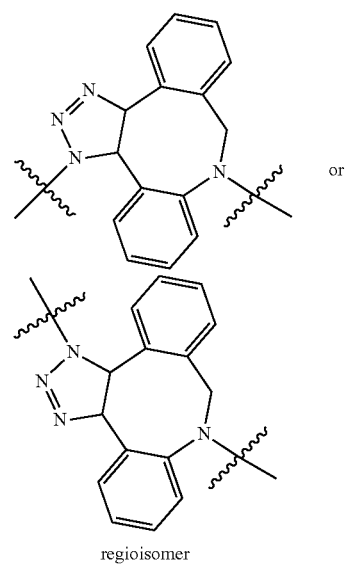

regioisomer wherein the wavy line indicates a bond to an adjacent atom.

In an embodiment, provided herein is a conjugate according to Formula (above), or a pharmaceutically acceptable salt, solvate, stereoisomer, or tautomer thereof; wherein QQ comprises a triazole ring. In an embodiment, provided herein is a conjugate according to Formula (above), or a pharmaceutically acceptable salt, solvate, stereoisomer, or tautomer thereof; wherein QQ is a triazole ring or fused cyclic group comprising a triazole ring. In an embodiment, provided herein is a conjugate according to Formula (above), or a pharmaceutically acceptable salt, solvate, stereoisomer, or tautomer thereof; wherein QQ is:

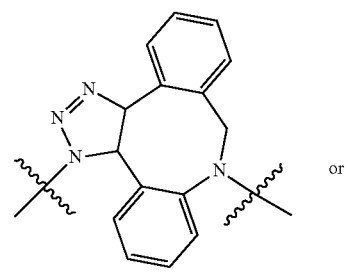

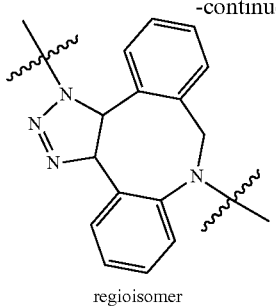

regioisomer wherein the wavy line indicates a bond to an adjacent atom.

In an aspect, provided herein is an IL-2 conjugate comprising water-soluble polymer, described herein, and an optional linker, described herein, linked to an TL-2 conjugate, wherein COMP is a residue of the IL-2 conjugate. In an embodiment, provided herein is an IL-2 conjugate according to Formula (above), or a pharmaceutically acceptable salt, solvate, stereoisomer, or tautomer thereof, wherein: COMP is a residue of the IL-2 moiety; and QQ comprises a triazole ring or fused cyclic group comprising a triazole ring. In an embodiment, provided herein is an IL-2 conjugate according to Formula (C1), or a pharmaceutically acceptable salt, solvate, stereoisomer, or tautomer thereof, wherein: COMP is a residue of the IL-2 moiety; and QQ is:

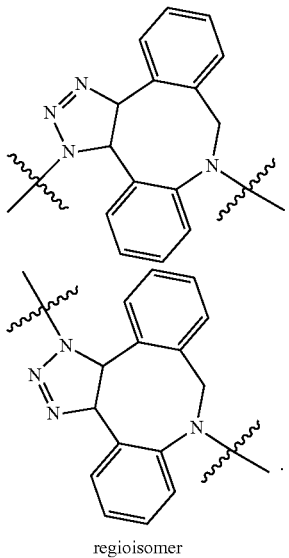

regioisomer wherein the wavy line indicates a bond to an adjacent atom.

In an embodiment, provided herein is a conjugate according to the following formula, wherein COMP indicates a non-natural amino acid residue of the IL-2 moiety, p is an integer from 1 to 10; n is an integer from 1 to 5,000; and, R is an end-capping group selected from methyl and H:

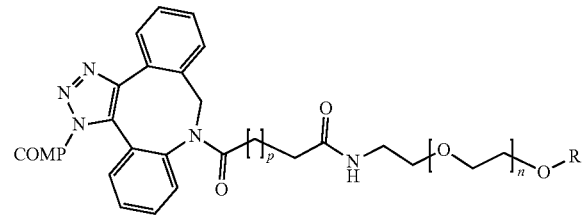

or regioisomer having the formula

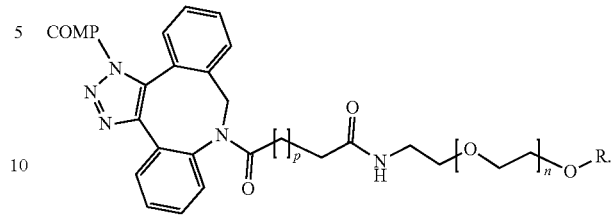

In particular embodiments, provided herein are IL-2 conjugates according to either wherein COMP indicates a residue of the non-natural amino acid at one or more IL-2 moiety positions selected from the group consisting of amino terminus, P1, T2, S3, S4, S5, T6, K7, K8, and T9, wherein the amino acid positions correspond to numbering scheme A. In certain embodiments, COMP indicates a residue of the non-natural amino acid at position S4.

In particular embodiments of the above conjugates, the non-natural amino acid residue within the IL-2 moiety having an azide functional group has the following formula:

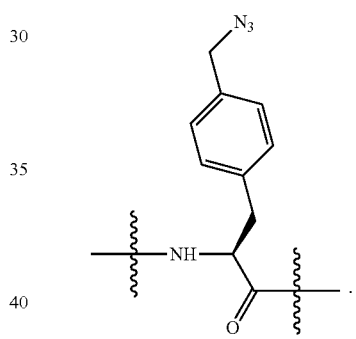

wherein the wavy line indicates a bond to adjacent amino acids of the IL-2 analog.

Exemplary compounds include conjugates having the following formula

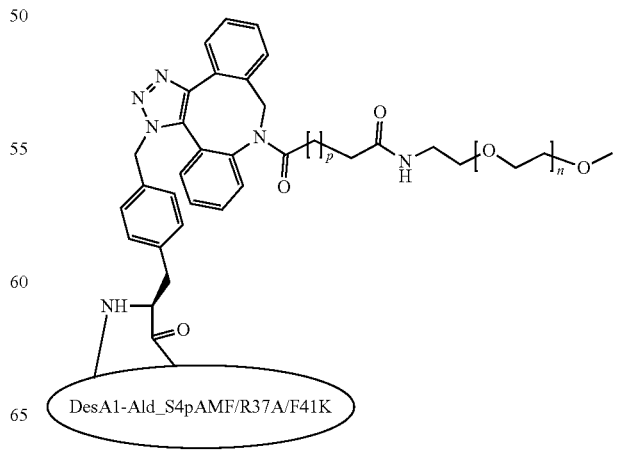

wherein p is an integer from 1 to 10 and n is an integer from 1 to 5,000 or its regioisomer having the formula
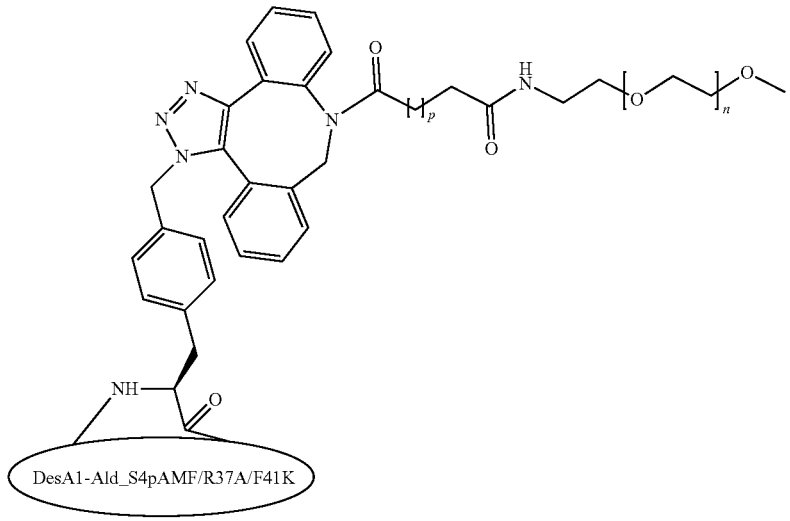
wherein p is an integer from 1 to 10 and n is an integer from 1 to 5,000, and
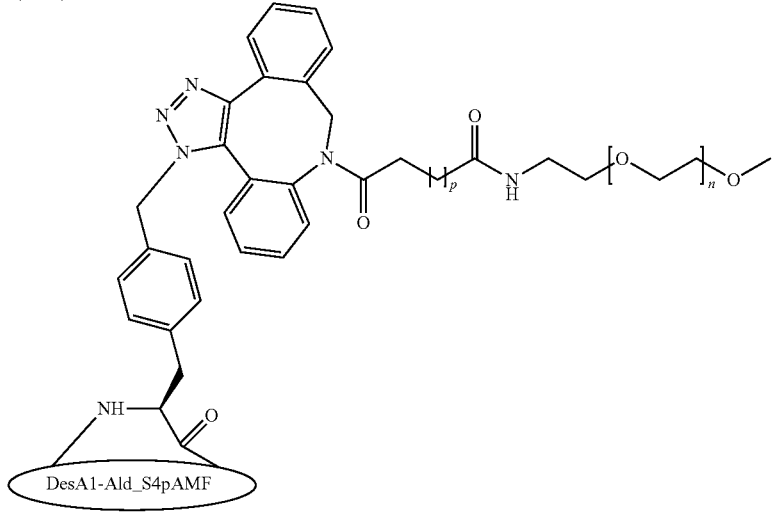
wherein p is an integer from 1 to 10 and n is an integer from 1 to 5,000, or its regioisomer having the formula
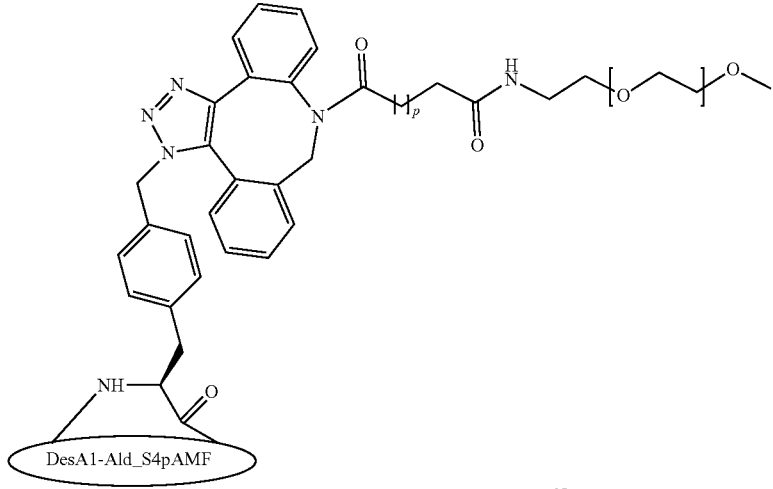
wherein p is an integer from 1 to 10 and n is an integer from 1 to 5,000.

Exemplary compounds include conjugates having the following formula
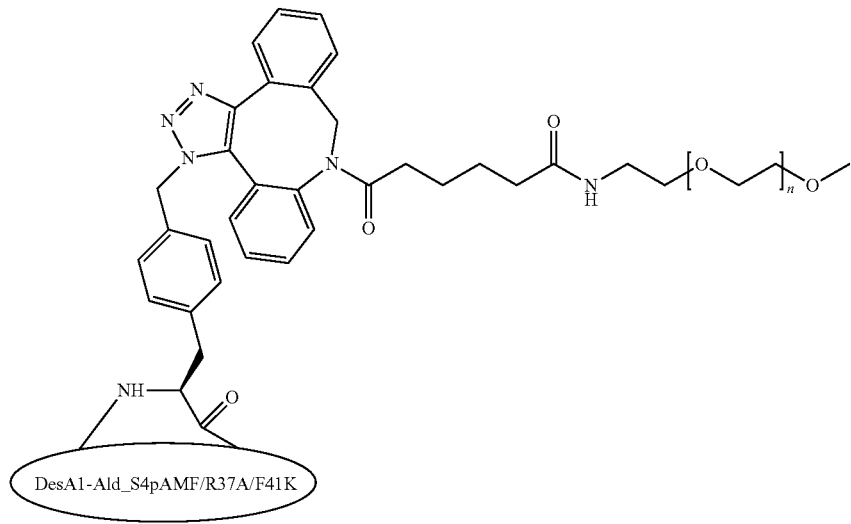
wherein n is an integer from 1 to 5,000 or its regioisomer having the formula
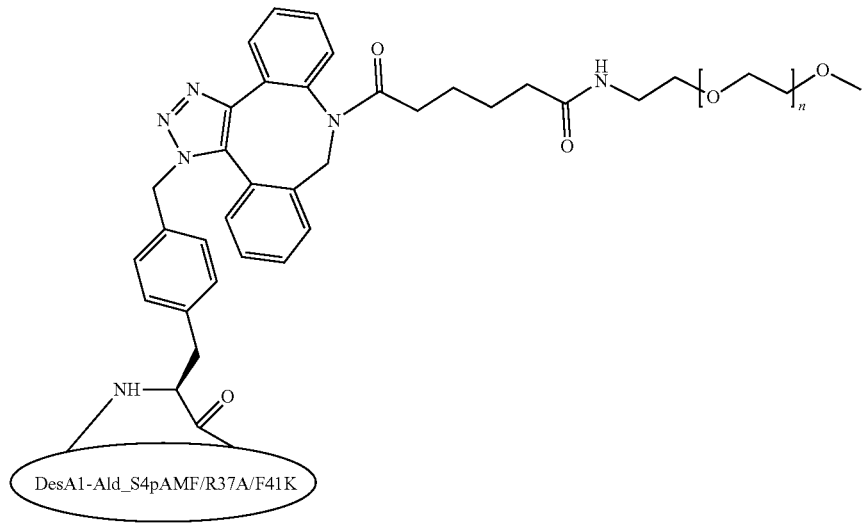
wherein n is an integer from 1 to 5,000, and
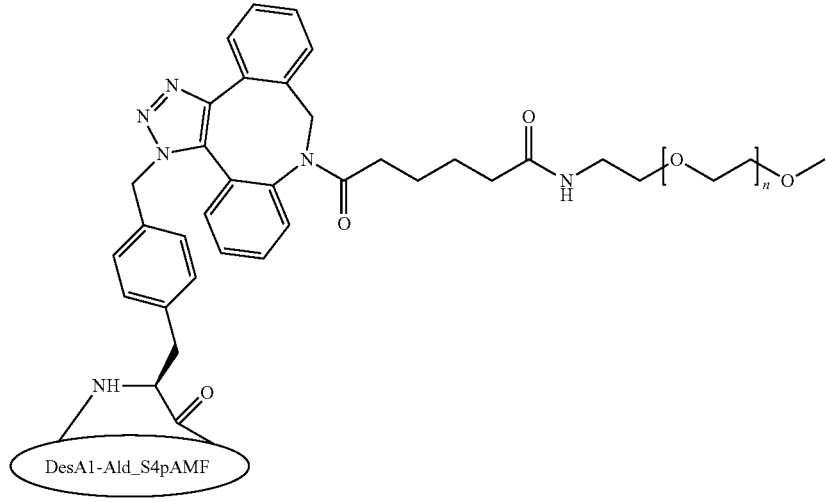

wherein n is an integer from 1 to 5,000, or its regioisomer having the formula
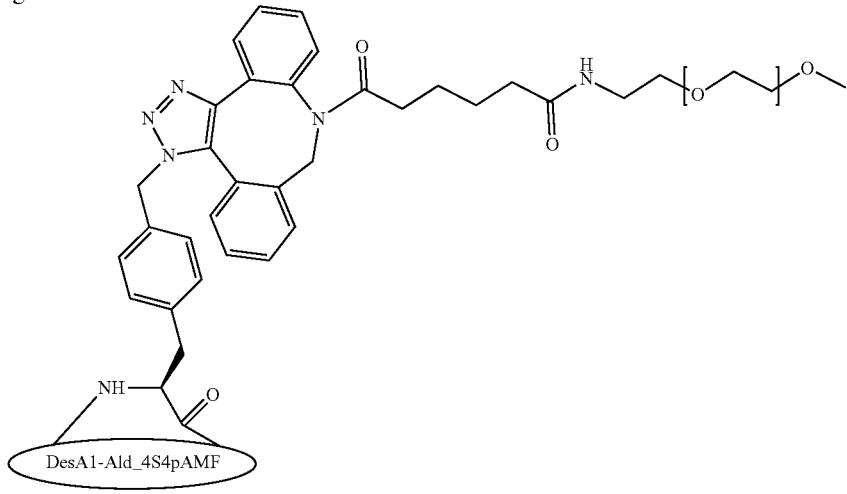
wherein n is an integer from 1 to 5,000.
Exemplary conjugates further include conjugates having the following formula:
CON1
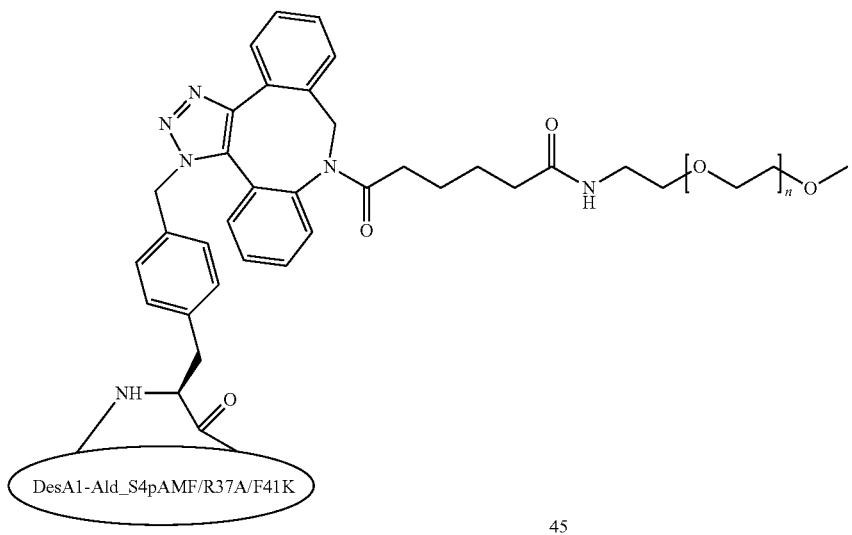
wherein n is about 681 or its regioisomer having the formula
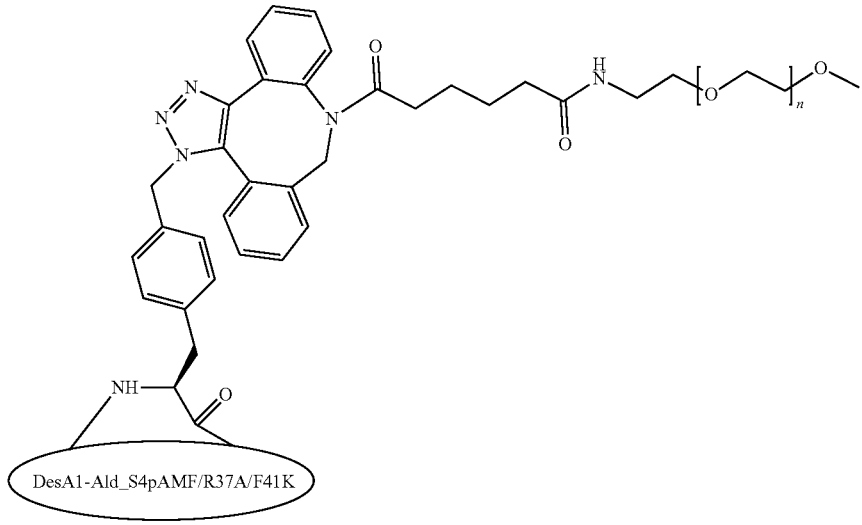

wherein n is about 681, and
CON2

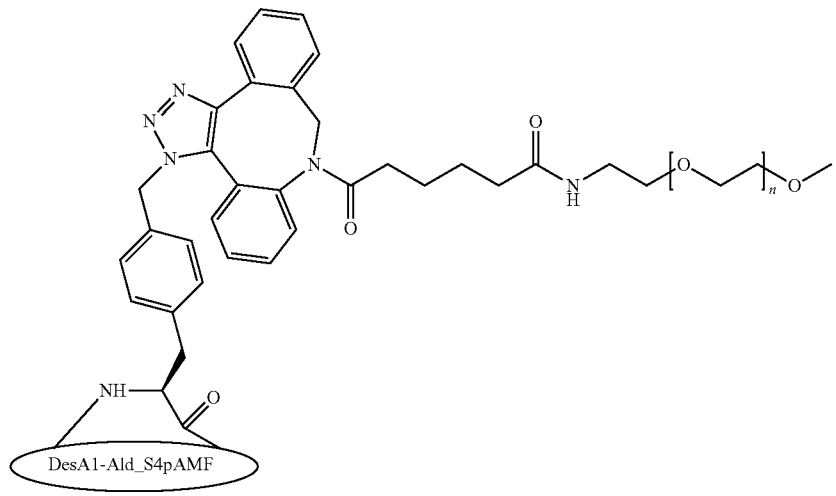

wherein n is about 681, or its regioisomer having the formula

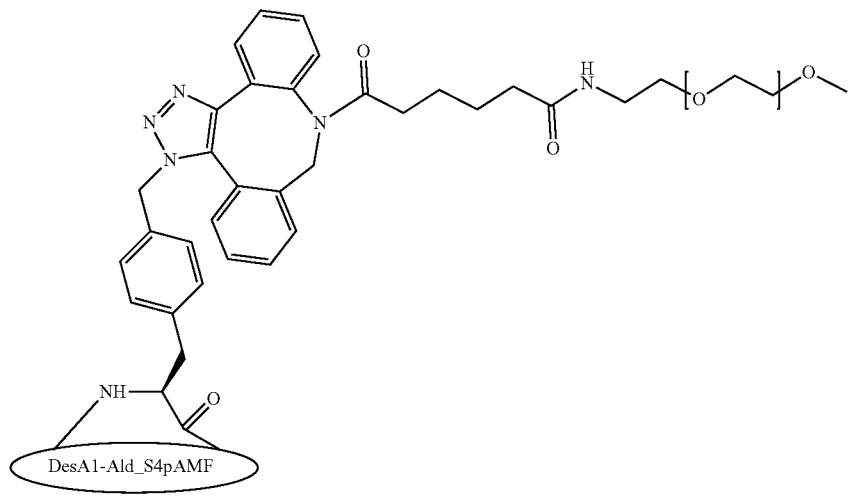

wherein n is about 681.

Preparation of IL-2 Conjugates

The IL-2 conjugates can be prepared by standard techniques. In certain embodiments, an IL-2 moiety is contacted with a nonpeptidic, water-soluble polymer precursor under conditions suitable for forming a bond from the IL-2 moiety to the nonpeptidic, water-soluble polymer precursor to form an IL-2 moiety-water-soluble polymer conjugate. In certain embodiments, an IL-2 moiety is contacted with a linker precursor under conditions suitable for forming a bond from the IL-2 moiety to the linker. The resulting IL-2 moiety-linker is contacted with a nonpeptidic, water-soluble polymer precursor under conditions suitable for forming a bond from the IL-2 moiety-linker to the nonpeptidic, water-soluble polymer precursor to form an IL-2 moiety-linker-nonpeptidic, water-soluble polymer conjugate. In certain embodiments, a nonpeptidic, water-soluble polymer precursor is contacted with a linker precursor under conditions suitable for forming a bond from the nonpeptidic, water-soluble polymer to the linker. The resulting water-soluble polymer-linker is contacted with an IL-2 moiety under conditions suitable for forming a bond from the nonpeptidic, water-soluble polymer-linker to the IL-2 moiety to form an IL-2 moiety-linker-nonpeptidic, water-soluble polymer conjugate. Suitable linkers for preparing the IL-2 conjugates are disclosed herein, and exemplary conditions for conjugation are described in the Examples below.

Embodiments are also directed to the provision of isolated nucleic acids encoding IL-2 moieties, vectors and host cells comprising the nucleic acids, and recombinant techniques for the production of IL-2 moieties.

For recombinant production of an IL-2 moiety, the nucleic acid(s) encoding it may be isolated and inserted into a replicable vector for further cloning (i.e., amplification of the DNA) or expression. In some embodiments, the nucleic acid may be produced by homologous recombination, for example as described in U.S. Pat. No. 5,204,244, incorporated by reference in its entirety.

Many different vectors are known in the art. The vector components generally include, but are not limited to, one or more of the following: a signal sequence, an origin of replication, one or more marker genes, an enhancer element, a promoter, and a transcription termination sequence, for example as described in U.S. Pat. No. 5,534,615, incorporated by reference in its entirety.

Expression of the IL-2 moiety, which comprises one or more non-natural amino acids, may be performed in an orthogonal biosynthetic translation system that is capable of site-specific substitution of any selected amino acid within the sequence of IL-2 with a non-natural amino acid. Such orthogonal biosynthetic translational machinery comprises orthogonal tRNAs and orthogonal-RS and orthogonal tRNAs/orthogonal-RS pairs, which when introduced into a host cell or cell-free translation system, can be used to incorporate a non-natural amino acid into a polypeptide (protein) of interest. The orthogonal tRNA delivers the non-natural amino acid in response to a selector codon and the orthogonal synthetase preferentially aminoacylates an orthogonal tRNA with the non-natural amino acid. The O—RS does not efficiently aminoacylate the orthogonal tRNA with any of the common twenty amino acids. Methods for constructing orthogonal biosynthetic translation system for cell-based or cell-free expression and using such systems for incorporating non-natural amino acids into a polypeptide at predetermined sites are known in the art and have been disclosed, for example, U.S. Pat. Nos. 9,797,908; 7,736,872; 9,163,271; 9,797,908; 97979908; 8445446; 7736872; 7846689; and US publication 20170292139; each of which is herein incorporated by reference in their entirety.

Once the IL-2 moiety incorporating the non-natural amino acid(s) has been produced in the host cell or cell-free orthogonal translation system, it can be extracted therefrom by a variety of techniques known in the art, including enzymatic, chemical and/or osmotic lysis and physical disruption. The cytokine (e.g., IL-2) polypeptide can be purified by standard techniques known in the art such as preparative chromatography, affinity purification or any other suitable technique.

Suitable host cells may include bacterial cells, for example *E. coli*, and eukaryote cells, for example insect cells (e.g. *Drosophila* such as *Drosophila melanogaster*), yeast cells, nematodes (e.g. *C. elegans*), mice (e.g. *Mus musculus*), or mammalian cells (such as Chinese hamster ovary cells (CHO) or COS cells, human 293T cells, HeLa cells, NIH 3T3 cells, and mouse erythroleukemia (MEL) cells) or human cells or other eukaryotic cells. Other suitable host cells are known to those skilled in the art.

When creating cell lines, it is generally preferred that stable cell lines are prepared. For stable transfection of mammalian cells for example, it is known that, depending upon the expression vector and transfection technique used, only a small fraction of cells may integrate the foreign DNA into their genome. In order to identify and select these integrants, a gene that encodes a selectable marker (for example, for resistance to antibiotics) is generally introduced into the host cells along with the gene of interest. Preferred selectable markers include those that confer resistance to drugs, such as G418, hygromycin, or methotrexate. Nucleic acid molecules encoding a selectable marker can be introduced into a host cell on the same vector or can be introduced on a separate vector. Cells stably transfected with the introduced nucleic acid molecule can be identified by drug selection (for example, cells that have incorporated the selectable marker gene will survive, while the other cells die).

In one embodiment, the conjugates described herein are integrated into the genome of the host cell. An advantage of stable integration is that the uniformity between individual cells or clones is achieved. Another advantage is that selection of the best producers may be performed. Accordingly, it is desirable to create stable cell lines. In another embodiment, the conjugates described herein are transfected into a host cell. An advantage of transfecting the conjugates into the host cell is that protein yields may be maximized. In one aspect, there is described a cell comprising the nucleic acid construct or the vector described herein.

Pharmaceutical Compositions and Methods of Administration

The IL-2 conjugates provided herein can be formulated into pharmaceutical compositions using methods available in the art and those disclosed herein. Any of the IL-2 conjugates provided herein can be provided in the appropriate pharmaceutical composition and be administered by a suitable route of administration.

The methods provided herein encompass administering pharmaceutical compositions comprising at least one IL-2 conjugate provided herein and one or more compatible and pharmaceutically acceptable earners. In this context, the term "pharmaceutically acceptable" means approved by a regulatory agency of the Federal or a state government or listed in the U.S. Pharmacopeia or other generally recognized pharmacopeia for use in animals, and more particularly in humans. The term "carrier" includes a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water can be used as a carrier when the pharmaceutical composition is administered intravenously. Saline solutions and aqueous dextrose and glycerol solutions can also be employed as liquid carriers, particularly for injectable solutions. Examples of suitable pharmaceutical earners are described in Martin, E. W., *Remington's Pharmaceutical Sciences*.

In clinical practice the pharmaceutical compositions or IL-2 conjugates provided herein may be administered by any route known in the art. Exemplary routes of administration include, but are not limited to, the inhalation, intraarterial, intradermal, intramuscular, intraperitoneal, intravenous, nasal, parenteral, pulmonary, and subcutaneous routes. In some embodiments, a pharmaceutical composition or IL-2 conjugate provided herein is administered parenterally.

The compositions for parenteral administration can be emulsions or sterile solutions. Parenteral compositions may include, for example, propylene glycol, polyethylene glycol, vegetable oils, and injectable organic esters (e.g., ethyl oleate). These compositions can also contain wetting, isotonizing, emulsifying, dispersing and stabilizing agents. Sterilization can be carried out in several ways, for example using a bacteriological filter, by radiation or by heating. Parenteral compositions can also be prepared in the form of sterile solid compositions which can be dissolved at the time of use in sterile water or any other injectable sterile medium.

In some embodiments, a composition provided herein is a pharmaceutical composition or a single unit dosage form. Pharmaceutical compositions and single unit dosage forms provided herein comprise a prophylactically or therapeutically effective amount of one or more prophylactic or therapeutic IL-2 conjugates.

The pharmaceutical composition may comprise one or more pharmaceutical excipients. Any suitable pharmaceutical excipient may be used, and one of ordinary skill in the art is capable of selecting suitable pharmaceutical excipients. Non-limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form depends on a variety of factors well known in the art including, but not limited to, the way in which the dosage form will be administered to a subject and the specific IL-2 moiety in the dosage form. The composition or single unit dosage form, if desired, can also contain minor amounts of wetting or emulsifying agents, or pH buffering agents. Accordingly, the pharmaceutical excipients provided below are intended to be illustrative, and not limiting. Additional pharmaceutical excipients include, for example, those described in the *Handbook of Pharmaceutical Excipients*, Rowe et al. (Eds.) 6th Ed. (2009), incorporated by reference in its entirety.

In some embodiments, the pharmaceutical composition comprises an anti-foaming agent. Any suitable anti-foaming agent may be used. In some aspects, the anti-foaming agent is selected from an alcohol, an ether, an oil, a wax, a silicone, a surfactant, and combinations thereof. In some aspects, the anti-foaming agent is selected from a mineral oil, a vegetable oil, ethylene bis stearamide, a paraffin wax, an ester wax, a fatty alcohol wax, a long chain fatty alcohol, a fatty acid soap, a fatty acid ester, a silicon glycol, a fluorosilicone, a polyethylene glycol-polypropylene glycol copolymer, polydimethylsiloxane-silicon dioxide, ether, octyl alcohol, capryl alcohol, sorbitan trioleate, ethyl alcohol, 2-ethylhexanol, dimethicone, oleyl alcohol, simethicone, and combinations thereof.

In some embodiments, the pharmaceutical composition comprises a co-solvent. Illustrative examples of co-solvents include ethanol, poly(ethylene) glycol, butylene glycol, dimethylacetamide, glycerin, and propylene glycol.

In some embodiments, the pharmaceutical composition comprises a buffer. Illustrative examples of buffers include acetate, borate, carbonate, lactate, malate, phosphate, citrate, hydroxide, diethanolamine, monoethanolamine, glycine, methionine, guar gum, and monosodium glutamate.

In some embodiments, the pharmaceutical composition comprises a carrier or filler. Illustrative examples of carriers or fillers include lactose, maltodextrin, mannitol, sorbitol, chitosan, stearic acid, xanthan gum, and guar gum.

In some embodiments, the pharmaceutical composition comprises a surfactant. Illustrative examples of surfactants include d-alpha tocopherol, benzalkonium chloride, benzethonium chloride, cetrimide, cetylpyridinium chloride, docusate sodium, glyceryl behenate, glyceryl monooleate, lauric acid, macrogol 15 hydroxystearate, myristyl alcohol, phospholipids, polyoxyethylene alkyl ethers, polyoxyethylene sorbitan fatty acid esters, polyoxyethylene stearates, polyoxylglycerides, sodium lauryl sulfate, sorbitan esters, and vitamin E polyethylene(glycol) succinate.

In some embodiments, the pharmaceutical composition comprises an anti-caking agent. Illustrative examples of anti-caking agents include calcium phosphate (tribasic), hydroxymethyl cellulose, hydroxypropyl cellulose, and magnesium oxide.

Other excipients that may be used with the pharmaceutical compositions include, for example, albumin, antioxidants, antibacterial agents, antifungal agents, bioabsorbable polymers, chelating agents, controlled release agents, diluents, dispersing agents, dissolution enhancers, emulsifying agents, gelling agents, ointment bases, penetration enhancers, preservatives, solubilizing agents, solvents, stabilizing agents, and sugars. Specific examples of each of these agents are described, for example, in the *Handbook of Pharmaceutical Excipients*, Rowe et al. (Eds.) 6th Ed. (2009), The Pharmaceutical Press, incorporated by reference in its entirety.

In some embodiments, the pharmaceutical composition comprises a solvent. In some aspects, the solvent is saline solution, such as a sterile isotonic saline solution or dextrose solution. In some aspects, the solvent is water for injection.

In some embodiments, the pharmaceutical compositions are in a particulate form, such as a microparticle or a nanoparticle. Microparticles and nanoparticles may be formed from any suitable material, such as a polymer or a lipid. In some aspects, the microparticles or nanoparticles are micelles, liposomes, or polymersomes.

Further provided herein are anhydrous pharmaceutical compositions and dosage forms comprising an IL-2 conjugate, since, in some embodiments, water can facilitate the degradation of some proteins.

Anhydrous pharmaceutical compositions and dosage forms provided herein can be prepared using anhydrous or low moisture containing ingredients and low moisture or low humidity conditions. Pharmaceutical compositions and dosage forms that comprise lactose and at least one active ingredient that comprises a primary or secondary amine can be anhydrous if substantial contact with moisture and/or humidity during manufacturing, packaging, and/or storage is expected.

An anhydrous pharmaceutical composition can be prepared and stored such that its anhydrous nature is maintained. Accordingly, anhydrous compositions can be packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Lactose-free compositions provided herein can comprise excipients that are well known in the art and are listed, for example, in the U.S. Pharmacopeia (USP) SP (XXI)/NF (XVI). In general, lactose-free compositions comprise an active ingredient, a binder/filler, and a lubricant in pharmaceutically compatible and pharmaceutically acceptable amounts. Exemplary lactose-free dosage forms comprise an active ingredient, microcrystalline cellulose, pre gelatinized starch, and magnesium stearate.

Also provided are pharmaceutical compositions and dosage forms that comprise one or more excipients that reduce the rate by which an IL-2 moiety or IL-2 conjugate will decompose. Such excipients, which are referred to herein as "stabilizers," include, but are not limited to, antioxidants such as ascorbic acid, pH buffers, or salt buffers.

Parenteral Dosage Forms

In certain embodiments, provided are parenteral dosage forms. Parenteral dosage forms can be administered to subjects by various routes including, but not limited to, subcutaneous, intravenous (including bolus injection), intramuscular, and intraarterial. Because their administration typically bypasses subjects' natural defenses against contaminants, parenteral dosage forms are typically, sterile or capable of being sterilized prior to administration to a subject. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Excipients that increase the solubility of one or more of the proteins disclosed herein can also be incorporated into the parenteral dosage forms.

Dosage and Unit Dosage Forms

In human therapeutics, the doctor will determine the posology which he considers most appropriate according to a preventive or curative treatment and according to the age, weight, condition and other factors specific to the subject to be treated.

In certain embodiments, a composition provided herein is a pharmaceutical composition or a single unit dosage form. Pharmaceutical compositions and single unit dosage forms provided herein comprise a prophylactically or therapeutically effective amount of one or more prophylactic or therapeutic proteins.

The amount of the IL-2 conjugate or composition which will be effective in the prevention or treatment of a disorder or one or more symptoms thereof will vary with the nature and severity of the disease or condition, and the route by which the IL-2 moiety is administered. The frequency and dosage will also vary according to factors specific for each subject depending on the specific therapy (e.g., therapeutic or prophylactic agents) administered, the severity of the disorder, disease, or condition, the route of administration, as well as age, body, weight, response, and the past medical history of the subject. Effective doses may be extrapolated from dose-response curves derived from in vitro or animal model test systems.

In certain embodiments, exemplary doses of a composition include milligram or microgram amounts of the IL-2 moiety per kilogram of subject or sample weight (e.g., about 10 micrograms per kilogram to about 50 milligrams per kilogram, about 100 micrograms per kilogram to about 25 milligrams per kilogram, or about 100 microgram per kilogram to about 10 milligrams per kilogram). In certain embodiment, the dosage of the IL-2 conjugate provided herein, based on weight of the IL-2 moiety, administered to prevent, treat, manage, or ameliorate a disorder, or one or more symptoms thereof in a subject is 0.1 mg/kg, 1 mg/kg, 2 mg/kg, 3 mg/kg, 4 mg/kg, 5 mg/kg, 6 mg/kg, 10 mg/kg, or 15 mg/kg or more of a subject's body weight.

The dose can be administered according to a suitable schedule, for example, once, two times, three times, or four times weekly. It may be necessary to use dosages of the IL-2 conjugate outside the ranges disclosed herein in some cases, as will be apparent to those of ordinary skill in the art. Furthermore, it is noted that the clinician or treating physician will know how and when to interrupt, adjust, or terminate therapy in conjunction with subject response.

Different therapeutically effective amounts may be applicable for different diseases and conditions, as will be readily known by those of ordinary skill in the art. Similarly, amounts sufficient to prevent, manage, treat or ameliorate such disorders, but insufficient to cause, or sufficient to reduce, adverse effects associated with the proteins provided herein are also encompassed by the herein described dosage amounts and dose frequency schedules. Further, when a subject is administered multiple dosages of a composition provided herein, not all of the dosages need be the same. For example, the dosage administered to the subject may be increased to improve the prophylactic or therapeutic effect of the composition or it may be decreased to reduce one or more side effects that a particular subject is experiencing.

In certain embodiments, treatment or prevention can be initiated with one or more loading doses of an IL-2 conjugate or composition provided herein followed by one or more maintenance doses.

In certain embodiments, a dose of an IL-2 conjugate or composition provided herein can be administered to achieve a steady-state concentration of the IL-2 moiety in blood or serum of the subject. The steady-state concentration can be determined by measurement according to techniques available to those of skill or can be based on the physical characteristics of the subject such as height, weight and age.

In certain embodiments, administration of the same composition may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same prophylactic or therapeutic agent may be repeated and the administration may be separated by at least 1 day, 2 days, 3 days, 5 days, 10 days, 15 days, 30 days, 45 days, 2 months, 75 days, 3 months, or 6 months.

Therapeutic Applications

For therapeutic applications, the IL-2 conjugates provided herein can be administered to a mammal, generally a human, in a pharmaceutically acceptable dosage form such as those known in the art and those discussed above. For example, the IL-2 conjugates may be administered to a human intravenously as a bolus or by continuous infusion over a period of time, by intramuscular, intraperitoneal, intra-cerebrospinal, subcutaneous, intra-articular, intrasynovial, intrathecal, or intratumoral routes. The IL-2 conjugates also are suitably administered by peritumoral, intralesional, or perilesional routes, to exert local as well as systemic therapeutic effects. The intraperitoneal route may be particularly useful, for example, in the treatment of ovarian tumors.

The IL-2 conjugates provided herein may be useful for the treatment of any disease or condition involving an IL2 receptor. In some embodiments, the disease or condition is a disease or condition that would benefit from stimulation or amplification of the immune response. In some embodiments, the disease or condition is a disease or condition that can benefit from treatment with an IL-2 moiety. In some embodiments, the disease or condition is a cancer. In some embodiments, the disease or condition is an infectious disease (e.g., HIV infection or HCV infection).

Any suitable cancer may be treated with the IL-2 conjugates provided herein. Illustrative suitable cancers include, for example, acute lymphoblastic leukemia (ALL), acute myeloid leukemia (AML), adrenocortical carcinoma, anal cancer, appendix cancer, astrocytoma, basal cell carcinoma, brain tumor, bile duct cancer, bladder cancer, bone cancer, breast cancer (including triple-negative breast cancer, or TNBC), bronchial tumor, carcinoma of unknown primary origin, cardiac tumor, cervical cancer, chordoma, colon cancer, colorectal cancer, craniopharyngioma, ductal carcinoma, embryonal tumor, endometrial cancer, ependymoma, esophageal cancer, esthesioneuroblastoma, fallopian tube carcinoma, fibrous histiocytoma, Ewing sarcoma, eye cancer, germ cell tumor, gallbladder cancer, gastric cancer, gastrointestinal carcinoid tumor, gastrointestinal stromal tumor, gestational trophoblastic disease, glioma, head and neck cancer, hepatocellular cancer, histiocytosis, Hodgkin lymphoma, hypopharyngeal cancer, intraocular melanoma, islet cell tumor, Kaposi sarcoma, kidney cancer, Langerhans cell histiocytosis, laryngeal cancer, lip and oral cavity cancer, liver cancer, lobular carcinoma in situ, lung cancer, macroglobulinemia, malignant fibrous histiocytoma, melanoma, Merkel cell carcinoma, mesothelioma, metastatic squamous neck cancer with occult primary, midline tract carcinoma involving NUT gene, mouth cancer, multiple endocrine neoplasia syndrome, multiple myeloma, mycosls fungoides, myelodysplastic syndrome, myelodysplastic/myeloproliferative neoplasm, nasal cavity and par nasal sinus cancer, nasopharyngeal cancer, neuroblastoma, non-small cell lung cancer (NSCLC), oropharyngeal cancer, osteosarcoma, ovarian cancer, pancreatic cancer, papillomatosis, paraganglioma, parathyroid cancer, penile cancer, pharyngeal cancer, pheochromocytomas, pituitary tumor, pleuropulmonary blastoma, primary central nervous system lymphoma, primary peritoneal carcinoma, prostate cancer, rectal cancer, renal cell cancer, renal pelvis and ureter cancer, retinoblastoma, rhabdoid tumor, salivary gland cancer, Sezary syndrome, skin cancer, small cell lung cancer, small intestine cancer, soft tissue sarcoma, spinal cord tumor, stomach cancer, T-cell lymphoma, teratoid tumor, testicular cancer, throat cancer, thymoma and thymic carcinoma, thyroid cancer, urethral cancer, uterine cancer, vaginal cancer, vulvar cancer, and Wilms tumor.

In some embodiments, the disease to be treated with the IL-2 conjugates provided herein is gastric cancer, colorectal cancer, renal cell carcinoma, cervical cancer, non-small cell lung carcinoma, ovarian cancer, uterine cancer, fallopian tube carcinoma, primary peritoneal carcinoma, uterine corpus carcinoma, endometrial carcinoma, prostate cancer, breast cancer, head and neck cancer, brain carcinoma, liver cancer, pancreatic cancer, mesothelioma, and/or a cancer of epithelial origin. In particular embodiments, the disease is colorectal cancer. In some embodiments, the disease is ovarian cancer. In some embodiments, the disease is breast cancer. In some embodiments, the disease is triple-negative breast cancer (TNBC). In some embodiments, the disease is lung cancer. In some embodiments, the disease is non-small cell lung cancer (NSCLC). In some embodiments, the disease is head and neck cancer. In some embodiments, the disease is renal cell carcinoma. In some embodiments, the disease is brain carcinoma. In some embodiments, the disease is endometrial cancer.

Combination Products

Further provided are combination products comprising an IL-2 conjugate or composition as disclosed herein. In particular embodiments, the IL-2 conjugate is contained within a medical delivery device. Medical delivery device has the definition set forth in Section 201(h) and includes but not limited to syringes, autoinjectors, medical pens, pumps, and the like.

In particular embodiments, the combination product comprises a therapeutic agent and an IL-2 conjugate that is physically, chemically, or otherwise combined or mixed and produced as a single entity.

The combination product further includes embodiments in which the IL-2 conjugate is packaged separately and is intended for use only with an approved individually specified therapeutic agent or device where both are required to achieve the intended use, indication, or effect and where upon approval of the IL-2 conjugate the labeling of the approved product would need to be changed, e.g., to reflect a change in intended use, dosage form, strength, route of administration, or significant change in dose.

The combination product further includes embodiments in which the IL-2 conjugate is packaged separately and which according to its proposed labeling is for use only with another individually specified investigational therapeutic agent or device where both are required to achieve the intended use, indication, or effect.

In particular embodiments, the therapeutic agent is a checkpoint inhibitor such as a PD-1 blocking agent is an anti-PD-1 antibody or anti-PD-L1 antibody. Exemplary anti-PD-1 antibodies that may be used in the combination therapy of the present invention include any antibody that binds PD-1 and inhibits PD-1 from binding PD-L1. In a further embodiment, the exemplary anti-PD-1 antibody is selected from the group consisting of nivolumab, pembrolizumab, and cemiplimab-rwlc. Exemplary antibodies include the following anti-PD-1 antibodies and compositions comprising an anti-PD1 antibody and a pharmaceutically acceptable carrier or salt.

Pembrolizumab, also known as KEYTRUDA, lambrolizumab, MK-3475 or SCH-900475, is a humanized anti-PD-1 antibody described in U.S. Pat. No. 8,354,509 and WO2009/114335 and disclosed, e.g., in Hamid, et al., New England J. Med. 369 (2): 134-144 (2013). Nivolumab, also known as OPDIVO, MDX-1106-04, ONO-4538, or BMS-936558, is a fully human IgG4 anti-PD-1 antibody described in WO2006/121168 and U.S. Pat. No. 8,008,449. Cemiplimab-rwlc, also known as cemiplimab, LIBTAYO or REGN2810, is a recombinant human IgG4 monoclonal antibody that is described in WO2015112800 and U.S. Pat. No. 9,987,500.

In particular embodiments, the therapeutic agent is a chemotherapy agent. Exemplary chemotherapy agents include but are not limited to (i) alkylating agents, including but not limited to, bifunctional alkylators, cyclophosphamide, mechlorethamine, chlorambucil, and melphalan;

(ii) monofunctional alkylators, including but not limited to, dacarbazine, nitrosoureas, and temozolomide (oral dacarbazine);

(iii) anthracyclines, including but not limited to, daunorubicin, doxorubicin, epirubicin, idarubicin, mitoxantrone, and valrubicin;

(iv) cytoskeletal disruptors (taxanes), including but not limited to, paclitaxel, docetaxel, abraxane, and taxotere;

(v) epothilones, including but not limited to, ixabepilone, and utidelone; (vi) histone deacetylase inhibitors, including but not limited to, vorinostat, and romidepsin;

(vii) inhibitors of topoisomerase i, including but not limited to, irinotecan, and topotecan; (viii) inhibitors of topoisomerase ii, including but not limited to, etoposide, teniposide, and tafluposide;

(ix) kinase inhibitors, including but not limited to, bortezomib, erlotinib, gefitinib, imatinib, vemurafenib, and vismodegib;

(x) nucleotide analogs and precursor analogs, including but not limited to, azacitidine, azathioprine, fluoropyrimidines (e.g., such as capecitabine, carmofur, doxifluridine, fluorouracil, and tegafur) cytarabine, gemcitabine, hydroxyurea, mercaptopurine, methotrexate, and tioguanine (formerly thioguanine);

(xi) peptide antibiotics, including but not limited to, bleomycin and actinomycin; a platinum-based agent, including but not limited to, carboplatin, cisplatin, and oxaliplatin;

(xii) retinoids, including but not limited to, tretinoin, alitretinoin, and bexarotene; and (xiii) vinca alkaloids and derivatives, including but not limited to, vinblastine, vincristine, vindesine, and vinorelbine.

Combination Therapy

The present invention provides combination therapies for the treatment of a human or animal individual comprising administering an IL-2 conjugate of the present invention and a second therapeutic agent consecutively or concurrently to the individual. In one embodiment, the IL-2 conjugate is administered to an individual at a time prior to a time the individual is administered the therapeutic agent. In another embodiment, the therapeutic agent is administered to an individual at a time before the individual is administered the IL-2 conjugate. The IL-2 conjugate and therapeutic agent may be administered in separate doses and in different formats.

In particular embodiments, the therapeutic agent is a checkpoint inhibitor such as a PD-1 blocking agent. The PD-1 blocking agent may be administered at the same dose, dosing frequency, and treatment duration as that approved for the PD-1 blocking agent in a monotherapy for particular indications. The dose of the IL-2 conjugate may be administered at the same dosing frequency and treatment duration as approved by the United States Food and Drug Administration (U.S. FDA) or at a dosing frequency and treatment duration as for the particular PD-1 blocking agent that is paired with IL-2 conjugate.

In particular embodiments, the PD-1 blocking agent is an anti-PD-1 antibody or anti-PD-L1 antibody. Exemplary anti-PD-1 antibodies that may be used in the combination therapy of the present invention include any antibody that binds PD-1 and inhibits PD-1 from binding PD-L1. In a further embodiment, the exemplary anti-PD-1 antibody is selected from the group consisting of nivolumab, pembrolizumab, and cemiplimab-rwlc. Exemplary antibodies include the following anti-PD-1 antibodies and compositions comprising an anti-PD1 antibody and a pharmaceutically acceptable salt.

The particular dose of the currently marketed anti-PD-1 antibodies vary between the antibodies, thus in particular embodiments of the combination therapy of the present invention, the dose, dosing frequency, and/or treatment duration may be at least the same as that approved by the U.S. FDA for the particular anti-PD-1 antibody for particular indications. For example, pembrolizumab is approved for a dose of 200 mg every three weeks as needed (pediatric individuals (two years up to 18 years) at 2 mg/kg up to 200 mg every three weeks as needed); nivolumab is approved at a dose of 3 mg/kg every 2 weeks; cemiplimab-rwlc is approved for a dose of 350 mg every three weeks as needed; atezolizumab is approved for a dose of 1200 mg every three weeks as needed; avelumab is approved for a dose of 10 mg/kg or 800 mg every two weeks as needed; and durvalumab is approved for a dose of 10 mg/kg every two weeks as needed.

In particular embodiments of the combination therapy, the PD-1 blocking agent is an anti-PD-1 antibody or anti-PD-1 antibody fragment, which may be administered at a dose from about 150 mg to about 250 mg, from about 175 mg to about 250 mg, from about 200 mg to about 250 mg, from about 150 mg to about 240 mg, from about 175 mg to about 240 mg, or from about 200 mg to about 240 mg. In some embodiments, the dose of the anti-PD-1 antibody or antigen binding fragment thereof is 150 mg, 175 mg, 200 mg, 225 mg, 240 mg, or 250 mg. In further embodiments, the anti-PD-1 antibody or anti-PD-1 antibody fragment may be administered at a frequency of every three weeks as needed. In another embodiment of the combination therapy of the present invention, the anti-PD-1 antibody or anti-PD-1 antibody fragment may be administered at dose greater than 250 mg, for example, a dose of about 400 mg at a frequency of every six weeks as needed.

In particular embodiments of the combination therapy, the PD-1 blocking agent is an anti-PD-1 antibody or anti-PD-1 antibody fragment, which may be administered at a dose from about 10 mg/kg to about 1200 mg. In further embodiments, the PD-1 blocking agent fragment may be administered at a frequency of every two to three weeks as needed.

While the PD-1 blocking agent may be administered at least at the doses, dosing frequencies, and treatment durations approved for the currently marketed PD-1 blocking agents in a monotherapy, the actual doses, dosing frequencies, and treatment durations for any particular combination of the present invention may differ from those that are approved for the PD-1 blocking agent monotherapies. Thus, in particular embodiments of the combination therapy of the present invention, the dose, dosing frequency, and treatment duration of any particular PD-1 blocking agent in the combination therapy will be determined from clinical trials conducted for the combination therapy.

In a particular embodiment of the combination therapy, the PD-1 blocking agent is nivolumab or an effector-silent variant of nivolumab, which is administered to an individual intravenously at a dose of 3 mg/kg over 30 to 60 minutes every two-three weeks as needed and wherein each dose of the IL-2 conjugate is administered intravenously following the administration of the PD-1 blocking agent for the same treatment duration as the PD-1 blocking agent or for duration less than or more than the PD-1 blocking agent duration. In a particular embodiment, the nivolumab or effector-silent variant of nivolumab is administered intravenously to an individual at an initial dose of 3 mg/kg intravenously over 30 minutes followed by administration of the IL-2 conjugate intravenously over 30 minutes on the same day, every three weeks for four doses, then nivolumab is administered intravenously at a fixed dose of 240 mg every two weeks over 30 minutes or 480 mg every four weeks over 30 minutes.

In a particular embodiments, the PD-1 blocking agent is pembrolizumab or effector-silent variant of pembrolizumab, which is administered to an adult individual intravenously at a dose of 200 mg over 30 minutes every three weeks as needed or to a pediatric individual intravenously at a dose of 2 mg/kg up to a maximum of about 200 mg over 30 minutes every three weeks wherein each treatment is followed by a dose of the IL-2 conjugate wherein each dose of the IL-2 conjugate is administered intravenously following administration of the PD-1 blocking agent for the same treatment duration as the PD-1 blocking agent or for duration less than or more than the PD-1 blocking agent duration.

In a particular embodiments, the PD-1 blocking agent is pembrolizumab or effector-silent variant of pembrolizumab, which is administered to an adult individual intravenously at a dose of 400 mg over 30 minutes every six weeks as needed wherein each treatment is followed by a dose of the IL-2 conjugate wherein each dose of the IL-2 conjugate is administered intravenously following the administration of the PD-1 blocking agent for the same treatment duration as the PD-1 blocking agent or for duration less than or more than the PD-1 blocking agent duration.

In a particular embodiment of the combination therapy, the PD-1 blocking agent is cemiplimab-rwlc or an effector-silent variant of cemiplimab-rwlc, which is administered to an individual intravenously at a dose of 350 mg over 30 minutes every three weeks as needed and wherein each dose of the IL-2 conjugate is administered intravenously following the administration of the PD-1 blocking agent for the same treatment duration as the PD-1 blocking agent or for duration less than or more than the PD-1 blocking agent duration. In a particular embodiment, the cemiplimab-rwlc or effector-silent variant of cemiplimab-rwlc is administered intravenously to an individual at an initial dose of 350 mg over 30 minutes followed by administration of the IL-2 conjugate over 30 minutes on the same day every three weeks as needed.

In a particular embodiment of the combination therapy, the PD-1 blocking agent is atezolizumab or an effector-silent variant of atezolizumab, which is administered to an individual intravenously at a dose of 1200 mg over 60 minutes every three weeks as needed and wherein each dose of the IL-2 conjugate is administered intravenously following the administration of the PD-1 blocking agent for the same treatment duration as the PD-1 blocking agent or for duration less than or more than the PD-1 blocking agent duration. In a particular embodiment, the atezolizumab or effector-silent variant of atezolizumab is administered intravenously to an individual at an initial dose of 1200 mg over 60 minutes followed by administration of the IL-2 conjugate over 30 minutes on the same day every three weeks as needed.

In a particular embodiment of the combination therapy, the PD-1 blocking agent is avelumab or an effector-silent variant of avelumab, which is administered to an individual intravenously at a dose of 10 mg/kg or 800 mg over 60 minutes every two weeks as needed and wherein each dose of the IL-2 conjugate is administered intravenously following the administration of the PD-1 blocking agent for the same treatment duration as the PD-1 blocking agent or for duration less than or more than the PD-1 blocking agent duration. In a particular embodiment, the avelumab or effector-silent variant of avelumab is administered intravenously to an individual at an initial dose of 10 mg/kg or 800 mg over 60 minutes followed by administration of the IL-2 conjugate over 30 minutes on the same day every two weeks as needed.

In a particular embodiment of the combination therapy, the PD-1 blocking agent is durvalumab or an effector-silent variant of durvalumab, which is administered to an individual intravenously at a dose of 10 mg/kg over 60 minutes every two weeks as needed and wherein each dose of the IL-2 conjugate is administered intravenously following the administration of the PD-1 blocking agent for the same treatment duration as the PD-1 blocking agent or for duration less than or more than the PD-1 blocking agent duration. In a particular embodiment, the durvalumab or effector-silent variant of durvalumab is administered intravenously to an individual at an initial dose of 10 mg/kg over 60 minutes followed by administration of the IL-2 conjugate over 30 minutes on the same day every two weeks as needed.

While the currently approved PD-1 blocking agents are provided in formulations at a concentration that permits intravenous administration to an individual over a 30 to 60 minute time frame, the combination therapies of the present invention contemplate embodiments in which the IL-2 conjugate and/or the PD-1 blocking agent are each provided in a formulation at a concentration that permits each to be separately administered to an individual in a single injection. Being able to provide at least one of the two blocking agents in a single injection would significantly reduce the time for administering both blocking agent to the individual.

In a further embodiment, the present invention provides a combination therapy in which the IL-2 conjugate and the PD-1 blocking agent are co-administered at the same time. Co-administration may be accomplished by providing the IL-2 conjugate and PD-1 blocking agents in separate formulations and simultaneously providing each formulation to the individual, either by separate IVs or mixing prior to administering the mixture by IV to the individual by IV, or by separate injection of each formulation into the individual. Co-administration may also be accomplished by providing the IL-2 conjugate and PD-1 blocking agents in a single formulation that is then administered to the individual in a single IV or in a single injection.

The combination therapy of the present invention may be administered to an individual having a cancer in combination with chemotherapy. The individual may undergo the chemotherapy at the same time the individual is undergoing the combination therapy of the present invention. The individual may undergo the combination therapy of the present invention after the individual has completed chemotherapy. The individual may be administered the chemotherapy after completion of the combination therapy. The combination therapy of the present invention may also be administered to an individual having recurrent or metastatic cancer with disease progression or relapse cancer and who is undergoing chemotherapy or who has completed chemotherapy.

Selecting a dose of the chemotherapy agent for chemotherapy depends on several factors, including the serum or tissue turnover rate of the entity, the level of symptoms, the immunogenicity of the entity, and the accessibility of the target cells, tissue or organ in the individual being treated. The dose of the additional therapeutic agent should be an amount that provides an acceptable level of side effects. Accordingly, the dose amount and dosing frequency of each additional therapeutic agent will depend in part on the particular therapeutic agent, the severity of the cancer being treated, and patient characteristics. Guidance in selecting appropriate doses of antibodies, cytokines, and small molecules are available. See, e.g., Wawrzynczak (1996) *Antibody Therapy*, Bios Scientific Pub. Ltd, Oxfordshire, UK; Kresina (ed.) (1991) *Monoclonal Antibodies, Cytokines and Arthritis*, Marcel Dekker, New York, NY; Bach (ed.) (1993) *Monoclonal Antibodies and Peptide Therapy in Autoimmune Diseases*, Marcel Dekker, New York, NY; Baert et al. (2003) *New Engl. J. Med.* 348:601-608; Milgrom et al. (1999) *New Engl. J. Med.* 341:1966-1973; Slamon et al. (2001) *New Engl. J. Med.* 344:783-792; Beniaminovitz et al. (2000) *New Engl. J. Med.* 342:613-619; Ghosh et al. (2003) *New Engl. J. Med.* 348:24-32; Lipsky et al. (2000) *New Engl. J. Med.* 343:1594-1602; Physicians' Desk Reference 2003 (Physicians' Desk Reference, 57th Ed); Medical Economics Company; ISBN: 1563634457; 57th edition (November 2002). Determination of the appropriate dose regimen may be made by the clinician, e.g., using parameters or factors known or suspected in the art to affect treatment or predicted to affect treatment, and will depend, for example, the individual's clinical history (e.g., previous therapy), the type and stage of the cancer to be treated and biomarkers of response to one or more of the therapeutic agents in the combination therapy.

For example, pembrolizumab is currently approved by the U.S. FDA for a combination therapy for (i) treating non-small cell lung cancer (NSCLC) comprising pembrolizumab with pemetrexed and platinum chemotherapy or carboplatin and either paclitaxel or nab-paclitaxel; and (ii) treating head and neck squamous cell cancer (HNSCC) comprising pembrolizumab and platinum-containing chemotherapy, and atezolizumab is currently approved for a combination therapy for treating NSCLC comprising bevacizumab (anti-VEGF-A antibody marketed under the tradename AVASTIN), paclitaxel, and carboplatin.

Thus, the present invention contemplates embodiments of the combination therapy of the present invention that further includes a chemotherapy step comprising platinum-containing chemotherapy, pemetrexed and platinum chemotherapy or carboplatin and either paclitaxel or nab-paclitaxel. In particular embodiments, the combination therapy with a chemotherapy step may be used for treating at least NSCLC and HNSCC.

The combination therapy further in combination with a chemotherapy step may be used for the treatment any proliferative disease, in particular, treatment of cancer. In particular embodiments, the combination therapy of the present invention may be used to treat melanoma, non-small cell lung cancer, head and neck cancer, urothelial cancer, breast cancer, gastrointestinal cancer, multiple myeloma, hepatocellular cancer, non-Hodgkin lymphoma, renal cancer, Hodgkin lymphoma, mesothelioma, ovarian cancer, small cell lung cancer, esophageal cancer, anal cancer, biliary tract cancer, colorectal cancer, cervical cancer, thyroid cancer, or salivary cancer.

In another embodiment, the combination therapy further in combination with a chemotherapy step may be used to treat pancreatic cancer, bronchus cancer, prostate cancer, pancreatic cancer, stomach cancer, ovarian cancer, urinary bladder cancer, brain or central nervous system cancer, peripheral nervous system cancer, uterine or endometrial cancer, cancer of the oral cavity or pharynx, liver cancer, kidney cancer, testicular cancer, biliary tract cancer, small bowel or appendix cancer, adrenal gland cancer, osteosarcoma, chondrosarcoma, or cancer of hematological tissues.

In particular embodiments, the combination therapy with a chemotherapy step may be used to treat one or more cancers selected from melanoma (metastatic or unresectable), primary mediastinal large B-cell lymphoma (PMBCL), urothelial carcinoma, MSIHC, gastric cancer, cervical cancer, hepatocellular carcinoma (HCC), Merkel cell carcinoma (MCC), renal cell carcinoma (including advanced), and cutaneous squamous carcinoma.

Combination Therapy Treatments

The combination therapy of the present invention may be used for the treatment any proliferative disease, in particular, treatment of cancer. In particular embodiments, the combination therapy of the present invention may be used to treat melanoma, non-small cell lung cancer, head and neck cancer, urothelial cancer, breast cancer, gastrointestinal cancer, multiple myeloma, hepatocellular cancer, non-Hodgkin lymphoma, renal cancer, Hodgkin lymphoma, mesothelioma, ovarian cancer, small cell lung cancer, esophageal cancer, anal cancer, biliary tract cancer, colorectal cancer, cervical cancer, thyroid cancer, or salivary cancer.

In another embodiment, the combination therapy of the present invention may be used to treat pancreatic cancer, bronchus cancer, prostate cancer, pancreatic cancer, stomach cancer, ovarian cancer, urinary bladder cancer, brain or central nervous system cancer, peripheral nervous system cancer, uterine or endometrial cancer, cancer of the oral cavity or pharynx, liver cancer, kidney cancer, testicular cancer, biliary tract cancer, small bowel or appendix cancer, adrenal gland cancer, osteosarcoma, chondrosarcoma, or cancer of hematological tissues.

The currently marketed PD-1 blocking agents are approved by the U.S. FDA to treat at least one or more cancers selected from melanoma (metastatic or unresectable), primary mediastinal large B-cell lymphoma (PMBCL), urothelial carcinoma, MSIHC, gastric cancer, cervical cancer, hepatocellular carcinoma (HCC), Merkel cell carcinoma (MCC), renal cell carcinoma (including advanced), and cutaneous squamous carcinoma. Thus, the combination therapy of the present invention may be used to treat at least one or more cancers selected from melanoma (metastatic or unresectable), primary mediastinal large B-cell lymphoma (PMBCL), urothelial carcinoma, MSIHC, gastric cancer, cervical cancer, hepatocellular carcinoma (HCC), Merkel cell carcinoma (MCC), renal cell carcinoma (including advanced), and cutaneous squamous carcinoma.

Kits

In some embodiments, an IL-2 conjugate provided herein is provided in the form of a kit, i.e., a packaged combination of reagents in predetermined amounts with instructions for performing a procedure. In some embodiments, the procedure is a diagnostic assay. In other embodiments, the procedure is a therapeutic procedure.

In some embodiments, the kit further comprises a solvent for the reconstitution of the IL-2 conjugate. In some embodiments, the IL-2 conjugate is provided in the form of a pharmaceutical composition. In some embodiments, the kit further includes a therapeutic agent other than the IL-2 conjugate. In a further embodiment, the kit comprises a combination product comprising the IL-2 conjugate contained within a medical delivery device.

The following examples are intended to promote a further understanding of the present invention.

General Methods

Standard methods in molecular biology are described in Sambrook, Fritsch and Maniatis (1982 & 1989 2nd Edition, 2001 3rd Edition) Molecular Cloning, A Laboratory Manual, Cold Spring Harbor Laboratory Press, Cold Spring Harbor, NY; and Sambrook and Russell (2001) Molecular Cloning, 3rd ed., Cold Spring Harbor Laboratory Press, Cold Spring Harbor, NY; Wu (1993) Recombinant DNA, Vol. 217, Academic Press, San Diego, CA). Standard methods also appear in Ausbel, et al. (2001), Current Protocols in Molecular Biology, Vols. 1-4, John Wiley and Sons, Inc. New York, NY, which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described (Coligan, et al. (2000) Current Protocols in Protein Science, Vol. 1, John Wiley and Sons, Inc., New York). Chemical analysis, chemical modification, post-translational modification, production of fusion proteins, and glycosylation of proteins are described (See, e.g., Coligan, et al. (2000) Current Protocols in Protein Science, Vol. 2, John Wiley and Sons, Inc., New York; Ausubel, et al. (2001) Current Protocols in Molecular Biology, Vol. 3, John Wiley and Sons, Inc., NY, NY, pp. 16.0.5-16.22.17 and Sigma-Aldrich, Co. (2001) Products for Life Science Research, St. Louis, MO; pp. 45-89; Amersham Pharmacia Biotech (2001) BioDirectory, Piscataway, N.J., pp. 384-391). Production, purification, and fragmentation of polyclonal and monoclonal antibodies have been described (See Coligan, et al. (2001) Current Protocols in Immunology, Vol. 1, John Wiley and Sons, Inc., New York and Harlow and Lane (1999) Using Antibodies, Cold Spring Harbor Laboratory Press, Cold Spring Harbor, NY). Standard techniques for characterizing ligand/receptor interactions are available (see, e.g., Coligan, et al. (2001) Current Protocols in Immunology, Vol. 4, John Wiley, Inc., New York).

Example 1

IL-2 Sites for Para Azidomethylphenylalanine (pAMF) Para-Azidomethylphenylalanine (pAMF) Incorporation and PEG Conjugation Individual IL-2 variants were designed to incorporate non-natural pAMF residues in place of specific residues using the Sutro Xpress CF+ cell-free expression platform (Yin et al Sci Rep 2017, 7, 1, 3026). Sites were chosen for pAMF incorporation to enable the conjugation of polyethylene glycol (PEG) moieties via copper-catalyzed azide-alkyne cycloaddition (CuAAC) or a copper-free conjugation method, e.g. strain-promoted azide-alkyne cycloaddition (SPAAC) through dibenzocyclooctyne (DBCO or DIBO).

The co-crystal structure of IL-2 bound to IL-2Rα, IL-2Rγ$_c$, and IL-2Rβ (Stauber et al., 2006, *Proc Natl Acad Sci USA* 103:2793; pdb code 2ERJ) was analyzed using PyMOL to identify which residues have side-chains that point to the solvent or to the IL-2Rα interface. Such residues were chosen for pAMF incorporation to enable conjugation to PEG. In particular, 12 residues near the N-terminus for pAMF incorporation were chosen that have side-chains pointing to the solvent. Conjugation of PEG to any of these sites are selected to increase the half-life of IL-2, lower the dose requirements, and/or increase the overall exposure. Incorporation of pAMF and/or conjugation of PEG at these sites are also selected to impact binding affinities for IL-2Rα, IL-2Rγ$_c$, and IL-2Rβ, which can be used to optimize the therapeutic properties as described below. IL-2 variants were made using standard mutagenesis or gene synthesis techniques and the positions for incorporating pAMF are shown in Table 1.

Aldesleukin (DesA1_IL-2_C124S, referred to as Ald; SEQ ID NO: 2) was modified to have a carboxyl-terminus HIS6-tag (SEQ ID NO: 54) (Ald-6HIS) linked via a Gly-Gly-Ser (GGS) linker and to have pAMF incorporated at the indicated sites shown in Table 1. These variants were expressed in Xpress+ CF in an overnight reaction in the presence of $^{14}$C-Leucine. The expressability of the IL-2 variants was estimated by $^{14}$C-incorporation (total yield), and the amount remaining in solution (soluble yield) was further measured following centrifugation at 14,000×g for 10 minutes. The measured yields are described in Table 1.

TABLE 1

Expression and solubility of Ald-6HIS with pAMF incorporation at the indicated site

| Position of pAMF incorporation in Ald-6HIS | Total Yield (µg/mL) | Soluble Yield (µg/mL) |
| --- | --- | --- |
| None | 692 | 463 |
| P1 | 600 | 276 |
| T2 | 585 | 278 |
| S3 | 549 | 286 |
| S4 | 579 | 308 |
| S5 | 606 | 304 |
| T6 | 631 | 211 |
| K7 | 639 | 322 |
| K8 | 637 | 226 |
| T9 | 614 | 127 |
| N25 | 653 | 244 |
| N28 | 708 | 158 |
| N29 | 607 | 241 |

The pAMF residues were chosen to allow conjugation of a non-degradable PEG. In this design, the conjugated PEG was intended to allow binding to all three IL-2R receptors and increase half-life. As in the above approach, it is desirable to have selective affinity for IL-2Rβ and IL-2Rγ$_c$ over IL-2Rα to increase the anti-tumor response of T-cells and NK-cells with minimal activation of immunosuppressive T$_{reg}$ cells. In this design, however, the resulting PEG-IL-2 conjugates are active upon initial dosing. As above, some binding to IL-2Rα may be beneficial, but dispensable, to reduce systemic toxicity through stimulation of T$_{reg}$ cells or other IL2Rα-expressing cell populations. Sites were scanned to identify those which yielded the optimal binding affinity for IL-2Rα, IL-2Rγ$_c$, and IL-2Rβ to maximize the therapeutic index. Overall, the long half-life and selective receptor engagement may have more preferable dosing and increased therapeutic index over standard IL-2 based therapies, e.g. aldesleukin.

The solubility of some variants appeared to be impacted by protein folding, stability, or aggregation-propensity of IL-2 with pAMF substitution at some sites. The top three IL-2 variants with the highest soluble yields were selected for further evaluation and were accordingly expressed and purified by IMAC resin purification followed by secondary purification with Capto Q resin. The IL-2 variants were then conjugated to a branched 20 kDa PEG (DBCO 2×10 kDa PEG) having the formula

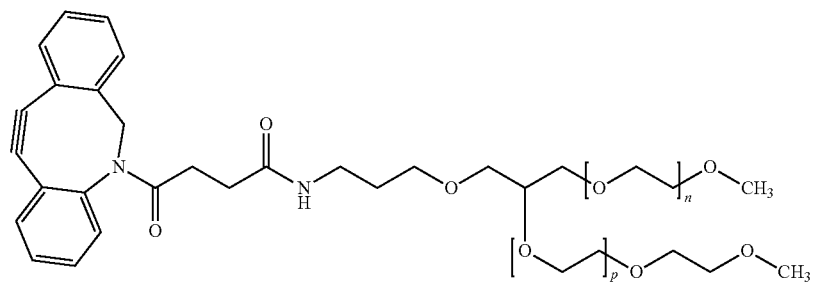

wherein n and p are each about 227. The unconjugated and PEG2-conjugated variants were also evaluated for thermostability (Table 2), IL-2Rα and IL-2Rβ binding (Table 3) and CTLL2 STAT5 reporter assay (Table 4).

TABLE 2

Thermostability of Ald-6HIS with pAMF incorporation at the indicated site

| Construct | Differential Scanning Fluorimetry, Tm (° C.) | |
|---|---|---|
| | Unconjugated | DBCO 2 × 10 kDa PEG (PEG2) |
| Ald-6HIS | 52.8 | NA |
| Ald-6HIS_S4pAMF | 50.4 | 58.8 |
| Ald-6HIS_S5pAMF | 51.7 | 57.0 |
| Ald-6HIS_K7pAMF | 49.3 | 57.4 |

NA = not applicable

TABLE 3

Kinetic affinity of Ald-6HIS variants (pAMF incorporated, with or without conjugation to DBCO-2 × 10 kDa PEG) to IL-2Rα-Fc and IL-2Rβ-Fc

| Construct | SPR IL-2Rα-Fc binding, (M) | | SPR IL-2Rβ-Fc binding, (M) | |
|---|---|---|---|---|
| | Unconjugated | DBCO 2 × 10 kDa PEG (PEG2) conjugated | Unconjugated | DBCO 2 × 10 kDa PEG (PEG2) conjugated |
| Ald-6HIS | 8E−09 | NA | 3E−07 | NA |
| Ald-6HIS_S4pAMF | 8E−09 | 1E−07 | 3E−07 | NC |
| Ald-6HIS_S5pAMF | 1E−08 | 7E−08 | 7E−07 | NC |
| Ald-6HIS_K7pAMF | 8E−09 | 8E−08 | 5E−07 | NC |

NA = not applicable
NC = not calculable
ND = not determined

TABLE 4

CTLL2 STAT5 reporter assay

| construct | Unconjugated EC50 (pM) | DBCO 2 × 10 kDa PEG (PEG2) conjugated EC50 (pM) |
|---|---|---|
| Ald-6HIS | 12 | NA |
| Ald-6HIS_S4pAMF | 11 | 209 |
| Ald-6HIS_S5pAMF | 10 | 169 |
| Ald-6HIS_K7pAMF | 10 | 245 |

Example 2

IL-2 Mutations for Lowering Affinity to IL2Rα

As described above, it is desirable to have an IL-2 variant for therapeutic purposes which shows lower affinity for IL-2Rα than natural IL-2 while maintaining binding to IL-2Rγ$_c$ and IL-2Rβ. This binding selectivity is expected to increase the anti-tumor response of T- and NK-cells with a lower response for immunosuppressive T$_{reg}$ cells relative to native IL-2.

To generate IL-2 variants that have a range of affinities for IL-2Rα, the co-crystal structure of IL-2 bound to IL-2Rα, IL-2Rγ$_c$, and IL-2Rβ (Stauber et al., 2006, *Proc Natl Acad Sci USA* 103:2793; pdb code 2ERJ) was first analyzed using PyMOL to identify which residues have side-chains that point to the IL-2Rα interface. Mutations were scanned at all of these sites using MOE (*Molecular Operating Environment (MOE)*, 2013.08; Chemical Computing Group ULC, 1010 Sherbooke St. West, Suite #910, Montreal, QC, Canada, H3A 2R7, 2018.) to identify mutations that are predicted to lower IL-2/IL-2Rα affinity without significantly impacting IL-2 stability.

In particular, 14 point mutations were chosen that were predicted to have desirable affinity and stability. These mutations were made in Ald-6HIS and consisted of the following substitutions: K34D, T36D, R37G, T40D, F41L, K42G, Y44V, E60T, E61S, K63G, P64A, E67G, L71I, and Y106A. Also, ten sets of triple mutations were chosen using combinations of these four substitutions P64A, E60T, E61S, Y106A, which were expected to further lower IL-2 affinity for IL-2Rα. The amino acid positions are numbered according to the numbering scheme A.

Figure 2A:
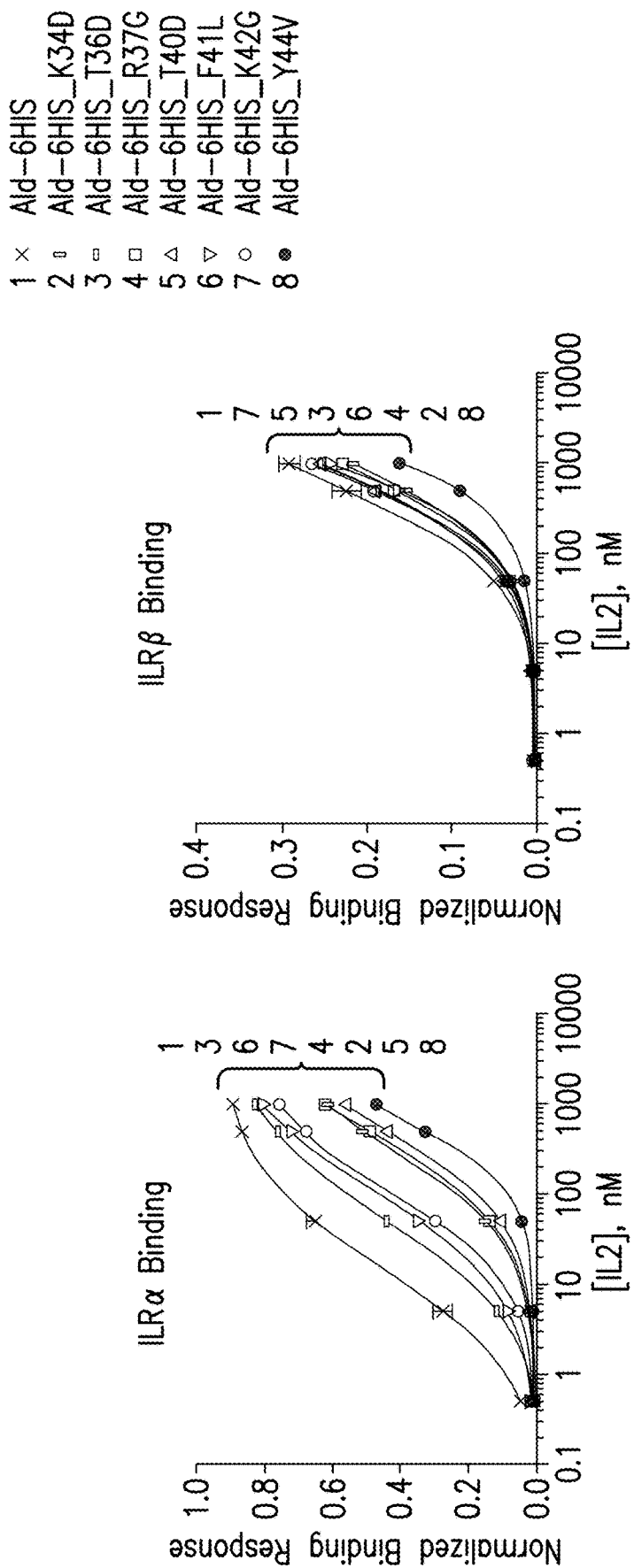
FIG. 2A shows the equilibrium binding of Ald-6HIS substitution variants K34D, T36D, R37G, T40D, F41L, K42G, and Y44V to immobilized biotin-labeled IL-2Rα or biotin-labeled IL-2Rβ.
Figure 2B:
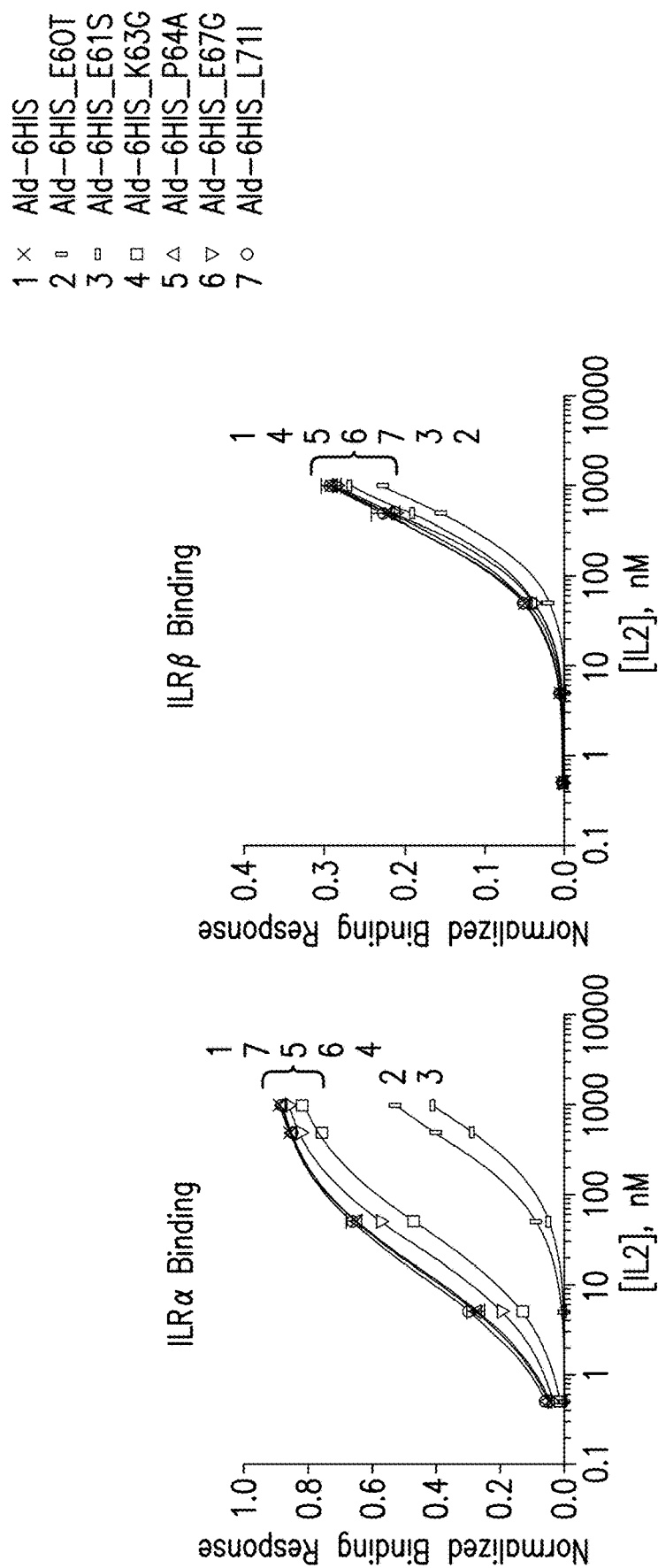
FIG. 2B shows the equilibrium binding of ald6HIS substitution variants E60T, E61S, K63G, P64A, E67G, and L71I to immobilized biotin-labeled IL-2Rα or biotin-labeled IL-2Rβ.
Figure 2C:
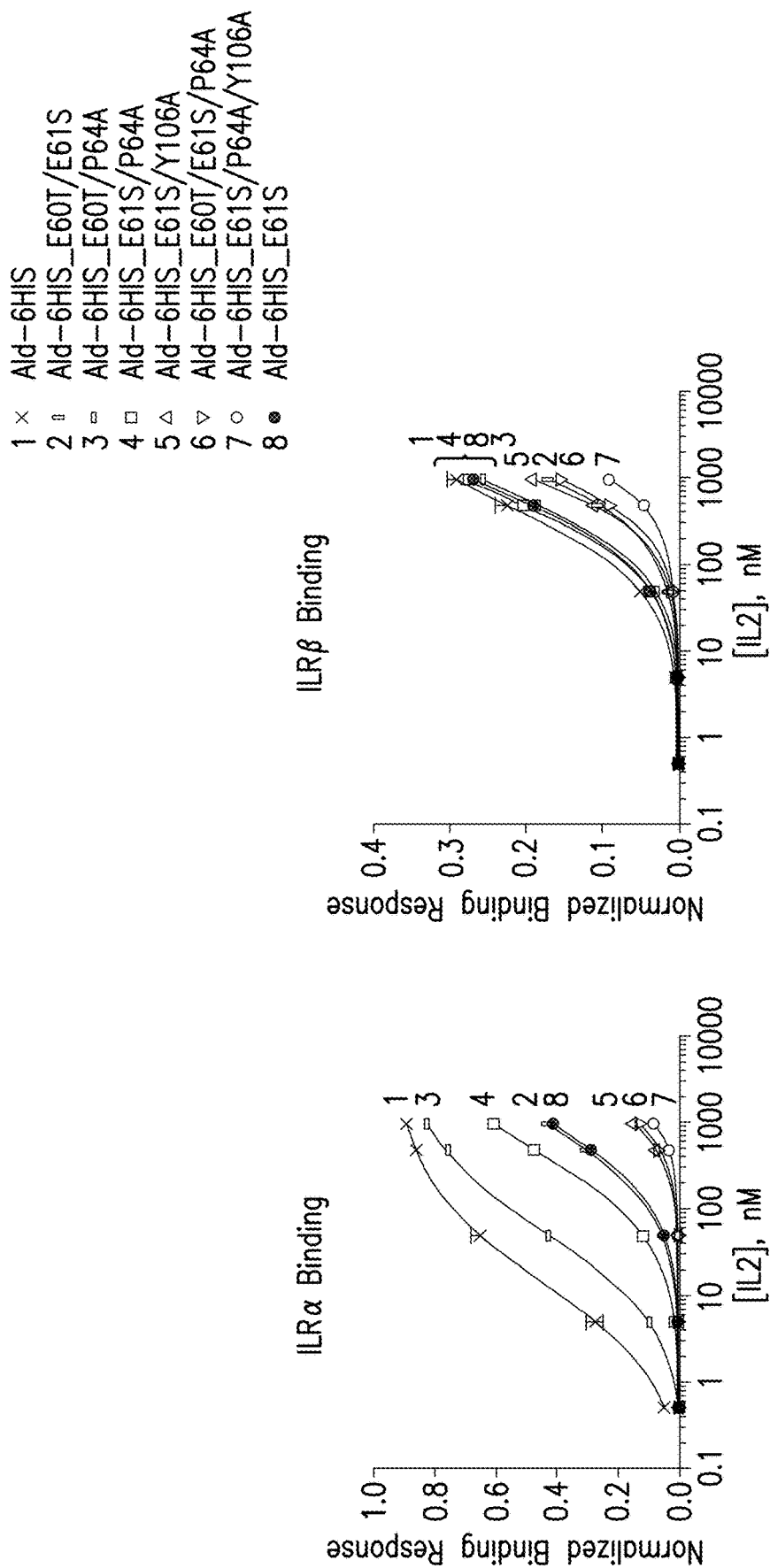
FIG. 2C shows the equilibrium binding Ald-6HIS substitution variants E60T/E61S, E60T/P64A, E61S/P64A, E61S/Y106A, E60T/E61S/P64A, E61S/P64A/Y106A, and E61S to immobilized biotin-labeled IL-2Rα or biotin-labeled IL-2Rβ.

FIG. 2A, FIG. 2B, and FIG. 2C show equilibrium binding of various IL-2 variants to immobilized biotin-IL-2Rα or biotin-IL-2Rβ.

The IL-2 variants that were synthesized using standard mutagenesis or gene synthesis techniques are shown in Table 5 below. Table 5 also shows IL-2Rα and IL-2Rβ binding data as determined by SPR on a Biacore T200 using the methods described in Example 9.

TABLE 5

Binding affinity determined by SPR

| Name | SPR Biotin-IL-2Rα-His (KD, M) | IL-2Rα binding (fold reduction over wt) | SPR Biotin-IL-2Rβ-His (KD, M) | IL-2Rβ binding (fold reduction over wt) |
|---|---|---|---|---|
| Ald-6HIS | 1.00E−08 | 1 | 4.00E−07 | 1 |
| Ald-6HIS_K34D | 3.00E−07 | 30 | 1.00E−06 | 3 |
| Ald-6HIS_T36D | 5.00E−08 | 5 | 8.00E−07 | 2 |
| Ald-6HIS_R37G | 5.00E−07 | 50 | 6.00E−07 | 2 |
| Ald-6HIS_T40D | 5.00E−07 | 50 | 6.00E−07 | 2 |
| Ald-6HIS_F41L | 1.00E−07 | 10 | 2.00E−06 | 5 |
| Ald-6HIS_K42G | 1.00E−07 | 10 | 6.00E−07 | 2 |
| Ald-6HIS_Y44V | 6.00E−07 | 60 | NC | |
| Ald-6HIS_E60T | 5.00E−07 | 50 | 8.00E−07 | 2 |
| Ald-6HIS_E61S | 9.00E−07 | 90 | 1.00E−06 | 3 |
| Ald-6HIS_K63G | 4.00E−08 | 4 | 5.00E−07 | 1 |
| Ald-6HIS_P64A | 1.00E−08 | 1 | 5.00E−07 | 1 |
| Ald-6HIS_E67G | 3.00E−08 | 3 | 6.00E−07 | 2 |
| Ald-6HIS_L71I | 1.00E−08 | 1 | 4.00E−07 | 1 |
| Ald-6HIS_Y106A | ND | ND | ND | ND |
| Ald-6HIS_E60T/E61S | 8.00E−07 | 80 | 2.00E−06 | 5 |
| Ald-6HIS_E60T/P64A | 6.00E−08 | 6 | 7.00E−07 | 2 |
| Ald-6HIS_E60T/Y106A | ND | ND | ND | ND |
| Ald-6HIS_E61S/P64A | 5.00E−07 | 50 | 5.00E−07 | 1 |
| Ald-6HIS_E61S/Y106A | NC | NC | 2.00E−06 | 5 |
| Ald-6HIS_P64A/Y106A | ND | ND | ND | ND |
| Ald-6HIS_E60T/E61S/P64A | 2.00E−06 | 200 | 1.00E−06 | 3 |
| Ald-6HIS_E60T/E61S/Y106A | ND | ND | ND | ND |
| Ald-6HIS_E60T/P64A/Y106A | ND | ND | ND | ND |
| Ald-6HIS_E61S/P64A/Y106A | NC | NC | NC | NC |

NC = not calculable
ND = not determined
wt = native IL-2 or aldesleukin activity The functional activity of the IL-2 variants was determined using the PathHunter U2OS IL2RB/IL2RG Dimerization Assay and the GboResponse STAT5-luc2-CTLL-2 Reporter Assay as described in Examples 11 and 12, respectively. The results are shown in Table 6.

TABLE 6

Cell-based assay measuring functional activity of IL-2 variants in reporter cell lines

| Name | U2OS-IL2Rbg EC50 (pM) | CTLL2-STAT5 EC50 (pM) |
|---|---|---|
| aldesleukin | 813 | 12 |
| Ald-6HIS_K34D | 865 | 12 |
| Ald-6HIS_T36D | 468 | 6 |
| Ald-6HIS_R37G | 753 | 18 |
| Ald-6HIS_T40D | 614 | 216 |
| Ald-6HIS_F41L | 1563 | 87 |
| Ald-6HIS_K42G | 1634 | 33 |
| Ald-6HIS_Y44V | 4188 | 679 |
| Ald-6HIS_E60T | 899 | 324 |
| Ald-6HIS_E61S | 623 | 5111 |
| Ald-6HIS_K63G | 485 | 5 |
| Ald-6HIS_P64A | 608 | 5 |
| Ald-6HIS_E67G | 879 | 7 |
| Ald-6HIS_L71I | 680 | 6 |
| Ald-6HIS_E60T_E61S | 1953 | 525 |
| Ald-6HIS_E60T_P64A | 499 | 24 |
| Ald-6HIS_E61S_P64A | 634 | 213 |
| Ald-6HIS_E61S_Y106A | 2868 | >7000 |
| Ald-6HIS_E60T_E61S_P64A | 1962 | 1093 |
| Ald-6HIS_E61S_P64A_Y106A | 5773 | >7000 |

>means "greater than"

To generate IL-2 variants with even lower affinity for IL-2Rα, another round of mutants was designed as shown in Table 7A-B. Specifically, from the first set described above, E60T, E61S, and T40D showed significant reductions in IL-2Rα binding and relatively low immunogenicity risk. R37A and F41K mutations were also included as they have been described previously to significantly lower binding to IL-2Rα (Heaton et al Cancer Res 1993, 53, 2597-2602). IL-2Rα and IL-2Rβ3 binding data as determined by SPR on a Biacore T200 using the methods described in Example 9.

TABLE 7A

Human IL-2Rα Binding Affinity Determined by SPR

| Name | ka (1/Ms) | kd (1/s) | KD (M) | Chi²/R max |
|---|---|---|---|---|
| Ald-6HIS | 1.2E+06 | 1.8E-01 | 1.6E-07 | 2.58% |
| Ald_F41/Y44A/l71G* | NC | NC | >1E-06 | 14.17% |
| Ald-6HIS_R37A/T40D | ND | ND | ND | |
| Ald-6HIS_R37A/F41K | ND | ND | ND | |
| Ald-6HIS_R37A/E60T | NC | NC | >1E-06 | 0.11% |
| Ald-6HIS_T40D/F41K | NC | NC | >1E-06 | 0.24% |
| Ald-6HIS_T40D/E60T | NC | NC | >1E-06 | 0.31% |
| Ald-6HIS_F41K/E60T | NC | NC | >1E-06 | 1.93% |
| Ald-6HIS_R37A/T40D/F41K | ND | ND | ND | |
| Ald-6HIS_R37A/T40D/E60T | ND | ND | ND | |
| Ald-6HIS_R37A/F41K/E60T | ND | ND | ND | |
| Ald-6HIS_T40D/F41K/E60T | ND | ND | ND | |

ND—not determined;
NC—not calculable
>—greater than

TABLE 7B

Human IL-2Rβ Binding Affinity Determined by SPR

| Name | Ka (1/Ms) | Kd (1/s) | KD (M) | Chi²/R max |
|---|---|---|---|---|
| Ald-6HIS | 2.5E+05 | 3.1E-01 | 1.2E-06 | 1% |
| Ald_F41/Y44A/l71G* | 3.9E+05 | 3.0E-01 | 7.7E-07 | 1% |
| Ald-6HIS_R37A/T40D | 3.4E+05 | 2.5E-01 | 7.3E-07 | 0% |
| Ald-6HIS_R37A/F41K | 3.0E+05 | 3.0E-01 | 1.0E-06 | 4% |
| Ald-6HIS_R37A/E60T | 7.5E+04 | 8.2E-02 | 1.1E-06 | 24% |
| Ald-6HIS_T40D/F41K | 3.3E+05 | 3.2E-01 | 9.8E-07 | 5% |
| Ald-6HIS_T40D/E60T | 3.6E+05 | 3.6E-01 | 9.9E-07 | 1% |
| Ald-6HIS_F41K/E60T | 4.4E+05 | 4.7E-01 | 1.1E-06 | 1% |
| Ald-6HIS_R37A/T40D/F41K | 4.1E+05 | 2.4E-01 | 5.9E-07 | 1% |
| Ald-6HIS_R37A/T40D/E60T | 2.2E+05 | 4.2E-01 | 1.9E-06 | 1% |
| Ald-6HIS_R37A/F41K/E60T | 1.5E+08 | 1.3E-02 | 8.6E-07 | 0% |
| Ald-6HIS_T40D/F41K/E60T | 3.5E+05 | 3.6E-01 | 1.0E-06 | 0% |

A protein thermal shift assay was carried out as described in Example 8 to determine the stability of the IL-2 variants.

TABLE 8

Thermostability Determined by Differential Scanning Fluorimetry

| Name | Baseline RFU | Tm1 (° C.) | ΔTm (° C.) |
|---|---|---|---|
| Ald-6HIS | 4222 | 51 | 0 |
| Ald-6HIS_F41/Y44A/L71G* | 4528 | 49 | -2 |
| Ald-6HIS_R37A/T40D | 4182 | 51.4 | 0.4 |
| Ald-6HIS_R37A/F41K | 4134 | 53.7 | 2.7 |
| Ald-6HIS_R37A/E60T | 4287 | 47.2 | -3.8 |
| Ald-6HIS_T40D/F41K | 4251 | 52.6 | 1.6 |
| Ald-6HIS_T40D/E60T | 4381 | 49.3 | -1.7 |
| Ald-6HIS_F41K/E60T | 4577 | 50.8 | -0.2 |
| Ald-6HIS_R37A/T40D/F41K | 4057 | 54.1 | 3.1 |
| Ald-6HIS_R37A/T40D/E60T | 4356 | 47.7 | -3.3 |
| Ald-6HIS_R37A/F41K/E60T | 4208 | 53.3 | 2.3 |
| Ald-6HIS_T40D/F41K/E60T | 4437 | 51.50 | 0.5 |

*disclosed in U.S. Pat. No. 9,266,938
RFU = relative fluorescence units

TABLE 9A

STAT5-CTLL2 Cell Assay Measuring Functional Activity of IL-2 Variants

| Name | EC$_{50}$ (nM) | EC$_{50}$ Fold Change |
|---|---|---|
| Ald-6HIS | 0.009 | 1.00 |
| Ald-6HIS_R37A/T40D | 0.101 | 11.19 |
| Ald-6HIS_R37A/F41K | 11.010 | 1218.59 |
| Ald-6HIS_R37A/E60T | 0.129 | 14.29 |
| Ald-6HIS_T40D/F41K | 6.314 | 698.84 |
| Ald-6HIS_T40D/E60T | 2.200 | 243.50 |
| Ald-6HIS_F41K/E60T | 103.400 | 11444.38 |
| Ald-6HIS_R37A/T40D/F41K | 12.690 | 1404.54 |
| Ald-6HIS_R37A/T40D/E60T | 6.221 | 688.54 |
| Ald-6HIS_R37A/F41K/E60T | 95.160 | 10532.37 |
| Ald-6HIS_T40D/F41K/E60T | 98.550 | 10907.58 |

TABLE 9B

NK-92 Cell Assay Measuring Functional Activity of IL-2 Variants

| Name | EC$_{50}$ (nM) | EC$_{50}$ Fold Change |
|---|---|---|
| Ald-6HIS | 0.007 | 1.00 |
| Ald-6HIS_R37A/T40D | 0.014 | 2.06 |
| Ald-6HIS_R37A/F41K | 0.051 | 7.31 |
| Ald-6HIS_R37A/E60T | 0.031 | 4.46 |
| Ald-6HIS_T40D/F41K | 0.020 | 2.81 |
| Ald-6HIS_T40D/E60T | 0.032 | 4.61 |
| Ald-6HIS_F41K/E60T | 0.079 | 11.38 |
| Ald-6HIS_R37A/T40D/F41K | 0.026 | 3.73 |
| Ald-6HIS_R37A/T40D/E60T | 0.076 | 10.96 |
| Ald-6HIS_R37A/F41K/E60T | 0.063 | 9.03 |
| Ald-6HIS_T40D/F41K/E60T | 0.063 | 9.09 |

TABLE 9C

U2OS B/BG Bridging Cell Assay Measuring Functional Activity of IL-2 Variants

| Name | EC$_{50}$ (nM) | EC$_{50}$ Fold Change |
|---|---|---|
| Ald-6HIS | 0.159 | 1.00 |
| Ald-6HIS_R37A/T40D | 0.451 | 2.83 |
| Ald-6HIS_R37A/F41K | 0.370 | 2.32 |
| Ald-6HIS_R37A/E60T | 0.522 | 3.28 |
| Ald-6HIS_T40D/F41K | 0.294 | 1.84 |
| Ald-6HIS_T40D/E60T | 0.492 | 3.09 |
| Ald-6HIS_F41K/E60T | 0.502 | 3.15 |
| Ald-6HIS_R37A/T40D/F41K | 0.185 | 1.16 |
| Ald-6HIS_R37A/T40D/E60T | 0.403 | 2.53 |
| Ald-6HIS_R37A/F41K/E60T | 0.325 | 2.04 |
| Ald-6HIS_T40D/F41K/E60T | 0.503 | 3.15 |

TABLE 9D

DERL7 Cell Assay Measuring Functional Activity of IL-2 Variants

| Name | EC$_{50}$ (nM) | EC$_{50}$ Fold Change |
|---|---|---|
| Ald-6HIS | 0.018 | 1.00 |
| Ald-6HIS_R37A/T40D | 0.023 | 1.31 |
| Ald-6HIS_R37A/F41K | 0.021 | 1.18 |
| Ald-6HIS_R37A/E60T | 0.038 | 2.14 |
| Ald-6HIS_T40D/F41K | 0.012 | 0.65 |
| Ald-6HIS_T40D/E60T | 0.028 | 1.55 |
| Ald-6HIS_F41K/E60T | 0.036 | 2.01 |
| Ald-6HIS_R37A/T40D/F41K | 0.013 | 0.71 |
| Ald-6HIS_R37A/T40D/E60T | 0.043 | 2.41 |
| Ald-6HIS_R37A/F41K/E60T | 0.026 | 1.46 |
| Ald-6HIS_T40D/F41K/E60T | 0.025 | 1.40 |

Example 3

Combining pAMF Site and Rα Mutations

Aldesleukin with an S4pAMF substitution is combined with Ru mutations R37A and F41K to generate IL-2 variant Ald_S4pAMF/R37A/F41K (MUT1). As shown in the scheme below, PEG1 is conjugated to the pAMF of MUT1 for half-life extension using SPAAC copper-free conjugation, as described in Example 6, to produce Ald_S4pAMF (PEG1)/R37A/F41K (CON1). As reference molecules for use as controls, variants without R37A and F41K mutations were generated in parallel Ald_S4pAMF (MUT2) and Ald_S4pAMF(PEG1) (CON2).

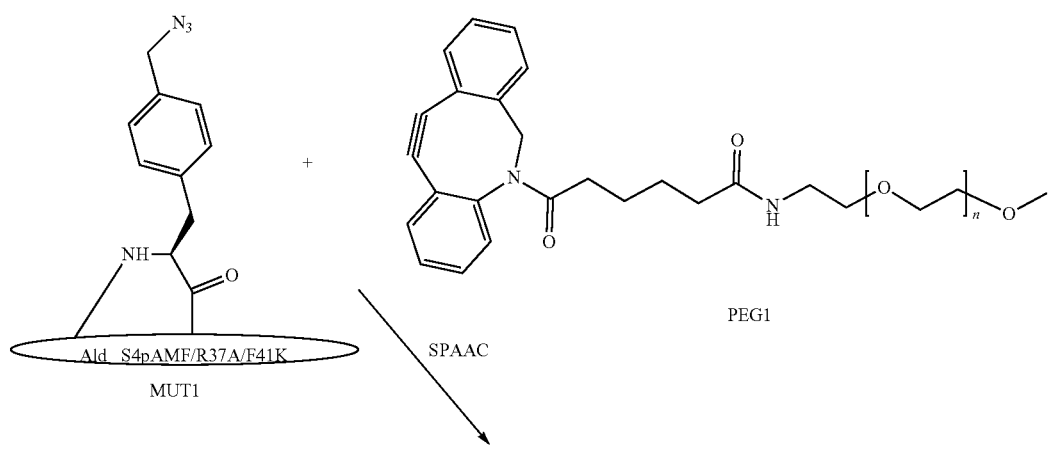

-continued

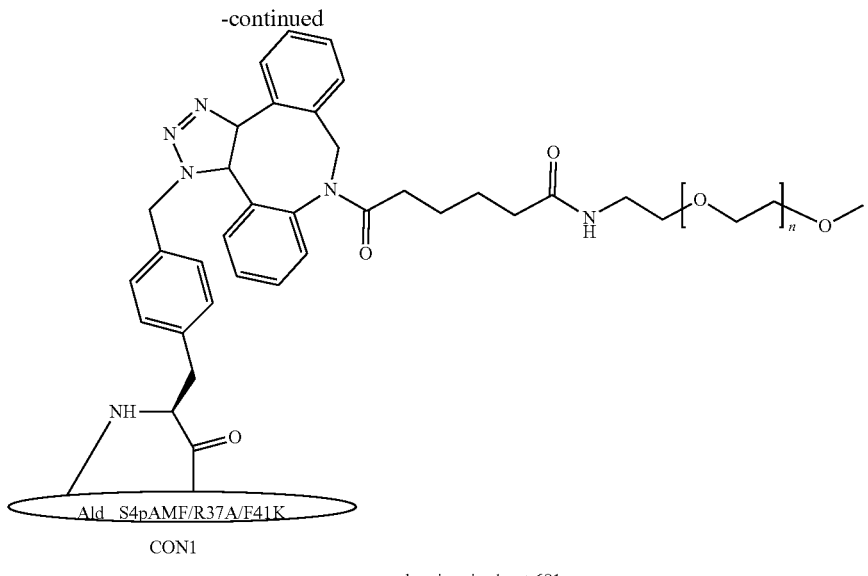

CON1 wherein n is about 681

Example 4

Cell-Free Expression of Recombinant IL-2 (rIL-2) and Variants Containing pAMF

The aldesleukin and variants are expressed in an Xpress+ CF™ reaction. The cell-free extracts are prepared from a mixture of four extracts derived from four engineered strains: (1) an OmpT sensitive RF1 attenuated E. coli strain engineered to overexpress E. coli DsbC and FkpA, (2) a similar RF1 attenuated E. coli strain engineered to produce an orthogonal CUA-encoding tRNA for non-natural amino acid insertion at an Amber Stop Codon, (3) a similar RF1 attenuated E. coli strain engineered to produce the pAMF-specific amino-acyl tRNA synthetase and (4) a similar RF1 attenuated E. coli strain engineered to produce T7 RNA polymerase. This cell-free extract 1 is treated with 50 μM iodoacetamide for 30 min at RT (20° C.) and added to a premix containing all other components. The final concentration in the protein synthesis reaction is 30% (v/v) cell extract 1, 1% (v/v) cell extract 2 or 5 μM orthogonal CUA-encoding tRNA, 0.6% (v/v) cell extract 3 or 5 uM engineered pAMF-specific amino-acyl tRNA synthetase, 0.5% (v/v) cell extract 4 or 100 nM T7 RNAP, 2 mM para-azidomethylphenylalanine (pAMF), 2 mM GSSG, 8 mM magnesium glutamate, 10 mM ammonium glutamate, 130 mM potassium glutamate, 35 mM sodium pyruvate, 1.2 mM AMP, 0.86 mM each of GMP, UMP, and CMP, 2 mM amino acids (except 0.5 mM for Tyrosine and Phenylalanine), 4 mM sodium oxalate, 1 mM putrescine, 1.5 mM spermidine, 15 mM potassium phosphate, 2.5-5 μg/mL IL2 or variants DNA. Cell-free reactions are performed at 20-30° C. for 12 hours on a shaker at 650 rpm in 96-well plates at 100 μL scale, in 24-well flower plates at 1 mL scale, in 100×10 mm petri dish at 8 mL scale or in stirred tanks at larger scales.

Example 5

Purification of Aldesleukin and Variants

Aldesleukin and variants are constructed with 6× Histidine tag at N- or C-terminus; cleavable affinity tags, e.g. His SUMO tag at N-terminus; or without a tag. Untagged aldesleukin and variants are purified by standard purification methods. His-tagged aldesleukin (Ald-6HIS) and variants are purified by standard immobilized metal affinity chromatography (IMAC) purification methods. Molecules with cleavable affinity tags are processed by enzymatic digestion followed by standard purification to remove tag and enzyme.

Example 6

Site-Specific PEGylation

Cu-free and Cu-catalyzed conjugation chemistry are utilized to conjugate PEG site specifically to aldesleukin variants containing pAMF.

SPAAC copper-free conjugation: Linear or branched mPEG (10 KDa, 20 KDa, 30 KDa, 40 KDa) is linked to dibenzocyclooctyne (DBCO) or dibenzocyclooctynol (DIBO). A 5 mM stock solution of DBCO/DIBO-mPEG is mixed with 1-50 mg/mL aldesleukin variants incorporated with pAMF at DBCO/DIBO-mPEG to pAMF ratio of 2-50 for 8 hours to 5 days at 22-35° C.

CuAAC conjugation: 5 mM stock solution of linear or branched alkyne-mPEG (10 KDa, 20 KDa, 30 KDa, 40 KDa) is mixed with 1-50 mg/mL aldesleukin variants incorporated with pAMF at alkyne-mPEG to pAMF ratio of 2-50 in 10× phosphate buffer (100 mM sodium phosphate, 150 mM NaCl, pH7.4). Copper reagent is prepared separately by mixing CuSO$_4$, ligand (triazole based such as tris(3-hydroxypropyltriazolylmethyl)amine, or benzimidazol based such as tripotassium 5,5',5''-[2,2',2''-nitrilotris(methylene) tris(1H-benzimidazole-2,1-diyl)]tripentanoate hydrate), reducing reagent (sodium ascorbate, DTT, or TCEP) and ROS scavenger (methionine, cysteine, or histidine). Aminoguanidine is added when sodium ascorbate is used as reducing reagent. Copper is added at alkyne to copper molar ratio of 1-15, ligand to copper molar ratio is 1-5, reducing reagent to copper molar ratio is 2-10, ascorbate to aminoguanidine ratio is molar 1-5. Copper reagent is then mixed with protein/drug mixture for 8 hours to 5 days at 22-35° C. When anaerobic condition is required, all solutions are purged with inert gas before mixing, and the reaction is kept under inert gas during the reaction.

Unconjugated PEG is removed. Unconjugated or PEG-conjugated aldesleukin variants are evaluated for conjugation efficiency, stability, and binding to IL-2Rα, IL-2Rβ, IL-2Rαβ, IL-2Rαβγ$_c$, and IL-2Rβγ$_c$ by ELISA or label-free technology such as SPR and/or biolayer interferometry (BLI).

Example 7

PEGylation Density PEGylation density is determined by a reversed phase HPLC assay. Protein is denatured in 5 M guanidine and reduced with 1 mM TCEP protein and run on a C8 column with an acetonitrile gradient of O-50%. PEGylation density is determined by integration of the UV trace at 280 nm. Unconjugated proteins and conjugates with non-hydrolysable PEGs of known PEGylation density are used as reference standards.

Example 8

Differential Scanning Fluorimetry (DSF)

A protein thermal shift assay is carried out by mixing the protein to be assayed with an environmentally sensitive dye (SYPRO Orange, Life Technologies Cat #5-6650) in a phosphate buffered solution (PBS), and monitoring the fluorescence of the mixture in real time as it undergoes controlled thermal denaturation. Protein solutions between 0.2-2 mg/mL are mixed at a 1-1 volumetric ratio with a 1-500 PBS-diluted solution of SYPRO Orange (SYPRO Orange stock dye is 5000× in DMSO). 10 µL aliquots of the protein-dye mixture were dispensed in quadruplicate in a 384-well microplate (Bio-Rad Cat #MSP-3852, plates preheated for 30 minutes at 95° C.), and the plate is sealed with an optically clear sealing film (Bio-Rad Cat #MSB-1001) and placed in a 384-well plate real-time thermocycler (Bio-Rad CFX384 Real Time System). The protein-dye mixture is heated from 25° C. to 95° C., at increments of 0.1° C. per cycle (about 1.5° C. per minute), allowing 3 seconds of equilibration at each temperature before taking a fluorescence measurement. At the end of the experiment, the transition melting temperature is determined using the Bio-Rad CFX manager software.

Example 9

Label-Free Kinetic Analysis with SPR or BLI

This example describes methods to identify aldesleukin variants that are pegylated at sites allowing for (1) limited/no impact on IL-2R binding, (2) reduction in IL-2Rα binding while maintaining similar IL-2Rβ, or (3) reduction in IL-2Rβγ$_c$ binding compared to rhIL-2. This example also provides methods to assess whether binding properties are altered only by PEG-conjugation. As such, a series of label-free assays are used to determine relative binding affinities between the aldesleukin variants and various components of the IL-2R complex.

Anti-Fc polyclonal antibodies are immobilized onto a CM5 chip (GE Life Sciences) using amine coupling chemistry (from Amine Coupling Kit, GE Life Sciences). The immobilization steps are carried out at a flow rate of 25 µL/minute in 1×HBS-EP+ buffer (GE Life Sciences; 10× Stock diluted before use). The sensor surfaces are activated for 7 min with a mixture of NHS (0.05 M) and EDC (0.2 M). The anti-Fc antibodies are injected over all four flow cells at a concentration of 25 µg/mL in 10 mM sodium acetate, pH 4.5, for seven minutes. Ethanolamine (1 M, pH 8.5) is injected for seven minutes to block any remaining activated groups. An average of 12,000 response units (RU) of capture antibody is immobilized on each flow cell.

Kinetic binding experiments are performed at 25° C. using 1×HBS-EP+ buffer. IL-2Rα-Fc or IL-2Rβ-Fc (Acro Biosystems, catalog #ILA-H5251, ILB-H5253) are injected over the anti-Fc surface at concentrations of 3-10 µg/mL for 12 seconds at a flow rate of 10 µL/minute on flow cells 2, 3 and 4, followed by a buffer wash for 30 seconds at the same flow rate. Kinetic characterization of conjugated or unconjugated aldesleukin or variants is carried out in a range of concentrations from 1 nM-10 µM and one injection of no antigen. After capturing ligand (IL-2Rα-Fc or IL-2Rβ-Fc) on the anti-Fc surface, the analyte (IL-2 variant) is bound for 180 seconds, followed by a 600 second dissociation phase at a flow rate of 50 L/min. Between each ligand capture and analyte binding cycle, regeneration is carried out using two injections of 10 mM Glycine pH 2.0 for 30 seconds at 30 µL/minute, followed by a 30 second buffer wash step. The data are fit with the Biacore T200 Evaluation software.

Similar methods are evaluated on a ForteBio Octet (Pall Life Sciences) and a MASS-1 (Sierra Sensors) to allow for more high throughput measurements. Anti-human capture (AHC) or streptavidin (SA) surfaces for the capture of Fc-fusion or biotinylated proteins, respectively, are also evaluated.

Example 10

Kit225STAT5-luc Assay

The human T lymphocyte Kit225 cell line (Hori et al., Blood 70:1069-1072 (1987)) was engineered with a STAT5 responsive luciferase reporter using the Promega pGL4.52 luc2P/STAT5 RE/Hygro vector (GenBank accession number JX206457) to produce Kit225-STAT5 reporter cells. This vector contains five copies of a STAT5 response element (STAT5 RE) that drives transcription of the luciferase reporter gene luc2P. To assess potency of IL-2 molecules, Kit225-STAT5 reporter cells cells were plated at $1 \times 10^4$ cell/well and rested overnight. Kit225 STAT5 luc cells were then treated with a serial dilution of IL-2 test articles, incubated for six hours, and then STAT5 activation was measured using a BrightGLO luciferase substrate kit (Promega).

Example 11

PathHunter U2OS IL2RB/IL2RG Dimerization Assay

U2OS IL2RB/IL2RG (DiscoverX, 93-0998C3) cells were thawed and cultured in complete DMEM/F-12 (Corning) with 100 IU Penicillin/100 µg/mL Streptomycin (Corning), 2 mM GlutaMax (Gibco), 10% heat-inactivated fetal bovine serum (FBS) (Sigma). Additional 250 µg/mL hygromycin, and 500 µg/mL G418 were added for selection. One day before the aldesleukin or variant treatment, 25 µL of cells were seeded at $0.075 \times 10^6$ cells/mL for a total of 1,875 cells per well in complete culture medium in a standard white TC-coated 384-well plate. On assay day, cells were treated with 25 µL of serial dilution of aldesleukin or variant samples (1:8 serial dilution of 1 µM starting concentration). Cells were incubated at 37° C., 5% $CO_2$ for 24 hours. 30 µL of reconstituted Beta-Glo (Promega) reagent was added and allowed to incubate for 25 minutes at room temperature with shaking. Plates were read on the Envision plate reader (PerkinElmer) and luminescence readings were converted to % relative signal using the 1 µM aldesleukin treated cells as controls. Data was fitted with non-linear regression analysis, using log (against) vs. response, variable slope, 4-parameter fit equation using GraphPad Prism. Data was expressed as % relative signal vs. dose of aldesleukin or variant samples in nM.

Example 12

GloResponse STAT5-luc2-CTLL-2 Reporter Assay

GboResponse STAT5-luc2-CTLL-2 (Promega, CD2018B05) cells were maintained in complete RPMI-1640 (Corning) with 100 IU Penicillin/100 µg/mL Streptomycin (Corning), 2 mM GlutaMax (Gibco), 20% heat-inactivated FBS (Sigma), and 10 ng/mL IL-2 (Peprotech). On assay day, cells were starved of IL-2 for at least 4 hours prior to treatment. 25 µL of cells were seeded at $0.075 \times 10^6$ cells/mL for a total of 1,875 cells per well in complete culture medium in a standard white TC-coated 384-well plate. Cells were treated with 25 µL of serial dilution of aldesleukin or variant samples (1:8 serial dilution of 1 µM starting concentration) and then incubated at 37° C., 5% $CO_2$ for 24 hours. 30 µL of reconstituted Bio-Glo (Promega) reagent was added and allowed to incubate for 25 minutes at room temperature with shaking. Plates were read on the Envision plate reader (PerkinElmer) and luminescence readings were converted to % relative signal using the 1 µM wild-type IL-2 (aldesleukin) treated cells as controls. Data was fitted with non-linear regression analysis, using log (against) vs. response, variable slope, four-parameter fit equation using GraphPad Prism. Data was expressed as % relative signal vs. dose of samples in nM.

Example 13

NK-92, M07-e and DERL-7 Cell Proliferation Assay

NK-92 (IL2RABG, ATCC, CRL-2407), M07-e (IL2RBG, DSMZ) and DERL-7 (IL2RBG, DSMZ, ACC 524) cells were maintained in complete RPMI-1640 (Corning) with 100 IU Penicillin/100 µg/mL Streptomycin (Corning), 2 mM GlutaMax (Gibco), 20% heat-inactivated FBS (Sigma), and 10 ng/mL IL-2 (Peprotech). On assay day, cells were starved of IL-2 for at least 4 hours prior to treatment. 25 µL of cells were seeded at $0.075 \times 10^6$ cells/mL for a total of 1,875 cells per well in complete culture medium in a standard white TC-coated 384-well plate. Cells were treated with 25 µL of serial dilution of aldesleukin or variant samples (1:8 serial dilution of 1 uM starting concentration) and then incubated at 37° C., 5% $CO_2$ for 24 hours. 30 µL of reconstituted CellTiter-Glo (Promega) reagent was added and allowed to incubate for 25 minutes at room temperature, with shaking. Plates were read on the Envision plate reader (PerkinElmer) and luminescence readings were converted to % relative signal using the 1 µM aldesleukin treated cells as controls. Data was fitted with non-linear regression analysis, using log (against) vs. response, variable slope, four-parameter fit equation using GraphPad Prism. Data was expressed as % relative signal vs. dose of samples in nM.

Example 14

In Vivo Activity of Aldesleukin Variants

Female C57BL/6 mice eight to ten weeks of age are anesthetized with isoflurane and implanted subcutaneously with $1 \times 10^6$ B16F10 cells into the right hind flank. Randomization and start of treatment (n=8 per group) is initiated when tumors are established (average tumor size approximately 125 or 130 mm³). Body weight and tumor size are monitored 3×/week until the group mean is approximately 1,500 mm³. For assessment of single agent efficacy, C57BL/6 animals bearing established B16F10 (melanoma) tumors are administered intravenously (IV) with vehicle and indicated dose of CON1 or CON2 every seven days for 2 doses (q7dx2).

Example 15

In Vivo Immune Cell Phenotyping

C57BL/6 non-tumor or B16F10 tumor bearing mice (as described above) are administered intravenously with a single administration of vehicle and indicated dose of CON1 or CON2. In B16F10 tumor bearing animals, tumors (n=five per group) are harvested 3, 7 or 10 days after start of treatment and subjected to mechanical and enzymatic digestion for analysis of immune cell sub-types by flow cytometry. In non-tumor bearing mice, spleens and peripheral blood (n=four per group) are collected 7 days post treatment for analysis. The number of lymphocytic cells or tumor infiltrating lymphocytes (TILs) and the ratio with a T-effector phenotype vs. a T-regulatory phenotype ($T_{eff}$:$T_{reg}$) are calculated. The drug candidates that induce an increased number of TILs and greater $T_{eff}$:$T_{reg}$ ratio are predicted to generate a superior therapeutic response to rhIL-2 and selected for further development.

Example 16

In Vivo Pharmacokinetic (PK) Assessment of Aldesleukin Variants

Pharmacokinetic (PK) profile of IL-2 variants is assessed in non-tumor bearing C57BL/6 animals. Mice receive a single bolus IV injection of 0.8 mg/kg CON1, CON2, or aldesleukin (n=3 per sampling time). Blood is collected in lithium heparinized tubes and plasma is harvested by centrifugation. All samples are stored at −80° C. until analysis. Samples are processed and analyzed by ELISA to determine plasma concentrations of variant IL-2 species. Analysis of PK parameters is conducted using Phoenix WinNonLin. The 30 kDa PEGylated IL-2 variant species with prolonged half-life (T½) and exposure (increase area under the curve, AUC) vs. aldesleukin are predicted to have greater therapeutic utility and are selected for further development.

Example 17

In Vitro Pharmacology

In vitro characterization of CON1 confirms an IL-2Rβγ$_c$-biased profile relative to aldesleukin and CON2. CON1 shows lack of binding to IL-2Rα (mouse, rat, rhesus, cynomolgus monkey, human) and binding to IL-2Rβ(human, cynomolgus monkey, rhesus monkey) within six-fold of aldesleukin when assessed by SPR. In cell lines expressing IL-2Rα, bioactivity for CON1 is reduced 100- to 5000-fold depending on the assay. The human DERL-7 cell line lacks expression of IL-2Rα and CON1 and CON2 potencies are within 2-fold of each other. Further comparison of the relative impact of PEGylation and muteins was enabled with an IL-2Rα knockout cell line which demonstrated that in the absence of IL2-Rα, the muteins in CON1 had no impact on potency. Experiments with human PBMCs measuring pSTAT5 activation and comparing to CON1 demonstrate CON1 induced greater reduction in activity in $T_{reg}$ cells (expressing IL-2Rαβγ$_c$) than the non-biased CON2, while similar reduction in activity was observed for both CON1 and CON2 on CD8 CTLs (expressing IL-2Rβγ$_c$).

Determination of CON1 Binding Affinity to Human, Cynomolgus Monkey, Rhesus Monkey, Mouse, and Rat IL-2-Rα and IL-2-Rβ by Surface Plasmon Resonance A Surface Plasmon Resonance (SPR) assay on a Biacore T200 (GE Healthcare) instrument was used to determine the monovalent affinities of pegylated aldesleukin variants against polyhistidine-tagged or Fc-tagged IL-2 Receptors. Biacore T200 Evaluation Software was used to fit each titration series to a 1:1 binding model or steady state affinity. The association ($k_{on}$, $M^{-1} s^{-1}$) and dissociation ($k_{off}$, $s^{-1}$) rate constants were determined for each set of titrations and used to calculate the dissociation constant, $K_D = k_{off}/k_{on}$, of each sample against each receptor. $k_{off}/k_{on}$ values are not reported herein.

To measure the affinity of CON1 and aldesleukin for IL-2R subunits, receptors were captured on either an anti-histidine or anti-hu Fc antibody surface. The affinity of aldesleukin for all species of IL-2Rα is between 9.9 and 29 nM while CON1 does not show detectable binding to any IL-2Rα when assayed at 2 μM (Table 10). Aldesleukin and CON1 do not show detectable binding to mouse and rat IL-2-Rβ. CON1 has a six-fold lower affinity for Human and Cynomolgus/Rhesus IL-2-Rβ than aldesleukin. Both aldesleukin and CON1 have affinities for Human and Cynomolgus/Rhesus IL-2-Rβ that are within 1.5-fold, 0.73 μM and 1.1 μM and 4.4 μM and 5.4 μM, respectively (Table 10).

TABLE 10

Assessment of Binding Affinities of Aldesleukin and CON1 to Human, Cynomolgus, Rhesus, Mouse, and Rat IL-2-Rα and IL-2-Rβ by SPR.[1]

| IL-2R Subunit | Species | Tag | Aldesleukin KD (M) | Aldesleukin KD/KD (human) | CON1 KD (M) | CON1 KD/KD (human) |
|---|---|---|---|---|---|---|
| alpha | Human | Fc | 1.8E−08 | 1.0 | NB[2] | n/a[3] |
| | Cynomolgus | | 1.2E−08 | 0.6 | NB | n/a |
| | Rhesus | | 1.3E−08 | 0.7 | NB | n/a |
| | Human | His | 1.6E−08 | 1.0 | NB | n/a |
| | Cynomolgus | | 9.9E−09 | 0.6 | NB | n/a |
| | Mouse | | 1.2E−08 | 0.8 | NB | n/a |
| | Rat | | 2.9E−08 | 1.8 | NB | n/a |
| beta | Human | His | 7.3E−07 | 1.0 | 4.4E−06 | 1.0 |
| | Cynomolgus/Rhesus[4] | | 1.1E−06 | 1.5 | 5.4E−06 | 1.2 |
| | Mouse | | NB | n/a | NB | n/a |
| | Rat | | NB | n/a | NB | n/a |

[1]Number of runs for all conditions = 2;
[2]NB (no binding observed at 2 μM CON1);
[3]n/a (not applicable);
[4]There is 100% amino acid identity between cynomolgus monkey and rhesus monkey IL-2Rβ extracellular region.

CON1 Show Great Activity Reduction on Cell Lines Expressing IL-2Rα

Figure 3:
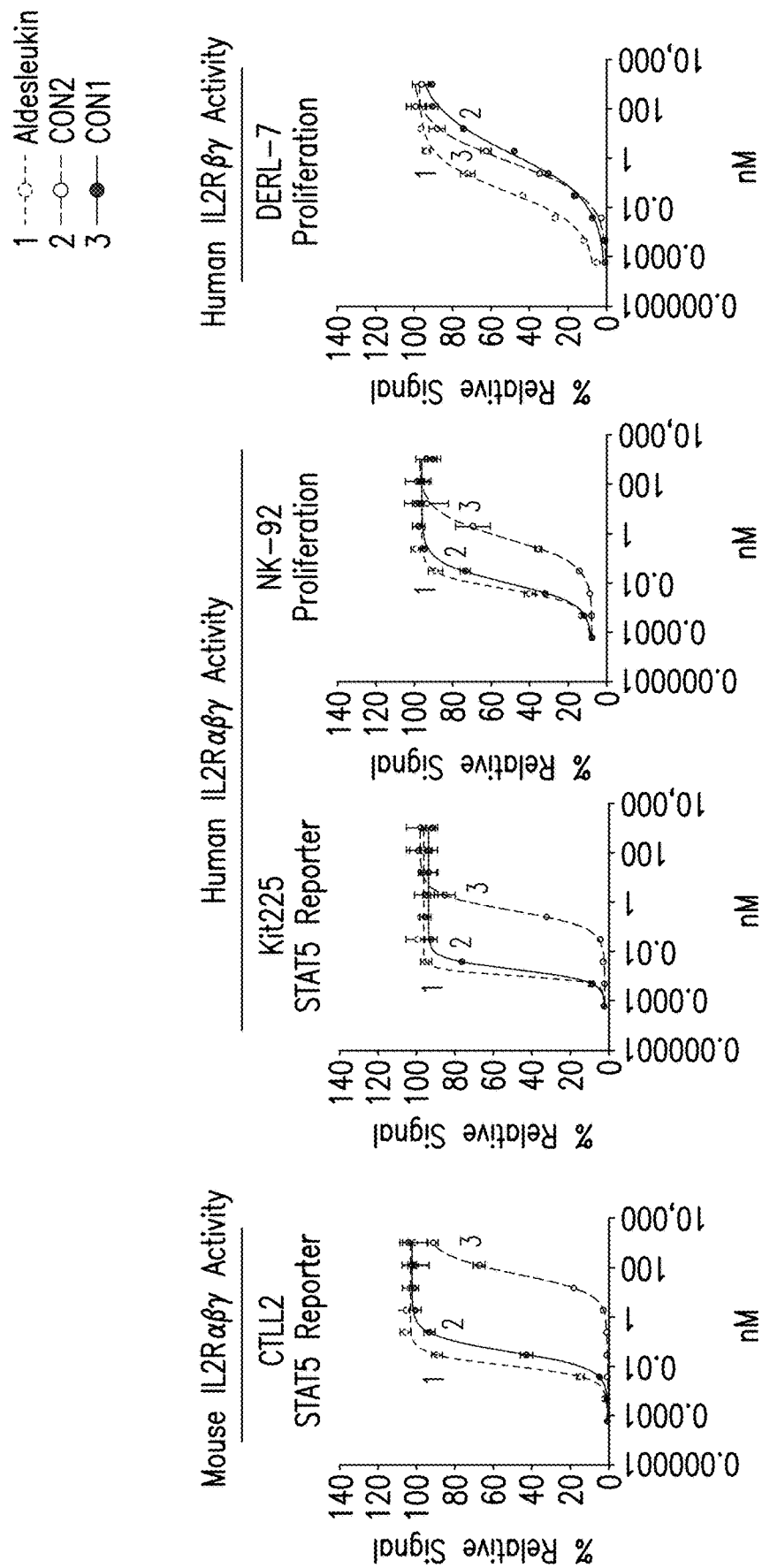
FIG. 3 shows (i) results of a mouse CTLL2 STAT5 reporter cell assay expressing IL-2Rαβγ$_c$ that compared activation of the STAT5 pathway by aldesleukin, CON2, and CON1; (ii) results of a human Kit225-STAT5 reporter cell assay expressing IL-2Rαβγ$_c$ that compared activation of the STAT5 pathway by aldesleukin, CON2, and CON1; (iii) results of a human NK92 cell assay expressing IL-2Rαβγ$_c$ that compared proliferation activity of aldesleukin, CON2, and CON1; and, (iv) results of a human DERL-7 cell assay expressing IL-2Rβγ$_c$ that compared proliferation activity of aldesleukin, CON2, and CON1. Representative data of three independent experiments are shown.

The activity of CON1 and CON2 to activate STAT5 pathway were accessed in mouse CTLL2-STAT5 reporter cells (expressing mouse IL-2Rαβγ$_c$), as well as in human Kit225-STAT5 reporter cells (expressing human IL-2Rαβγ$_c$). The activity of CON1 and CON2 to stimulate cell proliferation were also evaluated in human NK92 cells (expressing IL-2Rαβγ) and human DERL-7 cells (expressing IL-2βγ$_c$). Representative data of three independent experiments are shown in FIG. 3, the IL-2Rβγ$_c$ biased CON1 showed greater reduction in activity in cells expressing IL-2Rαβγ$_c$ (greater than 5000-fold on CTLL2-STAT5 reporter cells, greater than 400-fold on Kit225-STAT5 reporter cells and greater than 100-fold on NK92 cells, comparing to aldesleukin than the non-biased CON2 (less than 5-fold), while similar reduction in activity was observed for both CON1 (about 20-fold) and CON2 (about 40-fold) on cells expressing IL-2Rβγ$_c$ (DERL-7 cells) (Table 11).

TABLE 11

SP9849 Variants Induced pSTAT5 Activation and Cell Proliferation Activity

| Sample | Sample Description | STAT5-CTLL2 EC$_{50}$ (nM) | STAT5-CTLL2 EC$_{50}$ Fold-change | Kit225-STAT5 EC$_{50}$ (nM) | Kit225-STAT5 EC$_{50}$ Fold-change |
|---|---|---|---|---|---|
| Aldesleukin | aldesleukin | 0.011 | 1 | 0.001 | 1 |
| CON2 | Ald_S4pAMF(PEG1) | 0.04 | 4 | 0.002 | 2 |
| CON1 | Ald_S4pAMF (PEG1)/R37A/F41K | 57.4 | 5305 | 0.45 | 437 |

| Sample | Sample Description | NK-92 EC$_{50}$ (nM) | NK-92 EC$_{50}$ Fold-change | DERL-7 EC$_{50}$ (nM) | DERL-7 EC$_{50}$ Fold-change |
|---|---|---|---|---|---|
| Aldesleukin | aldesleukin | 0.006 | 1 | 0.044 | 1 |
| CON2 | Ald_S4pAMF(PEG1) | 0.01 | 2 | 1.69 | 38 |
| CON1 | Ald_S4pAMF (PEG1)/R37A/F41K | 0.68 | 117 | 0.73 | 17 |

CON1 Improves Relative Potency for CTLs Vs $T_{reg}$

Figure 4A:
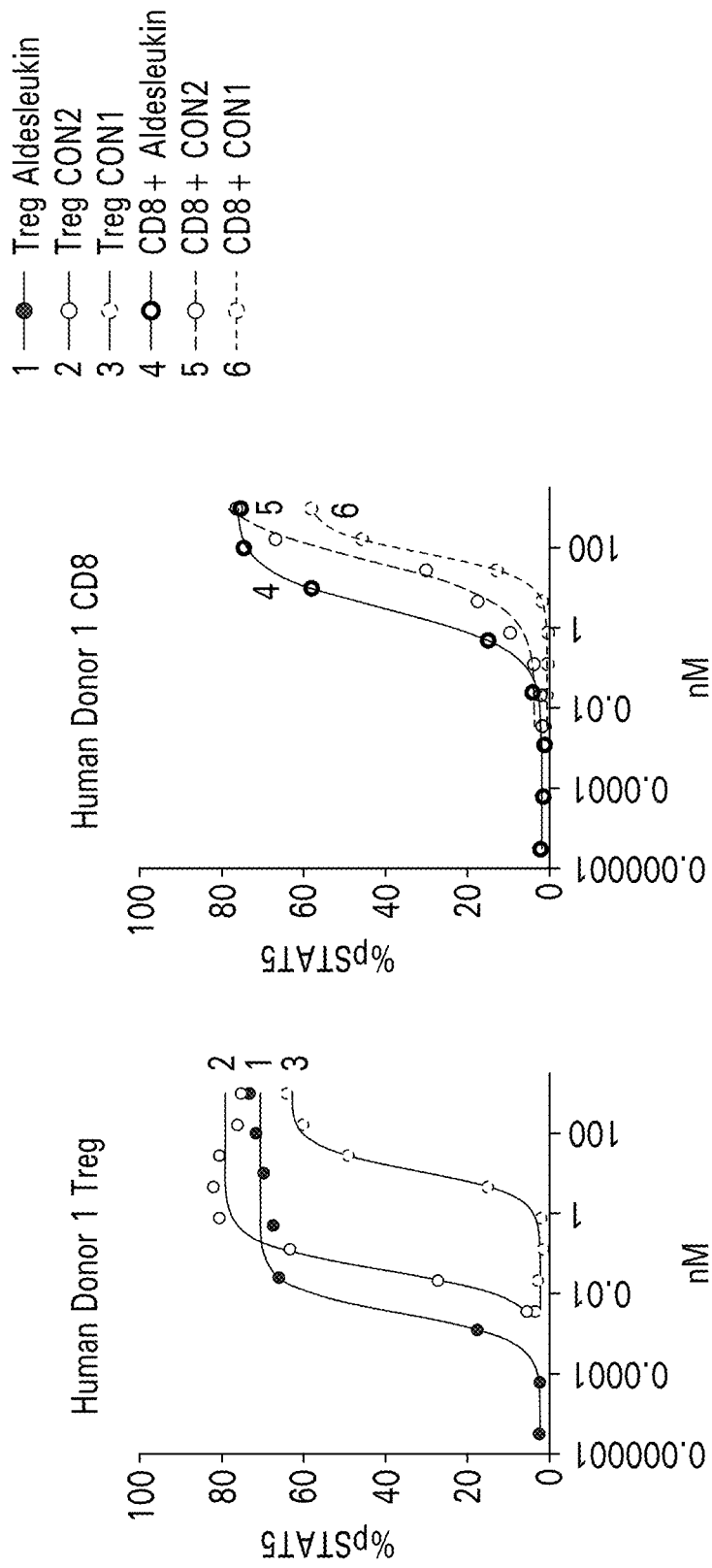
FIG. 4A compares the ability of CON1 and CON2 to activate the STAT5 pathway in primary human T$_{reg}$ cells (expressing IL2Rαβγ$_c$) and CD8$^+$ CTL cells (expressing IL2Rβγ$_c$) in peripheral blood mononuclear cells (PBMCs) isolated from human donor #1.
Figure 4B:
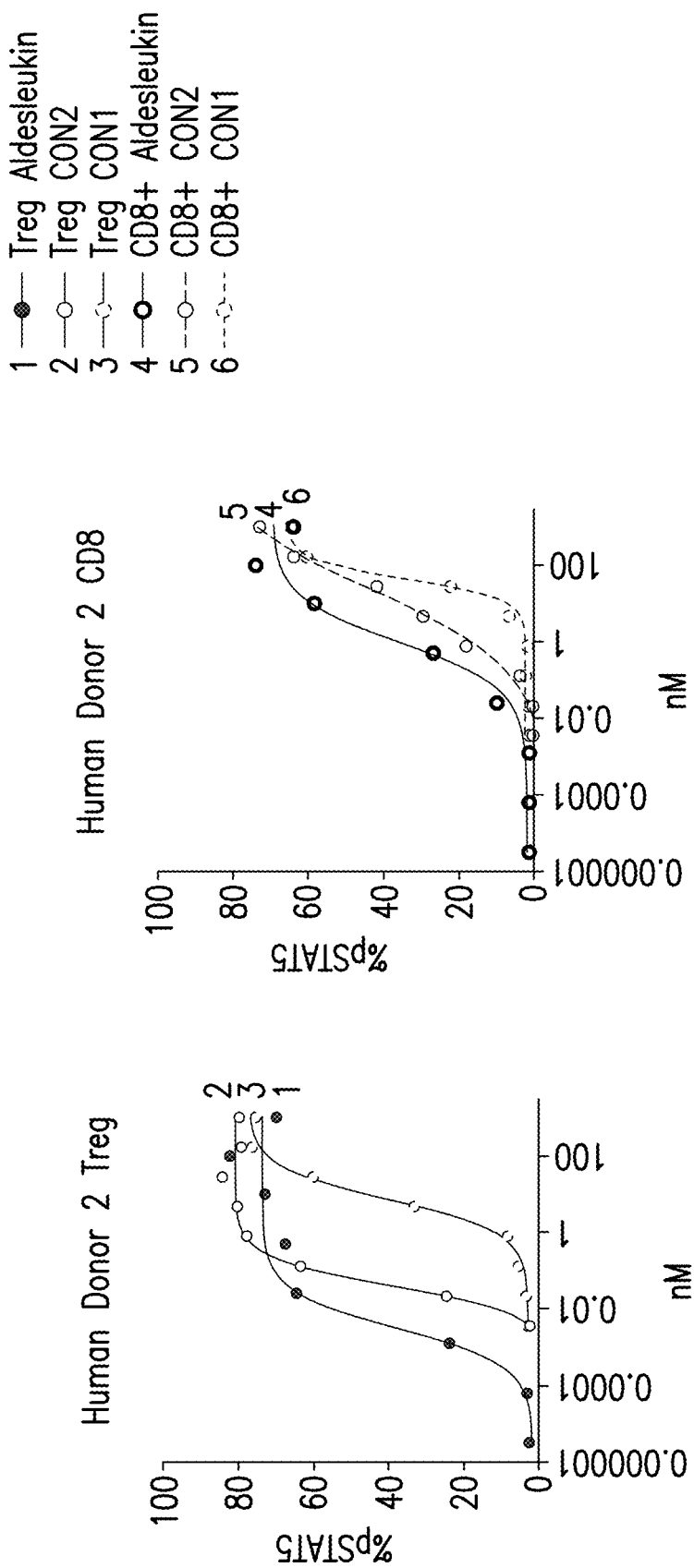
FIG. 4B compares the ability of CON1 and CON2 to activate the STAT5 pathway in primary human T$_{reg}$ cells (expressing IL2Rαβγ$_c$) and CD8$^+$ CTL cells (expressing IL2Rβγ$_c$) in PBMCs isolated from human donor #2.

The activity of CON1 and CON2 to activate STAT5 pathway in primary human $T_{reg}$ (expressing IL-2Rβγ$_c$) and CD8$^+$ CTL cells (expressing IL-2Rβγ$_c$) were evaluated in PBMCs isolated from different human donors. As shown in FIG. 4A, for human donor #1, the IL-2Rβγ$_c$ biased CON1 induced greater reduction in activity in $T_{reg}$ cells (about 3500-fold compared to aldesleukin) than the non-biased CON2 (about 10-fold compared to aldesleukin), while similar reduction in activity was observed for both CON1 and CON2 on CD8$^+$ CTLs (about 20-fold compared to aldesleukin). The difference in activity on $T_{reg}$ cells and CTLs for CON1 resulted in improved relative potency for CTLs/$T_{reg}$ cells (relative EC$_{50}$ is about six for CON1, compared to about 900 for aldesleukin and about 1200-fold for CON2). As shown in FIG. 4B, similar result was observed for CON1 and CON2 on $T_{reg}$ cells and CD8$^+$ CTLs from human donor #2 (Table 12).

TABLE 12

Aldesleukin Variants Induced pSTAT5 Activation in Human PBMC Donors

Human Donor #1

| Sample | $T_{reg}$ cells EC$_{50}$ nM | Fold-change from wt | CTLs EC$_{50}$ nM | Fold-change from wt | CTL vs. $T_{reg}$ potency shift |
|---|---|---|---|---|---|
| Aldesleukin | 0.003 | 1 | 2.83 | 1 | 867 |
| CON2 | 0.039 | 12 | 49.4 | 17 | 1252 |
| CON1 | 11.8 | 3623 | 71.9 | 25 | 6 |

Human Donor #2

| Sample | $T_{reg}$ cells EC$_{50}$ nM | Fold-change from wt | CTLs EC$_{50}$ nM | Fold-change from wt | CTL vs $T_{reg}$ potency shift |
|---|---|---|---|---|---|
| Aldesleukin | 0.003 | 1 | 0.97 | 1 | 312 |
| CON2 | 0.041 | 13 | 23.2 | 24 | 570 |
| CON1 | 7.29 | 2233 | 43.0 | 45 | 6 | wt = aldesleukin activity

CON1 Shows Greatly Reduced Activity on Human Cells Expressing IL-2Rα while in the Absence of IL-2Rα, IL-2βγ$_c$ Biased Muteins have No Impact on Potency.

The activity of CON2, MUT1 (Ald_S4pAMF/R37A/F41K), and CON1 to activate the STAT5 pathway was assessed in the Kit225-STAT5 reporter cells (expressing IL-2Rαβγ$_c$) as well as a CD25 knockout Kit225-STAT5 reporter cells (expressing only IL-2Rβγ) made using CRISPR-Cas9 genome editing technology. Test articles were selected to represent key attributes of engineered IL-2: CON2, which has wild-type IL-2 activity; MUT1, which is IL-2βγ$_c$ biased without PEGylation; and CON1, which is IL-2βγ$_c$ biased muteins with PEGylation.

Figure 5A:
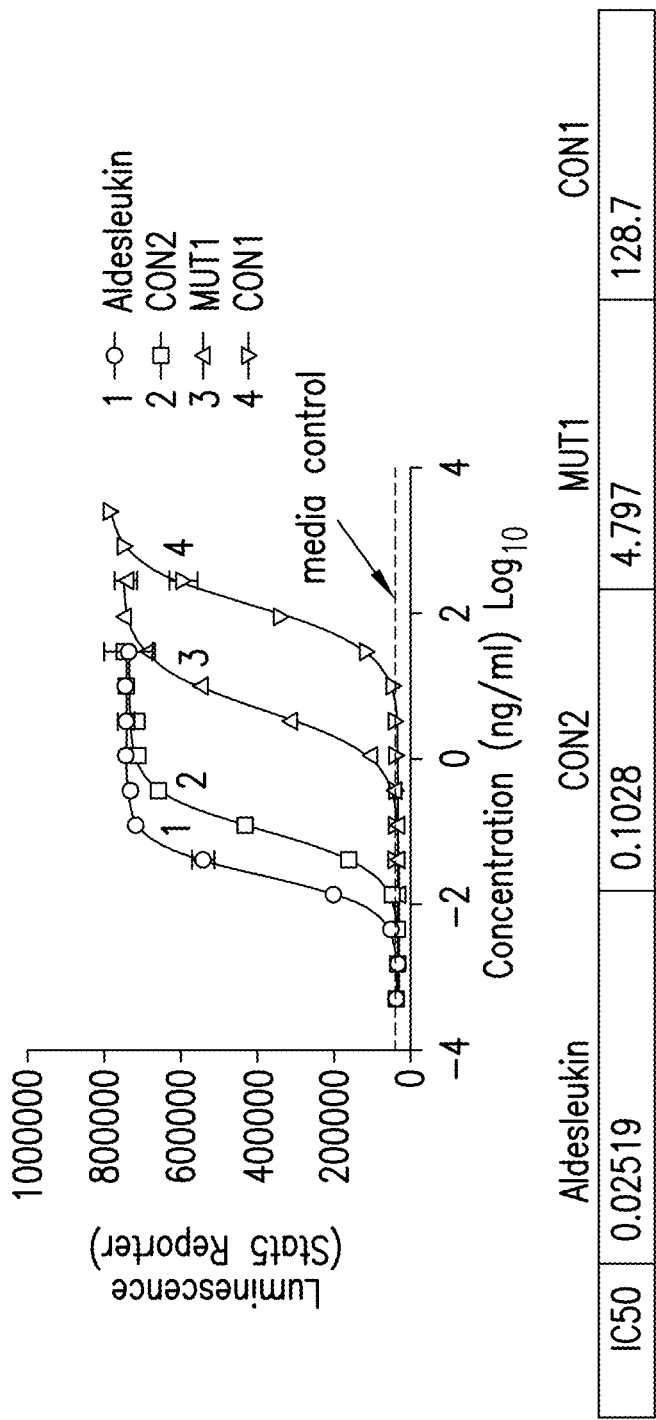
FIG. 5A shows results of an assay using Kit225-STAT5 reporter cells expressing IL-2Rαβγ$_c$ and a STAT5-luciferase reporter.
Figure 5B:
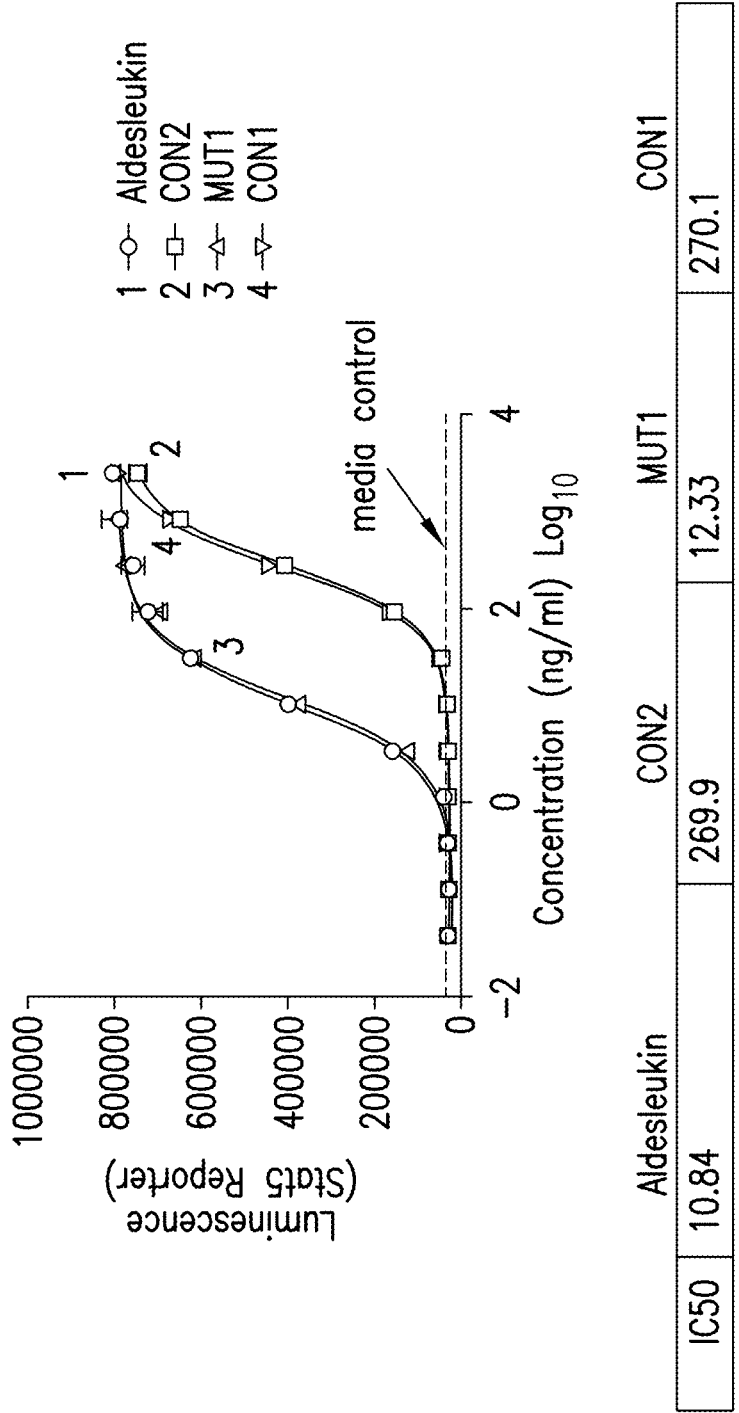
FIG. 5B shows the results of an assay using CD25 knockout Kit225-STAT5 reporter cells expressing IL-2Rβγ$_c$ only.

In Kit225-STAT5 reporter cells expressing IL-2Rαβγ$_c$, the IL-2Rβγ$_c$ biased muteins CON1 and MUT1 showed greater reduction in activity (190-fold and 5109-fold lower respectively) than non-biased CON2 (4-fold lower) compared to aldesleukin, which has wild-type IL-2 activity. In CD25 knockout Kit225-STAT5 reporter cells expressing only IL-2Rβγ$_c$, the reduction in activity was 24-fold lower for both CON2 and CON1 compared to aldesleukin. The activity of MUT1 was similar to that of aldesleukin. As shown in FIG. 5A and FIG. 5B, engineered human T cell lymphocyte Kit225 demonstrates impact of CD25-driven signaling on potency of STAT5 signaling and knockout of CD25 highlights that R37A/F41K muteins have no impact on IL-2R-βγ$_c$ driven signaling. In FIG. 5A, Kit225-STAT5 reporter cells expressing IL-2Rαβγ$_c$ and a STAT5-luciferase reporter, IL-2Rβγ$_c$ biased muteins MUT1 and CON1 show greater reduction in activity (190-fold and 5109-fold lower) than non-biased CON2 (4-fold lower) compared to aldesleukin. In FIG. 5B, CD25 knockout Kit225-STAT5 reporter cells expressing IL-2Rβγ$_c$ only, MUT1 shows activity similar to that of aldesleukin while CON1 shows 24-fold lower activity and is similar to the activity of CON2. In the absence of CD25 (IL-2Rα), IL-20γ$_c$ biased muteins have no impact on potency.

Example 18

In Vivo Pharmacology

In mice, immunophenotyping of peripheral blood shows CON1 increases CD8$^+$, $T_{eff}$ memory, and NK populations leading to an increased CD8$^+$ $T_{eff}$/$T_{reg}$ ratio. PEGylation dramatically improves the mouse pharmacokinetic profile of CON1 ($t_{1/2}$ ten hours) relative to aldesleukin ($t_{1/2}$ two hours). CON1 shows tumor growth inhibition (TGI) as monotherapy in the syngeneic mouse model B16F0, resulting in 47% TGI. CON2 showed improved efficacy (81% TGI); however, CON1 was better tolerated with little or no body weight loss at an equivalent dose of 5 mg/kg. The pharmacodynamic effects of CON1 on immune cell subtypes was assessed in B16F10 tumors. CON1 showed an increase in CD8/$T_{reg}$ ratio in the tumor; however, CON2 showed a greater magnitude and duration of response, which is consistent with greater tumor growth inhibition observed for CON2. The greater increase in the CD8 $T_{eff}$/$T_{reg}$ in CON2 compared to CON1 in the tumor microenvironment may be, in part, attributed to species differences in IL-2Rα binding affinity in rodents. CON1 and CON2 showed nearly identical kinetics of pSTAT5 phosphorylation after single doses in naïve mice and a prolonged pSTAT5 activation profile comparable to the NKTR-214 analog 5PEG in CD8$^+$ and NK cells with 5PEG showing an extended duration of response on CD4.

Figure 6:
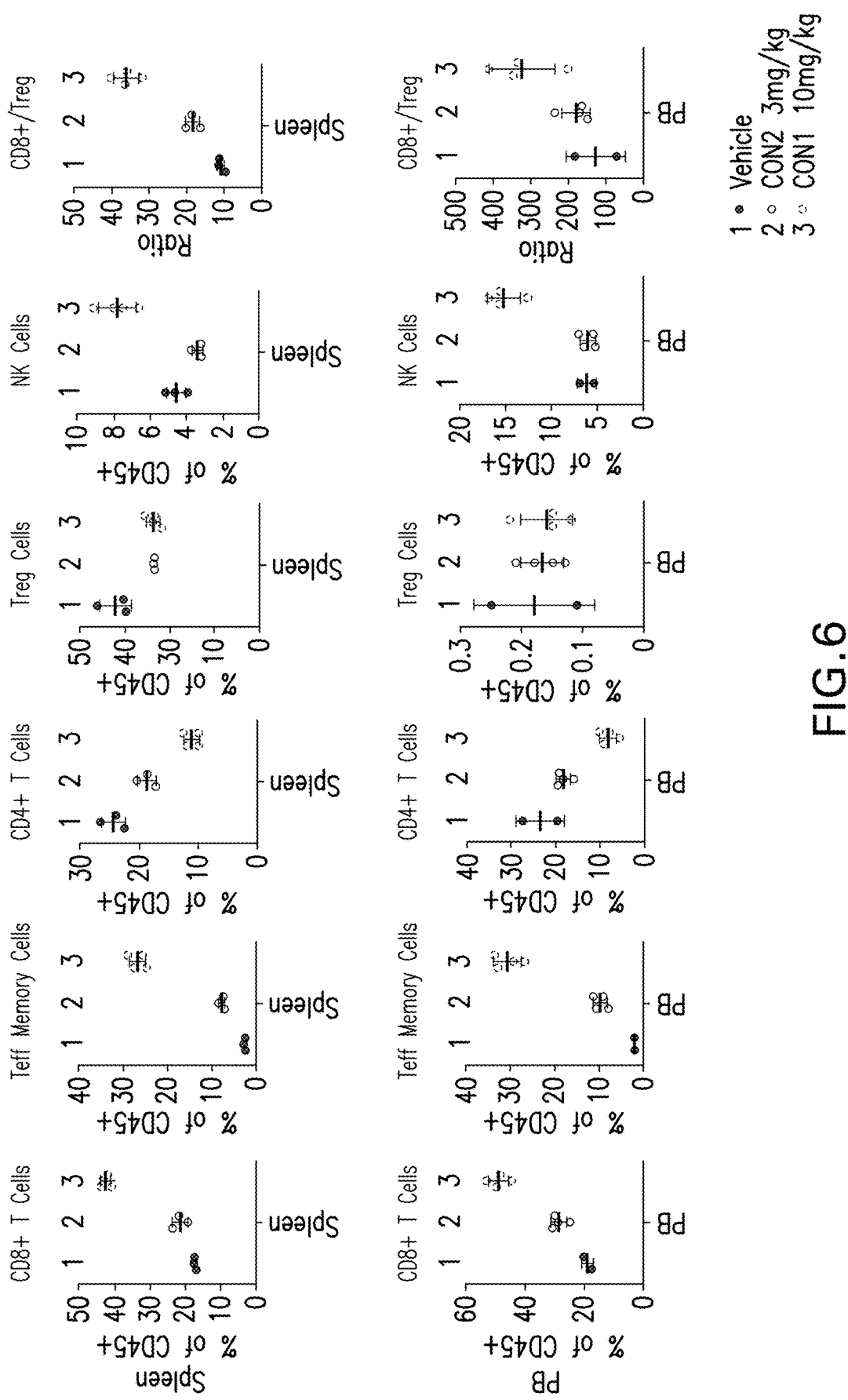
FIG. 6 shows single dose IV treatment of CON1 at 10 mg/kg for seven days in mice greatly increased % of CD8$^+$, T$_{eff}$ memory, and NK cells from spleen and PB, which resulted in an increase in CD8$^+$/T$_{reg}$ ratio. Each cell population was reported as % of CD45$^+$ immune cells from spleen and peripheral blood (PB) (four animals per treatment group). Lower cell counts in PB results in higher error bars. Two animals from the PB vehicle group, one animal from the spleen vehicle group and one animal from the spleen CON2 group were excluded from data analysis due to insufficient cells recovered.

CON1 Treatment in Mice Resulted in Increased CD8$^+$, $T_{eff}$ Memory and NK Cell Populations, as Well as Increased CD8$^+$/$T_{reg}$ Ratio in Peripheral Blood The in vivo activity of CON1 and CON2 to stimulate the immune cells in the spleen and peripheral blood (PB) were evaluated in female C57BL/6 mice with a single IV dose of 3 mg/kg for CON2 and 10 mg/kg for CON1 (dose selection based on in vivo efficacy). Seven days after the IV dosing, immune cells were isolated and stained with antibodies to label different immune cell populations. Comparing to aldesleukin, treatment of the IL-2Rβγ$_c$ biased CON1 greatly increased cell populations (as % of total immune cells) of CD8$^+$, $T_{eff}$ memory and NK cells, which resulted in an increase in CD8$^+$/$T_{reg}$ ratio. Similar results were observed in the PB of CON1 treated animals. Treatments with CON1 only showed slightly increased cell population in CD8$^+$ T cells and $T_{eff}$ memory cells, which resulted in a slightly increase in CD8$^+$/$T_{reg}$ ratio (FIG. 6). As shown in FIG. 6, single dose IV treatment of CON1 at 10 mg/kg for seven days in mice greatly increased % of CD8$^+$, $T_{eff}$ memory, and NK cells from spleen and PB, which resulted in an increase in CD8$^+$/$T_{reg}$ ratio.

Pharmacokinetic Profile of CON1 in C57BL/6 Mice

Figure 7:
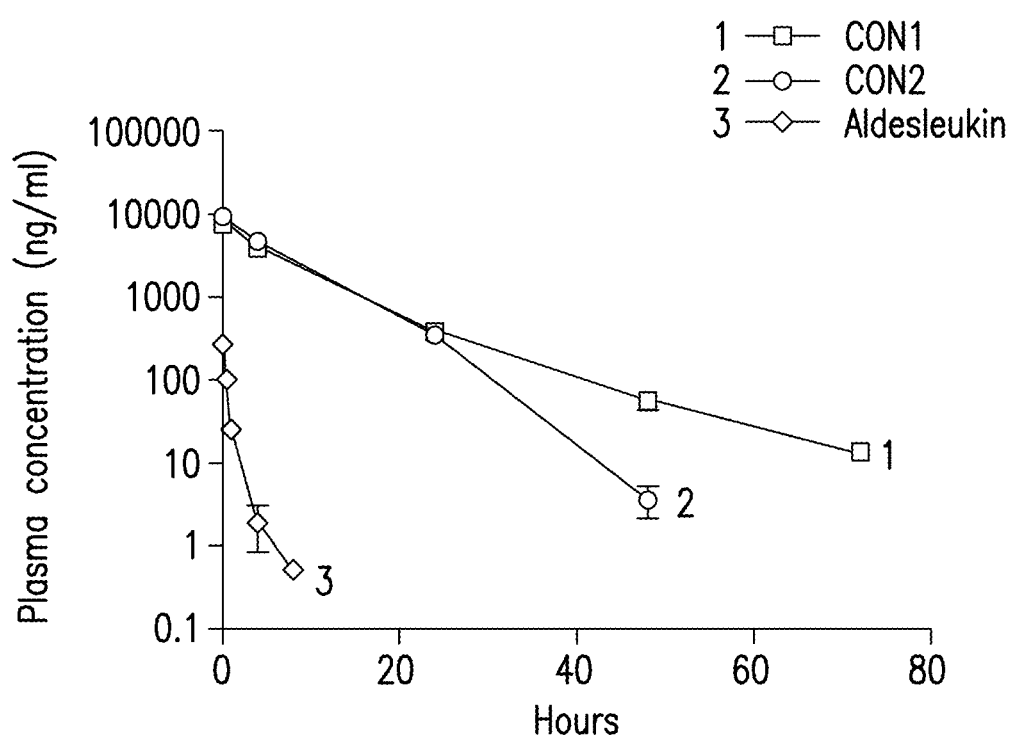
FIG. 7 shows IL-2 variants with 30 kDa PEG have extended PK profile compared to wild-type. Mean plasma concentration-time profile of CON1, CON2 and aldesleukin total antibody in C57BL/6 mice following IV bolus administration of a 0.8 mg/kg dose. Plasma concentrations were determined by ELISA using an anti-human IL-2 antibody. Data are presented as mean±standard deviation (SD).

The PK profile of CON1 was evaluated by total antibody levels following a single 0.8 mg/kg dose in non-tumor bearing C57BL/6 mice. Plasma samples were collected at several time points up to seven days for composite PK analysis. The mean plasma concentration profiles of IL-2 variants CON1, CON2, and aldesleukin are shown in FIG. 7. PK analysis showed that aldesleukin variants, CON1 and CON2, both conjugated to a non-releasable 30 kDa PEG, have longer $t_{1/2}$, lower clearance and higher exposure compared to aldesleukin having wild-type IL-2 profile (FIG. 7 and Table 13). All three molecules displayed comparable PK profiles in at least two independent experiments. It should be also noted that a representative aldesleukin data set from a different study was selected for comparison to the CON1 and CON2 aldesleukin variants. The reported terminal $t_{1/2}$ for aldesleukin is an estimate based on the last two timepoints.

As shown in FIG. 7, CON1 and CON2 have extended PK profile compared to aldesleukin.

TABLE 13

Summary of aldesleukin and variants PK Parameters in C57BL/6 Mice

| Treatment | Terminal $t_{1/2}$ (hr) | $C_0$ (ng/mL) | $C_{max}$ ± S.E. (ng/mL) | $AUC_{0\text{-}last}$ ± S.E. (day·ng/mL) | $AUC_{0\text{-}inf}$ (hr·ng/mL) | Clearance (mL/hr/kg) | $V_{ss}$ (mL/kg) |
|---|---|---|---|---|---|---|---|
| 0.8 mg/kg CON1 | 10.0 | 7970 | 7620 ± 320 | 71900 ± 1800 | 72100 | 11.1 | 73.9 |
| 0.8 mg/kg CON2 | 4.24 | 9980 | 9520 ± 700 | 83600 ± 4200 | 83700 | 9.56 | 47.1 |
| 0.8 mg/kg Aldesleukin | 2.08 | 734 | 276 ± 18 | 253 ± 10 | 254 | 3150 | 1660 |

Dose Response of CON1 in Syngeneic Mouse Model B16F10

Figure 8A:
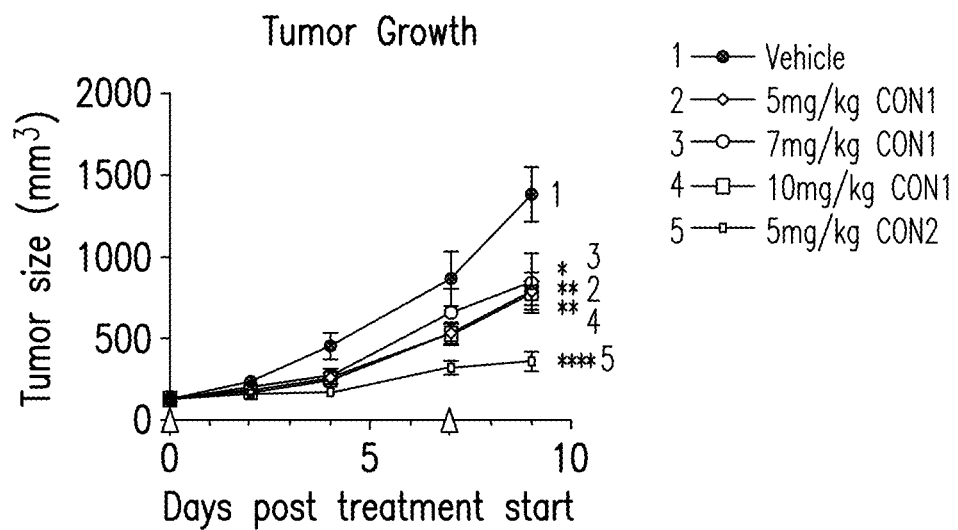
FIG. 8A shows tumor growth curves in response to indicated doses of CON1 or CON2 administered intravenously q7dx2 to animals bearing established B16F10 syngeneic mouse melanoma tumors. Arrowheads indicate treatment. Statistical analysis was performed on tumor sizes at day 9 using one-way ANOVA with Dunnett's multiple comparison test. A probability of less than 5% (p less than 0.05) was considered as significant. P-values: *=p less than 0.5, p less than 0.01, **p less than 0.0001.
Figure 8B:
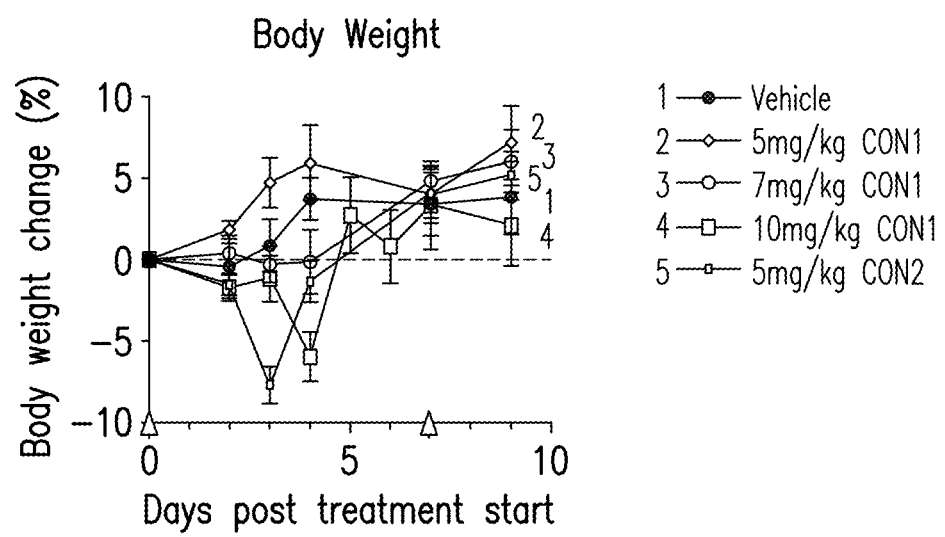
FIG. 8B shows percent body weight change in animals bearing syngeneic mouse melanoma tumor model B16F10 in response to treatment with indicated dose of CON1 or CON2. Percent body weight change was calculated relative to animal weight on the first day treatment was administered. Data is presented as mean values±SEM (n=8 per group). Arrowheads indicate treatment.

The dose-response relationship of CON1 was evaluated in syngeneic mouse melanoma tumor B16F10. Mice bearing established B16F10 tumors (about 125 mm³) were treated with 5, 7 and 10 mg/kg CON1 and 5 mg/kg of CON2 (q7dx2: every 7 days for two injections). Treatment with 5 mg/kg CON1 resulted in significant efficacy (47% TGI, p=0.0085) compared to vehicle control (FIG. 8A). Activity appeared to plateau at 5 mg/kg indicating a lack of dose dependence. The equivalent dose of CON2 at 5 mg/kg demonstrated improved efficacy compared to CON1 (81% TGI vs 47% respectively), suggesting that IL-2Rα binding contributes to efficacy (FIG. 8A). However, CON1 was better tolerated than CON2 with little or no body weight loss at 5 mg/kg (FIG. 8B). As shown in FIGS. 8A and 8B, CON1 exhibits significant anti-tumor activity in syngeneic mouse tumor model B16F10 and is well tolerated.

Efficacy of CON1 in Syngeneic Mouse Model B16F10

Figure 9A:
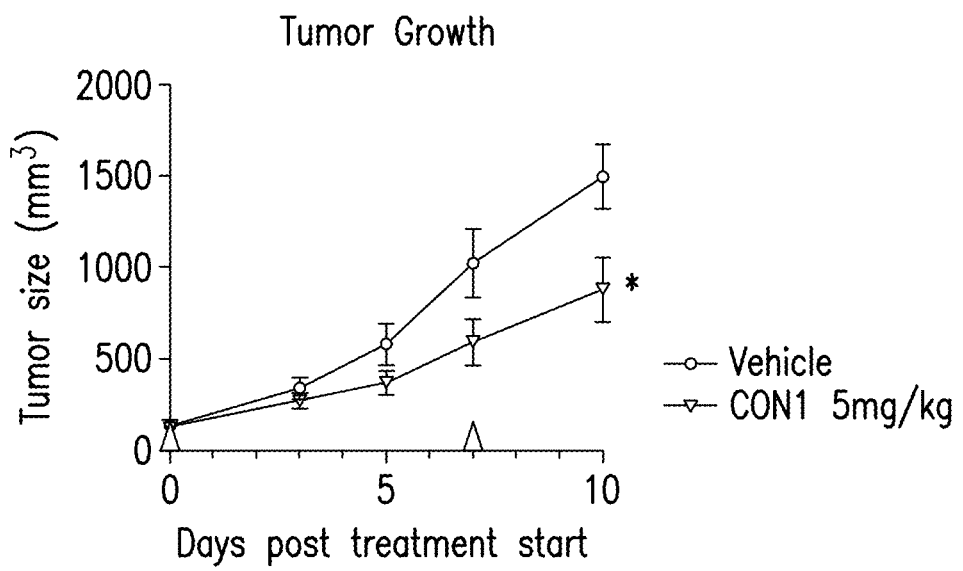
FIG. 9A shows tumor growth curves in response to 5 mg/kg CON1 administered intravenously q7dx2 to animals bearing established B16F10 syngeneic mouse melanoma tumors. Arrowheads indicate treatment. Statistical analysis was performed on tumor sizes at day 10 using one-way ANOVA with Dunnett's multiple comparison test. A probability of less than 5% (p less than 0.05) was considered as significant. *=p less than 0.5.
Figure 9B:
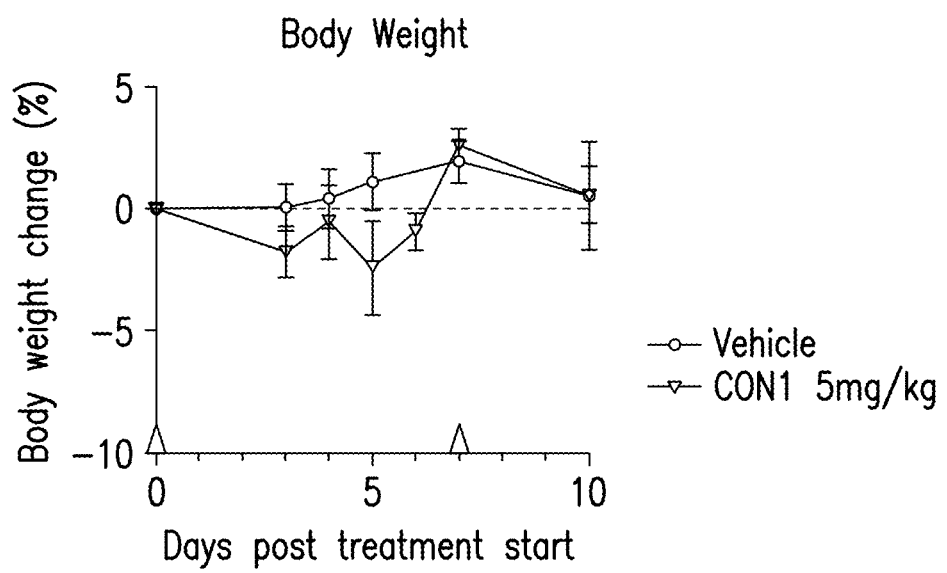
FIG. 9B shows percent body weight change in animals bearing syngeneic mouse melanoma tumor model B16F10 in response to treatment with CON1. Percent body weight change was calculated relative to animal weight on the first day treatment was administered. Arrowheads indicate treatment. Data is presented as mean values±SEM (n=8 per group).

The efficacy of CON1 was assessed in syngeneic mouse melanoma tumor B16F10. Mice bearing established B16F10 tumors (about 130 mm³) were treated with 5 mg/kg CON1 (q7dx2). Consistent with the preceding study, 5 mg/kg CON1 significantly inhibited B16F10 tumor growth compared to vehicle control (45% TGI, p=0.0197, FIG. 9A) and induced minimal body weight loss (FIG. 9B). As shown in FIGS. 9A and 9B, CON1 exhibits robust efficacy in syngeneic mouse tumor model B16F10 and is well tolerated.

Pharmacodynamic (PD) Effects of CON1 on B16F10 Tumors

The PD effects of CON1 on immune cell subtypes was assessed in B16F10 tumors. Mice bearing established B16F10 tumors (about 125 mm³) were treated with a single dose of 5 mg/kg CON1 or CON2. In order to explore longtitudinal immune responses in the tumor microenvironment, flow cytometry analysis was performed on tumors collected on days 3, 7 and 10 after treatment. Examination of immune infiltrates showed that the frequency (percent of live cells) of CD8⁺ T cells and granzyme B expressing (GmZ B+) CD8⁺ T cells was increased in both CON1 and CON2 treated animals (FIG. 10A and FIG. 10B). However, notable differences in the kinetics of T cell infiltration and activation was observed. CON1 induced an early increase in frequency of CD8 T cells and GmZ B+CD8 T cells on day three, while CON2 showed delayed activation which peaked at day 7 and decreased on day 10 (FIG. 10A and FIG. 10B). Both CON1 and CON2 significantly increased the frequency of total NK cells, NKT cells and GmZ B+ expressing NKT cells on day three compared to the vehicle treated group (FIG. 10E, FIG. 10F, and FIG. 10G). These populations decreased to similar levels as vehicle control by day seven and remained low until day 10 (FIG. 10E, FIG. 10F, and FIG. 10G). There was also a trend of lower or similar CD4 cells compared to vehicle following treatment with CON1 and CON2, except for increased levels of CON2 on day 10 (FIG. 10C).

Further analysis of the CD4 cell population revealed that CON1 and CON2 both promoted a remarkable decrease of $T_{reg}$ cells on day seven (relative to day three) followed by recovery on day 10 (FIG. 10D). The increase of CD8⁺ T cells or NKT cells and reduction of $T_{regs}$ led to an increase in these effector cell ratios in the tumor. An increase in CD8⁺ $T_{eff}/T_{reg}$ and NKT/$T_{reg}$ ratios was observed on day three in the CON1 treated group, whereas CON2 showed the highest increase in CD8⁺ $T_{eff}/T_{reg}$ and NKT/$T_{reg}$ ratio on days seven and three, respectively (FIG. 10H and FIG. 10I).

These results indicate that while both CON1 and CON2 are immunologically active, treatment with CON2 resulted in greater magnitude, sustained duration, and favorable kinetics of immune cells in the tumor microenvironment. This immune profile supports the slightly enhanced anti-tumor efficacy of CON2 relative to CON1 (FIG. 10J), which is consistent with trends observed in prior studies. In addition, it is noteworthy that the expansion of CD8⁺ T cells and increase in CD8/$T_{reg}$ ratio induced by CON2 on day seven complements the weekly dosing regimen typically employed in previous efficacy studies, which may further contribute to its enhanced efficacy in the B16F10 model. FIGS. 10A-J show IL-2 variant CON1 induces increase in CD8⁺ T cell, NK and NK T cells in the B16F10 tumor microenvironment.

Dynamics of STAT5 Phosphorylation in Naïve Mice after CON1 Treatments

The activity to induce phosphorylation of STAT5 by CON2, CON1, and NKTR-214 analog "5PEG" were assessed in naïve C57BL/6 mice at various time points (1 hour, 1, 3, 5, 7, and 10 days post injection) as indicated in FIG. 11. CON2 and CON1 showed a very similar kinetics for pSTAT5 in vivo activity throughout the time points where almost 100% of NK and CD8 T cells in the blood had pSTAT5 within 1 hour after the injection (FIG. 11). Loss of pSTAT5 activity took place over time up to 72 hours when pSTAT5 was no longer found in NK or CD8⁺ T cells. In CD4 T cells, CON2 and CON1 showed a slower induction (peaks at 24 hours post to injection) of pSTAT5 with a lower frequency (about 40%) of pSTAT5⁺ CD4 T cells. The reverse of pSTAT5 in CD4 T cells occurred in a slower kinetics as well, compared to NK or CD8⁺ T cells, where a complete loss of pSTAT5 was found at day 120 post-injection. 5PEG showed an overall slower kinetics to peak the pSTAT5 by 24 (NK or CD8$^+$) or 48 (CD4) hours with lower maximum pSTAT5 activation. While CON2 and CON1 showed nearly 100% pSTAT5$^+$ populations in NK or CD8$^+$ T cells, 5PEG IL-2 analog never reached similar magnitude as shown in FIG. 11. Thus, CON2 and CON1 showed a fast and robust pSTAT5 activity in vivo in blood of naïve mice compared to the 5PEG.

Example 19

Repeat-Dose Pharmacokinetic (PK) and Pharmacodynamic (PD) Study of CON1 and CON2 in Non-Human Primates (NHP)

In cancer patients, IL-2 treatment has been associated vascular leakage syndrome (VLS) that correlated with marked increases in circulating eosinophils. In NHP, results show dose-related increases in eosinophil counts following administration of CON1 and CON2. However, at matched doses of 0.3 mg/kg, CON2 had the greatest magnitude in eosinophilia relative to CON1 (FIG. 12A and FIG. 12B), suggesting a potential safety advantage of CON1.

Consistent with IL-2-based drugs, administration of CON1 and CON2 resulted in PD effects that included rapid decreases (margination) in total peripheral lymphocytes within 48 hours post dose, followed by concomitant lymphocyte increases (Days 4-8, FIG. 12C and FIG. 12D). These cyclical trends were observed for both drugs following the first and second dose and showed evidence of reversibility toward baseline levels by end of in-life. The data suggest a greater CON1-related magnitude in lymphocyte expansion relative to that of CON1 at matched doses of 0.3 mg/kg.

Flow cytometry analysis was used to characterize the various lymphocyte populations of interest, and ratios thereof, following administration CON1 and CON2. Consistent with total lymphocyte trends, both drugs elicited rapid decreases, followed by increases in cytotoxic T-cells [CTLs; CD3$^+$/CD8$^+$/CD4$^-$] (FIG. 12E and FIG. 12F), regulatory T-cells [CD3$^+$/CD4$^+$/CD25$^+$/CD127$^{low}$] (FIG. 12G and FIG. 12H), and natural killer (NK) cells [CD3$^-$/CD159$^+$] (FIG. 12I and FIG. 12J). Compared to CON2, a greater magnitude in NK cell expansion was noted with CON1 at ≥0.3 mg/kg, and a greater magnitude in CD8$^+$:T$_{reg}$ ratios (FIG. 13A and FIG. 13B).

Collectively, the data suggest a greater pharmacodynamic profile for CON1 (permanently R$\gamma_c$ biased) relative to that of CON2 (non β$\gamma_c$ biased) in NHP.

Site-specific PEGylation with a single non-releasable 30 kDa PEG at pAMF incorporated at position S4, confers significant half-life extension in mouse (10 hours) and NHP (17 hours.). Permanently β$\gamma_c$-bias via mutation of R37A/F41K eliminates binding to the IL-2Rα subunit and reduces αβ$\gamma_c$-driven activity 100- to 5000-fold in cell-based assays and 2000- to 3000-fold in PBMCs.

Example 20

This example provides data from a syngeneic mouse CT26 tumor model that shows that the efficacy of CON1 on tumor growth inhibition (TGI) can be enhanced by administrating in combination with an anti-mouse PD-1 antibody and that CON1 was well tolerated at 5 mg/kg and 10 mg/kg doses in a monotherapy or in combination with the anti-mouse PD1 antibody.

Mice

Wild-type C57BL/6J mice were obtained from Jackson laboratories. All animal procedures were approved by the Institutional Animal Care and Use Committee of MRL in accordance with guidelines of the Association for Assessment and Accreditation of Laboratory Animal Care. Study was conducted by HDBiosciences Inc. (6122 Nancy Ridge Drive, San Diego, CA).

Tumor Challenge and Treatment

For the syngeneic tumor experiments, 8- to 12-week-old C57BL/6J mice were subcutaneously (s.c.) injected with 3×10$^5$ CT26 cells on the flank. Tumor diameter was measured by electronic calipers and tumor volume was calculated by length×width×width×½. Treatments were started when tumors reached approximately 100 mm$^3$. The treatments were according to the doses, schedule, and route of administration as shown in Table 14.

TABLE 14

| Grp | Group treatment | Dose | Dosing Schedule | ROA | N | Day 15 TGI %/CR |
|---|---|---|---|---|---|---|
| 1 | Isotype Control + Vehicle | 10 mg/kg — | D 0, 5, 10, 15 D 0, 7, 14 | IP IV | 10 | |
| 2 | Isotype Control + Aldesleukin | 1 mg/kg | (BID 5D 2 days off) × 2 | IP | 10 | 68% 1CR |
| 3 | muDX400 + Vehicle | 10 mg/kg | D 0, 5, 10, 15 D 0, 7, 14 | IP IV | 10 | 25% |
| 4 | mDX400 + Aldesleukin | 10 mg/kg 1 mg/kg | D 0, 5, 10, 15 (BID 5D 2 days off) × 2 | IP IP | 10 | 85% 1CR |
| 5 | Isotype Control + CON1 | 10 mg/kg 5 mg/kg | D 0, 5, 10, 15 D 0, 7, 14 | IP IV | 10 | 24% |
| 6 | Isotype Control + CON1 | 10 mg/kg 10 mg/kg | D 0, 5, 10, 15 D 0, 7, 14 | IP IV | 10 | 49% |
| 7 | muDX400 + CON1 | 10 mg/kg 5 mg/kg | D 0, 5, 10, 15 D 0, 7, 14 | IP IV | 10 | 45% |
| 8 | muDX400 + CON1 | 10 mg/kg 10 mg/kg | D 0, 5, 10, 15 D 0, 7, 14 | IP IV | 10 | 69% 1PR |

TGI = tumor growth inhibition;
CR = complete response;
PR = partial response;
ROA = route of administration;
N = number of mice in group;
IP = Intraperitoneal injection;
IV = intravenous injection;
BID = twice a day;
D = day The anti-mouse PD-1 antibody mDX400 comprises the heavy and light chains having the amino acid sequences disclosed in International Patent Application No. WO2020185722 (see therein SEQ ID Nos. 63 and 64, respectively), which is incorporated herein by reference. To control for potential isotype effects, an anti-AD5-Hexon mouse IgGI (D265A) antibody was used as an IgGI isotype control. The vehicle for formulating the doses was 20 mM NaOAc, pH 5.5 buffer.

Aldesleukin dosed at 1 mg/kg showed similar efficacy for tumor growth inhibition (TGI) to historically observed effects (69% previously observed vs 68% in this example) (FIG. 16A). When aldesleukin dosed at 1 mg/kg was administered in combination with mDX400 dosed at 10 mg/kg, the efficacy of Aldesleukin on TGI was enhanced showing 85% TGI in the combination treatment compared to 69% for the monotherapy (FIG. 16A).

CON1 dosed at 5 mg/kg demonstrated efficacy for TGI, which was enhanced when CON1 dosed 5 mg/kg was administered in combination with mDX400 dosed at 10 mg/kg showing 45% TGI in the combination treatment compared to 24% for the CON1 monotherapy (FIG. 16B). The efficacy of CON1 dosed at 10 mg/kg demonstrated efficacy for TGI, which was enhanced when CON1 dosed 10 mg/kg was administered in combination with mDX400 dosed at 10 mg/kg showing 49% TGI in the combination treatment compared to 45% for the CON1 monotherapy (FIG. 16C).

FIGS. 17A-17B show the individual animal tumor volumes for each treatment group. Complete responses (CR) through Day 36 are presented for the responsive treatment groups. FIGS. 17A-17B show the mean tumor volume and standard error of the mean for each treatment group (starting number n=10/group). Tumor volumes from animals that were removed from the study due to large tumor volumes were carried forward in the mean until the last measurement was taken for that treatment group.

FIGS. 18A-18B show the change in body weight during the course of the experiments. The data show that CON1 was well tolerated at the 5 and 10 mg/kg doses, either as a monotherapy or in combination with mDX400.

SUMMARY

The mouse CT26 syngeneic tumor model has been used to demonstrate the benefit of combining IL-2 treatment with checkpoint blockade to improve tumor growth inhibition (TGI) for NKTR-214 (Charych et al, Clin Cancer Res; 22(3) 2016). Aldesleukin was administered for two courses of 1 mg/kg twice daily (BID) for five days alone or in combination with murine anti-PD1 antibody (mDX400) administered at 10 mg/kg every five days. CON1 was administered every seven days at 10 mg/kg alone or in combination with mDX400. The results shown hwerein demonstrate that Aldesleukin and CON1 both have tumor growth inhibition, and this was further enhanced upon combination with anti-PD1 antibody. TGI for CON1 was 45%, which increased to 69% when combined with mDX400, and TGI for aldesleukin was 68%, which increased to 85% when combined with mDX400. CON1 was also evaluated at 5 mg/kg and while TGI was less pronounced, combination benefit with mDX400 was still observed. Animal health was assessed by monitoring for body weight loss throughout the study and CON1 was shown to be well tolerated at both 5 and 10 mg/kg doses.

Table of Sequences

| SEQ ID NO: | Description | Sequence |
|---|---|---|
| 1 | Native Human IL-2 (mature) | APTSSSTKKTQLQLEHLLLDLQMILN GINNYKNPKLTRMLTFKFYMPKKAT ELKHLQCLEEELKPLEEVLNLAQSK NFHLRPRDLISNINVIVLELKGSETTF MCEYADETATIVEFLNRWITFCQSIIS TLT |
| 2 | DesA1_IL-2_C124S (mature) (aldesleukin) | PTSSSTKKTQLQLEHLLLDLQMILNG INNYKNPKLTRMLTFKFYMPKKATE LKHLQCLEEELKPLEEVLNLAQSKN FHLRPRDLISNINVIVLELKGSETTFM CEYADETATIVEFLNRWITFSQSIIST LT |
| 3 | IL-2 conjugate<br>X1 = A, another amino acid, NNAA, or absent<br>X2 = P, another amino acid, or NNAA<br>X3 = T, another amino acid, or NNAA<br>X4 = S, another amino acid, or NNAA<br>X5 = S, another amino acid, or NNAA<br>X6 = S, another amino acid, or NNAA<br>X7 = T, another amino acid, or NNAA<br>X8 = K, another amino acid, or NNAA<br>X9 = K, another amino acid, or NNAA<br>X10 = T, another amino acid, or NNAA<br>X1-X10 = proviso that 1-10 comprises only one NNAA and the NNAA is conjugated to a nonpeptidic, water soluble polymer | XXXXXXXXXXQLQLEHLLLDLQMI LNGINNYKNPXLXXMLXXXFXMPK KATELKHLQCLEXXLXXLEXVLNX AQSKNFHLRPRDLISNINVIVLELKG SETTFMCEXADETATIVEFLNRWITF XQSIISTLT |

| SEQ ID NO: | Description | Sequence |
|---|---|---|
| | X35 = K or another amino acid<br>X37 = T or another amino acid<br>X38 = R or another amino acid<br>X41 = T or another amino acid<br>X42 = F or another amino acid<br>X43 = K or another amino acid<br>X45 = Y or another amino acid<br>X61 = E or another amino acid<br>X62 = E or another amino acid<br>X64 = K or another amino acid<br>X65 = P or another amino acid<br>X68 = E or another amino acid<br>X72 = L or another amino acid<br>X107 = Y or another amino acid<br>X125 = C or another amino acid<br>X1-X133 = with the proviso that at least one of the amino acids at positions 37, 38, 41, 42, 43, 45, 61, 62, 64, 65, 68, 72, and 107 is not the amino acid at the corresponding position in native IL-2 | |
| 4 | IL-2 conjugate<br>X1 = P, another amino acid, or NNAA<br>X2 = T, another amino acid, or NNAA<br>X3 = S, another amino acid, or NNAA<br>X4 = S, another amino acid, or NNAA<br>X5 = S, another amino acid, or NNAA<br>X6 = T, another amino acid, or NNAA<br>X7 = K, another amino acid, or NNAA<br>X8 = K, another amino acid, or NNAA<br>X9 = T, another amino acid, or NNAA<br>X1-X9 = proviso that 1-9 comprises only one NNAA and the NNAA is conjugated to a nonpeptidic, water soluble polymer<br>X34 = K or another amino acid<br>X36 = T or another amino acid<br>X37 = R or another amino acid<br>X40 = T or another amino acid<br>X41 = F or another amino acid<br>X42 = K or another amino acid<br>X44 = Y or another amino acid<br>X60 = E or another amino acid<br>X61 = E or another amino acid<br>X63 = K or another amino acid<br>X64 = P or another amino acid<br>X67 = E or another amino acid<br>X71 = L or another amino acid<br>X106 = Y or another amino acid<br>X124 = C or another amino acid<br>X1-X132 = with the proviso that at least one of the amino acids at positions 36, 37, 40, 41, 42, 44, 60, 61, 63, 64, 69, 71, and 106 is not the amino acid at the corresponding position in aldesleukin | XXXXXXXXXQLQLEHLLLDLQMIL<br>NGINNYKNPXLXXMLXXXFXMPKK<br>ATELKHLQCLEXXLXXLEXVLNXA<br>QSKNFHLRPRDLISNINVIVLELKGSE<br>TTFMCEXADETATIVEFLNRWITFXQ<br>SIISTLT |
| 5 | IL-2 conjugate<br>X4 = NNAA conjugated to a nonpeptidic, water soluble polymer<br>X34 = K or another amino acid<br>X36 = T or another amino acid<br>X37 = R or another amino acid<br>X40 = T or another amino acid<br>X41 = F or another amino acid<br>X42 = K or another amino acid<br>X44 = Y or another amino acid<br>X60 = E or another amino acid<br>X61 = E or another amino acid<br>X63 = K or another amino acid<br>X64 = P or another amino acid<br>X67 = E or another amino acid<br>X71 = L or another amino acid | PTSXSTKKTQLQLEHLLLDLQMILN<br>GINNYKNPXLXXMLXXXFXMPKKA<br>TELKHLQCLEXXLXXLEXVLNXAQS<br>KNFHLRPRDLISNINVIVLELKGSETT<br>FMCEXADETATIVEFLNRWITFXQSII<br>STLT |

Table of Sequences

| SEQ ID NO: | Description | Sequence |
|---|---|---|
| | X106 = Y or another amino acid<br>X124 = C or another amino acid<br>X1-X132 = with the proviso that at least one of the amino acids at positions 36, 37, 40, 41, 42, 44, 60, 61, 63, 64, 69, 71, and 106 is not the amino acid at the corresponding position in native human IL-2 | |
| 6 | IL-2 conjugate<br>X4 = NNAA conjugated to a nonpeptidic, water soluble polymer<br>X37 = any amino acid except R<br>X41 = any amino acid except F<br>X124 = any amino acid except C | PTSXSTKKTQLQLEHLLLDLQMILN<br>GINNYKNPKLTXMLTXKFYMPKKA<br>TELKHLQCLEEELKPLEEVLNLAQS<br>KNFHLRPRDLISNINVIVLELKGSETT<br>FMCEYADETATIVEFLNRWITFXQSII<br>STLT |
| 7 | IL-2 conjugate<br>X5 = NNAA conjugated to a nonpeptidic, water soluble polymer<br>X38 = any amino acid except R<br>X42 = any amino acid except F<br>X125 = any amino acid except C | APTSXSTKKTQLQLEHLLLDLQMIL<br>NGINNYKNPKLTXMLTXKFYMPKK<br>ATELKHLQCLEEELKPLEEVLNLAQ<br>SKNFHLRPRDLISNINVIVLELKGSET<br>TFMCEYADETATIVEFLNRWITFXQS<br>IISTLT |
| 8 | IL-2 conjugate<br>X4 = NNAA conjugated to a nonpeptidic, water soluble polymer<br>X124 = A or S | PTSXSTKKTQLQLEHLLLDLQMILN<br>GINNYKNPKLTAMLTKKFYMPKKA<br>TELKHLQCLEEELKPLEEVLNLAQS<br>KNFHLRPRDLISNINVIVLELKGSETT<br>FMCEYADETATIVEFLNRWITFXQSII<br>STLT |
| 9 | IL-2 conjugate<br>X5 = NNAA conjugated to a nonpeptidic, water soluble polymer<br>X125 = A or S | APTSXSTKKTQLQLEHLLLDLQMIL<br>NGINNYKNPKLTAMLTKKFYMPKK<br>ATELKHLQCLEEELKPLEEVLNLAQ<br>SKNFHLRPRDLISNINVIVLELKGSET<br>TFMCEYADETATIVEFLNRWITFXQS<br>IISTLT |
| 10 | IL-2 conjugate DesA1_S4NNA(nonpeptidic, water soluble polymer)/R37A/F41K/C124S<br>X4 = NNAA conjugated to a nonpeptidic, water soluble polymer | PTSXSTKKTQLQLEHLLLDLQMILN<br>GINNYKNPKLTAMLTKKFYMPKKA<br>TELKHLQCLEEELKPLEEVLNLAQS<br>KNFHLRPRDLISNINVIVLELKGSETT<br>FMCEYADETATIVEFLNRWITFSQSII<br>STLT |
| 11 | IL-2 conjugate IL-2_S5NNA(nonpeptidic, water soluble polymer)/R38A/F42K/C125S<br>X5 = NNAA conjugated to a nonpeptidic, water soluble polymer | APTSXSTKKTQLQLEHLLLDLQMIL<br>NGINNYKNPKLTAMLTKKFYMPKK<br>ATELKHLQCLEEELKPLEEVLNLAQ<br>SKNFHLRPRDLISNINVIVLELKGSET<br>TFMCEYADETATIVEFLNRWITFSQS<br>IISTLT |
| 12 | IL-2 conjugate DesA1_IL-2_S4pAMF(nonpeptidic, water soluble polymer)/R37A/F41K/C124S<br>X4 = pAMF conjugated to a nonpeptidic, water soluble polymer | PTSXSTKKTQLQLEHLLLDLQMILN<br>GINNYKNPKLTAMLTKKFYMPKKA<br>TELKHLQCLEEELKPLEEVLNLAQS<br>KNFHLRPRDLISNINVIVLELKGSETT<br>FMCEYADETATIVEFLNRWITFSQSII<br>STLT |
| 13 | IL-2 conjugate IL-2_S5 pAMF(nonpeptidic, water soluble polymer)/R38A/F42K/C125S<br>X5 = pAMF conjugated to a nonpeptidic, water soluble polymer | APTSXSTKKTQLQLEHLLLDLQMIL<br>NGINNYKNPKLTAMLTKKFYMPKK<br>ATELKHLQCLEEELKPLEEVLNLAQ<br>SKNFHLRPRDLISNINVIVLELKGSET<br>TFMCEYADETATIVEFLNRWITFSQS<br>IISTLT |
| 14 | IL-2 conjugate DesA1_IL-2_S4 pAMF(PEG)/R37A/F41K/C124S<br>X4 = pAMF conjugated to PEG | PTSXSTKKTQLQLEHLLLDLQMILN<br>GINNYKNPKLTAMLTKKFYMPKKA<br>TELKHLQCLEEELKPLEEVLNLAQS<br>KNFHLRPRDLISNINVIVLELKGSETT<br>FMCEYADETATIVEFLNRWITFSQSII<br>STLT |

Table of Sequences

| SEQ ID NO: | Description | Sequence |
|---|---|---|
| 15 | IL-2 conjugate IL-2_S5 pAMF(PEG)/R38A/F42K/C125S X5 = pAMF conjugated to PEG | APTSXSTKKTQLQLEHLLLDLQMIL NGINNYKNPKLTAMLTKKFYMPKK ATELKHLQCLEEELKPLEEVLNLAQ SKNFHLRPRDLISNINVIVLELKGSET TFMCEYADETATIVEFLNRWITFSQS IISTLT |
| 16 | IL-2 conjugate DesA1_IL-2_S4 pAMF(PEG)/R37A/F41K/C124S X4 = pAMF conjugated to mPEG | PTSXSTKKTQLQLEHLLLDLQMILN GINNYKNPKLTAMLTKKFYMPKKA TELKHLQCLEEELKPLEEVLNLAQS KNFHLRPRDLISNINVIVLELKGSETT FMCEYADETATIVEFLNRWITFSQSII STLT |
| 17 | IL-2 conjugate IL-2_S5 pAMF(PEG)/R38A/F42K/C125S X5 = pAMF conjugated to mPEG | APTSXSTKKTQLQLEHLLLDLQMIL NGINNYKNPKLTAMLTKKFYMPKK ATELKHLQCLEEELKPLEEVLNLAQ SKNFHLRPRDLISNINVIVLELKGSET TFMCEYADETATIVEFLNRWITFSQS IISTLT |
| 18 | IL-2 conjugate DesA1_IL-2/S4 pAMF(30 kDa mPEG)/R37A/F41K/C124S X4 = pAMF conjugated to 30 kDa mPEG | PTSXSTKKTQLQLEHLLLDLQMILN GINNYKNPKLTAMLTKKFYMPKKA TELKHLQCLEEELKPLEEVLNLAQS KNFHLRPRDLISNINVIVLELKGSETT FMCEYADETATIVEFLNRWITFSQSII STLT |
| 19 | IL-2 conjugate IL-2_S5 pAMF(30 kDa mPEG)/R38A/F42K/C125S X5 = pAMF conjugated to 30 kDa mPEG | APTSXSTKKTQLQLEHLLLDLQMIL NGINNYKNPKLTAMLTKKFYMPKK ATELKHLQCLEEELKPLEEVLNLAQ SKNFHLRPRDLISNINVIVLELKGSET TFMCEYADETATIVEFLNRWITFSQS IISTLT |
| 20 | IL-2 conjugate Des-A1_IL-2_S4pAMF(PEG1)/R37A/F41K/C124S X4 = pAMF conjugated to PEG1 by a triazole linkage (CON1) | PTSXSTKKTQLQLEHLLLDLQMILN GINNYKNPKLTAMLTKKFYMPKKA TELKHLQCLEEELKPLEEVLNLAQS KNFHLRPRDLISNINVIVLELKGSETT FMCEYADETATIVEFLNRWITFSQSII STLT |
| 21 | IL-2 conjugate IL-2_S5pAMF(PEG1)/R38A/F42K/C125S X5 = pAMF conjugated to PEG1 by a triazole linkage | APTSXSTKKTQLQLEHLLLDLQMIL NGINNYKNPKLTAMLTKKFYMPKK ATELKHLQCLEEELKPLEEVLNLAQ SKNFHLRPRDLISNINVIVLELKGSET TFMCEYADETATIVEFLNRWITFSQS IISTLT |
| 22 | IL-2 conjugate DesA1/S4pMF(PEG1)/C124S X4 = pAMF conjugated to PEG1 by a triazole linkage (CON2) | PTSXSTKKTQLQLEHLLLDLQMILN GINNYKNPKLTRMLTFKFYMPKKAT ELKHLQCLEEELKPLEEVLNLAQSK NFHLRPRDLISNINVIVLELKGSETTF MCEYADETATIVEFLNRWITFSQSIIS TLT |
| 23 | Ald-6HIS_F41K/E60T/E61S | PTSSSTKKTQLQLEHLLLDLQMILNG INNYKNPKLTRMLTKKFYMPKKATE LKHLQCLETSLKPLEEVLNLAQSKN FHLRPRDLISNINVIVLELKGSETTFM CEYADETATIVEFLNRWITFSQSIIST LTGGSHHHHHH |
| 24 | Ald-6HIS_T40D/E60T/E61S | PTSSSTKKTQLQLEHLLLDLQMILNG INNYKNPKLTRMLDFKFYMPKKATE LKHLQCLETSLKPLEEVLNLAQSKN FHLRPRDLISNINVIVLELKGSETTFM CEYADETATIVEFLNRWITFSQSIIST LTGGSHHHHHH |

Table of Sequences

| SEQ ID NO: | Description | Sequence |
|---|---|---|
| 25 | Ald-6HIS_T40D/F41K/E61S | PTSSSTKKTQLQLEHLLLDLQMILNG INNYKNPKLTRMLDKKFYMPKKAT ELKHLQCLEESLKPLEEVLNLAQSK NFHLRPRDLISNINVIVLELKGSETTF MCEYADETATIVEFLNRWITFSQSIIS TLTGGSHHHHHH |
| 26 | Ald-6HIS_T40D/F41K/E60T | PTSSSTKKTQLQLEHLLLDLQMILNG INNYKNPKLTRMLDKKFYMPKKAT ELKHLQCLETELKPLEEVLNLAQSK NFHLRPRDLISNINVIVLELKGSETTF MCEYADETATIVEFLNRWITFSQSIIS TLTGGSHHHHHH |
| 27 | Ald-6HIS_R37A/E60T/E61S | PTSSSTKKTQLQLEHLLLDLQMILNG INNYKNPKLTAMLTFKFYMPKKATE LKHLQCLETSLKPLEEVLNLAQSKN FHLRPRDLISNINVIVLELKGSETTFM CEYADETATIVEFLNRWITFSQSIIST LTGGSHHHHHH |
| 28 | Ald-6HIS_R37A/F41K/E61S | PTSSSTKKTQLQLEHLLLDLQMILNG INNYKNPKLTAMLTKKFYMPKKAT ELKHLQCLEESLKPLEEVLNLAQSK NFHLRPRDLISNINVIVLELKGSETTF MCEYADETATIVEFLNRWITFSQSIIS TLTGGSHHHHHH |
| 29 | Ald-6HIS_R37A/F41K/E60T | PTSSSTKKTQLQLEHLLLDLQMILNG INNYKNPKLTAMLTKKFYMPKKAT ELKHLQCLETELKPLEEVLNLAQSK NFHLRPRDLISNINVIVLELKGSETTF MCEYADETATIVEFLNRWITFSQSIIS TLTGGSHHHHHH |
| 30 | Ald-6HIS_R37A/T40D/E61S | PTSSSTKKTQLQLEHLLLDLQMILNG INNYKNPKLTAMLDFKFYMPKKATE LKHLQCLEESLKPLEEVLNLAQSKN FHLRPRDLISNINVIVLELKGSETTFM CEYADETATIVEFLNRWITFSQSIIST LTGGSHHHHHH |
| 31 | Ald-6HIS_R37A/T40D/E60T | PTSSSTKKTQLQLEHLLLDLQMILNG INNYKNPKLTAMLDFKFYMPKKATE LKHLQCLETELKPLEEVLNLAQSKN FHLRPRDLISNINVIVLELKGSETTFM CEYADETATIVEFLNRWITFSQSIIST LTGGSHHHHHH |
| 32 | Ald-6HIS_R37A/T40D/F41K | PTSSSTKKTQLQLEHLLLDLQMILNG INNYKNPKLTAMLDKKFYMPKKAT ELKHLQCLEEELKPLEEVLNLAQSK NFHLRPRDLISNINVIVLELKGSETTF MCEYADETATIVEFLNRWITFSQSIIS TLTGGSHHHHHH |
| 33 | Ald-6HIS_F41K/E61S | PTSSSTKKTQLQLEHLLLDLQMILNG INNYKNPKLTRMLTKKFYMPKKATE LKHLQCLEESLKPLEEVLNLAQSKN FHLRPRDLISNINVIVLELKGSETTFM CEYADETATIVEFLNRWITFSQSIIST LTGGSHHHHHH |
| 34 | Ald-6HIS_F41K/E60T | PTSSSTKKTQLQLEHLLLDLQMILNG INNYKNPKLTRMLTKKFYMPKKATE LKHLQCLETELKPLEEVLNLAQSKN FHLRPRDLISNINVIVLELKGSETTFM CEYADETATIVEFLNRWITFSQSIIST LTGGSHHHHHH |

Table of Sequences

| SEQ ID NO: | Description | Sequence |
|---|---|---|
| 35 | Ald-6HIS_T40D/E61S | PTSSSTKKTQLQLEHLLLDLQMILNGINNYKNPKLTRMLDFKFYMPKKATELKHLQCLEESLKPLEEVLNLAQSKNFHLRPRDLISNINVIVLELKGSETTFMCEYADETATIVEFLNRWITFSQSIISTLTGGSHHHHHH |
| 36 | Ald-6HIS_T40D/E60T | PTSSSTKKTQLQLEHLLLDLQMILNGINNYKNPKLTRMLDFKFYMPKKATELKHLQCLETELKPLEEVLNLAQSKNFHLRPRDLISNINVIVLELKGSETTFMCEYADETATIVEFLNRWITFSQSIISTLTGGSHHHHHH |
| 37 | Ald-6HIS_T40D/F41K | PTSSSTKKTQLQLEHLLLDLQMILNGINNYKNPKLTRMLDKKFYMPKKATELKHLQCLEEELKPLEEVLNLAQSKNFHLRPRDLISNINVIVLELKGSETTFMCEYADETATIVEFLNRWITFSQSIISTLTGGSHHHHHH |
| 38 | Ald-6HIS_R37A/E61S | PTSSSTKKTQLQLEHLLLDLQMILNGINNYKNPKLTAMLTFKFYMPKKATELKHLQCLEESLKPLEEVLNLAQSKNFHLRPRDLISNINVIVLELKGSETTFMCEYADETATIVEFLNRWITFSQSIISTLTGGSHHHHHH |
| 39 | Ald-6HIS_R37A/E60T | PTSSSTKKTQLQLEHLLLDLQMILNGINNYKNPKLTAMLTFKFYMPKKATELKHLQCLETELKPLEEVLNLAQSKNFHLRPRDLISNINVIVLELKGSETTFMCEYADETATIVEFLNRWITFSQSIISTLTGGSHHHHHH |
| 40 | Ald-6HIS_R37A/F41K | PTSSSTKKTQLQLEHLLLDLQMILNGINNYKNPKLTAMLTKKFYMPKKATELKHLQCLEEELKPLEEVLNLAQSKNFHLRPRDLISNINVIVLELKGSETTFMCEYADETATIVEFLNRWITFSQSIISTLTGGSHHHHHH |
| 41 | Ald-6HIS_R37A/T40D | PTSSSTKKTQLQLEHLLLDLQMILNGINNYKNPKLTAMLDFKFYMPKKATELKHLQCLEEELKPLEEVLNLAQSKNFHLRPRDLISNINVIVLELKGSETTFMCEYADETATIVEFLNRWITFSQSIISTLTGGSHHHHHH |
| 42 | IL-2 moiety<br>X1 = A, another amino acid, NNAA, or absent<br>X2 = P, another amino acid, or NNAA<br>X3 = T, another amino acid, or NNAA<br>X4 = S, another amino acid, or NNAA<br>X5 = S, another amino acid, or NNAA<br>X6 = S, another amino acid, or NNAA<br>X7 = T, another amino acid, or NNAA<br>X8 = K, another amino acid, or NNAA<br>X9 = K, another amino acid, or NNAA<br>X10 = T, another amino acid, or NNAA<br>X1-X10 = proviso that 1-10 comprises only one NNAA<br>X35 = K or another amino acid<br>X37 = T or another amino acid<br>X38 = R or another amino acid<br>X41 = T or another amino acid<br>X42 = F or another amino acid<br>X43 = K or another amino acid<br>X45 = Y or another amino acid<br>X61 = E or another amino acid<br>X62 = E or another amino acid<br>X64 = K or another amino acid | XXXXXXXXXXQLQLEHLLLDLQMILNGINNYKNPXLXXMLXXXFXMPKKATELKHLQCLEXXLXXLEXVLNXAQSKNFHLRPRDLISNINVIVLELKGSETTFMCEXADETATIVEFLNRWITFXQSIISTLT |

Table of Sequences

| SEQ ID NO: | Description | Sequence |
|---|---|---|
| | X65 = P or another amino acid<br>X68 = E or another amino acid<br>X72 = L or another amino acid<br>X107 = Y or another amino acid<br>X125 = C or another amino acid<br>X1-X133 = with the proviso that at least one of the amino acids at positions 37, 38, 41, 42, 43, 45, 61, 62, 64, 65, 68, 72, and 107 is not the amino acid at the corresponding position in native IL-2 | |
| 43 | IL-2 moiety<br>X1 = P, another amino acid, or NNAA<br>X2 = T, another amino acid, or NNAA<br>X3 = S, another amino acid, or NNAA<br>X4 = S, another amino acid, or NNAA<br>X5 = S, another amino acid, or NNAA<br>X6 = T, another amino acid, or NNAA<br>X7 = K, another amino acid, or NNAA<br>X8 = K, another amino acid, or NNAA<br>X9 = T, another amino acid, or NNAA<br>X1-X9 = proviso that 1-9 comprises only one NNAA<br>X34 = K or another amino acid<br>X36 = T or another amino acid<br>X37 = R or another amino acid<br>X40 = T or another amino acid<br>X41 = F or another amino acid<br>X42 = K or another amino acid<br>X44 = Y or another amino acid<br>X60 = E or another amino acid<br>X61 = E or another amino acid<br>X63 = K or another amino acid<br>X64 = P or another amino acid<br>X67 = E or another amino acid<br>X71 = L or another amino acid<br>X106 = Y or another amino acid<br>X124 = C or another amino acid<br>X1-X132 = with the proviso that at least one of the amino acids at positions 36, 37, 40, 41, 42, 44, 60, 61, 63, 64, 69, 71, and 106 is not the amino acid at the corresponding position in aldesleukin | XXXXXXXXXQLQLEHLLLDLQMIL<br>NGINNYKNPXLXXMLXXXFXMPKK<br>ATELKHLQCLEXXLXXLEXVLNXA<br>QSKNFHLRPRDLISNINVIVLELKGSE<br>TTFMCEXADETATIVEFLNRWITFXQ<br>SIISTLT |
| 44 | IL-2 moiety<br>X4 = NNAA conjugated to a nonpeptidic, water-soluble polymer<br>X34 = K or another amino acid<br>X36 = T or another amino acid<br>X37 = R or another amino acid<br>X40 = T or another amino acid<br>X41 = F or another amino acid<br>X42 = K or another amino acid<br>X44 = Y or another amino acid<br>X60 = E or another amino acid<br>X61 = E or another amino acid<br>X63 = K or another amino acid<br>X64 = P or another amino acid<br>X67 = E or another amino acid<br>X71 = L or another amino acid<br>X106 = Y or another amino acid<br>X124 = C or another amino acid<br>X1-X132 = with the proviso that at least one of the amino acids at positions 36, 37, 40, 41, 42, 44, 60, 61, 63, 64, 69, 71, and 106 is not the amino acid at the corresponding position in native human IL-2 | PTSXSTKKTQLQLEHLLLDLQMILN<br>GINNYKNPXLXXMLXXXFXMPKKA<br>TELKHLQCLEXXLXXLEXVLNXAQS<br>KNFHLRPRDLISNINVIVLELKGSETT<br>FMCEXADETATIVEFLNRWITFXQSII<br>STLT |

-continued

Table of Sequences

| SEQ ID NO: | Description | Sequence |
|---|---|---|
| 45 | IL-2 moiety<br>X4 = NNAA<br>X37 = any amino acid except R<br>X41 = any amino acid except F<br>X124 = any amino acid except C | PTSXSTKKTQLQLEHLLLDLQMILN<br>GINNYKNPKLTXMLTXKFYMPKKA<br>TELKHLQCLEEELKPLEEVLNLAQS<br>KNFHLRPRDLISNINVIVLELKGSETT<br>FMCEYADETATIVEFLNRWITFXQSII<br>STLT |
| 46 | IL-2 moiety<br>X5 = NNAA<br>X38 = any amino acid except R<br>X42 = any amino acid except F<br>X125 = any amino acid except C | APTSXSTKKTQLQLEHLLLDLQMIL<br>NGINNYKNPKLTXMLTXKFYMPKK<br>ATELKHLQCLEEELKPLEEVLNLAQ<br>SKNFHLRPRDLISNINVIVLELKGSET<br>TFMCEYADETATIVEFLNRWITFXQS<br>IISTLT |
| 47 | IL-2 moiety<br>X4 = NNAA<br>X124 = A or S | PTSXSTKKTQLQLEHLLLDLQMILN<br>GINNYKNPKLTAMLTKKFYMPKKA<br>TELKHLQCLEEELKPLEEVLNLAQS<br>KNFHLRPRDLISNINVIVLELKGSETT<br>FMCEYADETATIVEFLNRWITFXQSII<br>STLT |
| 48 | IL-2 moiety<br>X5 = NNAA<br>X125 = A or S | APTSXSTKKTQLQLEHLLLDLQMIL<br>NGINNYKNPKLTAMLTKKFYMPKK<br>ATELKHLQCLEEELKPLEEVLNLAQ<br>SKNFHLRPRDLISNINVIVLELKGSET<br>TFMCEYADETATIVEFLNRWITFXQS<br>IISTLT |
| 49 | IL-2 moiety<br>DesA1_S4NNNA_R37A_F41K_C124S<br>X4 = NNAA | PTSXSTKKTQLQLEHLLLDLQMILN<br>GINNYKNPKLTAMLTKKFYMPKKA<br>TELKHLQCLEEELKPLEEVLNLAQS<br>KNFHLRPRDLISNINVIVLELKGSETT<br>FMCEYADETATIVEFLNRWITFSQSII<br>STLT |
| 50 | IL-2 moiety<br>IL-2_S5NNAA_R38A_F42K_C125S<br>X5 = NNAA | APTSXSTKKTQLQLEHLLLDLQMIL<br>NGINNYKNPKLTAMLTKKFYMPKK<br>ATELKHLQCLEEELKPLEEVLNLAQ<br>SKNFHLRPRDLISNINVIVLELKGSET<br>TFMCEYADETATIVEFLNRWITFSQS<br>IISTLT |
| 51 | IL-2 moiety DesA1_IL-2_S4pAMF_R37A_F41K_C124S<br>X4 = pAMF | PTSXSTKKTQLQLEHLLLDLQMILN<br>GINNYKNPKLTAMLTKKFYMPKKA<br>TELKHLQCLEEELKPLEEVLNLAQS<br>KNFHLRPRDLISNINVIVLELKGSETT<br>FMCEYADETATIVEFLNRWITFSQSII<br>STLT |
| 52 | IL-2 moiety IL-2_S5 pAMF_R38A_F42K_C125S<br>X5 = pAMF | APTSXSTKKTQLQLEHLLLDLQMIL<br>NGINNYKNPKLTAMLTKKFYMPKK<br>ATELKHLQCLEEELKPLEEVLNLAQ<br>SKNFHLRPRDLISNINVIVLELKGSET<br>TFMCEYADETATIVEFLNRWITFSQS<br>IISTLT |
| 53 | DesA1_IL-2 (mature) | PTSSSTKKTQLQLEHLLLDLQMILNG<br>INNYKNPKLTRMLTFKFYMPKKATE<br>LKHLQCLEEELKPLEEVLNLAQSKN<br>FHLRPRDLISNINVIVLELKGSETTFM<br>CEYADETATIVEFLNRWITFCQSIIST<br>LT |
| 54 | 6HIS-tag | HHHHHH |

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

What is claimed:

1. An interleukin 2 (IL-2) conjugate comprising an IL-2 polypeptide comprising an amino acid sequence with at least 80% identity to the amino acid sequence set forth in SEQ ID NO: 53 and further comprising:
   (i) one or more amino acid substitutions that reduce(s) affinity of the IL-2 polypeptide for the human IL-2 receptor αβγ$_c$ trimer (IL-2Rαβγ$_c$) relative to wild-type human IL-2; and
   (ii) a substitution of an amino acid at or near the N-terminus of the IL-2 polypeptide with a non-natural amino acid comprising an azide group, wherein the azide group is conjugated to an alkyne group of a nonpeptidic, water-soluble polymer having the formula

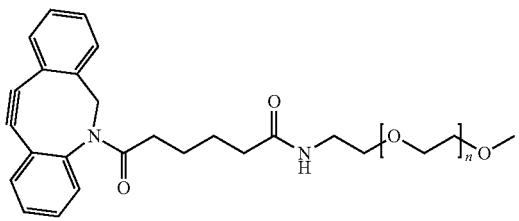

wherein n is about 681; and wherein the IL-2 polypeptide has substantially similar binding affinity for the human IL-2 receptor βγ$_c$ dimer (IL-βγ$_c$) relative to wild-type human IL-2.

2. The IL-2 conjugate of claim 1, wherein the IL-2 polypeptide comprises at least amino acids E15, H16, L19, D20, D84, N88, V91, Q126, T123, and I129, wherein the amino acid positions correspond to the positions set forth in the amino acid sequence of SEQ ID NO: 53 according to numbering scheme B.

3. The IL-2 conjugate of claim 1, wherein the IL-2 polypeptide conjugate has no detectable binding to the human IL-2 receptor α monomer (IL-2Rα) as determined by a Surface Plasmon Resonance assay.

4. The IL-2 conjugate of claim 1, wherein the one or more amino acid substitutions are located at amino acid positions independently selected from the group consisting of K34, T36, R37, T40, F41, K42, F43, Y44, E60, E61, K63, P64, E67, L71, M103, C104, and Y106, wherein the amino acid substitution positions correspond to the position of the amino acid in the amino acid sequence set forth in SEQ ID NO: 53 according to numbering scheme A.

5. The IL-2 conjugate of claim 4, wherein the one or more amino acid substitutions in the IL-2 polypeptide are at positions R37 and F41.

6. The IL-2 conjugate of claim 5, wherein the one or more amino acid substitutions in the IL-2 polypeptide are R37A and F41K.

7. The IL-2 conjugate of claim 1, wherein the IL-2 polypeptide further includes an amino acid substitution of the cysteine residue at position 124 with an amino acid selected from the group consisting of A and S, wherein the amino acid position corresponds to the position of the amino acid in the amino acid sequence set forth in SEQ ID NO: 53.

8. The IL-2 conjugate of claim 1, wherein the IL-2 polypeptide further includes an N-terminal alanine residue or an N-terminal methionine residue.

9. The IL-2 conjugate of claim 1, wherein the non-natural amino acid is substituted for an amino acid at position P1, T2, S3, S4, S5, T6, K7, K8, or T9 or linked to the N-terminal amino acid by an amide linkage, wherein the amino acid position corresponds to the position of the amino acid of SEQ ID NO: 53 according to numbering scheme A.

10. The IL-2 conjugate of claim 9, wherein the non-natural amino acid is located at the amino acid position corresponding to position S4 of the amino acid sequence set forth in SEQ ID NO: 2, wherein the amino acid position is according to numbering scheme A.

11. The IL-2 conjugate of claim 1, wherein the non-natural amino acid is selected from the group consisting of p-azidomethyl-L-phenylalanine, p-azido-L-phenylalanine, and N6-azidoethoxy-L-lysine.

12. The IL-2 conjugate of claim 1, wherein the non-natural amino acid is p-azidomethyl-L-phenylalanine.

13. The IL-2 conjugate of claim 1, wherein the IL-2 conjugate comprises the amino acid sequence set forth in SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO:
11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, or SEQ ID NO: 21.

14. An interleukin 2 (IL-2) conjugate comprising the formula (SEQ ID NO: 20)

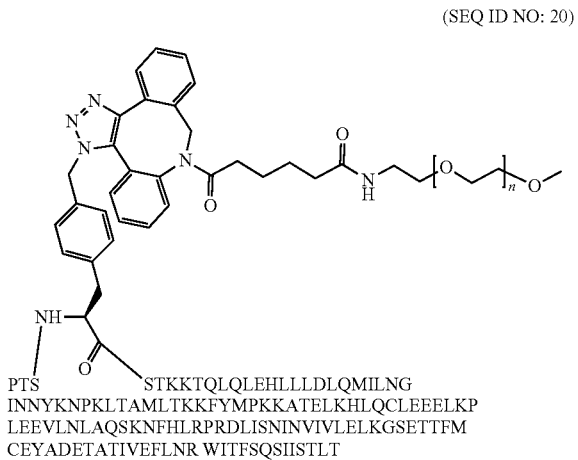

PTS STKKTQLQLEHLLLDLQMILNG
INNYKNPKLTAMLTKKFYMPKKATELKHLQCLEEELKP
LEEVLNLAQSKNFHLRPRDLISNINVIVLELKGSETTFM
CEYADETATIVEFLNR WITFSQSIISTLT wherein n is about 681, or a regioisomer thereof comprising the formula (SEQ ID NO: 20)

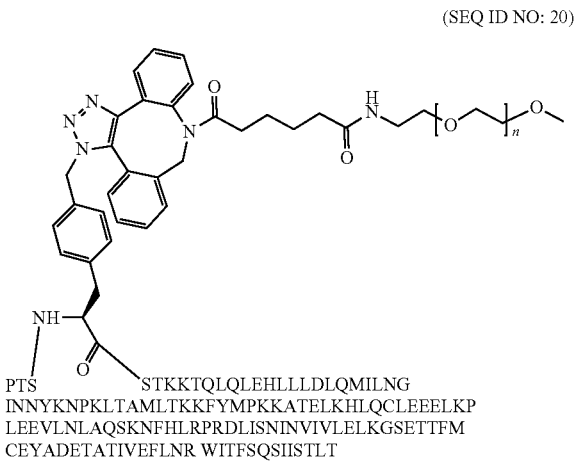

PTS STKKTQLQLEHLLLDLQMILNG
INNYKNPKLTAMLTKKFYMPKKATELKHLQCLEEELKP
LEEVLNLAQSKNFHLRPRDLISNINVIVLELKGSETTFM
CEYADETATIVEFLNR WITFSQSIISTLT wherein n is about 681.

15. A composition comprising:
the IL-2 conjugate of claim 1 and a pharmaceutically acceptable carrier or excipient.

16. A method for treating a proliferative disease or cancer in an individual, comprising:
administering a therapeutically effective amount of the IL-2 conjugate of claim 1 or composition of claim 15 to an individual in need thereof to treat the proliferative disease or cancer in the individual.

17. A combination therapy for treating a proliferative disease or cancer in an individual, comprising:

administering a therapeutically effective amount of the IL-2 conjugate of claim 1 or composition of claim 15 to an individual in need thereof, and
administering a therapeutically effective amount of a therapeutic agent to the individual, to treat the proliferative disease or cancer in the individual.

18. The combination therapy of claim 17, wherein the therapeutic agent is an anti-PD1 antibody or anti-PDL1 antibody.

19. The combination therapy of claim 17, wherein the IL-2 conjugate or composition is administered before the therapeutic agent is administered.

20. The combination therapy of claim 17, wherein the IL-2 conjugate or composition is administered after the therapeutic agent is administered.

21. The combination therapy of claim 17, wherein the IL-2 conjugate or composition is administered concurrently with the therapeutic agent.

22. An interleukin 2 (IL-2) conjugate comprising an IL-2 polypeptide comprising an amino acid sequence with at least 80% identity to the amino acid sequence set forth in SEQ ID NO: 53 and further comprising:
(i) one or more amino acid substitutions located at an amino acid position selected from the group consisting of K34, T36, R37, T40, F41, K42, F43, Y44, E60, E61, K63, P64, E67, L71, M103, C104, and Y106; and
(ii) a substitution of an amino acid at or near the N-terminus of the IL-2 polypeptide with a non-natural amino acid comprising an azide group, wherein the azide group is conjugated to an alkyne group of a nonpeptidic, water-soluble polymer having the formula

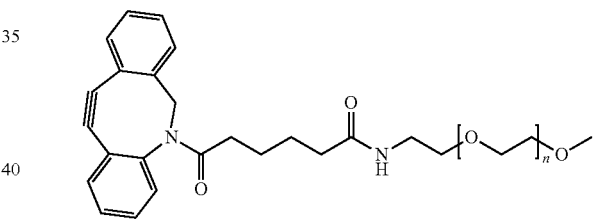

wherein n is about 681; and, wherein the amino acid positions correspond to the positions set forth in the amino acid sequence of SEQ ID NO: 53.

23. The IL-2 conjugate of claim 22, wherein the IL-2 polypeptide amino acid sequence comprises at least amino acids E15, H16, L19, D20, D84, N88, V91, Q126, T123, and I129, wherein the amino acid positions correspond to the positions set forth in the amino acid sequence of SEQ ID NO: 53 according to numbering scheme B.

24. The IL-2 conjugate of claim 22, wherein the one or more amino acid substitutions in the IL-2 polypeptide are at positions R37 and F41.

25. The IL-2 conjugate of claim 24, wherein the one or more amino acid substitutions in the IL-2 polypeptide are R37A and F41K.

26. The IL-2 conjugate of claim 22, wherein the IL-2 polypeptide further includes an amino acid substitution of the cysteine residue at position 124 with an amino acid selected from the group consisting of A and S, wherein the amino acid position corresponds to the position of the amino acid in SEQ ID NO: 53.

27. The IL-2 conjugate of claim 22, wherein the IL-2 polypeptide further includes an N-terminal alanine residue or an N-terminal methionine residue.

28. The IL-2 conjugate of claim 22, wherein the non-natural amino acid is substituted for an amino acid at position P1, T2, S3, S4, S5, T6, K7, K8, or T9 or linked to the N-terminal amino acid by an amide linkage, wherein the amino acid position corresponds to the position of the amino acid in SEQ ID NO: 53 according to numbering scheme A.

29. The IL-2 conjugate of claim 28, wherein the non-natural amino acid is located at the amino acid position corresponding to position S4 of the amino acid sequence set forth in SEQ ID NO: 2, wherein the amino acid position is according to numbering scheme A.

30. The IL-2 polypeptide conjugate of claim 22, wherein the non-natural amino acid is selected from the group consisting of p-azidomethyl-L-phenylalanine, p-azido-L-phenylalanine, and N6-azidoethoxy-L-lysine.

31. The IL-2 conjugate of claim 22, wherein the non-natural amino acid is p-azidomethyl-L-phenylalanine.

32. The IL-2 conjugate of claim 22, wherein the IL-2 conjugate comprises the amino acid sequence set forth in SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, or SEQ ID NO: 21.

33. A composition comprising:
the IL-2 conjugate of claim 22 and a pharmaceutically acceptable carrier or excipient.

34. A method for treating a proliferative disease or cancer in an individual, comprising:
administering a therapeutically effective amount of the IL-2 conjugate of claim 22 or the composition of claim 33 to an individual in need thereof to treat the proliferative disease or cancer in the individual.

35. A combination therapy for treating a proliferative disease or cancer in an individual, comprising:
administering a therapeutically effective amount of the IL-2 conjugate of claim 22 or the composition of claim 33 to an individual in need thereof, and
administering a therapeutically effective amount of a therapeutic agent to the individual, to treat the proliferative disease or cancer in the individual.

36. The combination therapy of claim 35, wherein the therapeutic agent is an anti-PD1 antibody or anti-PDL1 antibody.

37. An interleukin 2 (IL-2) conjugate comprising an IL-2 polypeptide comprising an amino acid sequence with at least 80% identity to the amino acid sequence set forth in SEQ ID NO: 53 and further comprising:
a substitution of an amino acid at or near the N-terminus of the IL-2 polypeptide with a non-natural amino acid comprising an azide group, wherein the azide group is conjugated to an alkyne group of a nonpeptidic, water-soluble polymer having the formula having the formula

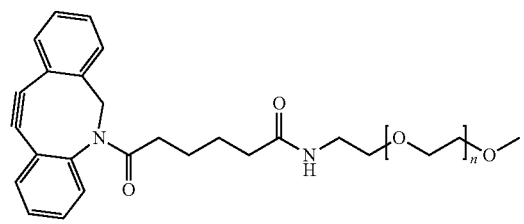

wherein n is about 681, with the proviso that the IL-2 polypeptide comprises at least amino acids (i) E15, H16, L19, D20, D84, N88, V91, Q126, T123, and I129 in which the amino acid positions correspond to the positions set forth in the amino acid sequence of SEQ ID NO: 53 according to numbering scheme B, and
(ii) K34, T36, R37, T40, F41, K42, F43, Y44, E60, E61, K63, P64, E67, L71, M103, C104, and Y106 in which the amino acid positions correspond to the positions set forth in the amino acid sequence of SEQ ID NO: 53 according to numbering scheme A.

38. The IL-2 conjugate of claim 37, wherein the IL-2 polypeptide further includes an amino acid substitution of the cysteine residue at position 124 with an amino acid selected from the group consisting of A and S, wherein the amino acid position corresponds to the position of the amino acid in SEQ ID NO: 53.

39. The IL-2 conjugate of claim 37, wherein the IL-2 polypeptide further includes an N-terminal alanine residue or an N-terminal methionine residue.

40. The IL-2 conjugate of claim 37, wherein the non-natural amino acid is substituted for an amino acid at position P1, T2, S3, S4, S5, T6, K7, K8, or T9 or linked to the N-terminal amino acid by an amide linkage, wherein the amino acid position corresponds to the position of the amino acid in SEQ ID NO: 53 according to numbering scheme A.

41. The IL-2 conjugate of claim 40, wherein the non-natural amino acid is located at the amino acid position corresponding to position S4 of the amino acid sequence set forth in SEQ ID NO: 2, wherein the amino acid position is according to numbering scheme A.

42. The IL-2 polypeptide conjugate of claim 37, wherein the non-natural amino acid is selected from the group consisting of p-azidomethyl-L-phenylalanine, p-azido-L-phenylalanine, and N6-azidoethoxy-L-lysine.

43. The IL-2 conjugate of claim 37, wherein the non-natural amino acid is p-azidomethyl-L-phenylalanine.

44. The interleukin 2 (IL-2) conjugate of claim 14, wherein the IL-2 conjugate further includes an N-terminal methionine residue.

45. The interleukin 2 (IL-2) conjugate of claim 14, wherein the IL-2 conjugate further includes an N-terminal alanine residue.

46. A composition comprising:
the IL-2 conjugate of claim 22 and a pharmaceutically acceptable carrier or excipient.

47. A method for treating a proliferative disease or cancer in an individual, comprising:
administering a therapeutically effective amount of the composition of claim 46 to an individual in need thereof to treat the proliferative disease or cancer in the individual.

48. A combination therapy for treating a proliferative disease or cancer in an individual, comprising:
administering a therapeutically effective amount of the composition of claim 46 to an individual in need thereof, and
administering a therapeutically effective amount of a therapeutic agent to the individual, to treat the proliferative disease or cancer in the individual.

49. The IL-2 conjugate of claim 1, wherein the IL-2 polypeptide comprises an amino acid sequence with at least 90% identity to the amino acid sequence set forth in SEQ ID NO: 53.

50. The IL-2 conjugate of claim 1, wherein the IL-2 polypeptide comprises an amino acid sequence with at least 95% identity to the amino acid sequence set forth in SEQ ID NO: 53.

51. The IL-2 conjugate of claim 22, wherein the IL-2 polypeptide comprises an amino acid sequence with at least 90% identity to the amino acid sequence set forth in SEQ ID NO: 53.

52. The IL-2 conjugate of claim 22 wherein the IL-2 polypeptide comprises an amino acid sequence with at least 95% identity to the amino acid sequence set forth in SEQ ID NO: 53.

53. The IL-2 conjugate of claim 37, wherein the IL-2 polypeptide comprises an amino acid sequence with at least 90% identity to the amino acid sequence set forth in SEQ ID NO: 53.

54. The IL-2 conjugate of claim 37 wherein the IL-2 polypeptide comprises an amino acid sequence with at least 95% identity to the amino acid sequence set forth in SEQ ID NO: 53.

* * * * *